(12) United States Patent
Koike et al.

(10) Patent No.: US 9,624,170 B2
(45) Date of Patent: Apr. 18, 2017

(54) 4-(PIPERRAZIN-1-YL)-PYRROLIDIN-2-ONE COMPOUNDS AS MONOACYLGLYCEROL LIPASE (MAGL) INHIBITORS

(71) Applicant: TAKEDA PHARMACEUTICAL COMPANY LIMITED, Osaka-shi, Osaka (JP)

(72) Inventors: Tatsuki Koike, Fujisawa (JP); Makoto Fushimi, Fujisawa (JP); Jumpei Aida, Fujisawa (JP); Shuhei Ikeda, Fujisawa (JP); Tomokazu Kusumoto, Fujisawa (JP); Hideyuki Sugiyama, Fujisawa (JP); Hidekazu Tokuhara, Fujisawa (JP)

(73) Assignee: TAKEDA PHARMACEUTICAL COMPANY LIMITED, Osaka-shi, Osaka (JP)

( * ) Notice: Subject to any disclaimer, the term of this patent is extended or adjusted under 35 U.S.C. 154(b) by 0 days.

(21) Appl. No.: 15/108,000

(22) PCT Filed: Dec. 25, 2014

(86) PCT No.: PCT/JP2014/084752
§ 371 (c)(1),
(2) Date: Jun. 24, 2016

(87) PCT Pub. No.: WO2015/099196
PCT Pub. Date: Jul. 2, 2015

(65) Prior Publication Data
US 2016/0318864 A1    Nov. 3, 2016

(30) Foreign Application Priority Data
Dec. 26, 2013 (JP) .............................. 2013-269244

(51) Int. Cl.
| | | |
|---|---|---|
| *C07D 207/273* | (2006.01) | |
| *C07D 401/12* | (2006.01) | |
| *C07D 403/12* | (2006.01) | |
| *C07D 403/14* | (2006.01) | |
| *C07D 409/12* | (2006.01) | |
| *C07D 471/04* | (2006.01) | |
| *C07D 405/12* | (2006.01) | |
| *C07D 417/14* | (2006.01) | |
| *C07D 417/12* | (2006.01) | |
| *C07D 413/12* | (2006.01) | |
| *C07D 403/04* | (2006.01) | |
| *C07D 401/14* | (2006.01) | |

(52) U.S. Cl.
CPC ....... *C07D 207/273* (2013.01); *C07D 401/12* (2013.01); *C07D 401/14* (2013.01); *C07D 403/04* (2013.01); *C07D 403/12* (2013.01); *C07D 403/14* (2013.01); *C07D 405/12* (2013.01); *C07D 409/12* (2013.01); *C07D 413/12* (2013.01); *C07D 417/12* (2013.01); *C07D 417/14* (2013.01); *C07D 471/04* (2013.01)

(58) Field of Classification Search
None
See application file for complete search history.

(56) References Cited

FOREIGN PATENT DOCUMENTS

| GB | 1080680 A | 8/1967 |
|---|---|---|
| WO | 2010/124082 A1 | 10/2010 |
| WO | 2010/124086 A1 | 10/2010 |
| WO | 2010/124121 A1 | 10/2010 |
| WO | 2010/124122 A1 | 10/2010 |
| WO | 2011/041713 A2 | 4/2011 |
| WO | 2012/044613 A1 | 4/2012 |
| WO | 2012/054716 A1 | 4/2012 |
| WO | 2012/030907 A1 | 8/2012 |
| WO | 2013/049289 A1 | 4/2013 |
| WO | 2013/049293 A1 | 4/2013 |

OTHER PUBLICATIONS

ISR issued in corresponding international application No. PCT/JP2014/084752 mailed Mar. 11, 2015.
Neurochemical Research, vol. 36, pp. 1520-1525, 2011.
Neuropsychopharmacology, vol. 39, pp. 1763-1776, 2014.
Journal of Headache and Pain, vol. 15, No. 14, 2014.
Brain Research, vol. 1298, pp. 13-23, 2009.
Brain Research, vol. 1474, pp. 91-99, 2012.
PLoS One (2012), 7(8), e42120/CODEN: POLNCL; ISSN: 1932-6203.
Petty, A., et al., "A small molecule agonist of EphA2 receptor tyrosine kinase inhibits tumor cell migration in vitro and prostate cancer metastasis in vivo", PLoS One (2012), 7(8), e42120, CODEN: POLNCL; ISSN: 1932-6203.

(Continued)

*Primary Examiner* — Brian J Davis
(74) *Attorney, Agent, or Firm* — Nath, Goldberg & Meyer; Joshua B. Goldberg; Scott H. Blackman

(57) ABSTRACT

The present invention aims to provide a compound having an MAGL inhibitory action, and useful as a prophylactic or therapeutic agent for neurodegenerative diseases (e.g., Alzheimer's disease, Huntington's disease, Parkinson's disease, amyotrophic lateral sclerosis, traumatic brain injury, glaucoma, multiple sclerosis and the like), anxiety disorder, pain (e.g., inflammatory pain, carcinomatous pain, nervous pain and the like), epilepsy and the like. The present invention relates to a compound represented by the formula (I):

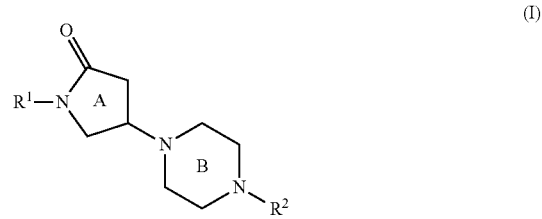

wherein each symbol is as described in the DESCRIPTION, or a salt thereof.

16 Claims, 3 Drawing Sheets

(56) References Cited

OTHER PUBLICATIONS

Science, vol. 294, pp. 1871-1875, 2001.
Molecular Neurobiology, vol. 41, pp. 115-128, 2010.
Neuron, vol. 53, pp. 337-351, 2007.
Nature Reviews Neurology, vol. 6, pp. 193-201, 2010.
Chemistry and Physics of Lipids, vol. 121, pp. 149-158, 2002.
Cell Report, vol. 1, p. 617-623, 2012.
Biochemical Pharmacology, vol. 50, 83-90, 1995.
Molecular Pharmacology, vol. 34, pp. 605-613, 1988.
Neuroscience Letters, vol. 396, pp. 113-116, 2006.
Journal of Alzheimer's Disease, vol. 30, pp. 439-459, 2012.
Neuroscience, vol. 178, pp. 159-168, 2011.
Annals of Neurology, vol. 57, pp. 168-175, 2005.
Science, vol. 334, pp. 809-813, 2011.
Neurobiology of Disease, vol. 15, pp. 601-609, 2004.
European Journal of Pharmacology, vol. 542, pp. 100-105, 2006.
Brain, vol. 132, pp. 3152-3164, 2009.
Brain Research, vol. 1390, pp. 126-141, 2011.
Nature, vol. 413, pp. 527-531, 2001.
Experimental Eye Research, vol. 87, pp. 106-114, 2008.
Behavioural Brain Research, vol. 252, pp. 10-17, 2013.
British Journal of Pharmacology, vol. 150, pp. 693-701, 2007.
Pharmacological Research, vol. 64, pp. 60-67, 2011.
Nature of Medicine, vol. 16, pp. 413-419, 2010.

ated on Jun. 23, 2016, 1 KB), is incorporated herein by reference.
4-(PIPERRAZIN-1-YL)-PYRROLIDIN-2-ONE COMPOUNDS AS MONOACYLGLYCEROL LIPASE (MAGL) INHIBITORS This is a National Phase Application filed under 35 U.S.C. 371 as a national stage of PCT/JP2014/084752, filed Dec. 25, 2014, an application claiming the benefit of Japanese Application No. 2013-269244, filed Dec. 26, 2013, the content of each of which is hereby incorporated by reference in its entirety.

TECHNICAL FIELD

The present invention relates to a heterocyclic compound having a monoacylglycerol lipase (sometimes to be abbreviated as "MAGL" in the present specification) inhibitory action, a pharmaceutical composition containing same and the like.

The Sequence Listing submitted in text format (.txt) filed on Jun. 24, 2014, named "3064SequenceListing.txt", (created on Jun. 23, 2016, 1 KB), is incorporated herein by reference.

BACKGROUND OF THE INVENTION

Arachidonic acid (sometimes to be abbreviated as "AA" in the present specification), and eicosanoid, which is a product in vivo, have been reported to cause inflammation in the central nervous system and peripheral [non-patent document 1: Science, vol. 294, pages 1871-1875, 2001]. An inhibitor that suppresses arachidonic acid production pathway, and eicosanoid production pathway is promising as a therapeutic drug for inflammatory diseases, and non-steroidal anti-inflammatory drugs such as cyclooxygenase inhibitor and the like have been used as therapeutic drugs for inflammatory pain. However, when a cyclooxygenase inhibitor is used for a long time, digestive tract disorders are sometimes developed as side effects, thus posing a problem. In addition, circulatory side effects such as myocardial infarction, cerebral infarction and the like also pose problems in recent years.

Neuroinflammation accompanied by activation of glial cells has been suggested to be a pathological change characteristic of neurodegenerative diseases (e.g., Alzheimer's disease etc.) [non-patent document 2: Molecular Neurobiology (Mol. Neurobiol), vol. 41, pages 115-128, 2010]. It has been reported that anti-inflammatory drugs suppress activation of glial cells and suppress neurodegenerative progression in an animal model of tau overexpression (human variant tau transgenic mouse etc.) which is a pathological characteristic of Alzheimer's disease [non-patent document 3: Neuron, vol. 53, pages 337-351, 2007]. In addition, the effectiveness of suppression of neuroinflammation for the treatment of neurodegenerative diseases such as Alzheimer's disease and the like has been suggested [non-patent document 4: Nature Reviews Neurology (Nat. Rev. Neurol.), vol. 6, pages 193-201, 2010], and a therapeutic drug that suppresses neuroinflammation is promising as a therapeutic or prophylactic drug for neurodegenerative diseases.

Monoacylglycerol lipase (MAGL) is an enzyme that hydrolyzes monoacylglycerol into fatty acid and glycerol. In the central nervous system, the substrate of MAGL is 2-arachidonoylglycerol (also referred to as 2-AG in the present specification) which is decomposed into arachidonic acid and glycerol [non-patent document 5: Chemistry and Physics of Lipids (Chem phys Lipids) vol. 121, pages 149-158, 2002]. In recent years, suppression of production of arachidonic acid and eicosanoids, suppression of activation of glial cell, suppression of production of inflammatory cytokine, and a decreasing action on the accumulation of Aβ plaque which is a pathologic finding of Alzheimer's disease have been reported in a crossbred animal of MAGL deficient mouse and amyloid β (to be also referred to as Aβ in the present specification) overexpressing animal model (APP/PS1 double transgenic mouse etc.) [non-patent document 6: Cell Report (Cell Rep.), vol. 1, pages 617-623, 2012], and an inhibitor etc. that suppress the action of MAGL are promising as a therapeutic or prophylactic drug for Alzheimer's disease.

In addition, as receptors of 2-AG, which is a substrate of MAGL, cannabinoid receptor 1 (to be referred to as CB1 in the present specification), and cannabinoid receptor 2 (to be referred to as CB2 in the present specification) have been identified [non-patent document 7: Biochemical Pharmacology (Biochem. Pharmcol.) vol. 50, 83-90, 1995]. CB1 is mainly expressed in the brain region [non-patent document 8: Molecular Pharmacology (Mol. Pharmacol.), vol. 34, pages 605-613, 1988], and CB2 is expressed in immunocyte, and microglial cell in the brain region [non-patent document 9: Neuroscience Letters (Neurosci. Lett.), vol. 396, pages 113-116, 2006]. In recent years, it has been reported that CB1 receptor agonist improves cognition function [non-patent document 10: Journal of Alzheimer's Disease (J. Alzheimers. Dis.), vol. 30, pages 439-459, 2012], and 2-AG, which is the substrate of MAGL, shows a protective action against nerve cell death due to Aβ [non-patent document 11: Neuroscience, vol. 178, pages 159-168, 2011]. Therefore, MAGL inhibitor that suppresses decomposition of 2-AG is promising as a therapeutic or prophylactic drug that suppresses neuroinflammation, nerve cell death, Aβ accumulation and the like observed in Alzheimer's disease and having not only a symptomatic relief action but also a disease-modifying action.

Parkinson's disease, which is one of the neurodegenerative diseases, is a disease associated with movement disorders caused by the degeneration of midbrain substantia nigra dopamine nerve cells, for which activation of glial cell has been reported [non-patent document 12: Annals of Neurology (Ann. Neurol.) vol. 57, pages 168-175, 2005]. While 1-methyl-4-phenyl-1,2,3,6-tetrahydropyridine(1-methyl-4-phenyl-1,2,3,6-tetrahydropyridine) is known to induce midbrain substantia nigra dopamine nerve cell death, it has been reported to show a protective action against nerve cell death in MAGL deficient mouse [non-patent document 13: Science, vol. 334, pages 809-813, 2011]. Therefore, an inhibitor etc. that suppress the action of MAGL are promising as new therapeutic drugs for Parkinson's disease.

Amyotrophic lateral sclerosis (to be referred to as ALS in the present specification) is a disease associated with degeneration of motor neuron, and an effective treatment method does not exist at present. Activation of glial cell in ALS has been reported [non-patent document 14: Neurobiology of Disease (Neurobiol. Dis.) vol. 15, pages 601-609, 2004]. It has also been reported that activation of CB2 suppresses progression of the disease in mutant superoxide dismutase overexpression mouse, which is an animal model of ALS [non-patent document 15: European Journal of Pharmacology (Eur. J. Pharmacol.), vol. 542, pages 100-105, 2006]. In addition, it has been reported that neuroinflammation in MAGL deficient mouse is suppressed by decreasing arachidonic acid, which is a product of MAGL in the living body

[non-patent document 13: Science, vol. 334, pages 809-813, 2011]. Therefore, an MAGL inhibitor is promising as a new therapeutic drug for ALS.

Huntington's disease which is one of the neurodegenerative diseases is a disease wherein a neurological function is lost by nerve cell death and neuroinflammation due to polyglutamine aggregation. It has been reported that activation of CB2 suppresses neuroinflammation and shows a neuroprotective action in R6/2 mouse which is an animal model of Huntington's disease [non-patent document 16: Brain, vol. 132, pages 3152-3164, 2009]. In addition, it has been reported that neuroinflammation is suppressed by decreasing arachidonic acid, which is a resultant product of MAGL, in MAGL deficient mouse [non-patent document 13: Science, vol. 334, pages 809-813, 2011]. Therefore, an MAGL inhibitor is promising as a new therapeutic drug for Huntington's disease.

2-AG, which is a substrate of MAGL, has been reported to suppress progression of the disease state in an autoimmune encephalomyelitis model, i.e., an animal model of multiple sclerosis which is one of the central demyelination diseases [non-patent document 17: Brain Research (Brain Res.), vol. 1390, pages 126-141, 2011]. In addition, it has been reported that neuroinflammation is suppressed in MAGL deficient mouse by decreasing arachidonic acid, which is a resultant product of MAGL [non-patent document 13: Science, vol. 334, pages 809-813, 2011]. Therefore, an MAGL inhibitor is promising as a new therapeutic drug for multiple sclerosis.

Traumatic brain injury (TBI) is a condition exerting an extremely harmful influence on the health of individuals, and an effective treatment method does not exist at present. 2-AG, which is a substrate of MAGL, has been reported to have a protective action against nerve cell death in a closed head injury animal model [non-patent document 18: Nature, vol. 413, pages 527-531, 2001]. Therefore, an MAGL inhibitor is promising as a new therapeutic or prophylactic drug for traumatic brain injury.

Glaucoma most often causes loss of eyesight, and is considered a serious social problem. 2-AG, which is a substrate of MAGL, has been reported to activate aqueous outflow in an intraocular perfusion model [non-patent document 19: Experimental Eye Research (Exp. Eye Res.), vol. 87, pages 106-114, 2008]. Therefore, an MAGL inhibitor is promising as a new therapeutic or prophylactic drug for glaucoma.

Anxiety disorder is a mental disease that occurs highly frequently, and greatly influences the quality of life. 2-AG, which is a substrate of MAGL, has been reported to show an anti-anxiety action in an elevated plus maze test, which is an effective test system of anxiety disorder [non-patent document 20: Behavioural Brain Research (Behav. Brain Res.), vol. 252, pages 10-17, 2013]. Therefore, an MAGL inhibitor is promising as a new therapeutic drug for anxiety disorders.

2-AG, which is a substrate of MAGL, has been reported to show an antinociceptive effect in a formalin test [non-patent document 21: British Journal of Pharmacology, vol. 150, pages 693-701, 2007]. In addition, 2-AG has been reported to show effect in a mechanical hyperalgesia test which is a carcinomatous pain model [non-patent document 22: Pharmacological Research (Pharmacol. Res.), vol. 64, pages 60-67, 2011]. Therefore, an MAGL inhibitor is promising as a new therapeutic drug for inflammatory pain and nervous pain.

Epilepsy greatly influences daily life. It is known that neuroinflammation has been induced in the hippocampus of temporal lobe epilepsy patients, and neuroinflammation accompanied by activation of glial cells is involved in convulsive attack [non-patent document 23: Nature Medicine (Nature Med.), vol. 16, pages 413-419, 2010]. 2-AG, which is a substrate of MAGL, has a suppressive action on pentylenetetrazole-induced convulsive attack, which is an acute convulsion model [non-patent document 24: Neurochemical Research (Neurochem. Res.), vol. 36, pages 1520-1525, 2011]. Therefore, an MAGL inhibitor is promising as a new therapeutic drug for epilepsy.

Depression is a disease that occurs highly frequently in the modern society, and greatly influences the quality of life. 2-AG, which is a substrate of MAGL, has been reported to show an anti-depression action on chronicle stress model which is an effective test system of depression [non-patent document 25: Neuropsychopharmacology, vol. 39, pages 1763-1776, 2014]. Therefore, an MAGL inhibitor is promising as a new therapeutic drug for depression.

Migraine is a disease that occurs highly frequently in the modern society, and greatly influences the quality of life. One of the factors that develop migraine is neuroinflammation. Activation of CB2 has been reported to have an analgesic action in nitroglycerin-administered rat, which is an effective test system of migraine [non-patent document 26: Journal of Headache and Pain, vol. 15, No. 14, 2014]. Therefore, an MAGL inhibitor is promising as a new therapeutic drug for migraine.

Cerebral edema is a disease developed in association with various encephalopathies. One of the causes of cerebral edema is collapse of blood-brain barrier. Arachidonic acid and eicosanoids are known to collapse blood-brain barrier [non-patent document 27: Brain Research, vol. 1298, pages 13-23, 2009]. An inhibitor that suppresses the action of MAGL decreases production of arachidonic acid by MAGL. Therefore, an MAGL inhibitor is promising as a new therapeutic drug for cerebral edema.

Cerebral ischemia is one factor causing the onset of cerebral infarction. 2-AG, which is a substrate of MAGL, has been reported to have a brain protective action in a test system effective for cerebral ischemia [non-patent document 28: Brain Research, vol. 1474, pages 91-99, 2012]. Therefore, an MAGL inhibitor is promising as a new therapeutic drug for cerebral ischemia.

As the heterocyclic compound, the following compounds are known. Patent document 1 describes that a compound represented by the following formula (I):

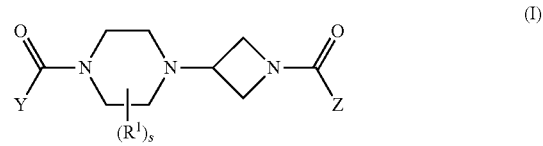

wherein each symbol is as defined in patent document 1, is an MAGL inhibitor and useful for the treatment of pain and the like.

Patent document 2 describes that a compound represented by the following formula (I):

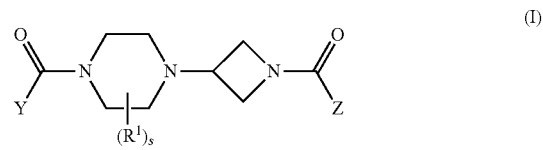

wherein each symbol is as defined in patent document 2, is an MAGL inhibitor and useful for the treatment of pain and the like.

patent document 3 describes that a compound represented by the following formula (I):

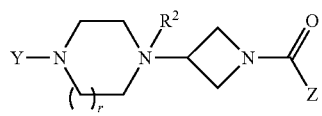

(1)

wherein each symbol is as defined in patent document 3, is an MAGL inhibitor, and useful for the treatment of pain and the like.

Patent document 4 describes that a compound represented by the following formula (I):

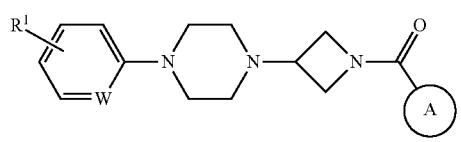

(I)

wherein each symbol is as defined in patent document 4, is an MAGL inhibitor, and useful for the treatment of pain and the like.

Patent document 5 describes that a compound represented by the following formula:

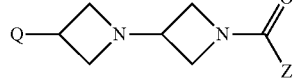

wherein each symbol is as defined in patent document 5, is useful as an MAGL inhibitor.

Patent document 6 describes that a compound represented by the following formula:

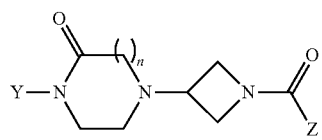

wherein each symbol is as defined in patent document 6, and a compound represented by the following formula:

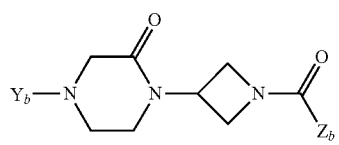

wherein each symbol is as defined in patent document 6, is useful as an MAGL inhibitor.

Patent document 7 describes that a compound represented by the following formula:

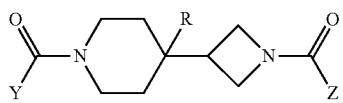

wherein each symbol is as defined in patent document 7, is useful as an MAGL inhibitor.

Patent document 8 describes that a compound represented by the following formula (I):

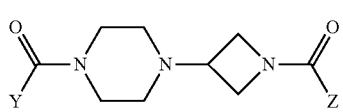

(I)

wherein each symbol is as defined in patent document 8, is an MAGL inhibitor, and useful for the treatment, improvement or prophylaxis of metabolic diseases (obesity, diabetes).

Patent document 9 describes that a compound represented by the following formula (I):

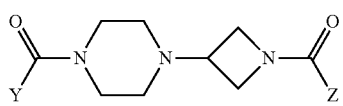

(I)

wherein each symbol is as defined in patent document 9, is an MAGL inhibitor, and useful for the treatment, improvement or prophylaxis of metabolic diseases (obesity, diabetes).

Patent document 10 describes that a compound represented by the following formula (I):

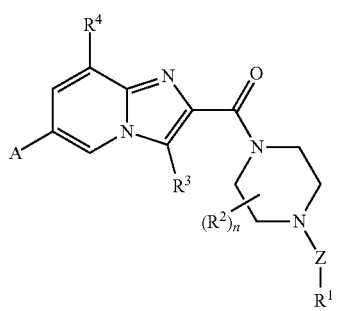

wherein each symbol is as defined in patent document 10, is useful as a therapeutic drug for virus infection with HCV and the like.

In addition, a compound represented by the following formula:

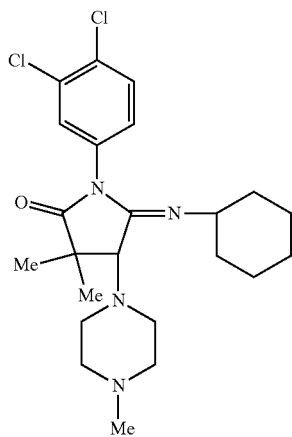 [SMILES: CN1CCN(C2C(=NC3CCCCC3)N(c3ccc(Cl)c(Cl)c3)C(=O)C2(C)C)CC1]

(CAS registry number: 7738-09-2),
a compound represented by the following formula:

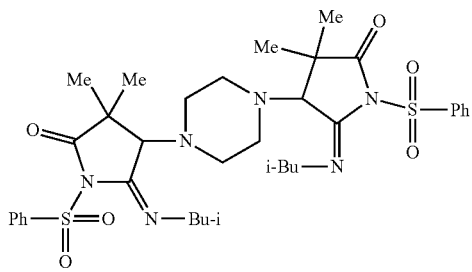

(CAS registry number: 1195573-79-5),
a compound represented by the following formula:

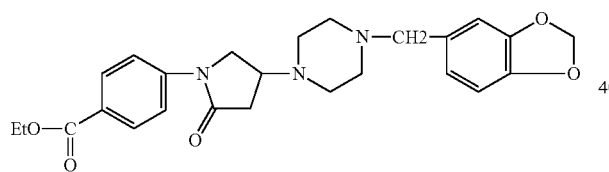

(CAS registry number: 1438897-72-3),
a compound represented by the following formula:

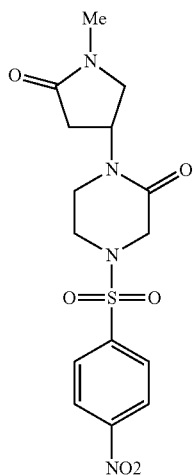 [SMILES: CN1CC(N2CCN(S(=O)(=O)c3ccc([N+](=O)[O-])cc3)CC2=O)CC1=O]

(CAS registry number: 1284249-15-5), a compound represented by the following formula:

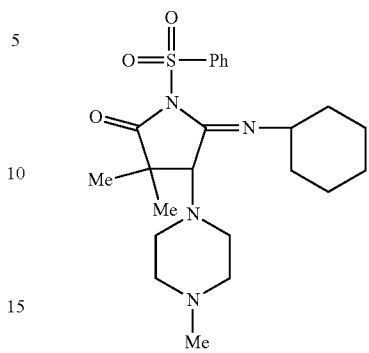

(CAS registry number: 18146-33-3),
a compound represented by the following formula:

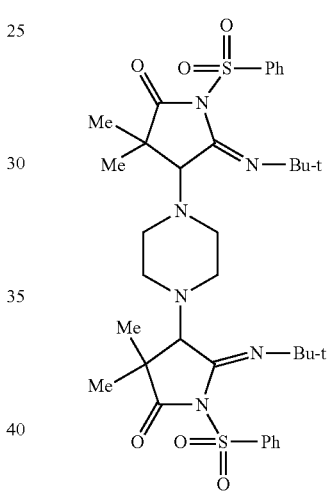

(CAS registry number: 18146-34-4),
a compound represented by the following formula:

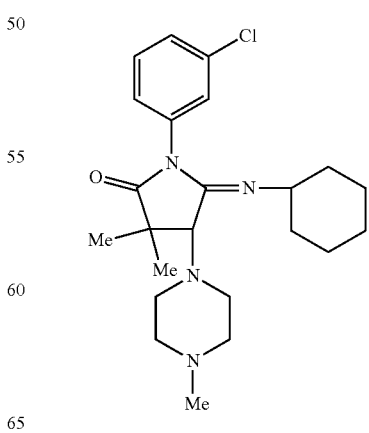

(CAS registry number: 7776-81-0), a compound represented by the following formula:

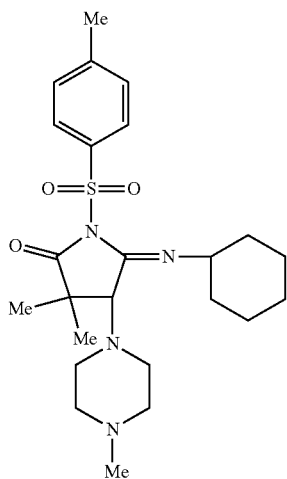 [SMILES: Cc1ccc(S(=O)(=O)N2C(=O)C(C)(C)C(N3CCN(C)CC3)C2=NC2CCCCC2)cc1]

(CAS registry number: 7776-83-2),
a compound represented by the following formula:

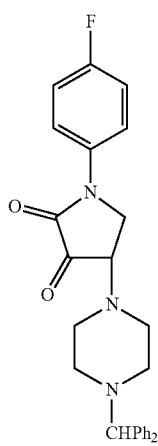

(CAS registry number: 1024432-22-1),
a compound represented by the following formula:

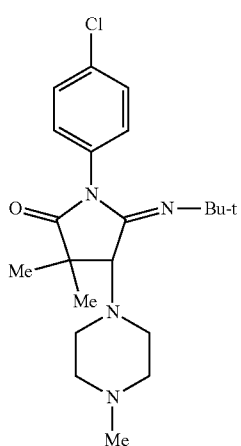

(CAS registry number: 1021295-46-4), a compound represented by the following formula:

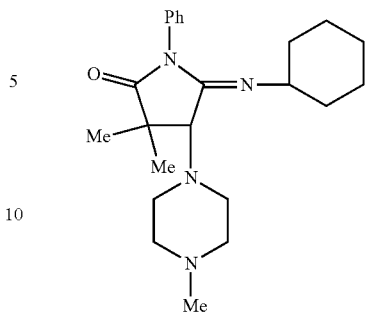

(CAS registry number: 1021295-42-0),
a compound represented by the following formula:

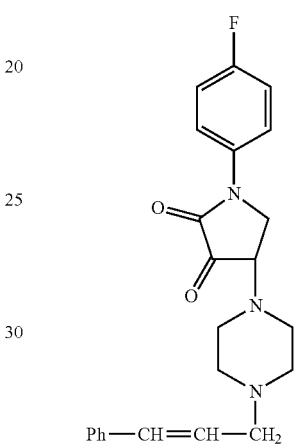

(CAS registry number: 664308-10-5),
a compound represented by the following formula:

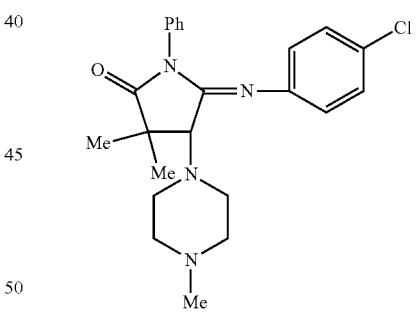

(CAS registry number: 933233-84-2),
a compound represented by the following formula:

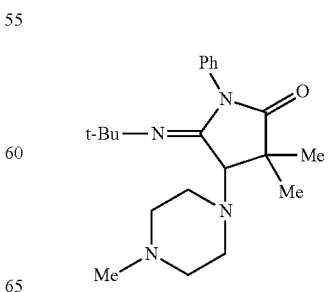

(CAS registry number: 1021295-34-0), a compound represented by the following formula:

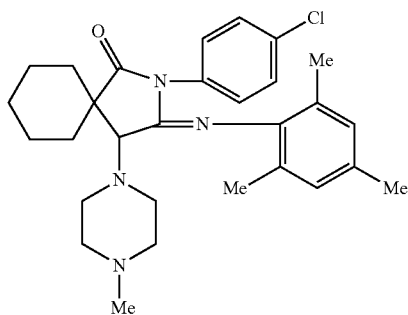

(CAS registry number: 1021295-73-7),
a compound represented by the following formula:

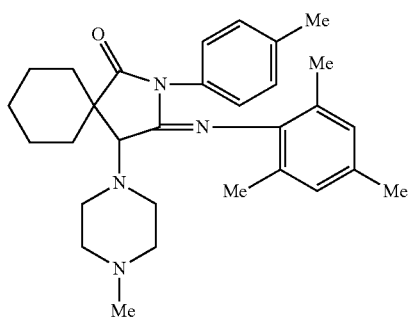 [SMILES: Cc1cc(C)c(N=C2C(N3CCN(C)CC3)C3(CCCCC3)C(=O)N2c2ccc(Cl)cc2)c(C)c1]

(CAS registry number: 1021295-70-4),
a compound represented by the following formula:

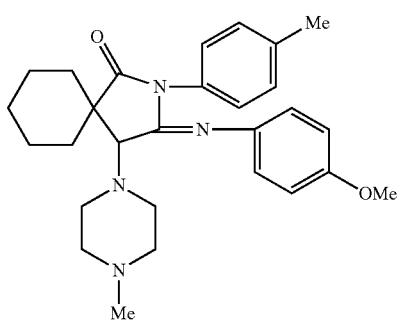 [SMILES: COc1ccc(N=C2C(N3CCN(C)CC3)C3(CCCCC3)C(=O)N2c2ccc(C)cc2)cc1]

(CAS registry number: 1021295-67-9),
a compound represented by the following formula:

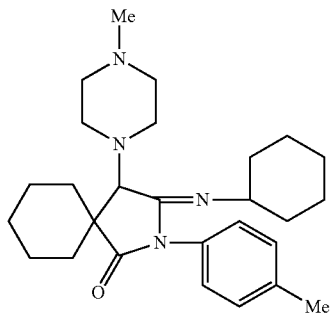 [SMILES: Cc1ccc(N2C(=O)C3(CCCCC3)C(N3CCN(C)CC3)C2=NC2CCCCC2)cc1]

(CAS registry number: 1021295-64-6), a compound represented by the following formula:

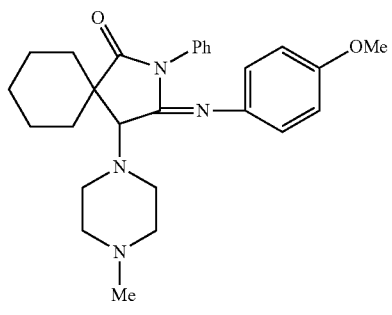 [SMILES: COc1ccc(N=C2C(N3CCN(C)CC3)C3(CCCCC3)C(=O)N2c2ccccc2)cc1]

(CAS registry number: 942028-84-4),
a compound represented by the following formula:

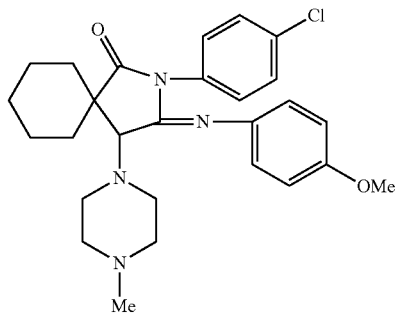 [SMILES: COc1ccc(N=C2C(N3CCN(C)CC3)C3(CCCCC3)C(=O)N2c2ccc(Cl)cc2)cc1]

(CAS registry number: 942025-61-8),
a compound represented by the following formula:

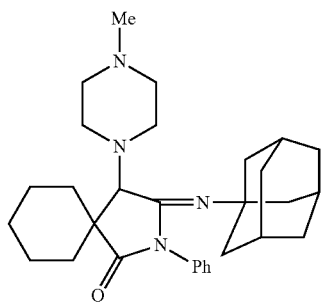 [SMILES: CN1CCN(C2C(=NC34CC5CC(CC(C5)C3)C4)N(c3ccccc3)C(=O)C23CCCCC3)CC1]

(CAS registry number: 942028-82-2),
a compound represented by the following formula

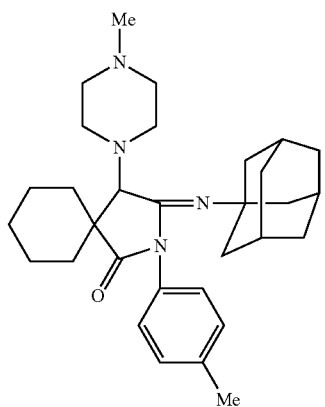 [SMILES: Cc1ccc(N2C(=O)C3(CCCCC3)C(N3CCN(C)CC3)C2=NC23CC4CC(CC(C4)C2)C3)cc1]

(CAS registry number: 942025-59-4), a compound represented by the following formula

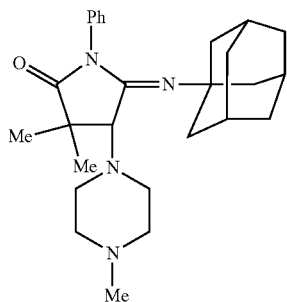 [SMILES: CN1CCN(C2C(=NC34CC5CC(CC(C5)C3)C4)N(c3ccccc3)C(=O)C2(C)C)CC1]

(CAS registry number: 933208-31-2),
a compound represented by the following formula

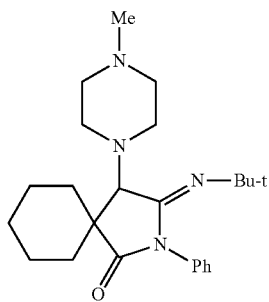

(CAS registry number: 942028-80-0),
a compound represented by the following formula

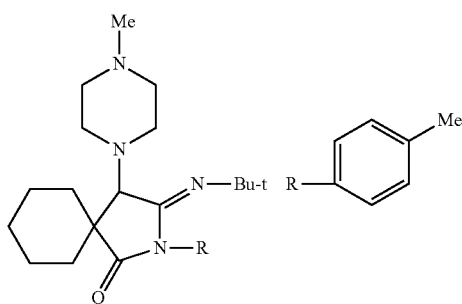

(CAS registry number: 942025-57-2), and
a compound represented by the following formula

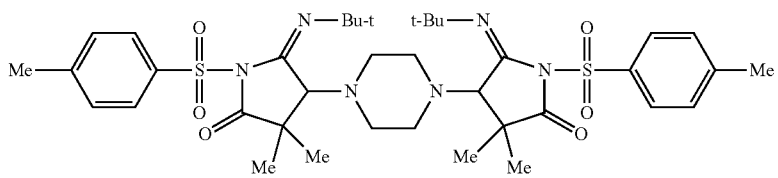

(CAS registry number: 7739-84-6) are known.

DOCUMENT LIST

Patent Documents patent document 1: WO 2010/124082
patent document 2: WO 2010/124086
patent document 3: WO 2010/124121
patent document 4: WO 2010/124122
patent document 5: WO 2012/030907
patent document 6: WO 2012/044613
patent document 7: WO 2012/054716
patent document 8: WO 2013/049289
patent document 9: WO 2013/049293
patent document 10: WO 2011/041713

Non-Patent Documents non-patent document 1: Science, vol. 294, pages 1871-1875, 2001
non-patent document 2: Molecular Neurobiology (Mol. Neurobiol), vol. 41, pages 115-128, 2010
non-patent document 3: Neuron, vol. 53, pages 337-351, 2007
non-patent document 4: Nature Reviews Neurology (Nat. Rev. Neurol.), vol. 6, pages 193-201, 2010
non-patent document 5: Chemistry and Physics of Lipids (Chem phys Lipids) vol. 121, pages 149-158, 2002
non-patent document 6: Cell Report (Cell Rep.), vol. 1, page 617-623, 2012
non-patent document 7: Biochemical Pharmacology (Biochem. Pharmcol.) vol. 50, 83-90, 1995
non-patent document 8: Molecular Pharmacology (Mol. Pharmacol.), vol. 34, pages 605-613, 1988
non-patent document 9: Neuroscience Letters (Neurosci. Lett.), vol. 396, pages 113-116, 2006
non-patent document 10: Journal of Alzheimer's Disease (J. Alzheimers. Dis.), vol. 30, pages 439-459, 2012
non-patent document 11: Neuroscience, vol. 178, pages 159-168, 2011
non-patent document 12: Annals of Neurology (Ann. Neurol.) vol. 57, pages 168-175, 2005
non-patent document 13: Science, vol. 334, pages 809-813, 2011 non-patent document 14: Neurobiology of Disease (Neurobiol. Dis.) vol. 15, pages 601-609, 2004
non-patent document 15: European Journal of Pharmacology (Eur. J. Pharmacol.), vol. 542, pages 100-105, 2006
non-patent document 16: Brain, vol. 132, pages 3152-3164, 2009
non-patent document 17: Brain Research (Brain Res.), vol. 1390, pages 126-141, 2011
non-patent document 18: Nature, vol. 413, pages 527-531, 2001
non-patent document 19: Experimental Eye Research (Exp. Eye Res.), vol. 87, pages 106-114, 2008
non-patent document 20: Behavioural Brain Research (Behav. Brain Res.), vol. 252, pages 10-17, 2013
non-patent document 21: British Journal of Pharmacology, vol. 150, pages 693-701, 2007
non-patent document 22: Pharmacological Research (Pharmacol. Res.), vol. 64, pages 60-67, 2011 non-patent document 23: Nature Medicine (Nature Med.), vol. 16, pages 413-419, 2010 non-patent document 24: Neurochemical Research (Neurochem. Res.), vol. 36, pages 1520-1525, 2011
non-patent document 25: Neuropsychopharmacology, vol. 39, pages 1763-1776, 2014
non-patent document 26: Journal of Headache and Pain, vol. 15, No. 14, 2014
non-patent document 27: Brain Research, vol. 1298, pages 13-23, 2009
non-patent document 28: Brain Research, vol. 1474, pages 91-99, 2012

SUMMARY OF THE INVENTION

Problems to be Solved by the Invention

An object of the present invention is to provide a compound having an MAGL inhibitory action, and useful as a prophylactic or therapeutic agent for neurodegenerative disease (e.g., Alzheimer's disease, Huntington's disease, Parkinson's disease, amyotrophic lateral sclerosis, traumatic brain injury, glaucoma, multiple sclerosis and the like), anxiety disorder, pain (e.g., inflammatory pain, carcinomatous pain, nervous pain and the like), epilepsy and the like.

Means of Solving the Problems

The present inventors have conducted intensive studies in an attempt to solve the above-mentioned problems and found that a compound represented by the following formula (I) has an MAGL inhibitory action, and therefore, is useful as a prophylactic or therapeutic agent for neurodegenerative disease (e.g., Alzheimer's disease, Huntington's disease, Parkinson's disease, amyotrophic lateral sclerosis, traumatic brain injury, glaucoma, multiple sclerosis and the like), anxiety disorder, pain (e.g., inflammatory pain, carcinomatous pain, nervous pain and the like), epilepsy and the like, which resulted in the completion of the present invention.

Accordingly, the present invention provides the following.

[1] A compound represented by the formula (I):

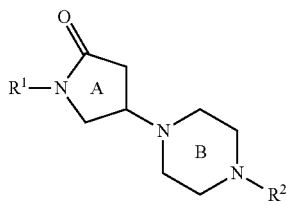

(I)

wherein
ring A is a pyrrolidin-2-one ring optionally substituted by 1 or 2 additional substituents selected from a halogen atom, a cyano group, an optionally substituted hydroxy group, an optionally substituted amino group, an optionally substituted sulfanyl group, an acyl group, an optionally substituted hydrocarbon group, and an optionally substituted heterocyclic group,
ring B is a piperazine ring optionally substituted by 1 to 3 additional substituents selected from a halogen atom, a cyano group, an optionally substituted hydroxy group, an optionally substituted amino group, an optionally substituted sulfanyl group, an acyl group, an optionally substituted hydrocarbon group, and an optionally substituted heterocyclic group,
$R^1$ is an optionally substituted hydrocarbon group or an optionally substituted heterocyclic group, and
$R^2$ is an acyl group, an optionally substituted $C_{6-14}$ aryl group,
or an optionally substituted heterocyclic group,
or a salt thereof (hereinafter to be also referred to as compound (I)).
[2] The compound or salt of the above-mentioned [1], wherein ring A is a pyrrolidin-2-one ring optionally substituted by 1 or 2 additional substituents selected from a halogen atom, a hydroxy group and a $C_{1-6}$ alkyl group; and ring B is a piperazine ring optionally further substituted by 1 to 3 $C_{1-6}$ alkyl groups.
[3] The compound or salt of the above-mentioned [1] or [2], wherein the both ring A and ring B are not substituted by the additional substituents.
[4] The compound or salt of the above-mentioned [1] or [2], wherein $R^1$ is
(1) a $C_{6-14}$ aryl group optionally substituted by 1 to 3 substituents selected from
   (i) an optionally substituted hydrocarbon group,
   (ii) an optionally substituted heterocyclic group,
   (iii) an acyl group,
   (iv) an optionally substituted amino group,
   (v) an optionally substituted hydroxy group,
   (vi) a halogen atom, and
   (vii) a cyano group;
(2) a 5- to 14-membered aromatic heterocyclic group optionally substituted by 1 to 3 substituents selected from
   (i) an optionally substituted hydrocarbon group,
   (ii) an optionally substituted heterocyclic group,
   (iii) an acyl group,
   (iv) an optionally substituted amino group,
   (v) an optionally substituted hydroxy group, and
   (vi) a halogen atom;
(3) a 3- to 14-membered non-aromatic heterocyclic group optionally substituted by 1 to 3 substituents selected from
   (i) an optionally substituted hydrocarbon group,
   (ii) an optionally substituted heterocyclic group,
   (iii) an acyl group, and
   (iv) a halogen atom;
(4) a $C_{1-6}$ alkyl group optionally substituted by 1 to 3 optionally substituted hydrocarbon groups, or (5) a $C_{3-10}$ cycloalkenyl group.
[5] The compound or salt of any of the above-mentioned [1], [2] and [4], wherein $R^1$ is
(1) a $C_{6-14}$ aryl group optionally substituted by 1 to 3 substituents selected from
   (i) a $C_{6-14}$ aryloxy group optionally substituted by 1 to 3 substituents selected from
      (a) a $C_{1-6}$ alkoxy group, and
      (b) a halogen atom,
   (ii) a halogen atom,
   (iii) a cyano group,
   (iv) an optionally halogenated $C_{1-6}$ alkoxy group,
   (v) a $C_{1-6}$ alkyl group optionally substituted by 1 to 3 substituents selected from
      (a) a halogen atom,
      (b) a cyano group,
      (c) a $C_{6-14}$ aryl group, and
      (d) a 3- to 14-membered non-aromatic heterocyclic group optionally substituted by 1 to 3 $C_{1-6}$ alkyl groups,
   (vi) a $C_{7-16}$ aralkyloxy group,
   (vii) a $C_{3-10}$ cycloalkyl group,
   (viii) a $C_{6-14}$ aryl group optionally substituted by 1 to substituents selected from (a) a halogen atom,
(b) a cyano group,
(c) a $C_{1-6}$ alkyl group optionally substituted by 1 to 3 substituents selected from a halogen atom, a hydroxy group and a carbamoyl group,
(d) an optionally halogenated $C_{1-6}$ alkoxy group,
(e) a carboxy group,
(f) a mono- or di-$C_{1-6}$ alkyl-carbonylamino group,
(g) a mono- or di-$C_{1-6}$ alkylsulfonylamino group,
(h) a sulfamoyl group,
(i) a mono- or di-$C_{1-6}$ alkylsulfamoyl group,
(j) a carbamoyl group,
(k) a mono- or di-$C_{1-6}$ alkyl-carbamoyl group,
(l) a 3- to 14-membered non-aromatic heterocyclylcarbonyl group,
(m) a $C_{6-14}$ aryl group,
(n) a $C_{6-14}$ aryloxy group, and
(o) a 3- to 14-membered non-aromatic heterocyclic group,
(ix) a 5- to 14-membered aromatic heterocyclic group optionally substituted by 1 to 3 substituents selected from
(a) a halogen atom,
(b) an optionally halogenated $C_{1-6}$ alkyl group, and
(c) a $C_{1-6}$ alkoxy group,
(x) a 3- to 14-membered non-aromatic heterocyclic group optionally substituted by 1 to 3 substituents selected from
(a) a $C_{1-6}$ alkyl group,
(b) a $C_{1-6}$ alkoxy group, and
(c) an oxo group,
(xi) a 5- to 14-membered aromatic heterocyclyloxy group,
(xii) a mono- or di-$C_{6-14}$ arylamino group optionally substituted by 1 to 3 substituents selected from
(a) a halogen atom,
(b) a mono- or di-$C_{1-6}$ alkyl-carbonylamino group,
(c) a ($C_{1-6}$ alkyl) ($C_{1-6}$ alkyl-carbonyl)amino group, and
(d) a pyrrolidinyl group optionally substituted by 1 to 3 oxo groups,
(xiii) a mono- or di-$C_{6-14}$ aryl-carbamoyl group,
(xiv) a $C_{3-10}$ cycloalkylamino group, and
(xv) a 3- to 14-membered non-aromatic heterocyclylamino group optionally substituted by 1 to 3 substituents selected from
(a) a $C_{1-6}$ alkyl group,
(b) a $C_{1-6}$ alkyl-carbonyl group, and
(c) an oxo group,
(2) a 5- or 6-membered monocyclic aromatic heterocyclic group optionally substituted by 1 to 3 substituents selected from
(i) a halogen atom,
(ii) a $C_{6-14}$ aryl group,
(iii) a $C_{6-14}$ aryloxy group, and
(iv) a 5- to 14-membered aromatic heterocyclic group optionally substituted by 1 to 3 $C_{1-6}$ alkyl groups,
(3) a 8- to 14-membered fused polycyclic aromatic heterocyclic group or a 9- to 14-membered fused polycyclic non-aromatic heterocyclic group, each of which is optionally substituted by 1 to 3 substituents selected from
(i) a halogen atom,
(ii) a $C_{6-14}$ aryl group optionally substituted by 1 to 3 substituents selected from
(a) a halogen atom,
(b) an optionally halogenated $C_{1-6}$ alkyl group, and
(c) a $C_{1-6}$ alkoxy group, (iii) a 5- to 14-membered aromatic heterocyclic group optionally substituted by 1 to 3 substituents selected from
(a) a halogen atom,
(b) an optionally halogenated $C_{1-6}$ alkyl group, and
(c) a $C_{1-6}$ alkoxy group,
(iv) a $C_{1-6}$ alkyl group optionally substituted by 1 to 3 $C_{6-14}$ aryl groups optionally substituted by 1 to 3 halogen atoms,
(v) a $C_{1-6}$ alkyl-carbonyl group optionally substituted by 1 to 3 substituents selected from
(a) a halogen atom,
(b) a $C_{6-14}$ aryl group optionally substituted by 1 to 3 halogen atoms,
(c) a $C_{3-10}$ cycloalkyl group,
(d) a 5- to 14-membered aromatic heterocyclic group optionally substituted by 1 to 3 substituents selected from a halogen atom and a $C_{1-6}$ alkoxy group, and
(e) a 3- to 14-membered non-aromatic heterocyclic group,
(vi) a $C_{1-6}$ alkoxy-carbonyl group,
(vii) a $C_{6-14}$ aryl-carbonyl group,
(viii) a 3- to 14-membered non-aromatic heterocyclylcarbonyl group, and
(ix) a $C_{3-10}$ cycloalkyl group,
(4) a $C_{1-6}$ alkyl group optionally substituted by 1 to 3 $C_{6-14}$ aryl groups, or
(5) a $C_{3-10}$ cycloalkenyl group.
[6] The compound or salt of any of the above-mentioned [1], [2], [4] and [5], wherein $R^2$ is
(1) a 5- to 14-membered aromatic heterocyclylcarbonyl group optionally substituted by 1 to 3 substituents selected from
(i) a halogen atom, and
(ii) a $C_{1-6}$ alkyl group,
(2) a 3- to 14-membered non-aromatic heterocyclylcarbonyl group,
(3) a $C_{1-6}$ alkyl-carbonyl group optionally substituted by 1 to 3 substituents selected from
(i) a halogen atom,
(ii) a mono- or di-$C_{1-6}$ alkylamino group, and
(iii) a 5- to 14-membered aromatic heterocyclic group,
(4) a $C_{6-14}$ aryl-carbonyl group,
(5) an optionally halogenated $C_{3-10}$ cycloalkyl-carbonyl group,
(6) a $C_{1-6}$ alkoxy-carbonyl group,
(7) a 5- to 14-membered aromatic heterocyclylsulfonyl group,
(8) a $C_{6-14}$ aryl group, or
(9) a 5- to 14-membered aromatic heterocyclic group optionally substituted by 1 to 3 cyano groups.
[7] The compound or salt of any of the above-mentioned [1], [2], [4] and [6], wherein ring A is a pyrrolidin-2-one ring optionally substituted by 1 or 2 additional substituents selected from a halogen atom, a hydroxy group and a $C_{1-6}$ alkyl group;
ring B is a piperazine ring optionally further substituted by 1 to 3 $C_{1-6}$ alkyl groups;
$R^1$ is
(1) a $C_{6-14}$ aryl group optionally substituted by 1 to 3 substituents selected from
(i) a $C_{6-14}$ aryloxy group optionally substituted by 1 to 3 substituents selected from
(a) a $C_{1-6}$ alkoxy group, and
(b) a halogen atom, (ii) a halogen atom,
(iii) a cyano group,
(iv) an optionally halogenated $C_{1-6}$ alkoxy group,
(v) a $C_{1-6}$ alkyl group optionally substituted by 1 to 3 substituents selected from
  (a) a halogen atom,
  (b) a cyano group,
  (c) a $C_{6-14}$ aryl group, and
  (d) a 3- to 14-membered non-aromatic heterocyclic group optionally substituted by 1 to 3 $C_{1-6}$ alkyl groups,
(vi) a $C_{7-16}$ aralkyloxy group,
(vii) a $C_{3-10}$ cycloalkyl group,
(viii) a $C_{6-14}$ aryl group optionally substituted by 1 to 5 substituents selected from
  (a) a halogen atom,
  (b) a cyano group,
  (c) a $C_{1-6}$ alkyl group optionally substituted by 1 to 3 substituents selected from a halogen atom, a hydroxy group and a carbamoyl group,
  (d) an optionally halogenated $C_{1-6}$ alkoxy group,
  (e) a carboxy group,
  (f) a mono- or di-$C_{1-6}$ alkyl-carbonylamino group,
  (g) a mono- or di-$C_{1-6}$ alkylsulfonylamino group,
  (h) a sulfamoyl group,
  (i) a mono- or di-$C_{1-6}$ alkylsulfamoyl group,
  (j) a carbamoyl group,
  (k) a mono- or di-$C_{1-6}$ alkyl-carbamoyl group,
  (l) a 3- to 14-membered non-aromatic heterocyclylcarbonyl group,
  (m) a $C_{6-14}$ aryl group,
  (n) a $C_{6-14}$ aryloxy group, and
  (o) a 3- to 14-membered non-aromatic heterocyclic group,
(ix) a 5- to 14-membered aromatic heterocyclic group optionally substituted by 1 to 3 substituents selected from
  (a) a halogen atom,
  (b) an optionally halogenated $C_{1-6}$ alkyl group, and
  (c) a $C_{1-6}$ alkoxy group,
(x) a 3- to 14-membered non-aromatic heterocyclic group optionally substituted by 1 to 3 substituents selected from
  (a) a $C_{1-6}$ alkyl group,
  (b) a $C_{1-6}$ alkoxy group, and
  (c) an oxo group,
(xi) a 5- to 14-membered aromatic heterocyclyloxy group,
(xii) a mono- or di-$C_{6-14}$ arylamino group optionally substituted by 1 to 3 substituents selected from
  (a) a halogen atom,
  (b) a mono- or di-$C_{1-6}$ alkyl-carbonylamino group,
  (c) a ($C_{1-6}$ alkyl)($C_{1-6}$ alkyl-carbonyl)amino group, and
  (d) a pyrrolidinyl group optionally substituted by 1 to 3 oxo groups,
(xiii) a mono- or di-$C_{6-14}$ aryl-carbamoyl group,
(xiv) a $C_{3-10}$ cycloalkylamino group, and
(xv) a 3- to 14-membered non-aromatic heterocyclylamino group optionally substituted by 1 to 3 substituents selected from
  (a) a $C_{1-6}$ alkyl group,
  (b) a $C_{1-6}$ alkyl-carbonyl group, and
  (c) an oxo group,
(2) a 5- or 6-membered monocyclic aromatic heterocyclic group optionally substituted by 1 to 3 substituents selected from
  (i) a halogen atom,
  (ii) a $C_{6-14}$ aryl group,
  (iii) a $C_{6-14}$ aryloxy group, and
  (iv) a 5- to 14-membered aromatic heterocyclic group optionally substituted by 1 to 3 $C_{1-6}$ alkyl groups,
(3) a 8- to 14-membered fused polycyclic aromatic heterocyclic group or a 9- to 14-membered fused polycyclic non-aromatic heterocyclic group, each of which is optionally substituted by 1 to 3 substituents selected from
  (i) a halogen atom,
  (ii) a $C_{6-14}$ aryl group optionally substituted by 1 to 3 substituents selected from
    (a) a halogen atom,
    (b) an optionally halogenated $C_{1-6}$ alkyl group, and
    (c) a $C_{1-6}$ alkoxy group,
  (iii) a 5- to 14-membered aromatic heterocyclic group optionally substituted by 1 to 3 substituents selected from
    (a) a halogen atom,
    (b) an optionally halogenated $C_{1-6}$ alkyl group, and
    (c) a $C_{1-6}$ alkoxy group,
  (iv) a $C_{1-6}$ alkyl group optionally substituted by 1 to 3 $C_{6-14}$ aryl groups optionally substituted by 1 to 3 halogen atoms,
  (v) a $C_{1-6}$ alkyl-carbonyl group optionally substituted by 1 to 3 substituents selected from
    (a) a halogen atom,
    (b) a $C_{6-14}$ aryl group optionally substituted by 1 to 3 halogen atoms,
    (c) a $C_{3-10}$ cycloalkyl group,
    (d) a 5- to 14-membered aromatic heterocyclic group optionally substituted by 1 to 3 substituents selected from a halogen atom and a $C_{1-6}$ alkoxy group, and
    (e) a 3- to 14-membered non-aromatic heterocyclic group,
  (vi) a $C_{1-6}$ alkoxy-carbonyl group,
  (vii) a $C_{6-14}$ aryl-carbonyl group,
  (viii) a 3- to 14-membered non-aromatic heterocyclylcarbonyl group, and
  (ix) a $C_{3-10}$ cycloalkyl group,
(4) a $C_{1-6}$ alkyl group optionally substituted by 1 to 3 $C_{6-14}$ aryl groups, or
(5) a $C_{3-10}$ cycloalkenyl group; and
$R^2$ is
(1) a 5- to 14-membered aromatic heterocyclylcarbonyl group optionally substituted by 1 to 3 substituents selected from
  (i) a halogen atom, and
  (ii) a $C_{1-6}$ alkyl group,
(2) a 3- to 14-membered non-aromatic heterocyclylcarbonyl group,
(3) a $C_{1-6}$ alkyl-carbonyl group optionally substituted by 1 to 3 substituents selected from
  (i) a halogen atom,
  (ii) a mono- or di-$C_{1-6}$ alkylamino group, and
  (iii) a 5- to 14-membered aromatic heterocyclic group,
(4) a $C_{6-14}$ aryl-carbonyl group,
(5) an optionally halogenated $C_{3-10}$ cycloalkyl-carbonyl group,
(6) a $C_{1-6}$ alkoxy-carbonyl group,
(7) a 5- to 14-membered aromatic heterocyclylsulfonyl group,
(8) a $C_{6-14}$ aryl group, or
(9) a 5- to 14-membered aromatic heterocyclic group optionally substituted by 1 to 3 cyano groups.
[8] The compound or salt of any of the above-mentioned [1], [2], [4] and [7], wherein ring A is a pyrrolidin-2-one ring optionally substituted by 1 or 2 additional substituents selected from a halogen atom, a hydroxy group and a $C_{1-6}$ alkyl group;
ring B is a piperazine ring optionally further substituted by 1 to 3 $C_{1-6}$ alkyl groups;
$R^1$ is
(1) a phenyl group or a naphthyl group, each of which is optionally substituted by 1 to 3 substituents selected from
- (i) a phenoxy group optionally substituted by 1 to 3 substituents selected from
  - (a) a $C_{1-6}$ alkoxy group, and
  - (b) a halogen atom,
- (ii) a halogen atom,
- (iii) a cyano group,
- (iv) an optionally halogenated $C_{1-6}$ alkoxy group,
- (v) a $C_{1-6}$ alkyl group optionally substituted by 1 to 3 substituents selected from
  - (a) a halogen atom,
  - (b) a cyano group,
  - (c) a phenyl group,
  - (d) a piperazinyl group optionally substituted by 1 to 3 $C_{1-6}$ alkyl groups, and
  - (e) a morpholinyl group,
- (vi) a benzyloxy group,
- (vii) a $C_{3-10}$ cycloalkyl group,
- (viii) a phenyl group optionally substituted by 1 to 5 substituents selected from
  - (a) a halogen atom,
  - (b) a cyano group,
  - (c) a $C_{1-6}$ alkyl group optionally substituted by 1 to 3 substituents selected from a halogen atom, a hydroxy group and a carbamoyl group,
  - (d) an optionally halogenated $C_{1-6}$ alkoxy group,
  - (e) a carboxy group,
  - (f) a mono- or di-$C_{1-6}$ alkyl-carbonylamino group,
  - (g) a mono- or di-$C_{1-6}$ alkylsulfonylamino group,
  - (h) a sulfamoyl group,
  - (i) a mono- or di-$C_{1-6}$ alkylsulfamoyl group,
  - (j) a carbamoyl group,
  - (k) a mono- or di-$C_{1-6}$ alkyl-carbamoyl group,
  - (l) a pyrrolidinylcarbonyl group,
  - (m) a phenyl group,
  - (n) a phenoxy group, and
  - (o) a morpholinyl group,
- (ix) a pyridyl group optionally substituted by 1 to 3 substituents selected from
  - (a) a halogen atom,
  - (b) an optionally halogenated $C_{1-6}$ alkyl group, and
  - (c) a $C_{1-6}$ alkoxy group,
- (x) a dihydropyridyl group optionally substituted by 1 to 3 substituents selected from
  - (a) a $C_{1-6}$ alkyl group, and
  - (b) an oxo group,
- (xi) a thiazolyl group optionally substituted by 1 to 3 optionally halogenated $C_{1-6}$ alkyl groups,
- (xii) a morpholinyl group,
- (xiii) a pyridyloxy group,
- (xiv) a mono- or di-phenylamino group optionally substituted by 1 to 3 substituents selected from
  - (a) a halogen atom,
  - (b) a mono- or di-$C_{1-6}$ alkyl-carbonylamino group,
  - (c) a ($C_{1-6}$ alkyl)($C_{1-6}$ alkyl-carbonyl)amino group, and
  - (d) a pyrrolidinyl group optionally substituted by 1 to 3 oxo groups,
- (xv) a mono- or di-phenylcarbamoyl group,
- (xvi) a thienyl group optionally substituted by 1 to 3 substituents selected from
  - (a) an optionally halogenated $C_{1-6}$ alkyl group, and
  - (b) a $C_{1-6}$ alkoxy group,
- (xvii) a furyl group,
- (xviii) a pyrazinyl group optionally substituted by 1 to 3 $C_{1-6}$ alkyl groups,
- (xix) a pyrazolyl group optionally substituted by 1 to 3 optionally halogenated $C_{1-6}$ alkyl groups,
- (xx) a pyrimidinyl group optionally substituted by 1 to 3 $C_{1-6}$ alkyl groups,
- (xxi) an isoxazolyl group optionally substituted by 1 to 3 $C_{1-6}$ alkyl groups,
- (xxii) an imidazolyl group optionally substituted by 1 to 3 $C_{1-6}$ alkyl groups,
- (xxiii) a naphthyl group,
- (xxiv) a dihydroindolyl group optionally substituted by 1 to 3 substituents selected from
  - (a) a $C_{1-6}$ alkyl group,
  - (b) a $C_{1-6}$ alkoxy group, and
  - (c) an oxo group,
- (xxv) an indolyl group,
- (xxvi) an indazolyl group optionally substituted by 1 to 3 $C_{1-6}$ alkyl groups,
- (xxvii) an imidazopyridyl group optionally substituted by 1 to 3 $C_{1-6}$ alkyl groups,
- (xxviii) an isobenzothiazolyl group,
- (xxix) a pyrazolopyridyl group,
- (xxx) a thienopyridyl group,
- (xxxi) a dihydropyrrolopyridyl group optionally substituted by 1 to 3 oxo group,
- (xxxii) a pyrrolopyridyl group optionally substituted by 1 to 3 $C_{1-6}$ alkoxy groups,
- (xxxiii) a benzothiophenyl group,
- (xxxiv) a benzofuranyl group,
- (xxxv) a dihydrobenzofuranyl group,
- (xxxvi) a $C_{3-10}$ cycloalkylamino group,
- (xxxvii) a piperidylamino group optionally substituted by 1 to 3 substituents selected from
  - (a) a $C_{1-6}$ alkyl group,
  - (b) a $C_{1-6}$ alkyl-carbonyl group, and
  - (c) an oxo group,
- (xxxviii) a tetrahydropyranylamino group,
- (xxxix) a 1,4-dihydrobenzoxazinylamino group optionally substituted by 1 to 3 oxo groups, and
- (xxxx) a tetrahydroquinolylamino group optionally substituted by 1 to 3 oxo groups, (2) a pyridyl group, an imidazolyl group or a pyrazolyl group, each of which is optionally substituted by 1 to 3 substituents selected from
- (i) a halogen atom,
- (ii) a phenyl group,
- (iii) a phenoxy group, and
- (iv) a pyridyl group optionally substituted by 1 to 3 $C_{1-6}$ alkyl groups, (3) an indolyl group, an indazolyl group, a pyrrolopyridyl group, a dibenzofuranyl group, an imidazopyridyl group, a dihydroindolyl group, a benzothiophenyl group or a benzoxazolyl group, each of which is optionally substituted by 1 to 3 substituents selected from
- (i) a halogen atom,
- (ii) a phenyl group optionally substituted by 1 to 3 substituents selected from
  - (a) a halogen atom,
  - (b) an optionally halogenated $C_{1-6}$ alkyl group, and
  - (c) a $C_{1-6}$ alkoxy group, (iii) a pyridyl group optionally substituted by 1 to 3 substituents selected from
  (a) a halogen atom, and
  (b) an optionally halogenated $C_{1-6}$ alkyl group,
(iv) a pyrimidinyl group optionally substituted by 1 to 3 substituents selected from
  (a) a halogen atom,
  (b) an optionally halogenated $C_{1-6}$ alkyl group, and
  (c) a $C_{1-6}$ alkoxy group,
(v) a pyridazinyl group optionally substituted by 1 to 3 optionally halogenated $C_{1-6}$ alkyl groups,
(vi) a pyrazinyl group optionally substituted by 1 to 3 optionally halogenated $C_{1-6}$ alkyl groups,
(vii) a $C_{1-6}$ alkyl group optionally substituted by 1 to 3 phenyl groups optionally substituted by 1 to 3 halogen atoms,
(viii) a $C_{1-6}$ alkyl-carbonyl group optionally substituted by 1 to 3 substituents selected from
  (a) a halogen atom,
  (b) a phenyl group optionally substituted by 1 to 3 halogen atoms,
  (c) a $C_{3-10}$ cycloalkyl group,
  (d) a pyridyl group optionally substituted by 1 to 3 substituents selected from a halogen atom and a $C_{1-6}$ alkoxy group, and
  (e) a tetrahydropyranyl group,
(ix) a $C_{1-6}$ alkoxy-carbonyl group,
(x) a benzoyl group,
(xi) a tetrahydropyranylcarbonyl group, and
(xii) a $C_{3-10}$ cycloalkyl group,
(4) a $C_{1-6}$ alkyl group optionally substituted by 1 to 3 phenyl groups, or
(5) a $C_{3-10}$ cycloalkenyl group; and
$R^2$ is
(1) a thiazolylcarbonyl group, a thienylcarbonyl group, a furylcarbonyl group, a pyrrolylcarbonyl group, a pyrazolylcarbonyl group, an imidazolylcarbonyl group, an oxazolylcarbonyl group or a quinolylcarbonyl group, each of which is optionally substituted by 1 to 3 substituents selected from
  (i) a halogen atom, and
  (ii) a $C_{1-6}$ alkyl group,
(2) a pyrrolidinylcarbonyl group,
(3) a $C_{1-6}$ alkyl-carbonyl group optionally substituted by 1 to 3 substituents selected from
  (i) a halogen atom,
  (ii) a mono- or di-$C_{1-6}$ alkylamino group, and
  (iii) a pyridyl group,
(4) a benzoyl group,
(5) an optionally halogenated $C_{3-10}$ cycloalkyl-carbonyl group,
(6) a $C_{1-6}$ alkoxy-carbonyl group,
(7) a pyridylsulfonyl group,
(8) a phenyl group, or
(9) a pyridyl group or a pyrimidinyl group, each of which is optionally substituted by 1 to 3 cyano groups.

[9] The compound or salt of any of the above-mentioned [1], [2], [4] and [8], wherein ring A is a pyrrolidin-2-one ring optionally substituted by 1 or 2 additional substituents selected from a halogen atom, a hydroxy group and a $C_{1-6}$ alkyl group;
ring B is a piperazine ring optionally further substituted by 1 to 3 $C_{1-6}$ alkyl groups;
$R^1$ is
(1) a phenyl group or a naphthyl group, each of which is optionally substituted by 1 to 3 substituents selected from
  (i) a phenoxy group optionally substituted by 1 to 3 substituents selected from
    (a) a $C_{1-6}$ alkoxy group, and
    (b) a halogen atom,
  (ii) a halogen atom,
  (iii) an optionally halogenated $C_{1-6}$ alkoxy group,
  (iv) a $C_{1-6}$ alkyl group optionally substituted by 1 to 3 phenyl groups,
  (v) a benzyloxy group,
  (vi) a $C_{3-10}$ cycloalkyl group,
  (vii) a phenyl group optionally substituted by 1 to 5 substituents selected from
    (a) a halogen atom,
    (b) a cyano group,
    (c) a $C_{1-6}$ alkyl group optionally substituted by 1 to 3 substituents selected from a halogen atom, a hydroxy group and a carbamoyl group,
    (d) an optionally halogenated $C_{1-6}$ alkoxy group,
    (e) a carboxy group,
    (f) a mono- or di-$C_{1-6}$ alkyl-carbonylamino group,
    (g) a mono- or di-$C_{1-6}$ alkylsulfonylamino group,
    (h) a sulfamoyl group,
    (i) a mono- or di-$C_{1-6}$ alkylsulfamoyl group,
    (j) a carbamoyl group,
    (k) a mono- or di-$C_{1-6}$ alkyl-carbamoyl group,
    (l) a pyrrolidinylcarbonyl group,
    (m) a phenyl group,
    (n) a phenoxy group, and
    (o) a morpholinyl group,
  (viii) a pyridyl group optionally substituted by 1 to 3 substituents selected from
    (a) a halogen atom,
    (b) an optionally halogenated $C_{1-6}$ alkyl group, and
    (c) a $C_{1-6}$ alkoxy group,
  (ix) a thiazolyl group optionally substituted by 1 to 3 optionally halogenated $C_{1-6}$ alkyl groups,
  (x) a pyridyloxy group,
  (xi) a mono- or di-phenylamino group optionally substituted by 1 to 3 substituents selected from
    (a) a halogen atom,
    (b) a mono- or di-$C_{1-6}$ alkyl-carbonylamino group,
    (c) a ($C_{1-6}$ alkyl)($C_{1-6}$ alkyl-carbonyl)amino group, and
    (d) a pyrrolidinyl group optionally substituted by 1 to 3 oxo groups,
  (xii) a thienyl group optionally substituted by 1 to 3 substituents selected from
    (a) an optionally halogenated $C_{1-6}$ alkyl group, and
    (b) a $C_{1-6}$ alkoxy group,
  (xiii) a furyl group,
  (xiv) a pyrazinyl group optionally substituted by 1 to 3 $C_{1-6}$ alkyl groups,
  (xv) a pyrazolyl group optionally substituted by 1 to 3 optionally halogenated $C_{1-6}$ alkyl groups,
  (xvi) a pyrimidinyl group optionally substituted by 1 to 3 $C_{1-6}$ alkyl groups,
  (xvii) an isoxazolyl group optionally substituted by 1 to 3 $C_{1-6}$ alkyl groups,
  (xviii) an imidazolyl group optionally substituted by 1 to 3 $C_{1-6}$ alkyl groups,
  (xix) a naphthyl group,
  (xx) a dihydroindolyl group optionally substituted by 1 to 3 substituents selected from
    (a) a $C_{1-6}$ alkyl group,
    (b) a $C_{1-6}$ alkoxy group, and
    (c) an oxo group,
  (xxi) an indolyl group,
  (xxii) an indazolyl group optionally substituted by 1 to 3 $C_{1-6}$ alkyl groups, (xxiii) an imidazopyridyl group optionally substituted by 1 to 3 $C_{1-6}$ alkyl groups,
(xxiv) an isobenzothiazolyl group,
(xxv) a pyrazolopyridyl group,
(xxvi) a thienopyridyl group,
(xxvii) a dihydropyrrolopyridyl group optionally substituted by 1 to 3 oxo groups,
(xxviii) a pyrrolopyridyl group optionally substituted by 1 to 3 $C_{1-6}$ alkoxy groups,
(xxix) a benzothiophenyl group,
(xxx) a benzofuranyl group,
(xxxi) a dihydrobenzofuranyl group,
(xxxii) a $C_{3-10}$ cycloalkylamino group,
(xxxiii) a piperidylamino group optionally substituted by 1 to 3 substituents selected from
  (a) a $C_{1-6}$ alkyl group, and
  (b) an oxo group,
(xxxiv) a 1,4-dihydrobenzoxazinylamino group optionally substituted by 1 to 3 oxo groups, and
(xxxv) a tetrahydroquinolylamino group optionally substituted by 1 to 3 oxo groups,
(2) a pyridyl group optionally substituted by 1 to 3 substituents selected from
  (i) a halogen atom,
  (ii) a phenyl group,
  (iii) a phenoxy group, and
  (iv) a pyridyl group optionally substituted by 1 to 3 $C_{1-6}$ alkyl groups, or
(3) an indolyl group, an indazolyl group, a pyrrolopyridyl group, a dibenzofuranyl group, a dihydroindolyl group, a benzothiophenyl group or a benzoxazolyl group, each of which is optionally substituted by 1 to 3 substituents selected from
  (i) a halogen atom,
  (ii) a phenyl group optionally substituted by 1 to 3 substituents selected from
    (a) a halogen atom,
    (b) an optionally halogenated $C_{1-6}$ alkyl group, and
    (c) a $C_{1-6}$ alkoxy group,
  (iii) a pyridyl group optionally substituted by 1 to 3 substituents selected from
    (a) a halogen atom, and
    (b) an optionally halogenated $C_{1-6}$ alkyl group,
  (iv) a pyrimidinyl group optionally substituted by 1 to 3 substituents selected from
    (a) a halogen atom,
    (b) an optionally halogenated $C_{1-6}$ alkyl group, and
    (c) a $C_{1-6}$ alkoxy group,
  (v) a pyridazinyl group optionally substituted by 1 to 3 optionally halogenated $C_{1-6}$ alkyl groups,
  (vi) a pyrazinyl group optionally substituted by 1 to 3 optionally halogenated $C_{1-6}$ alkyl groups,
  (vii) a $C_{1-6}$ alkyl group optionally substituted by 1 to 3 phenyl groups optionally substituted by 1 to 3 halogen atoms,
  (viii) a $C_{1-6}$ alkyl-carbonyl group optionally substituted by 1 to 3 substituents selected from
    (a) a halogen atom,
    (b) a phenyl group optionally substituted by 1 to 3 halogen atoms,
    (c) a $C_{3-10}$ cycloalkyl group,
    (d) a pyridyl group optionally substituted by 1 to 3 substituents selected from a halogen atom and a $C_{1-6}$ alkoxy group, and
    (e) a tetrahydropyranyl group,
  (ix) a $C_{1-6}$ alkoxy-carbonyl group,
  (x) a benzoyl group,
  (xi) a tetrahydropyranylcarbonyl group, and
  (xii) a $C_{3-10}$ cycloalkyl group; and
$R^2$ is
(1) a thiazolylcarbonyl group, a thienylcarbonyl group, a furylcarbonyl group or an oxazolylcarbonyl group, each of which is optionally substituted by 1 to 3 halogen atoms,
(2) a pyrrolidinylcarbonyl group, or
(3) a pyridyl group or a pyrimidinyl group, each of which is optionally substituted by 1 to 3 cyano groups.
[10] The compound or salt of any of the above-mentioned [1] to [9], wherein ring A is a pyrrolidin-2-one ring not substituted by the additional substituents;
ring B is a piperazine ring not substituted by the additional substituents;
$R^1$ is
(1) a phenyl group substituted by 1 to 3 substituents selected from
  (i) a halogen atom, and
  (ii) a pyridyl group substituted by 1 to 3 $C_{1-6}$ alkyl groups, or
(2) an indolyl group or an indazolyl group, each of which is substituted by 1 to 3 substituents selected from
  (i) a phenyl group substituted by 1 to 3 substituents selected from
    (a) a halogen atom, and
    (b) a halogenated $C_{1-6}$ alkyl group, and
  (ii) a pyrimidinyl group substituted by 1 to 3 halogenated $C_{1-6}$ alkyl groups; and
$R^2$ is a thiazolylcarbonyl group or a pyrimidinyl group.
[11] (4R)-4-(4-(1,3-thiazol-2-ylcarbonyl)piperazin-1-yl)-1-(1-(5-(trifluoromethyl)pyrimidin-2-yl)-1H-indol-5-yl)pyrrolidin-2-one, or a salt thereof.
[12] (4R)-4-(4-(1,3-thiazol-4-ylcarbonyl)piperazin-1-yl)-1-(1-(4-(trifluoromethyl)phenyl)-1H-indol-5-yl)pyrrolidin-2-one, or a salt thereof.
[13] (4R)-1-(3-fluoro-5-(2-methylpyridin-3-yl)phenyl)-4-(4-(pyrimidin-2-yl)piperazin-1-yl)pyrrolidin-2-one, or a salt thereof.
[14] A medicament comprising the compound or salt of any of the above-mentioned [1] to [13].
[15] The medicament of the above-mentioned [14], which is a monoacylglycerol lipase inhibitor.
[16] The medicament of the above-mentioned [14], which is a prophylactic or therapeutic agent for Alzheimer's disease, Parkinson's disease, pain or epilepsy.
[17] The compound or salt of any of the above-mentioned [1] to [13] for use for the prophylaxis or treatment of Alzheimer's disease, Parkinson's disease, pain or epilepsy.
[18] A method of inhibiting monoacylglycerol lipase in a mammal, comprising administering an effective amount of the compound or salt of any of the above-mentioned [1] to [13] to the mammal.
[19] A method of preventing or treating Alzheimer's disease, Parkinson's disease, pain or epilepsy in a mammal, comprising administering an effective amount of the compound or salt of any of the above-mentioned [1] to [13] to the mammal.
[20] Use of the compound or salt of any of the above-mentioned [1] to [13] in the production of a prophylactic or therapeutic agent for Alzheimer's disease, Parkinson's disease, pain or epilepsy.

Effect of the Invention

According to the present invention, a compound having a superior MAGL inhibitory action and useful as a prophylactic or therapeutic agent for neurodegenerative diseases (e.g., Alzheimer's disease, Huntington's disease, Parkinson's disease, amyotrophic lateral sclerosis, traumatic brain injury, glaucoma, multiple sclerosis and the like), anxiety disorder, pain (e.g., inflammatory pain, carcinomatous pain, nervous pain and the like), epilepsy and the like can be provided.

DETAILED DESCRIPTION OF THE INVENTION

Figure 1:
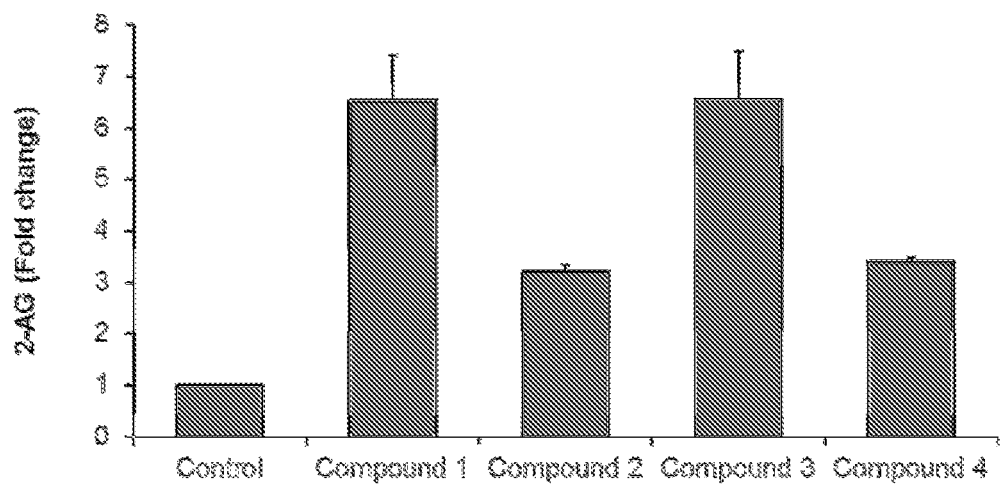
FIG. 1 shows an effect of compounds 1-4 to increase 2-AG.

The present invention is described in detail in the following.

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxycarbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ arylcarbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following substituent group A.

[substituent group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl)($C_{1-6}$ alkyl-carbonyl)amino group (e.g., N-acetyl-N-methylamino),
(52) a $C_{6-14}$ aryl-carbonylamino group (e.g., phenylcarbonylamino, naphthylcarbonylamino),

(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),

(54) a $C_{7-16}$ aralkyloxy-carbonylamino group (e.g., benzyloxycarbonylamino),

(55) a $C_{1-6}$ alkylsulfonylamino group (e.g., methylsulfonylamino, ethylsulfonylamino),

(56) a $C_{6-14}$ arylsulfonylamino group optionally substituted by a $C_{1-6}$ alkyl group (e.g., phenylsulfonylamino, toluenesulfonylamino),

(57) an optionally halogenated $C_{1-6}$ alkyl group,

(58) a $C_{2-6}$ alkenyl group,

(59) a $C_{2-6}$ alkynyl group,

(60) a $C_{3-10}$ cycloalkyl group,

(61) a $C_{3-10}$ cycloalkenyl group and

(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 hetero atoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 hetero atoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, triazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi- or tri-cyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 hetero atoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi- or tri-cyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the aforementioned substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkyl-phosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted amino group include an amino group, a mono- or di-(optionally halogenated $C_{1-6}$ alkyl)amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) amino group (e.g., methylcarbamoylamino), a (mono- or di-$C_{7-16}$ aralkyl-carbamoyl)amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl)($C_{1-6}$ alkyl-carbonyl)amino group (e.g., N-acetyl-N-methylamino) and a ($C_{1-6}$ alkyl)($C_{6-14}$ aryl-carbonyl)amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from substituent group A".

Preferable examples of the optionally substituted silyl group include a tri-$C_{1-6}$ alkylsilyl group (e.g., trimethylsilyl, tert-butyl(dimethyl)silyl).

The definition of each symbol in the formula (I) is described in detail in the following.

Ring A is a pyrrolidin-2-one ring optionally substituted by 1 or 2 additional substituents selected from a halogen atom, a cyano group, an optionally substituted hydroxy group, an optionally substituted amino group, an optionally substituted sulfanyl group, an acyl group, an optionally substituted hydrocarbon group, and an optionally substituted heterocyclic group.

When the number of the additional substituents of ring A is two, the respective substituents may be the same or different.

Ring A is preferably a pyrrolidin-2-one ring optionally substituted by 1 or 2 additional substituents selected from an optionally substituted hydrocarbon group.

Ring A is more preferably a pyrrolidin-2-one ring optionally substituted by 1 or 2 additional substituents selected from an optionally substituted $C_{1-6}$ alkyl group and an optionally substituted $C_{3-10}$ cycloalkyl group.

Ring A is further preferably a pyrrolidin-2-one ring optionally substituted by 1 or 2 additional substituents selected from a methyl group, an ethyl group and an isopropyl group.

In another embodiment, ring A is preferably a pyrrolidin-2-one ring optionally substituted by 1 or 2 additional substituents selected from a halogen atom (e.g., a fluorine atom), a hydroxy group and a $C_{1-6}$ alkyl group (e.g., methyl).

Ring A is particularly preferably a pyrrolidin-2-one ring not substituted by the additional substituents.

Ring B is a piperazine ring optionally substituted by 1 to 3 additional substituents selected from a halogen atom, a cyano group, an optionally substituted hydroxy group, an optionally substituted amino group, an optionally substituted sulfanyl group, an acyl group, an optionally substituted hydrocarbon group, and an optionally substituted heterocyclic group.

When the number of the additional substituents of ring B is two or more, the respective substituents may be the same or different.

Ring B is preferably a piperazine ring optionally substituted by 1 to 3 additional substituents selected from an optionally substituted hydrocarbon group.

Ring B is more preferably a piperazine ring optionally substituted by 1 to 3 additional substituents selected from an optionally substituted $C_{1-6}$ alkyl group and an optionally substituted $C_{3-10}$ cycloalkyl group.

Ring B is further preferably a piperazine ring optionally substituted by 1 to 3 additional substituents selected from a methyl group, an ethyl group and an isopropyl group.

In another embodiment, ring B is more preferably a piperazine ring optionally substituted by 1 to 3 additional substituents selected from a $C_{1-6}$ alkyl group (e.g., methyl).

Ring B is particularly preferably a piperazine ring not substituted by the additional substituents.

$R^1$ is an optionally substituted hydrocarbon group or an optionally substituted heterocyclic group.

As the "hydrocarbon group" of the "optionally substituted hydrocarbon group" for $R^1$, a $C_{1-6}$ alkyl group, a $C_{7-16}$ aralkyl group, a $C_{3-10}$ cycloalkyl group and a $C_{6-14}$ aryl group are preferable, a $C_{6-14}$ aryl group is more preferable, phenyl and naphthyl are further preferable, and phenyl is particularly preferable.

As the "heterocyclic group" of the "optionally substituted heterocyclic group" for $R^1$, a 5- to 14-membered aromatic heterocyclic group is preferable, and a 5- or 6-membered monocyclic aromatic heterocyclic group and a 8- to 14-membered fused polycyclic (preferably, bi- or tri-cyclic) aromatic heterocyclic group are more preferable.

The "hydrocarbon group" of the "optionally substituted hydrocarbon group" and the "heterocyclic group" of the "optionally substituted heterocyclic group" for $R^1$ may be further substituted by, for example, substituent(s) selected from the aforementioned substituent group A, and the number of the substituents is, for example, 1 to 3. When the number of the substituents is two or more, the respective substituents may be the same or different.

$R^1$ is preferably an optionally substituted $C_{1-6}$ alkyl group, an optionally substituted $C_{7-16}$ aralkyl group, an optionally substituted $C_{3-10}$ cycloalkyl group, an optionally substituted $C_{6-14}$ aryl group, an optionally substituted 5- to 14-membered aromatic heterocyclic group, or a 3- to 14-membered optionally substituted non-aromatic heterocyclic group.

$R^1$ is more preferably an optionally substituted $C_{6-14}$ aryl group, an optionally substituted 5- or 6-membered monocyclic aromatic heterocyclic group, or an optionally substituted 8- to 14-membered fused polycyclic (preferably, bi- or tri-cyclic) aromatic heterocyclic group.

$R^1$ is further preferably
(1) a $C_{6-14}$ aryl group optionally substituted by 1 to 3 substituents selected from
  (i) an optionally substituted hydrocarbon group,
  (ii) an optionally substituted heterocyclic group,
  (iii) an acyl group,
  (iv) an optionally substituted amino group,
  (v) an optionally substituted hydroxy group,
  (vi) a halogen atom, and
  (vii) a cyano group;
(2) a 5- or 6-membered monocyclic aromatic heterocyclic group optionally substituted by 1 to 3 substituents selected from
  (i) an optionally substituted hydrocarbon group,
  (ii) an optionally substituted heterocyclic group,
  (iii) an acyl group,
  (iv) an optionally substituted amino group, and
  (v) an optionally substituted hydroxy group; or
(3) a 8- to 14-membered fused polycyclic (preferably, bi- or tri-cyclic) aromatic heterocyclic group optionally substituted by 1 to 3 substituents selected from
  (i) an optionally substituted hydrocarbon group,
  (ii) an optionally substituted heterocyclic group, and
  (iii) a halogen atom.

$R^1$ is furthermore preferably
(1) a $C_{6-14}$ aryl group (e.g., phenyl, naphthyl) optionally substituted by 1 to 3 substituents selected from
  (i) a $C_{6-14}$ aryloxy group (e.g., phenoxy) optionally substituted by 1 to 3 substituents selected from
    (a) a $C_{1-6}$ alkoxy group (e.g., methoxy), and
    (b) a halogen atom (e.g., a fluorine atom),
  (ii) a halogen atom (e.g., a chlorine atom, a bromine atom, an iodine atom),
  (iii) a cyano group,
  (iv) an optionally halogenated $C_{1-6}$ alkoxy group (e.g., methoxy, trifluoromethoxy),
  (v) a $C_{1-6}$ alkyl group (e.g., methyl) optionally substituted by 1 to 3 substituents selected from
    (a) a $C_{6-14}$ aryl group (e.g., phenyl), and
    (b) a 3- to 14-membered non-aromatic heterocyclic group (preferably, a 3- to 8-membered monocyclic non-aromatic heterocyclic group (e.g., piperazinyl)) optionally substituted by 1 to 3 $C_{1-6}$ alkyl groups (e.g., methyl),
  (vi) a $C_{7-16}$ aralkyloxy group (e.g., benzyloxy),
  (vii) a $C_{3-10}$ cycloalkyl group (e.g., cyclopropyl),
  (viii) a $C_{6-14}$ aryl group (e.g., phenyl) optionally substituted by 1 to 3 halogen atoms (e.g., a fluorine atom, a chlorine atom),
  (ix) a 5- to 14-membered aromatic heterocyclic group (preferably, a 5- or 6-membered monocyclic aromatic heterocyclic group (e.g., pyridyl, thiazolyl)) optionally substituted by 1 to 3 $C_{1-6}$ alkyl groups (e.g., methyl),
  (x) a 3- to 14-membered non-aromatic heterocyclic group (preferably, a 3- to 8-membered monocyclic non-aromatic heterocyclic group (e.g., morpholinyl)),
  (xi) a 5- to 14-membered aromatic heterocyclyloxy group (preferably, a 5- or 6-membered monocyclic aromatic heterocyclyloxy group (e.g., pyridyloxy)),
  (xii) a mono- or di-$C_{6-14}$ arylamino group (e.g., phenylamino) optionally substituted by 1 to 3 halogen atoms (e.g., a fluorine atom), and
  (xiii) a mono- or di-$C_{6-14}$ aryl-carbamoyl group (e.g., phenylcarbamoyl);
(2) a 5- or 6-membered monocyclic aromatic heterocyclic group (e.g., pyridyl, imidazolyl, pyrazolyl) optionally substituted by 1 to 3 substituents selected from
  (i) a $C_{6-14}$ aryl group (e.g., phenyl), and
  (ii) a $C_{6-14}$ aryloxy group (e.g., phenoxy); or
(3) a 8- to 14-membered fused polycyclic (preferably, bi- or tri-cyclic) aromatic heterocyclic group (e.g., indolyl, indazolyl, pyrrolopyridyl, dibenzofuranyl, imidazopyridyl) optionally substituted by 1 to 3 substituents selected from
  (i) a $C_{6-14}$ aryl group (e.g., phenyl) optionally substituted by 1 to 3 halogen atoms (e.g., a fluorine atom),
  (ii) a 5- to 14-membered aromatic heterocyclic group (preferably, a 5- or 6-membered monocyclic aromatic heterocyclic group (e.g., pyrimidinyl, pyridyl)) optionally substituted by 1 to 3 substituents selected from
    (a) a halogen atom (e.g., a fluorine atom, a chlorine atom), and
    (b) an optionally halogenated $C_{1-6}$ alkyl group (e.g., trifluoromethyl), and
  (iii) a halogen atom (e.g., a bromine atom).

$R^1$ is still further preferably
(1) a $C_{6-14}$ aryl group (e.g., phenyl, naphthyl) optionally substituted by 1 to 3 substituents selected from
  (i) a $C_{6-14}$ aryloxy group (e.g., phenoxy) optionally substituted by 1 to 3 substituents selected from (a) a $C_{1-6}$ alkoxy group (e.g., methoxy), and
(b) a halogen atom (e.g., a fluorine atom),
(ii) a halogen atom (e.g., a bromine atom, an iodine atom),
(iii) a $C_{1-6}$ alkoxy group (e.g., methoxy),
(iv) a $C_{7-16}$ aralkyl group (e.g., benzyl),
(v) a $C_{7-16}$ aralkyloxy group (e.g., benzyloxy),
(vi) a $C_{3-10}$ cycloalkyl group (e.g., cyclopropyl),
(vii) a $C_{6-14}$ aryl group (e.g., phenyl) optionally substituted by 1 to 3 halogen atoms (e.g., a fluorine atom, a chlorine atom),
(viii) a 5- to 14-membered aromatic heterocyclic group (preferably, a 5- or 6-membered monocyclic aromatic heterocyclic group (e.g., pyridyl)),
(ix) a 5- to 14-membered aromatic heterocyclyloxy group (preferably, a 5- or 6-membered monocyclic aromatic heterocyclyloxy group (e.g., pyridyloxy)), and
(x) a mono- or di-$C_{6-14}$ arylamino group (e.g., phenylamino) optionally substituted by 1 to 3 halogen atoms (e.g., a fluorine atom);
(2) a 5- or 6-membered monocyclic aromatic heterocyclic group (e.g., pyridyl) optionally substituted by 1 to 3 $C_{6-14}$ aryloxy groups (e.g., phenoxy); or
(3) a 8- to 14-membered fused polycyclic (preferably, bi- or tri-cyclic) aromatic heterocyclic group (e.g., indolyl, indazolyl, pyrrolopyridyl, dibenzofuranyl) optionally substituted by 1 to 3 substituents selected from
(i) a $C_{6-14}$ aryl group (e.g., phenyl) optionally substituted by 1 to 3 halogen atoms (e.g., a fluorine atom), and
(ii) a 5- to 14-membered aromatic heterocyclic group (preferably, a 5- or 6-membered monocyclic aromatic heterocyclic group (e.g., pyrimidinyl, pyridyl)) optionally substituted by 1 to 3 substituents selected from
(a) a halogen atom (e.g., a fluorine atom, a chlorine atom), and
(b) an optionally halogenated $C_{1-6}$ alkyl group (e.g., trifluoromethyl).

$R^1$ is further still more preferably
(1) a $C_{6-14}$ aryl group (e.g., phenyl) optionally substituted by 1 to 3 substituents selected from
(i) a $C_{6-14}$ aryloxy group (e.g., phenoxy) optionally substituted by 1 to 3 halogen atoms (e.g., a fluorine atom),
(ii) a $C_{1-6}$ alkoxy group (e.g., methoxy),
(iii) a $C_{3-10}$ cycloalkyl group (e.g., cyclopropyl),
(iv) a $C_{6-14}$ aryl group (e.g., phenyl), and
(v) a $C_{7-16}$ aralkyloxy group (e.g., benzyloxy); or
(2) a 8- to 14-membered fused polycyclic (preferably, bi- or tri-cyclic) aromatic heterocyclic group (e.g., indolyl, indazolyl, dibenzofuranyl) optionally substituted by 1 to 3 substituents selected from
(i) a $C_{6-14}$ aryl group (e.g., phenyl) optionally substituted by 1 to 3 halogen atoms (e.g., a fluorine atom), and
(ii) a 5- to 14-membered aromatic heterocyclic group (preferably, a 5- or 6-membered aromatic heterocyclic group (e.g., pyrimidinyl, pyridyl)) optionally substituted by 1 to 3 optionally halogenated $C_{1-6}$ alkyl groups (e.g., trifluoromethyl).

In another embodiment, $R^1$ is more preferably
(1) a $C_{6-14}$ aryl group optionally substituted by 1 to 3 substituents selected from
(i) an optionally substituted hydrocarbon group,
(ii) an optionally substituted heterocyclic group,
(iii) an acyl group,
(iv) an optionally substituted amino group,
(v) an optionally substituted hydroxy group,
(vi) a halogen atom, and
(vii) a cyano group;

(2) a 5- to 14-membered aromatic heterocyclic group optionally substituted by 1 to 3 substituents selected from
(i) an optionally substituted hydrocarbon group,
(ii) an optionally substituted heterocyclic group,
(iii) an acyl group,
(iv) an optionally substituted amino group,
(v) an optionally substituted hydroxy group, and
(vi) a halogen atom;
(3) a 3- to 14-membered non-aromatic heterocyclic group optionally substituted by 1 to 3 substituents selected from
(i) an optionally substituted hydrocarbon group,
(ii) an optionally substituted heterocyclic group,
(iii) an acyl group, and
(iv) a halogen atom;
(4) a $C_{1-6}$ alkyl group optionally substituted by 1 to 3 optionally substituted hydrocarbon groups; or
(5) a $C_{3-10}$ cycloalkenyl group.

In another embodiment, $R^1$ is furthermore preferably (1) a $C_{6-14}$ aryl group (e.g., phenyl, naphthyl) optionally substituted by 1 to 3 substituents selected from
(i) a $C_{6-14}$ aryloxy group (e.g., phenoxy) optionally substituted by 1 to 3 substituents selected from
(a) a $C_{1-6}$ alkoxy group (e.g., methoxy), and
(b) a halogen atom (e.g., a fluorine atom),
(ii) a halogen atom (e.g., a fluorine atom, a chlorine atom, a bromine atom, an iodine atom),
(iii) a cyano group,
(iv) an optionally halogenated $C_{1-6}$ alkoxy group (e.g., methoxy, trifluoromethoxy),
(v) a $C_{1-6}$ alkyl group (e.g., methyl, isopropyl) optionally substituted by 1 to 3 substituents selected from
(a) a halogen atom (e.g., a fluorine atom),
(b) a cyano group,
(c) a $C_{6-14}$ aryl group (e.g., phenyl), and
(d) a 3- to 14-membered non-aromatic heterocyclic group (preferably, a 3- to 8-membered monocyclic non-aromatic heterocyclic group (e.g., piperazinyl, morpholinyl)) optionally substituted by 1 to 3 $C_{1-6}$ alkyl groups (e.g., methyl),
(vi) a $C_{7-16}$ aralkyloxy group (e.g., benzyloxy),
(vii) a $C_{3-10}$ cycloalkyl group (e.g., cyclopropyl), (viii) a $C_{6-14}$ aryl group (e.g., phenyl, naphthyl) optionally substituted by 1 to 5 substituents selected from
(a) a halogen atom (e.g., a fluorine atom, a chlorine atom),
(b) a cyano group,
(c) a $C_{1-6}$ alkyl group (e.g., methyl, ethyl) optionally substituted by 1 to 3 substituents selected from a halogen atom (e.g., a fluorine atom), a hydroxy group and a carbamoyl group,
(d) an optionally halogenated $C_{1-6}$ alkoxy group (e.g., methoxy, ethoxy, isopropoxy, trifluoromethoxy),
(e) a carboxy group,
(f) a mono- or di-$C_{1-6}$ alkyl-carbonylamino group (e.g., acetylamino),
(g) a mono- or di-$C_{1-6}$ alkylsulfonylamino group (e.g., methylsulfonylamino),
(h) a sulfamoyl group,
(i) a mono- or di-$C_{1-6}$ alkylsulfamoyl group (e.g., methylsulfamoyl),
(j) a carbamoyl group,
(k) a mono- or di-$C_{1-6}$ alkyl-carbamoyl group (e.g., methylcarbamoyl),
(l) a 3- to 14-membered non-aromatic heterocyclylcarbonyl group (preferably, a 3- to 8-membered monocyclic non-aromatic heterocyclylcarbonyl group (e.g., pyrrolidinylcarbonyl)), (m) a $C_{6-14}$ aryl group (e.g., phenyl),
(n) a $C_{6-14}$ aryloxy group (e.g., phenoxy), and
(o) a 3- to 14-membered non-aromatic heterocyclic group (preferably, a 3- to 8-membered monocyclic non-aromatic heterocyclic group (e.g., morpholinyl)), (ix) a 5- to 14-membered aromatic heterocyclic group (e.g., pyridyl, thiazolyl, thienyl, furyl, pyrazinyl, pyrazolyl, pyrimidinyl, isoxazolyl, imidazolyl, indolyl, indazolyl, imidazopyridyl, isobenzothiazolyl, pyrazolopyridyl, thienopyridyl, pyrrolopyridyl, benzothiophenyl, benzofuranyl) optionally substituted by 1 to 3 substituents selected from
(a) a halogen atom (e.g., a chlorine atom),
(b) an optionally halogenated $C_{1-6}$ alkyl group (e.g., methyl, ethyl, isopropyl, trifluoromethyl), and
(c) a $C_{1-6}$ alkoxy group (e.g., methoxy), (x) a 3- to 14-membered non-aromatic heterocyclic group (e.g., dihydropyridyl, morpholinyl, dihydroindolyl, dihydropyrrolopyridyl, dihydrobenzofuranyl) optionally substituted by 1 to 3 substituents selected from
(a) a $C_{1-6}$ alkyl group (e.g., methyl),
(b) a $C_{1-6}$ alkoxy group (e.g., methoxy), and
(c) an oxo group, (xi) a 5- to 14-membered aromatic heterocyclyloxy group (preferably, a 5- or 6-membered monocyclic aromatic heterocyclyloxy group (e.g., pyridyloxy)), (xii) a mono- or di-$C_{6-14}$ arylamino group (e.g., phenylamino) optionally substituted by 1 to 3 substituents selected from
(a) a halogen atom (e.g., a fluorine atom),
(b) a mono- or di-$C_{1-6}$ alkyl-carbonylamino group (e.g., acetylamino),
(c) a ($C_{1-6}$ alkyl)($C_{1-6}$ alkyl-carbonyl)amino group (e.g., methyl(acetyl)amino), and
(d) a pyrrolidinyl group optionally substituted by 1 to 3 oxo groups, (xiii) a mono- or di-$C_{6-14}$ aryl-carbamoyl group (e.g., phenylcarbamoyl), (xiv) a $C_{3-10}$ cycloalkylamino group (e.g., cyclohexylamino), and (xv) a 3- to 14-membered non-aromatic heterocyclylamino group (e.g., piperidylamino, tetrahydropyranylamino, 1,4-dihydrobenzoxazinylamino, tetrahydroquinolylamino) optionally substituted by 1 to 3 substituents selected from
(a) a $C_{1-6}$ alkyl group (e.g., methyl),
(b) a $C_{1-6}$ alkyl-carbonyl group (e.g., acetyl), and (c) an oxo group, (2) a 5- or 6-membered monocyclic aromatic heterocyclic group (e.g., pyridyl, imidazolyl, pyrazolyl) optionally substituted by 1 to 3 substituents selected from
(i) a halogen atom (e.g., a bromine atom),
(ii) a $C_{6-14}$ aryl group (e.g., phenyl),
(iii) a $C_{6-14}$ aryloxy group (e.g., phenoxy), and
(iv) a 5- to 14-membered aromatic heterocyclic group (preferably, a 5- or 6-membered monocyclic aromatic heterocyclic group (e.g., pyridyl)) optionally substituted by 1 to 3 $C_{1-6}$ alkyl groups (e.g., methyl), (3) a 8- to 14-membered fused polycyclic aromatic heterocyclic group (e.g., indolyl, indazolyl, pyrrolopyridyl, dibenzofuranyl, imidazopyridyl, benzothiophenyl, benzoxazolyl) or a 9- to 14-membered fused polycyclic non-aromatic heterocyclic group (e.g., dihydroindolyl), each of which is optionally substituted by 1 to 3 substituents selected from
(i) a halogen atom (e.g., a fluorine atom, a chlorine atom, a bromine atom), (ii) a $C_{6-14}$ aryl group (e.g., phenyl) optionally substituted by 1 to 3 substituents selected from
(a) a halogen atom (e.g., a fluorine atom, a chlorine atom),
(b) an optionally halogenated $C_{1-6}$ alkyl group (e.g., methyl, trifluoromethyl), and
(c) a $C_{1-6}$ alkoxy group (e.g., methoxy), (iii) a 5- to 14-membered aromatic heterocyclic group (preferably, a 5- or 6-membered monocyclic aromatic heterocyclic group (e.g., pyridyl, pyrimidinyl, pyridazinyl, pyrazinyl)) optionally substituted by 1 to 3 substituents selected from
(a) a halogen atom (e.g., a fluorine atom, a chlorine atom),
(b) an optionally halogenated $C_{1-6}$ alkyl group (e.g., methyl, trifluoromethyl), and
(c) a $C_{1-6}$ alkoxy group (e.g., methoxy), (iv) a $C_{1-6}$ alkyl group (e.g., methyl) optionally substituted by 1 to 3 $C_{6-14}$ aryl groups (e.g., phenyl) optionally substituted by 1 to 3 halogen atoms (e.g., a fluorine atom), (v) a $C_{1-6}$ alkyl-carbonyl group (e.g., acetyl, ethylcarbonyl, isobutylcarbonyl, neopentylcarbonyl) optionally substituted by 1 to 3 substituents selected from
(a) a halogen atom (e.g., a fluorine atom),
(b) a $C_{6-14}$ aryl group (e.g., phenyl) optionally substituted by 1 to 3 halogen atoms (e.g., a fluorine atom, a chlorine atom),
(c) a $C_{3-10}$ cycloalkyl group (e.g., cyclopropyl),
(d) a 5- to 14-membered aromatic heterocyclic group (preferably, a 5- or 6-membered monocyclic aromatic heterocyclic group (e.g., pyridyl)) optionally substituted by 1 to 3 substituents selected from a halogen atom (e.g., a chlorine atom) and a $C_{1-6}$ alkoxy group (e.g., methoxy), and
(e) a 3- to 14-membered non-aromatic heterocyclic group (preferably, a 3- to 8-membered monocyclic non-aromatic heterocyclic group (e.g., tetrahydropyranyl)), (vi) a $C_{1-6}$ alkoxy-carbonyl group (e.g., tert-butoxycarbonyl), (vii) a $C_{6-14}$ aryl-carbonyl group (e.g., benzoyl), (viii) a 3- to 14-membered non-aromatic heterocyclylcarbonyl group (preferably, a 3- to 8-membered monocyclic non-aromatic heterocyclylcarbonyl group (e.g., tetrahydropyranylcarbonyl)), and (ix) a $C_{3-10}$ cycloalkyl group (e.g., cyclopropyl), (4) a $C_{1-6}$ alkyl group (e.g., methyl) optionally substituted by 1 to 3 $C_{6-14}$ aryl groups (e.g., phenyl), or (5) a $C_{3-10}$ cycloalkenyl group (e.g., cyclohexenyl).

In another embodiment, $R^1$ is further still more preferably
(1) a phenyl group or a naphthyl group, each of which is optionally substituted by 1 to 3 substituents selected from
(i) a phenoxy group optionally substituted by 1 to 3 substituents selected from
(a) a $C_{1-6}$ alkoxy group (e.g., methoxy), and
(b) a halogen atom (e.g., a fluorine atom),
(ii) a halogen atom (e.g., a fluorine atom, a chlorine atom, a bromine atom, an iodine atom),
(iii) a cyano group,
(iv) an optionally halogenated $C_{1-6}$ alkoxy group (e.g., methoxy, trifluoromethoxy),
(v) a $C_{1-6}$ alkyl group (e.g., methyl, isopropyl) optionally substituted by 1 to 3 substituents selected from
(a) a halogen atom (e.g., a fluorine atom),
(b) a cyano group,
(c) a phenyl group, (d) a piperazinyl group optionally substituted by 1 to 3 $C_{1-6}$ alkyl groups (e.g., methyl), and
(e) a morpholinyl group,
(vi) a benzyloxy group,
(vii) a $C_{3-10}$ cycloalkyl group (e.g., cyclopropyl),
(viii) a phenyl group optionally substituted by 1 to 5 substituents selected from
  (a) a halogen atom (e.g., a fluorine atom, a chlorine atom),
  (b) a cyano group,
  (c) a $C_{1-6}$ alkyl group (e.g., methyl, ethyl) optionally substituted by 1 to 3 substituents selected from a halogen atom (e.g., a fluorine atom), a hydroxy group and a carbamoyl group,
  (d) an optionally halogenated $C_{1-6}$ alkoxy group (e.g., methoxy, ethoxy, isopropoxy, trifluoromethoxy),
  (e) a carboxy group,
  (f) a mono- or di-$C_{1-6}$ alkyl-carbonylamino group (e.g., acetylamino),
  (g) a mono- or di-$C_{1-6}$ alkylsulfonylamino group (e.g., methylsulfonylamino),
  (h) a sulfamoyl group,
  (i) a mono- or di-$C_{1-6}$ alkylsulfamoyl group (e.g., methylsulfamoyl),
  (j) a carbamoyl group,
  (k) a mono- or di-$C_{1-6}$ alkyl-carbamoyl group (e.g., methylcarbamoyl),
  (l) a pyrrolidinylcarbonyl group,
  (m) a phenyl group,
  (n) a phenoxy group, and
  (o) a morpholinyl group,
(ix) a pyridyl group optionally substituted by 1 to 3 substituents selected from
  (a) a halogen atom (e.g., a chlorine atom),
  (b) an optionally halogenated $C_{1-6}$ alkyl group (e.g., methyl, trifluoromethyl), and
  (c) a $C_{1-6}$ alkoxy group (e.g., methoxy),
(x) a dihydropyridyl group optionally substituted by 1 to 3 substituents selected from
  (a) a $C_{1-6}$ alkyl group (e.g., methyl), and
  (b) an oxo group,
(xi) a thiazolyl group optionally substituted by 1 to 3 optionally halogenated $C_{1-6}$ alkyl groups (e.g., methyl, trifluoromethyl),
(xii) a morpholinyl group,
(xiii) a pyridyloxy group,
(xiv) a mono- or di-phenylamino group optionally substituted by 1 to 3 substituents selected from
  (a) a halogen atom (e.g., a fluorine atom),
  (b) a mono- or di-$C_{1-6}$ alkyl-carbonylamino group (e.g., acetylamino),
  (c) a ($C_{1-6}$ alkyl)($C_{1-6}$ alkyl-carbonyl)amino group (e.g., methyl(acetyl)amino), and
  (d) a pyrrolidinyl group optionally substituted by 1 to 3 oxo groups,
(xv) a mono- or di-phenylcarbamoyl group,
(xvi) a thienyl group optionally substituted by 1 to 3 substituents selected from
  (a) an optionally halogenated $C_{1-6}$ alkyl group (e.g., methyl, trifluoromethyl), and
  (b) a $C_{1-6}$ alkoxy group (e.g., methoxy),
(xvii) a furyl group,
(xviii) a pyrazinyl group optionally substituted by 1 to 3 $C_{1-6}$ alkyl groups (e.g., methyl),
(xix) a pyrazolyl group optionally substituted by 1 to 3 optionally halogenated $C_{1-6}$ alkyl groups (e.g., methyl, ethyl, isopropyl, trifluoromethyl),
(xx) a pyrimidinyl group optionally substituted by 1 to 3 $C_{1-6}$ alkyl groups (e.g., methyl),
(xxi) an isoxazolyl group optionally substituted by 1 to 3 $C_{1-6}$ alkyl groups (e.g., methyl),
(xxii) an imidazolyl group optionally substituted by 1 to 3 $C_{1-6}$ alkyl groups (e.g., methyl),
(xxiii) a naphthyl group,
(xxiv) a dihydroindolyl group optionally substituted by 1 to 3 substituents selected from
  (a) a $C_{1-6}$ alkyl group (e.g., methyl),
  (b) a $C_{1-6}$ alkoxy group (e.g., methoxy), and
  (c) an oxo group,
(xxv) an indolyl group,
(xxvi) an indazolyl group optionally substituted by 1 to 3 $C_{1-6}$ alkyl groups (e.g., methyl),
(xxvii) an imidazopyridyl group optionally substituted by 1 to 3 $C_{1-6}$ alkyl groups (e.g., methyl),
(xxviii) an isobenzothiazolyl group,
(xxix) a pyrazolopyridyl group,
(xxx) a thienopyridyl group,
(xxxi) a dihydropyrrolopyridyl group optionally substituted by 1 to 3 oxo groups,
(xxxii) a pyrrolopyridyl group optionally substituted by 1 to 3 $C_{1-6}$ alkoxy groups (e.g., methoxy),
(xxxiii) a benzothiophenyl group,
(xxxiv) a benzofuranyl group,
(xxxv) a dihydrobenzofuranyl group,
(xxxvi) a $C_{3-10}$ cycloalkylamino group (e.g., cyclohexylamino),
(xxxvii) a piperidylamino group optionally substituted by 1 to 3 substituents selected from
  (a) a $C_{1-6}$ alkyl group (e.g., methyl),
  (b) a $C_{1-6}$ alkyl-carbonyl group (e.g., acetyl), and
  (c) an oxo group,
(xxxviii) a tetrahydropyranylamino group,
(xxxix) a 1,4-dihydrobenzoxazinylamino group optionally substituted by 1 to 3 oxo groups, and
(xxxx) a tetrahydroquinolylamino group optionally substituted by 1 to 3 oxo groups,
(2) a pyridyl group, an imidazolyl group or a pyrazolyl group, each of which is optionally substituted by 1 to 3 substituents selected from
  (i) a halogen atom (e.g., a bromine atom),
  (ii) a phenyl group,
  (iii) a phenoxy group, and
  (iv) a pyridyl group optionally substituted by 1 to 3 $C_{1-6}$ alkyl groups (e.g., methyl),
(3) an indolyl group, an indazolyl group, a pyrrolopyridyl group, a dibenzofuranyl group, an imidazopyridyl group, a dihydroindolyl group, a benzothiophenyl group or a benzoxazolyl group, each of which is optionally substituted by 1 to 3 substituents selected from
  (i) a halogen atom (e.g., a fluorine atom, a chlorine atom, a bromine atom),
  (ii) a phenyl group optionally substituted by 1 to 3 substituents selected from
    (a) a halogen atom (e.g., a fluorine atom, a chlorine atom),
    (b) an optionally halogenated $C_{1-6}$ alkyl group (e.g., methyl, trifluoromethyl), and
    (c) a $C_{1-6}$ alkoxy group (e.g., methoxy),
  (iii) a pyridyl group optionally substituted by 1 to 3 substituents selected from
    (a) a halogen atom (e.g., a fluorine atom, a chlorine atom), and
    (b) an optionally halogenated $C_{1-6}$ alkyl group (e.g., methyl, trifluoromethyl), (iv) a pyrimidinyl group optionally substituted by 1 to 3 substituents selected from
  (a) a halogen atom (e.g., a fluorine atom, a chlorine atom),
  (b) an optionally halogenated $C_{1-6}$ alkyl group (e.g., methyl, trifluoromethyl), and
  (c) a $C_{1-6}$ alkoxy group (e.g., methoxy),
(v) a pyridazinyl group optionally substituted by 1 to 3 optionally halogenated $C_{1-6}$ alkyl groups (e.g., trifluoromethyl),
(vi) a pyrazinyl group optionally substituted by 1 to 3 optionally halogenated $C_{1-6}$ alkyl groups (e.g., trifluoromethyl),
(vii) a $C_{1-6}$ alkyl group (e.g., methyl) optionally substituted by 1 to 3 phenyl groups optionally substituted by 1 to 3 halogen atoms (e.g., a fluorine atom),
(viii) a $C_{1-6}$ alkyl-carbonyl group (e.g., acetyl, ethylcarbonyl, isobutylcarbonyl, neopentylcarbonyl) optionally substituted by 1 to 3 substituents selected from
  (a) a halogen atom (e.g., a fluorine atom),
  (b) a phenyl group optionally substituted by 1 to 3 halogen atoms (e.g., a fluorine atom, a chlorine atom),
  (c) a $C_{3-10}$ cycloalkyl group (e.g., cyclopropyl),
  (d) a pyridyl group optionally substituted by 1 to 3 substituents selected from a halogen atom (e.g., a chlorine atom) and a $C_{1-6}$ alkoxy group (e.g., methoxy), and
  (e) a tetrahydropyranyl group,
(ix) a $C_{1-6}$ alkoxy-carbonyl group (e.g., tert-butoxycarbonyl),
(x) a benzoyl group,
(xi) a tetrahydropyranylcarbonyl group, and
(xii) a $C_{3-10}$ cycloalkyl group (e.g., cyclopropyl), (4) a $C_{1-6}$ alkyl group (e.g., methyl) optionally substituted by 1 to 3 phenyl groups, or
(5) a $C_{3-10}$ cycloalkenyl group (e.g., cyclohexenyl).

In another embodiment, $R^1$ is further still more preferably (1) a phenyl group or a naphthyl group, each of which is optionally substituted by 1 to 3 substituents selected from
  (i) a phenoxy group optionally substituted by 1 to 3 substituents selected from
    (a) a $C_{1-6}$ alkoxy group (e.g., methoxy), and
    (b) a halogen atom (e.g., a fluorine atom),
  (ii) a halogen atom (e.g., a fluorine atom, a bromine atom, an iodine atom),
  (iii) an optionally halogenated $C_{1-6}$ alkoxy group (e.g., methoxy, trifluoromethoxy),
  (iv) a $C_{1-6}$ alkyl group (e.g., methyl) optionally substituted by 1 to 3 phenyl groups,
  (v) a benzyloxy group,
  (vi) a $C_{3-10}$ cycloalkyl group (e.g., cyclopropyl),
  (vii) a phenyl group optionally substituted by 1 to 5 substituents selected from
    (a) a halogen atom (e.g., a fluorine atom, a chlorine atom),
    (b) a cyano group,
    (c) a $C_{1-6}$ alkyl group (e.g., methyl, ethyl) optionally substituted by 1 to 3 substituents selected from a halogen atom (e.g., a fluorine atom), a hydroxy group and a carbamoyl group,
    (d) an optionally halogenated $C_{1-6}$ alkoxy group (e.g., methoxy, ethoxy, isopropoxy, trifluoromethoxy),
    (e) a carboxy group,
    (f) a mono- or di-$C_{1-6}$ alkyl-carbonylamino group (e.g., acetylamino),
    (g) a mono- or di-$C_{1-6}$ alkylsulfonylamino group (e.g., methylsulfonylamino),
    (h) a sulfamoyl group,
    (i) a mono- or di-$C_{1-6}$ alkylsulfamoyl group (e.g., methylsulfamoyl),
    (j) a carbamoyl group,
    (k) a mono- or di-$C_{1-6}$ alkyl-carbamoyl group (e.g., methylcarbamoyl),
    (l) a pyrrolidinylcarbonyl group,
    (m) a phenyl group,
    (n) a phenoxy group, and
    (o) a morpholinyl group,
  (viii) a pyridyl group optionally substituted by 1 to 3 substituents selected from
    (a) a halogen atom (e.g., a chlorine atom),
    (b) an optionally halogenated $C_{1-6}$ alkyl group (e.g., methyl, trifluoromethyl), and
    (c) a $C_{1-6}$ alkoxy group (e.g., methoxy),
  (ix) a thiazolyl group optionally substituted by 1 to 3 optionally halogenated $C_{1-6}$ alkyl groups (e.g., methyl, trifluoromethyl),
  (x) a pyridyloxy group,
  (xi) a mono- or di-phenylamino group optionally substituted by 1 to 3 substituents selected from
    (a) a halogen atom (e.g., a fluorine atom),
    (b) a mono- or di-$C_{1-6}$ alkyl-carbonylamino group (e.g., acetylamino),
    (c) a ($C_{1-6}$ alkyl)($C_{1-6}$ alkyl-carbonyl)amino group (e.g., methyl(acetyl)amino), and
    (d) a pyrrolidinyl group optionally substituted by 1 to 3 oxo groups,
  (xii) a thienyl group optionally substituted by 1 to 3 substituents selected from
    (a) an optionally halogenated $C_{1-6}$ alkyl group (e.g., methyl, trifluoromethyl), and
    (b) a $C_{1-6}$ alkoxy group (e.g., methoxy),
  (xiii) a furyl group,
  (xiv) a pyrazinyl group optionally substituted by 1 to 3 $C_{1-6}$ alkyl groups (e.g., methyl),
  (xv) a pyrazolyl group optionally substituted by 1 to 3 optionally halogenated $C_{1-6}$ alkyl groups (e.g., methyl, ethyl, isopropyl, trifluoromethyl),
  (xvi) a pyrimidinyl group optionally substituted by 1 to 3 $C_{1-6}$ alkyl groups (e.g., methyl),
  (xvii) an isoxazolyl group optionally substituted by 1 to 3 $C_{1-6}$ alkyl groups (e.g., methyl),
  (xviii) an imidazolyl group optionally substituted by 1 to 3 $C_{1-6}$ alkyl groups (e.g., methyl),
  (xix) a naphthyl group,
  (xx) a dihydroindolyl group optionally substituted by 1 to 3 substituents selected from
    (a) a $C_{1-6}$ alkyl group (e.g., methyl),
    (b) a $C_{1-6}$ alkoxy group (e.g., methoxy), and
    (c) an oxo group,
  (xxi) an indolyl group,
  (xxii) an indazolyl group optionally substituted by 1 to 3 $C_{1-6}$ alkyl groups (e.g., methyl),
  (xxiii) an imidazopyridyl group optionally substituted by 1 to 3 $C_{1-6}$ alkyl groups (e.g., methyl),
  (xxiv) an isobenzothiazolyl group,
  (xxv) a pyrazolopyridyl group,
  (xxvi) a thienopyridyl group,
  (xxvii) a dihydropyrrolopyridyl group optionally substituted by 1 to 3 oxo groups,
  (xxviii) a pyrrolopyridyl group optionally substituted by 1 to 3 $C_{1-6}$ alkoxy groups (e.g., methoxy),
  (xxix) a benzothiophenyl group, (xxx) a benzofuranyl group,
(xxxi) a dihydrobenzofuranyl group,
(xxxii) a $C_{3-10}$ cycloalkylamino group (e.g., cyclohexylamino),
(xxxiii) a piperidylamino group optionally substituted by 1 to 3 substituents selected from
  (a) a $C_{1-6}$ alkyl group (e.g., methyl), and
  (b) an oxo group,
(xxxiv) a 1,4-dihydrobenzoxazinylamino group optionally substituted by 1 to 3 oxo groups, and
(xxxv) a tetrahydroquinolylamino group optionally substituted by 1 to 3 oxo groups,
(2) a pyridyl group optionally substituted by 1 to 3 substituents selected from
  (i) a halogen atom (e.g., a bromine atom),
  (ii) a phenyl group,
  (iii) a phenoxy group, and
  (iv) a pyridyl group optionally substituted by 1 to 3 $C_{1-6}$ alkyl groups (e.g., methyl), or
(3) an indolyl group, an indazolyl group, a pyrrolopyridyl group, a dibenzofuranyl group, a dihydroindolyl group, a benzothiophenyl group or a benzoxazolyl group, each of which is optionally substituted by 1 to 3 substituents selected from
  (i) a halogen atom (e.g., a fluorine atom, a chlorine atom),
  (ii) a phenyl group optionally substituted by 1 to 3 substituents selected from
    (a) a halogen atom (e.g., a fluorine atom, a chlorine atom),
    (b) an optionally halogenated $C_{1-6}$ alkyl group (e.g., methyl, trifluoromethyl), and
    (c) a $C_{1-6}$ alkoxy group (e.g., methoxy),
  (iii) a pyridyl group optionally substituted by 1 to 3 substituents selected from
    (a) a halogen atom (e.g., a fluorine atom, a chlorine atom), and
    (b) an optionally halogenated $C_{1-6}$ alkyl group (e.g., methyl, trifluoromethyl),
  (iv) a pyrimidinyl group optionally substituted by 1 to 3 substituents selected from
    (a) a halogen atom (e.g., a fluorine atom, a chlorine atom),
    (b) an optionally halogenated $C_{1-6}$ alkyl group (e.g., methyl, trifluoromethyl), and
    (c) a $C_{1-6}$ alkoxy group (e.g., methoxy),
  (v) a pyridazinyl group optionally substituted by 1 to 3 optionally halogenated $C_{1-6}$ alkyl groups (e.g., trifluoromethyl),
  (vi) a pyrazinyl group optionally substituted by 1 to 3 optionally halogenated $C_{1-6}$ alkyl groups (e.g., trifluoromethyl),
  (vii) a $C_{1-6}$ alkyl group (e.g., methyl) optionally substituted by 1 to 3 phenyl groups optionally substituted by 1 to 3 halogen atoms (e.g., a fluorine atom),
  (viii) a $C_{1-6}$ alkyl-carbonyl group (e.g., acetyl, ethylcarbonyl, isobutylcarbonyl, neopentylcarbonyl) optionally substituted by 1 to 3 substituents selected from
    (a) a halogen atom (e.g., a fluorine atom),
    (b) a phenyl group optionally substituted by 1 to 3 halogen atoms (e.g., a fluorine atom, a chlorine atom),
    (c) a $C_{3-10}$ cycloalkyl group (e.g., cyclopropyl),
    (d) a pyridyl group optionally substituted by 1 to 3 substituents selected from a halogen atom (e.g., a chlorine atom) and a $C_{1-6}$ alkoxy group (e.g., methoxy), and
    (e) a tetrahydropyranyl group,
  (ix) a $C_{1-6}$ alkoxy-carbonyl group (e.g., tert-butoxycarbonyl),
  (x) a benzoyl group,
  (xi) a tetrahydropyranylcarbonyl group, and
  (xii) a $C_{3-10}$ cycloalkyl group (e.g., cyclopropyl).

In still another embodiment, $R^1$ is further still more preferably
(1) a phenyl group optionally substituted by 1 to 3 substituents selected from
  (i) a phenoxy group optionally substituted by 1 to 3 halogen atoms (e.g., a fluorine atom),
  (ii) a halogen atom (e.g., a fluorine atom, a bromine atom),
  (iii) a $C_{1-6}$ alkoxy group (e.g., methoxy),
  (iv) an optionally halogenated $C_{1-6}$ alkyl group (e.g., trifluoromethyl),
  (v) a benzyloxy group,
  (vi) a $C_{3-10}$ cycloalkyl group (e.g., cyclopropyl),
  (vii) a phenyl group optionally substituted by 1 to 5 halogen atoms (e.g., a fluorine atom, a chlorine atom),
  (viii) a pyridyl group optionally substituted by 1 to 3 $C_{1-6}$ alkyl groups (e.g., methyl),
  (ix) a monophenylamino group optionally substituted by 1 to 3 halogen atoms (e.g., a fluorine atom),
  (x) a pyrimidinyl group optionally substituted by 1 to 3 $C_{1-6}$ alkyl groups (e.g., methyl), and
  (xi) a dihydroindolyl group optionally substituted by 1 to 3 substituents selected from
    (a) a $C_{1-6}$ alkoxy group (e.g., methoxy), and
    (b) an oxo group,
(2) an indolyl group, an indazolyl group, a dibenzofuranyl group, a dihydroindolyl group or a benzothiophenyl group, each of which is optionally substituted by 1 to 3 substituents selected from
  (i) a halogen atom (e.g., a fluorine atom, a chlorine atom),
  (ii) a phenyl group optionally substituted by 1 to 3 substituents selected from
    (a) a halogen atom (e.g., a fluorine atom, a chlorine atom), and
    (b) an optionally halogenated $C_{1-6}$ alkyl group (e.g., trifluoromethyl),
  (iii) a pyridyl group optionally substituted by 1 to 3 optionally halogenated $C_{1-6}$ alkyl groups (e.g., trifluoromethyl),
  (iv) a pyrimidinyl group optionally substituted by 1 to 3 optionally halogenated $C_{1-6}$ alkyl groups (e.g., trifluoromethyl),
  (v) a $C_{1-6}$ alkyl group (e.g., methyl) optionally substituted by 1 to 3 phenyl groups optionally substituted by 1 to 3 halogen atoms (e.g., a fluorine atom),
  (vi) a $C_{1-6}$ alkyl-carbonyl group (e.g., acetyl, neopentylcarbonyl) optionally substituted by 1 to 3 substituents selected from
    (a) a halogen atom (e.g., a fluorine atom), and
    (b) a phenyl group optionally substituted by 1 to 3 halogen atoms (e.g., a chlorine atom),
  (vii) a $C_{1-6}$ alkoxy-carbonyl group (e.g., tert-butoxycarbonyl), and
  (viii) a $C_{3-10}$ cycloalkyl group (e.g., cyclopropyl), or
(3) a $C_{1-6}$ alkyl group (e.g., methyl) optionally substituted by 1 to 3 phenyl groups.

$R^1$ is particularly preferably
(1) a phenyl group substituted by 1 to 3 substituents selected from
  (i) a halogen atom (e.g., a fluorine atom), and
  (ii) a pyridyl group substituted by 1 to 3 $C_{1-6}$ alkyl groups (e.g., methyl), or (2) an indolyl group or an indazolyl group, each of which is substituted by 1 to 3 substituents selected from
  (i) a phenyl group substituted by 1 to 3 substituents selected from
    (a) a halogen atom (e.g., a fluorine atom), and
    (b) a halogenated $C_{1-6}$ alkyl group (e.g., trifluoromethyl), and
  (ii) a pyrimidinyl group substituted by 1 to 3 halogenated $C_{1-6}$ alkyl groups (e.g., trifluoromethyl).

$R^2$ is an acyl group, an optionally substituted $C_{6-14}$ aryl group or an optionally substituted heterocyclic group.

As the "acyl group" for $R^2$, an optionally substituted 5- to 14-membered aromatic heterocyclylcarbonyl group, an optionally substituted 3- to 14-membered non-aromatic heterocyclylcarbonyl group, an optionally substituted $C_{1-6}$ alkyl-carbonyl group, an optionally substituted $C_{6-14}$ aryl-carbonyl group, an optionally substituted $C_{3-10}$ cycloalkyl-carbonyl group, an optionally substituted $C_{1-6}$ alkoxy-carbonyl group, and an optionally substituted 5- to 14-membered aromatic heterocyclylsulfonyl group are preferable,
an optionally substituted 5- or 6-membered monocyclic aromatic heterocyclylcarbonyl group and an optionally substituted 3- to 8-membered monocyclic non-aromatic heterocyclylcarbonyl group are more preferable,
a 5- or 6-membered monocyclic aromatic heterocyclylcarbonyl group is further preferable,
thiazolylcarbonyl, thienylcarbonyl, furylcarbonyl, pyrrolylcarbonyl, pyrazolylcarbonyl, imidazolylcarbonyl and oxazolylcarbonyl are still more preferable, and thiazolylcarbonyl and oxazolylcarbonyl are particularly preferable.

The "5- to 14-membered aromatic heterocyclylcarbonyl group" of the "optionally substituted 5- to 14-membered aromatic heterocyclylcarbonyl group", the "3- to 14-membered non-aromatic heterocyclylcarbonyl group" of the above-mentioned "optionally substituted 3- to 14-membered non-aromatic heterocyclylcarbonyl group", the "$C_{1-6}$ alkyl-carbonyl group" of the above-mentioned "optionally substituted $C_{1-6}$ alkyl-carbonyl group", the "$C_{6-14}$ aryl-carbonyl group" of the above-mentioned "optionally substituted $C_{6-14}$ aryl-carbonyl group", the "$C_{3-10}$ cycloalkyl-carbonyl group" of the above-mentioned "optionally substituted $C_{3-10}$ cycloalkyl-carbonyl group", the "$C_{1-6}$ alkoxy-carbonyl group" of the above-mentioned "optionally substituted $C_{1-6}$ alkoxy-carbonyl group", and the "5- to 14-membered aromatic heterocyclylsulfonyl group" of the above-mentioned "optionally substituted 5- to 14-membered aromatic heterocyclylsulfonyl group" may be further substituted by, for example, substituent(s) selected from the aforementioned substituent group A, and the number of the substituents is, for example, 1 to 3. When the number of the substituents is two or more, the respective substituents may be the same or different.

As the "heterocyclic group" of the "optionally substituted heterocyclic group" for $R^2$, a 5- to 14-membered aromatic heterocyclic group is preferable, a 5- or 6-membered monocyclic aromatic heterocyclic group is more preferable, pyridyl and pyrimidinyl are further preferable, and pyridyl is particularly preferable.

As the "$C_{6-14}$ aryl group" of the "optionally substituted $C_{6-14}$ aryl group" for $R^2$, phenyl is preferable.

The "$C_{6-14}$ aryl group" of the "optionally substituted $C_{6-14}$ aryl group" and the "heterocyclic group" of the "optionally substituted heterocyclic group" for $R^2$ may be further substituted by, for example, substituent(s) selected from the aforementioned substituent group A, and the number of the substituents is, for example, 1 to 3. When the number of the substituents is two or more, the respective substituents may be the same or different.

$R^2$ is preferably an optionally substituted 5- to 14-membered aromatic heterocyclylcarbonyl group, an optionally substituted 3- to 14-membered non-aromatic heterocyclylcarbonyl group, an optionally substituted $C_{1-6}$ alkyl-carbonyl group, an optionally substituted $C_{6-14}$ aryl-carbonyl group, an optionally substituted $C_{3-10}$ cycloalkyl-carbonyl group, an optionally substituted $C_{1-6}$ alkoxy-carbonyl group, an optionally substituted 5- to 14-membered aromatic heterocyclylsulfonyl group, an optionally substituted $C_{6-14}$ aryl group, or an optionally substituted 5- to 14-membered aromatic heterocyclic group.

Specifically, $R^2$ is preferably
(1) a 5- to 14-membered aromatic heterocyclylcarbonyl group (preferably, a 5- or 6-membered monocyclic aromatic heterocyclylcarbonyl group (e.g., thiazolylcarbonyl, thienylcarbonyl, furylcarbonyl, pyrrolylcarbonyl, pyrazolylcarbonyl, imidazolylcarbonyl, oxazolylcarbonyl) or a 8- to 14-membered fused polycyclic (preferably, bi- or tri-cyclic) aromatic heterocyclylcarbonyl group (e.g., quinolylcarbonyl)), which is optionally substituted by 1 to 3 substituents selected from
  (i) a halogen atom (e.g., a chlorine atom), and
  (ii) a $C_{1-6}$ alkyl group (e.g., methyl),
(2) a 3- to 14-membered non-aromatic heterocyclylcarbonyl group (preferably, a 3- to 8-membered monocyclic non-aromatic heterocyclylcarbonyl group (e.g., pyrrolidinylcarbonyl)),
(3) a $C_{1-6}$ alkyl-carbonyl group (e.g., acetyl) optionally substituted by 1 to 3 substituents selected from
  (i) a halogen atom (e.g., a fluorine atom),
  (ii) a mono- or di-$C_{1-6}$ alkylamino group (e.g., dimethylamino), and
  (iii) a 5- to 14-membered aromatic heterocyclic group (preferably, a 5- or 6-membered monocyclic aromatic heterocyclic group (e.g., pyridyl)),
(4) a $C_{6-14}$ aryl-carbonyl group (e.g., benzoyl),
(5) an optionally halogenated $C_{3-10}$ cycloalkyl-carbonyl group (e.g., difluorocyclopropylcarbonyl),
(6) a $C_{1-6}$ alkoxy-carbonyl group (e.g., tert-butoxycarbonyl),
(7) a 5- to 14-membered aromatic heterocyclylsulfonyl group (preferably, a 5- or 6-membered monocyclic aromatic heterocyclylsulfonyl group (e.g., pyridylsulfonyl)),
(8) a $C_{6-14}$ aryl group (e.g., phenyl), or
(9) a 5- to 14-membered aromatic heterocyclic group (preferably, a 5- or 6-membered monocyclic aromatic heterocyclic group (e.g., pyridyl, pyrimidinyl)) optionally substituted by 1 to 3 cyano groups.

$R^2$ is more preferably an optionally substituted 5- to 14-membered aromatic heterocyclylcarbonyl group, an optionally substituted 3- to 14-membered non-aromatic heterocyclylcarbonyl group, an optionally substituted $C_{1-6}$ alkyl-carbonyl group, or an optionally substituted 5- to 14-membered aromatic heterocyclic group.

Specifically, $R^2$ is more preferably
(1) a 5- to 14-membered aromatic heterocyclylcarbonyl group (preferably, a 5- or 6-membered monocyclic aromatic heterocyclylcarbonyl group (e.g., thiazolylcarbonyl, thienylcarbonyl, furylcarbonyl, oxazolylcarbonyl) optionally substituted by 1 to 3 halogen atoms (e.g., a chlorine atom),
(2) a 3- to 14-membered non-aromatic heterocyclylcarbonyl group (preferably, a 3- to 8-membered monocyclic non-aromatic heterocyclylcarbonyl group (e.g., pyrrolidinylcarbonyl)), or (3) a 5- to 14-membered aromatic heterocyclic group (preferably, a 5- or 6-membered monocyclic aromatic heterocyclic group (e.g., pyridyl, pyrimidinyl)) optionally substituted by 1 to 3 cyano groups.

Specifically, $R^2$ is further preferably
(1) a 5- to 14-membered aromatic heterocyclylcarbonyl group (preferably, a 5- or 6-membered monocyclic aromatic heterocyclylcarbonyl group (e.g., thiazolylcarbonyl, oxazolylcarbonyl)),
(2) a 3- to 14-membered non-aromatic heterocyclylcarbonyl group (preferably, a 3- to 8-membered monocyclic non-aromatic heterocyclylcarbonyl group (e.g., pyrrolidinylcarbonyl), or
(3) a 5- to 14-membered aromatic heterocyclic group (preferably, a 5- or 6-membered monocyclic aromatic heterocyclic group (e.g., pyridyl)) optionally substituted by 1 to 3 cyano groups.

In another embodiment, $R^2$ is specifically preferably
(1) a thiazolylcarbonyl group, a thienylcarbonyl group, a furylcarbonyl group, a pyrrolylcarbonyl group, a pyrazolylcarbonyl group, an imidazolylcarbonyl group, an oxazolylcarbonyl group or a quinolylcarbonyl group, each of which is optionally substituted by 1 to 3 substituents selected from
    (i) a halogen atom (e.g., a chlorine atom), and
    (ii) a $C_{1-6}$ alkyl group (e.g., methyl),
(2) a pyrrolidinylcarbonyl group,
(3) a $C_{1-6}$ alkyl-carbonyl group (e.g., acetyl) optionally substituted by 1 to 3 substituents selected from
    (i) a halogen atom (e.g., a fluorine atom),
    (ii) a mono- or di-$C_{1-6}$ alkylamino group (e.g., dimethylamino), and
    (iii) a pyridyl group,
(4) a benzoyl group,
(5) an optionally halogenated $C_{3-10}$ cycloalkyl-carbonyl group (e.g., difluorocyclopropylcarbonyl),
(6) a $C_{1-6}$ alkoxy-carbonyl group (e.g., tert-butoxycarbonyl),
(7) a pyridylsulfonyl group,
(8) a phenyl group, or
(9) a pyridyl group or a pyrimidinyl group, each of which is optionally substituted by 1 to 3 cyano groups.

Specifically, $R^2$ is more preferably
(1) a thiazolylcarbonyl group, a thienylcarbonyl group, a furylcarbonyl group or an oxazolylcarbonyl group, each of which is optionally substituted by 1 to 3 halogen atoms (e.g., a chlorine atom),
(2) a pyrrolidinylcarbonyl group, or
(3) a pyridyl group or a pyrimidinyl group, each of which is optionally substituted by 1 to 3 cyano groups.

Specifically, $R^2$ is further preferably
(1) a thiazolylcarbonyl group or an oxazolylcarbonyl group,
(2) a pyrrolidinylcarbonyl group, or
(3) a pyridyl group or a pyrimidinyl group, each of which is optionally substituted by 1 to 3 cyano groups.

Specifically, $R^2$ is particularly preferably a thiazolylcarbonyl group or a pyrimidinyl group.

Preferable examples of compound (I) include the following compounds.

[Compound A]

Compound (I) wherein
ring A is a pyrrolidin-2-one ring not substituted by the additional substituents;
ring B is a piperazine ring not substituted by the additional substituents;

$R^1$ is
(1) a $C_{6-14}$ aryl group (e.g., phenyl, naphthyl) optionally substituted by 1 to 3 substituents selected from
    (i) a $C_{6-14}$ aryloxy group (e.g., phenoxy) optionally substituted by 1 to 3 substituents selected from
        (a) a $C_{1-6}$ alkoxy group (e.g., methoxy), and
        (b) a halogen atom (e.g., a fluorine atom),
    (ii) a halogen atom (e.g., a chlorine atom, a bromine atom, an iodine atom),
    (iii) a cyano group,
    (iv) an optionally halogenated $C_{1-6}$ alkoxy group (e.g., methoxy, trifluoromethoxy),
    (v) a $C_{1-6}$ alkyl group (e.g., methyl) optionally substituted by 1 to 3 substituents selected from
        (a) a $C_{6-14}$ aryl group (e.g., phenyl), and
        (b) a 3- to 14-membered non-aromatic heterocyclic group (preferably, a 3- to 8-membered monocyclic non-aromatic heterocyclic group (e.g., piperazinyl)) optionally substituted by 1 to 3 $C_{1-6}$ alkyl groups (e.g., methyl),
    (vi) a $C_{7-16}$ aralkyloxy group (e.g., benzyloxy),
    (vii) a $C_{3-10}$ cycloalkyl group (e.g., cyclopropyl),
    (viii) a $C_{6-14}$ aryl group (e.g., phenyl) optionally substituted by 1 to 3 halogen atoms (e.g., a fluorine atom, a chlorine atom),
    (ix) a 5- to 14-membered aromatic heterocyclic group (preferably, a 5- or 6-membered monocyclic aromatic heterocyclic group (e.g., pyridyl, thiazolyl)) optionally substituted by 1 to 3 $C_{1-6}$ alkyl groups (e.g., methyl),
    (x) a 3- to 14-membered non-aromatic heterocyclic group (preferably, a 3- to 8-membered monocyclic non-aromatic heterocyclic group (e.g., morpholinyl)),
    (xi) a 5- to 14-membered aromatic heterocyclyloxy group (preferably, a 5- or 6-membered monocyclic aromatic heterocyclyloxy group (e.g., pyridyloxy)),
    (xii) a mono- or di-$C_{6-14}$ arylamino group (e.g., phenylamino) optionally substituted by 1 to 3 halogen atoms (e.g., a fluorine atom), and
    (xiii) a mono- or di-$C_{6-14}$ aryl-carbamoyl group (e.g., phenylcarbamoyl);
(2) a 5- or 6-membered monocyclic aromatic heterocyclic group (e.g., pyridyl, imidazolyl, pyrazolyl) optionally substituted by 1 to 3 substituents selected from
    (i) a $C_{6-14}$ aryl group (e.g., phenyl), and
    (ii) a $C_{6-14}$ aryloxy group (e.g., phenoxy); or
(3) a 8- to 14-membered fused polycyclic (preferably, bi- or tri-cyclic) aromatic heterocyclic group (e.g., indolyl, indazolyl, pyrrolopyridyl, dibenzofuranyl, imidazopyridyl) optionally substituted by 1 to 3 substituents selected from
    (i) a $C_{6-14}$ aryl group (e.g., phenyl) optionally substituted by 1 to 3 halogen atoms (e.g., a fluorine atom),
    (ii) a 5- to 14-membered aromatic heterocyclic group (preferably, a 5- or 6-membered monocyclic aromatic heterocyclic group (e.g., pyrimidinyl, pyridyl)) optionally substituted by 1 to 3 substituents selected from
        (a) a halogen atom (e.g., a fluorine atom, a chlorine atom), and
        (b) an optionally halogenated $C_{1-6}$ alkyl group (e.g., trifluoromethyl), and
    (iii) a halogen atom (e.g., a bromine atom); and
$R^2$ is
(1) a 5- to 14-membered aromatic heterocyclylcarbonyl group (preferably, a 5- or 6-membered monocyclic aromatic heterocyclylcarbonyl group (e.g., thiazolylcarbonyl, thienylcarbonyl, furylcarbonyl, pyrrolylcarbonyl, pyrazolylcarbonyl, imidazolylcarbonyl, oxazolylcarbonyl) or a 8- to 14-membered fused polycyclic (preferably, bi- or tri-cyclic)

aromatic heterocyclylcarbonyl group (e.g., quinolylcarbonyl)), which is optionally substituted by 1 to 3 substituents selected from
- (i) a halogen atom (e.g., a chlorine atom), and
- (ii) a $C_{1-6}$ alkyl group (e.g., methyl), (2) a 3- to 14-membered non-aromatic heterocyclylcarbonyl group (preferably, a 3- to 8-membered monocyclic non-aromatic heterocyclylcarbonyl group (e.g., pyrrolidinylcarbonyl)), (3) a $C_{1-6}$ alkyl-carbonyl group (e.g., acetyl) optionally substituted by 1 to 3 substituents selected from
- (i) a halogen atom (e.g., a fluorine atom),
- (ii) a mono- or di-$C_{1-6}$ alkylamino group (e.g., dimethylamino), and
- (iii) a 5- to 14-membered aromatic heterocyclic group (preferably, a 5- or 6-membered monocyclic aromatic heterocyclic group (e.g., pyridyl)), (4) a $C_{6-14}$ aryl-carbonyl group (e.g., benzoyl), (5) an optionally halogenated $C_{3-10}$ cycloalkyl-carbonyl group (e.g., difluorocyclopropylcarbonyl), (6) a $C_{1-6}$ alkoxy-carbonyl group (e.g., tert-butoxycarbonyl), (7) a 5- to 14-membered aromatic heterocyclylsulfonyl group (preferably, a 5- or 6-membered monocyclic aromatic heterocyclylsulfonyl group (e.g., pyridylsulfonyl)), (8) a $C_{6-14}$ aryl group (e.g., phenyl), or (9) a 5- to 14-membered aromatic heterocyclic group (preferably, a 5- or 6-membered monocyclic aromatic heterocyclic group (e.g., pyridyl, pyrimidinyl)) optionally substituted by 1 to 3 cyano groups.

[Compound B]

Compound (I) wherein ring A is a pyrrolidin-2-one ring not substituted by the additional substituents;

ring B is a piperazine ring not substituted by the additional substituents;

$R^1$ is (1) a $C_{6-14}$ aryl group (e.g., phenyl, naphthyl) optionally substituted by 1 to 3 substituents selected from
- (i) a $C_{6-14}$ aryloxy group (e.g., phenoxy) optionally substituted by 1 to 3 substituents selected from
  - (a) a $C_{1-6}$ alkoxy group (e.g., methoxy), and
  - (b) a halogen atom (e.g., a fluorine atom),
- (ii) a halogen atom (e.g., a bromine atom, an iodine atom),
- (iii) a $C_{1-6}$ alkoxy group (e.g., methoxy),
- (iv) a $C_{7-16}$ aralkyl group (e.g., benzyl),
- (v) a $C_{7-16}$ aralkyloxy group (e.g., benzyloxy),
- (vi) a $C_{3-10}$ cycloalkyl group (e.g., cyclopropyl),
- (vii) a $C_{6-14}$ aryl group (e.g., phenyl) optionally substituted by 1 to 3 halogen atoms (e.g., a fluorine atom, a chlorine atom),
- (viii) a 5- to 14-membered aromatic heterocyclic group (preferably, a 5- or 6-membered monocyclic aromatic heterocyclic group (e.g., pyridyl)),
- (ix) a 5- to 14-membered aromatic heterocyclyloxy group (preferably, a 5- or 6-membered monocyclic aromatic heterocyclyloxy group (e.g., pyridyloxy)), and
- (x) a mono- or di-$C_{6-14}$ arylamino group (e.g., phenylamino) optionally substituted by 1 to 3 halogen atoms (e.g., a fluorine atom);

(2) a 5- or 6-membered monocyclic aromatic heterocyclic group (e.g., pyridyl) optionally substituted by 1 to 3 $C_{6-14}$ aryloxy groups (e.g., phenoxy); or (3) a 8- to 14-membered fused polycyclic (preferably, bi- or tri-cyclic) aromatic heterocyclic group (e.g., indolyl, indazolyl, pyrrolopyridyl, dibenzofuranyl) optionally substituted by 1 to 3 substituents selected from
- (i) a $C_{6-14}$ aryl group (e.g., phenyl) optionally substituted by 1 to 3 halogen atoms (e.g., a fluorine atom), and
- (ii) a 5- to 14-membered aromatic heterocyclic group (preferably, a 5- or 6-membered monocyclic aromatic heterocyclic group (e.g., pyrimidinyl, pyridyl)) optionally substituted by 1 to 3 substituents selected from
  - (a) a halogen atom (e.g., a fluorine atom, a chlorine atom), and
  - (b) an optionally halogenated $C_{1-6}$ alkyl group (e.g., trifluoromethyl); and $R^2$ is (1) a 5- to 14-membered aromatic heterocyclylcarbonyl group (preferably, a 5- or 6-membered monocyclic aromatic heterocyclylcarbonyl group (e.g., thiazolylcarbonyl, thienylcarbonyl, furylcarbonyl, oxazolylcarbonyl) optionally substituted by 1 to 3 halogen atoms (e.g., a chlorine atom), (2) a 3- to 14-membered non-aromatic heterocyclylcarbonyl group (preferably, a 3- to 8-membered monocyclic non-aromatic heterocyclylcarbonyl group (e.g., pyrrolidinylcarbonyl)), or (3) a 5- to 14-membered aromatic heterocyclic group (preferably, a 5- or 6-membered monocyclic aromatic heterocyclic group (e.g., pyridyl, pyrimidinyl)) optionally substituted by 1 to 3 cyano groups.

[Compound C]

Compound (I) wherein ring A is a pyrrolidin-2-one ring not substituted by the additional substituents;

ring B is a piperazine ring not substituted by the additional substituents;

$R^1$ is (1) a $C_{6-14}$ aryl group (e.g., phenyl) optionally substituted by 1 to 3 substituents selected from
- (i) a $C_{6-14}$ aryloxy group (e.g., phenoxy) optionally substituted by 1 to 3 halogen atoms (e.g., a fluorine atom),
- (ii) a $C_{1-6}$ alkoxy group (e.g., methoxy),
- (iii) a $C_{3-10}$ cycloalkyl group (e.g., cyclopropyl),
- (iv) a $C_{6-14}$ aryl group (e.g., phenyl), and
- (v) a $C_{7-16}$ aralkyloxy group (e.g., benzyloxy); or (2) a 8- to 14-membered fused polycyclic (preferably, bi- or tri-cyclic) aromatic heterocyclic group (e.g., indolyl, indazolyl, dibenzofuranyl) optionally substituted by 1 to 3 substituents selected from
- (i) a $C_{6-14}$ aryl group (e.g., phenyl) optionally substituted by 1 to 3 halogen atoms (e.g., a fluorine atom), and
- (ii) a 5- to 14-membered aromatic heterocyclic group (preferably, a 5- or 6-membered aromatic heterocyclic group (e.g., pyrimidinyl, pyridyl)) optionally substituted by 1 to 3 optionally halogenated $C_{1-6}$ alkyl groups (e.g., trifluoromethyl); and $R^2$ is (1) a 5- to 14-membered aromatic heterocyclylcarbonyl group (preferably, a 5- or 6-membered monocyclic aromatic heterocyclylcarbonyl group (e.g., thiazolylcarbonyl, oxazolylcarbonyl)), (2) a 3- to 14-membered non-aromatic heterocyclylcarbonyl group (preferably, a 3- to 8-membered monocyclic non-aromatic heterocyclylcarbonyl group (e.g., pyrrolidinylcarbonyl)), or (3) a 5- to 14-membered aromatic heterocyclic group (preferably, a 5- or 6-membered monocyclic aromatic heterocyclic group (e.g., pyridyl)) optionally substituted by 1 to 3 cyano groups.

[Compound D]
Compound (I) wherein
ring A is a pyrrolidin-2-one ring optionally substituted by 1 or 2 additional substituents selected from a halogen atom (e.g., a fluorine atom), a hydroxy group and a $C_{1-6}$ alkyl group (e.g., methyl);
ring B is a piperazine ring further optionally substituted by 1 to 3 $C_{1-6}$ alkyl groups (e.g., methyl);
$R^1$ is
(1) a $C_{6-14}$ aryl group (e.g., phenyl, naphthyl) optionally substituted by 1 to 3 substituents selected from
  (i) a $C_{6-14}$ aryloxy group (e.g., phenoxy) optionally substituted by 1 to 3 substituents selected from
    (a) a $C_{1-6}$ alkoxy group (e.g., methoxy), and
    (b) a halogen atom (e.g., a fluorine atom),
  (ii) a halogen atom (e.g., a fluorine atom, a chlorine atom, a bromine atom, an iodine atom),
  (iii) a cyano group,
  (iv) an optionally halogenated $C_{1-6}$ alkoxy group (e.g., methoxy, trifluoromethoxy),
  (v) a $C_{1-6}$ alkyl group (e.g., methyl, isopropyl) optionally substituted by 1 to 3 substituents selected from
    (a) a halogen atom (e.g., a fluorine atom),
    (b) a cyano group,
    (c) a $C_{6-14}$ aryl group (e.g., phenyl), and
    (d) a 3- to 14-membered non-aromatic heterocyclic group (preferably, a 3- to 8-membered monocyclic non-aromatic heterocyclic group (e.g., piperazinyl, morpholinyl)) optionally substituted by 1 to 3 $C_{1-6}$ alkyl groups (e.g., methyl),
  (vi) a $C_{7-16}$ aralkyloxy group (e.g., benzyloxy),
  (vii) a $C_{3-10}$ cycloalkyl group (e.g., cyclopropyl),
  (viii) a $C_{6-14}$ aryl group (e.g., phenyl, naphthyl) optionally substituted by 1 to 5 substituents selected from
    (a) a halogen atom (e.g., a fluorine atom, a chlorine atom),
    (b) a cyano group,
    (c) a $C_{1-6}$ alkyl group (e.g., methyl, ethyl) optionally substituted by 1 to 3 substituents selected from a halogen atom (e.g., a fluorine atom), a hydroxy group and a carbamoyl group,
    (d) an optionally halogenated $C_{1-6}$ alkoxy group (e.g., methoxy, ethoxy, isopropoxy, trifluoromethoxy),
    (e) a carboxy group,
    (f) a mono- or di-$C_{1-6}$ alkyl-carbonylamino group (e.g., acetylamino),
    (g) a mono- or di-$C_{1-6}$ alkylsulfonylamino group (e.g., methylsulfonylamino),
    (h) a sulfamoyl group,
    (i) a mono- or di-$C_{1-6}$ alkylsulfamoyl group (e.g., methylsulfamoyl),
    (j) a carbamoyl group,
    (k) a mono- or di-$C_{1-6}$ alkyl-carbamoyl group (e.g., methylcarbamoyl),
    (l) a 3- to 14-membered non-aromatic heterocyclylcarbonyl group (preferably, a 3- to 8-membered monocyclic non-aromatic heterocyclylcarbonyl group (e.g., pyrrolidinylcarbonyl)),
    (m) a $C_{6-14}$ aryl group (e.g., phenyl),
    (n) a $C_{6-14}$ aryloxy group (e.g., phenoxy), and
    (o) a 3- to 14-membered non-aromatic heterocyclic group (preferably, a 3- to 8-membered monocyclic non-aromatic heterocyclic group (e.g., morpholinyl)),
  (ix) a 5- to 14-membered aromatic heterocyclic group (e.g., pyridyl, thiazolyl, thienyl, furyl, pyrazinyl, pyrazolyl, pyrimidinyl, isoxazolyl, imidazolyl, indolyl, indazolyl, imidazopyridyl, isobenzothiazolyl, pyrazolopyridyl, thienopyridyl, pyrrolopyridyl, benzothiophenyl, benzofuranyl) optionally substituted by 1 to 3 substituents selected from
    (a) a halogen atom (e.g., a chlorine atom),
    (b) an optionally halogenated $C_{1-6}$ alkyl group (e.g., methyl, ethyl, isopropyl, trifluoromethyl), and
    (c) a $C_{1-6}$ alkoxy group (e.g., methoxy),
  (x) a 3- to 14-membered non-aromatic heterocyclic group (e.g., dihydropyridyl, morpholinyl, dihydroindolyl, dihydropyrrolopyridyl, dihydrobenzofuranyl) optionally substituted by 1 to 3 substituents selected from
    (a) a $C_{1-6}$ alkyl group (e.g., methyl),
    (b) a $C_{1-6}$ alkoxy group (e.g., methoxy), and
    (c) an oxo group,
  (xi) a 5- to 14-membered aromatic heterocyclyloxy group (preferably, a 5- or 6-membered monocyclic aromatic heterocyclyloxy group (e.g., pyridyloxy)),
  (xii) a mono- or di-$C_{6-14}$ arylamino group (e.g., phenylamino) optionally substituted by 1 to 3 substituents selected from
    (a) a halogen atom (e.g., a fluorine atom),
    (b) a mono- or di-$C_{1-6}$ alkyl-carbonylamino group (e.g., acetylamino),
    (c) a ($C_{1-6}$ alkyl) ($C_{1-6}$ alkyl-carbonyl)amino group (e.g., methyl(acetyl)amino), and
    (d) a pyrrolidinyl group optionally substituted by 1 to 3 oxo groups,
  (xiii) a mono- or di-$C_{6-14}$ aryl-carbamoyl group (e.g., phenylcarbamoyl),
  (xiv) a $C_{3-10}$ cycloalkylamino group (e.g., cyclohexylamino), and
  (xv) a 3- to 14-membered non-aromatic heterocyclylamino group (e.g., piperidylamino, tetrahydropyranylamino, 1,4-dihydrobenzoxazinylamino, tetrahydroquinolylamino) optionally substituted by 1 to 3 substituents selected from
    (a) a $C_{1-6}$ alkyl group (e.g., methyl),
    (b) a $C_{1-6}$ alkyl-carbonyl group (e.g., acetyl), and
    (c) an oxo group,
(2) a 5- or 6-membered monocyclic aromatic heterocyclic group (e.g., pyridyl, imidazolyl, pyrazolyl) optionally substituted by 1 to 3 substituents selected from
  (i) a halogen atom (e.g., a bromine atom),
  (ii) a $C_{6-14}$ aryl group (e.g., phenyl),
  (iii) a $C_{6-14}$ aryloxy group (e.g., phenoxy), and
  (iv) a 5- to 14-membered aromatic heterocyclic group (preferably, a 5- or 6-membered monocyclic aromatic heterocyclic group (e.g., pyridyl)) optionally substituted by 1 to 3 $C_{1-6}$ alkyl groups (e.g., methyl),
(3) a 8- to 14-membered fused polycyclic aromatic heterocyclic group (e.g., indolyl, indazolyl, pyrrolopyridyl, dibenzofuranyl, imidazopyridyl, benzothiophenyl, benzoxazolyl) or a 9- to 14-membered fused polycyclic non-aromatic heterocyclic group (e.g., dihydroindolyl), each of which is optionally substituted by 1 to 3 substituents selected from
  (i) a halogen atom (e.g., a fluorine atom, a chlorine atom, a bromine atom),
  (ii) a $C_{6-14}$ aryl group (e.g., phenyl) optionally substituted by 1 to 3 substituents selected from
    (a) a halogen atom (e.g., a fluorine atom, a chlorine atom),
    (b) an optionally halogenated $C_{1-6}$ alkyl group (e.g., methyl, trifluoromethyl), and
    (c) a $C_{1-6}$ alkoxy group (e.g., methoxy),
  (iii) a 5- to 14-membered aromatic heterocyclic group (preferably, a 5- or 6-membered monocyclic aromatic heterocyclic group (e.g., pyridyl, pyrimidinyl, pyridazinyl, pyrazinyl)) optionally substituted by 1 to 3 substituents selected from
  (a) a halogen atom (e.g., a fluorine atom, a chlorine atom),
  (b) an optionally halogenated $C_{1-6}$ alkyl group (e.g., methyl, trifluoromethyl), and
  (c) a $C_{1-6}$ alkoxy group (e.g., methoxy),
(iv) a $C_{1-6}$ alkyl group (e.g., methyl) optionally substituted by 1 to 3 $C_{6-14}$ aryl groups (e.g., phenyl) optionally substituted by 1 to 3 halogen atoms (e.g., a fluorine atom),
(v) a $C_{1-6}$ alkyl-carbonyl group (e.g., acetyl, ethylcarbonyl, isobutylcarbonyl, neopentylcarbonyl) optionally substituted by 1 to 3 substituents selected from
  (a) a halogen atom (e.g., a fluorine atom),
  (b) a $C_{6-14}$ aryl group (e.g., phenyl) optionally substituted by 1 to 3 halogen atoms (e.g., a fluorine atom, a chlorine atom),
  (c) a $C_{3-10}$ cycloalkyl group (e.g., cyclopropyl),
  (d) a 5- to 14-membered aromatic heterocyclic group (preferably, a 5- or 6-membered monocyclic aromatic heterocyclic group (e.g., pyridyl)) optionally substituted by 1 to 3 substituents selected from a halogen atom (e.g., a chlorine atom) and a $C_{1-6}$ alkoxy group (e.g., methoxy), and
  (e) a 3- to 14-membered non-aromatic heterocyclic group (preferably, a 3- to 8-membered monocyclic non-aromatic heterocyclic group (e.g., tetrahydropyranyl)),
(vi) a $C_{1-6}$ alkoxy-carbonyl group (e.g., tert-butoxycarbonyl),
(vii) a $C_{6-14}$ aryl-carbonyl group (e.g., benzoyl),
(viii) a 3- to 14-membered non-aromatic heterocyclylcarbonyl group (preferably, a 3- to 8-membered monocyclic non-aromatic heterocyclylcarbonyl group (e.g., tetrahydropyranylcarbonyl)), and
(ix) a $C_{3-10}$ cycloalkyl group (e.g., cyclopropyl),
(4) a $C_{1-6}$ alkyl group (e.g., methyl) optionally substituted by 1 to 3 $C_{6-14}$ aryl groups (e.g., phenyl), or
(5) a $C_{3-10}$ cycloalkenyl group (e.g., cyclohexenyl); and
$R^2$ is
(1) a 5- to 14-membered aromatic heterocyclylcarbonyl group (preferably, a 5- or 6-membered monocyclic aromatic heterocyclylcarbonyl group (e.g., thiazolylcarbonyl, thienylcarbonyl, furylcarbonyl, pyrrolylcarbonyl, pyrazolylcarbonyl, imidazolylcarbonyl, oxazolylcarbonyl) or a 8- to 14-membered fused polycyclic (preferably, bi- or tri-cyclic) aromatic heterocyclylcarbonyl group (e.g., quinolylcarbonyl)), which is optionally substituted by 1 to 3 substituents selected from
  (i) a halogen atom (e.g., a chlorine atom), and
  (ii) a $C_{1-6}$ alkyl group (e.g., methyl),
(2) a 3- to 14-membered non-aromatic heterocyclylcarbonyl group (preferably, a 3- to 8-membered monocyclic non-aromatic heterocyclylcarbonyl group (e.g., pyrrolidinylcarbonyl)),
(3) a $C_{1-6}$ alkyl-carbonyl group (e.g., acetyl) optionally substituted by 1 to 3 substituents selected from
  (i) a halogen atom (e.g., a fluorine atom),
  (ii) a mono- or di-$C_{1-6}$ alkylamino group (e.g., dimethylamino), and
  (iii) a 5- to 14-membered aromatic heterocyclic group (preferably, a 5- or 6-membered monocyclic aromatic heterocyclic group (e.g., pyridyl)),
(4) a $C_{6-14}$ aryl-carbonyl group (e.g., benzoyl),
(5) an optionally halogenated $C_{3-10}$ cycloalkyl-carbonyl group (e.g., difluorocyclopropylcarbonyl),
(6) a $C_{1-6}$ alkoxy-carbonyl group (e.g., tert-butoxycarbonyl),
(7) a 5- to 14-membered aromatic heterocyclylsulfonyl group (preferably, a 5- or 6-membered monocyclic aromatic heterocyclylsulfonyl group (e.g., pyridylsulfonyl)),
(8) a $C_{6-14}$ aryl group (e.g., phenyl), or
(9) a 5- to 14-membered aromatic heterocyclic group (preferably, a 5- or 6-membered monocyclic aromatic heterocyclic group (e.g., pyridyl, pyrimidinyl)) optionally substituted by 1 to 3 cyano groups.
[Compound E]
Compound (I) wherein
ring A is a pyrrolidin-2-one ring optionally substituted by 1 or 2 additional substituents selected from a halogen atom (e.g., a fluorine atom), a hydroxy group and a $C_{1-6}$ alkyl group (e.g., methyl);
ring B is a piperazine ring further optionally substituted by 1 to 3 $C_{1-6}$ alkyl groups (e.g., methyl);
$R^1$ is
(1) a phenyl group or a naphthyl group, each of which is optionally substituted by 1 to 3 substituents selected from
  (i) a phenoxy group optionally substituted by 1 to 3 substituents selected from
    (a) a $C_{1-6}$ alkoxy group (e.g., methoxy), and
    (b) a halogen atom (e.g., a fluorine atom),
  (ii) a halogen atom (e.g., a fluorine atom, a chlorine atom, a bromine atom, an iodine atom),
  (iii) a cyano group,
  (iv) an optionally halogenated $C_{1-6}$ alkoxy group (e.g., methoxy, trifluoromethoxy),
  (v) a $C_{1-6}$ alkyl group (e.g., methyl, isopropyl) optionally substituted by 1 to 3 substituents selected from
    (a) a halogen atom (e.g., a fluorine atom),
    (b) a cyano group,
    (c) a phenyl group,
    (d) a piperazinyl group optionally substituted by 1 to 3 $C_{1-6}$ alkyl groups (e.g., methyl), and
    (e) a morpholinyl group,
  (vi) a benzyloxy group,
  (vii) a $C_{3-10}$ cycloalkyl group (e.g., cyclopropyl),
  (viii) a phenyl group optionally substituted by 1 to 5 substituents selected from
    (a) a halogen atom (e.g., a fluorine atom, a chlorine atom),
    (b) a cyano group,
    (c) a $C_{1-6}$ alkyl group (e.g., methyl, ethyl) optionally substituted by 1 to 3 substituents selected from a halogen atom (e.g., a fluorine atom), a hydroxy group and a carbamoyl group,
    (d) an optionally halogenated $C_{1-6}$ alkoxy group (e.g., methoxy, ethoxy, isopropoxy, trifluoromethoxy),
    (e) a carboxy group,
    (f) a mono- or di-$C_{1-6}$ alkyl-carbonylamino group (e.g., acetylamino),
    (g) a mono- or di-$C_{1-6}$ alkylsulfonylamino group (e.g., methylsulfonylamino),
    (h) a sulfamoyl group,
    (i) a mono- or di-$C_{1-6}$ alkylsulfamoyl group (e.g., methylsulfamoyl),
    (j) a carbamoyl group,
    (k) a mono- or di-$C_{1-6}$ alkyl-carbamoyl group (e.g., methylcarbamoyl),
    (l) a pyrrolidinylcarbonyl group,
    (m) a phenyl group,
    (n) a phenoxy group, and
    (o) a morpholinyl group, (ix) a pyridyl group optionally substituted by 1 to 3 substituents selected from
  (a) a halogen atom (e.g., a chlorine atom),
  (b) an optionally halogenated $C_{1-6}$ alkyl group (e.g., methyl, trifluoromethyl), and
  (c) a $C_{1-6}$ alkoxy group (e.g., methoxy),
(x) a dihydropyridyl group optionally substituted by 1 to 3 substituents selected from
  (a) a $C_{1-6}$ alkyl group (e.g., methyl), and
  (b) an oxo group,
(xi) a thiazolyl group optionally substituted by 1 to 3 optionally halogenated $C_{1-6}$ alkyl groups (e.g., methyl, trifluoromethyl),
(xii) a morpholinyl group,
(xiii) a pyridyloxy group,
(xiv) a mono- or di-phenylamino group optionally substituted by 1 to 3 substituents selected from
  (a) a halogen atom (e.g., a fluorine atom),
  (b) a mono- or di-$C_{1-6}$ alkyl-carbonylamino group (e.g., acetylamino),
  (c) a ($C_{1-6}$ alkyl)($C_{1-6}$ alkyl-carbonyl)amino group (e.g., methyl(acetyl)amino), and
  (d) a pyrrolidinyl group optionally substituted by 1 to 3 oxo groups,
(xv) a mono- or di-phenylcarbamoyl group,
(xvi) a thienyl group optionally substituted by 1 to 3 substituents selected from
  (a) an optionally halogenated $C_{1-6}$ alkyl group (e.g., methyl, trifluoromethyl), and
  (b) a $C_{1-6}$ alkoxy group (e.g., methoxy),
(xvii) a furyl group,
(xviii) a pyrazinyl group optionally substituted by 1 to 3 $C_{1-6}$ alkyl groups (e.g., methyl),
(xix) a pyrazolyl group optionally substituted by 1 to 3 optionally halogenated $C_{1-6}$ alkyl groups (e.g., methyl, ethyl, isopropyl, trifluoromethyl),
(xx) a pyrimidinyl group optionally substituted by 1 to 3 $C_{1-6}$ alkyl groups (e.g., methyl),
(xxi) an isoxazolyl group optionally substituted by 1 to 3 $C_{1-6}$ alkyl groups (e.g., methyl),
(xxii) an imidazolyl group optionally substituted by 1 to 3 $C_{1-6}$ alkyl groups (e.g., methyl),
(xxiii) a naphthyl group,
(xxiv) a dihydroindolyl group optionally substituted by 1 to 3 substituents selected from
  (a) a $C_{1-6}$ alkyl group (e.g., methyl),
  (b) a $C_{1-6}$ alkoxy group (e.g., methoxy), and
  (c) an oxo group,
(xxv) an indolyl group,
(xxvi) an indazolyl group optionally substituted by 1 to 3 $C_{1-6}$ alkyl groups (e.g., methyl),
(xxvii) an imidazopyridyl group optionally substituted by 1 to 3 $C_{1-6}$ alkyl groups (e.g., methyl),
(xxviii) an isobenzothiazolyl group,
(xxix) a pyrazolopyridyl group,
(xxx) a thienopyridyl group,
(xxxi) a dihydropyrrolopyridyl group optionally substituted by 1 to 3 oxo groups,
(xxxii) a pyrrolopyridyl group optionally substituted by 1 to 3 $C_{1-6}$ alkoxy groups (e.g., methoxy),
(xxxiii) a benzothiophenyl group,
(xxxiv) a benzofuranyl group,
(xxxv) a dihydrobenzofuranyl group,
(xxxvi) a $C_{3-10}$ cycloalkylamino group (e.g., cyclohexylamino),
(xxxvii) a piperidylamino group optionally substituted by 1 to 3 substituents selected from
  (a) a $C_{1-6}$ alkyl group (e.g., methyl),
  (b) a $C_{1-6}$ alkyl-carbonyl group (e.g., acetyl), and (c) an oxo group,
(xxxviii) a tetrahydropyranylamino group,
(xxxix) a 1,4-dihydrobenzoxazinylamino group optionally substituted by 1 to 3 oxo groups, and
(xxxx) a tetrahydroquinolylamino group optionally substituted by 1 to 3 oxo groups,
(2) a pyridyl group, an imidazolyl group or a pyrazolyl group, each of which is optionally substituted by 1 to 3 substituents selected from
  (i) a halogen atom (e.g., a bromine atom),
  (ii) a phenyl group,
  (iii) a phenoxy group, and
  (iv) a pyridyl group optionally substituted by 1 to 3 $C_{1-6}$ alkyl groups (e.g., methyl),
(3) an indolyl group, an indazolyl group, a pyrrolopyridyl group, a dibenzofuranyl group, an imidazopyridyl group, a dihydroindolyl group, a benzothiophenyl group or a benzoxazolyl group, each of which is optionally substituted by 1 to 3 substituents selected from
  (i) a halogen atom (e.g., a fluorine atom, a chlorine atom, a bromine atom),
  (ii) a phenyl group optionally substituted by 1 to 3 substituents selected from
    (a) a halogen atom (e.g., a fluorine atom, a chlorine atom),
    (b) an optionally halogenated $C_{1-6}$ alkyl group (e.g., methyl, trifluoromethyl), and
    (c) a $C_{1-6}$ alkoxy group (e.g., methoxy),
  (iii) a pyridyl group optionally substituted by 1 to 3 substituents selected from
    (a) a halogen atom (e.g., a fluorine atom, a chlorine atom), and
    (b) an optionally halogenated $C_{1-6}$ alkyl group (e.g., methyl, trifluoromethyl),
  (iv) a pyrimidinyl group optionally substituted by 1 to 3 substituents selected from
    (a) a halogen atom (e.g., a fluorine atom, a chlorine atom),
    (b) an optionally halogenated $C_{1-6}$ alkyl group (e.g., methyl, trifluoromethyl), and
    (c) a $C_{1-6}$ alkoxy group (e.g., methoxy),
  (v) a pyridazinyl group optionally substituted by 1 to 3 optionally halogenated $C_{1-6}$ alkyl groups (e.g., trifluoromethyl),
  (vi) a pyrazinyl group optionally substituted by 1 to 3 optionally halogenated $C_{1-6}$ alkyl groups (e.g., trifluoromethyl),
  (vii) a $C_{1-6}$ alkyl group (e.g., methyl) optionally substituted by 1 to 3 phenyl groups optionally substituted by 1 to 3 halogen atoms (e.g., a fluorine atom),
  (viii) a $C_{1-6}$ alkyl-carbonyl group (e.g., acetyl, ethylcarbonyl, isobutylcarbonyl, neopentylcarbonyl) optionally substituted by 1 to 3 substituents selected from
    (a) a halogen atom (e.g., a fluorine atom),
    (b) a phenyl group optionally substituted by 1 to 3 halogen atoms (e.g., a fluorine atom, a chlorine atom),
    (c) a $C_{3-10}$ cycloalkyl group (e.g., cyclopropyl),
    (d) a pyridyl group optionally substituted by 1 to 3 substituents selected from a halogen atom (e.g., a chlorine atom) and a $C_{1-6}$ alkoxy group (e.g., methoxy), and
    (e) a tetrahydropyranyl group, (ix) a $C_{1-6}$ alkoxy-carbonyl group (e.g., tert-butoxycarbonyl),
(x) a benzoyl group,
(xi) a tetrahydropyranylcarbonyl group, and
(xii) a $C_{3-10}$ cycloalkyl group (e.g., cyclopropyl),
(4) a $C_{1-6}$ alkyl group (e.g., methyl) optionally substituted by 1 to 3 phenyl groups, or
(5) a $C_{3-10}$ cycloalkenyl group (e.g., cyclohexenyl); and
$R^2$ is
(1) a thiazolylcarbonyl group, a thienylcarbonyl group, a furylcarbonyl group, a pyrrolylcarbonyl group, a pyrazolylcarbonyl group, an imidazolylcarbonyl group, an oxazolylcarbonyl group or a quinolylcarbonyl group, each of which is optionally substituted by 1 to 3 substituents selected from
    (i) a halogen atom (e.g., a chlorine atom), and
    (ii) a $C_{1-6}$ alkyl group (e.g., methyl),
(2) a pyrrolidinylcarbonyl group,
(3) a $C_{1-6}$ alkyl-carbonyl group (e.g., acetyl) optionally substituted by 1 to 3 substituents selected from
    (i) a halogen atom (e.g., a fluorine atom),
    (ii) a mono- or di-$C_{1-6}$ alkylamino group (e.g., dimethylamino), and
    (iii) a pyridyl group,
(4) a benzoyl group,
(5) an optionally halogenated $C_{3-10}$ cycloalkyl-carbonyl group (e.g., difluorocyclopropylcarbonyl),
(6) a $C_{1-6}$ alkoxy-carbonyl group (e.g., tert-butoxycarbonyl),
(7) a pyridylsulfonyl group,
(8) a phenyl group, or
(9) a pyridyl group or a pyrimidinyl group, each of which is optionally substituted by 1 to 3 cyano groups.

[Compound F]
Compound (I) wherein
ring A is a pyrrolidin-2-one ring optionally substituted by 1 or 2 additional substituents selected from a halogen atom (e.g., a fluorine atom), a hydroxy group and a $C_{1-6}$ alkyl group (e.g., methyl);
ring B is a piperazine ring further optionally substituted by 1 to 3 $C_{1-6}$ alkyl groups (e.g., methyl);
$R^1$ is
(1) a phenyl group or a naphthyl group, each of which is optionally substituted by 1 to 3 substituents selected from
    (i) a phenoxy group optionally substituted by 1 to 3 substituents selected from
        (a) a $C_{1-6}$ alkoxy group (e.g., methoxy), and
        (b) a halogen atom (e.g., a fluorine atom),
    (ii) a halogen atom (e.g., a fluorine atom, a bromine atom, an iodine atom),
    (iii) an optionally halogenated $C_{1-6}$ alkoxy group (e.g., methoxy, trifluoromethoxy),
    (iv) a $C_{1-6}$ alkyl group (e.g., methyl) optionally substituted by 1 to 3 phenyl groups,
    (v) a benzyloxy group,
    (vi) a $C_{3-10}$ cycloalkyl group (e.g., cyclopropyl),
    (vii) a phenyl group optionally substituted by 1 to 5 substituents selected from
        (a) a halogen atom (e.g., a fluorine atom, a chlorine atom),
        (b) a cyano group,
        (c) a $C_{1-6}$ alkyl group (e.g., methyl, ethyl) optionally substituted by 1 to 3 substituents selected from a halogen atom (e.g., a fluorine atom), a hydroxy group and a carbamoyl group,
        (d) an optionally halogenated $C_{1-6}$ alkoxy group (e.g., methoxy, ethoxy, isopropoxy, trifluoromethoxy),
        (e) a carboxy group,
        (f) a mono- or di-$C_{1-6}$ alkyl-carbonylamino group (e.g., acetylamino),
        (g) a mono- or di-$C_{1-6}$ alkylsulfonylamino group (e.g., methylsulfonylamino),
        (h) a sulfamoyl group,
        (i) a mono- or di-$C_{1-6}$ alkylsulfamoyl group (e.g., methylsulfamoyl),
        (j) a carbamoyl group,
        (k) a mono- or di-$C_{1-6}$ alkyl-carbamoyl group (e.g., methylcarbamoyl),
        (l) a pyrrolidinylcarbonyl group,
        (m) a phenyl group,
        (n) a phenoxy group, and
        (o) a morpholinyl group,
    (viii) a pyridyl group optionally substituted by 1 to 3 substituents selected from
        (a) a halogen atom (e.g., a chlorine atom),
        (b) an optionally halogenated $C_{1-6}$ alkyl group (e.g., methyl, trifluoromethyl), and
        (c) a $C_{1-6}$ alkoxy group (e.g., methoxy),
    (ix) a thiazolyl group optionally substituted by 1 to 3 optionally halogenated $C_{1-6}$ alkyl groups (e.g., methyl, trifluoromethyl),
    (x) a pyridyloxy group,
    (xi) a mono- or di-phenylamino group optionally substituted by 1 to 3 substituents selected from
        (a) a halogen atom (e.g., a fluorine atom),
        (b) a mono- or di-$C_{1-6}$ alkyl-carbonylamino group (e.g., acetylamino),
        (c) a ($C_{1-6}$ alkyl) ($C_{1-6}$ alkyl-carbonyl)amino group (e.g., methyl(acetyl)amino), and
        (d) a pyrrolidinyl group optionally substituted by 1 to 3 oxo groups,
    (xii) a thienyl group optionally substituted by 1 to 3 substituents selected from
        (a) an optionally halogenated $C_{1-6}$ alkyl group (e.g., methyl, trifluoromethyl), and
        (b) a $C_{1-6}$ alkoxy group (e.g., methoxy),
    (xiii) a furyl group,
    (xiv) a pyrazinyl group optionally substituted by 1 to 3 $C_{1-6}$ alkyl groups (e.g., methyl),
    (xv) a pyrazolyl group optionally substituted by 1 to 3 optionally halogenated $C_{1-6}$ alkyl groups (e.g., methyl, ethyl, isopropyl, trifluoromethyl),
    (xvi) a pyrimidinyl group optionally substituted by 1 to 3 $C_{1-6}$ alkyl groups (e.g., methyl),
    (xvii) an isoxazolyl group optionally substituted by 1 to 3 $C_{1-6}$ alkyl groups (e.g., methyl),
    (xviii) an imidazolyl group optionally substituted by 1 to 3 $C_{1-6}$ alkyl groups (e.g., methyl),
    (xix) a naphthyl group,
    (xx) a dihydroindolyl group optionally substituted by 1 to 3 substituents selected from
        (a) a $C_{1-6}$ alkyl group (e.g., methyl),
        (b) a $C_{1-6}$ alkoxy group (e.g., methoxy), and
        (c) an oxo group,
    (xxi) an indolyl group,
    (xxii) an indazolyl group optionally substituted by 1 to 3 $C_{1-6}$ alkyl groups (e.g., methyl),
    (xxiii) an imidazopyridyl group optionally substituted by 1 to 3 $C_{1-6}$ alkyl groups (e.g., methyl),
    (xxiv) an isobenzothiazolyl group,
    (xxv) a pyrazolopyridyl group,
    (xxvi) a thienopyridyl group,
    (xxvii) a dihydropyrrolopyridyl group optionally substituted by 1 to 3 oxo groups, (xxviii) a pyrrolopyridyl group optionally substituted by 1 to 3 $C_{1-6}$ alkoxy groups (e.g., methoxy),
(xxix) a benzothiophenyl group,
(xxx) a benzofuranyl group,
(xxxi) a dihydrobenzofuranyl group,
(xxxii) a $C_{3-10}$ cycloalkylamino group (e.g., cyclohexylamino),
(xxxiii) a piperidylamino group optionally substituted by 1 to 3 substituents selected from
  (a) a $C_{1-6}$ alkyl group (e.g., methyl), and
  (b) an oxo group,
(xxxiv) a 1,4-dihydrobenzoxazinylamino group optionally substituted by 1 to 3 oxo groups, and
(xxxv) a tetrahydroquinolylamino group optionally substituted by 1 to 3 oxo groups,
(2) a pyridyl group optionally substituted by 1 to 3 substituents selected from
  (i) a halogen atom (e.g., a bromine atom),
  (ii) a phenyl group,
  (iii) a phenoxy group, and
  (iv) a pyridyl group optionally substituted by 1 to 3 $C_{1-6}$ alkyl groups (e.g., methyl), or
(3) an indolyl group, an indazolyl group, a pyrrolopyridyl group, a dibenzofuranyl group, a dihydroindolyl group, a benzothiophenyl group or a benzoxazolyl group, each of which is optionally substituted by 1 to 3 substituents selected from
  (i) a halogen atom (e.g., a fluorine atom, a chlorine atom),
  (ii) a phenyl group optionally substituted by 1 to 3 substituents selected from
    (a) a halogen atom (e.g., a fluorine atom, a chlorine atom),
    (b) an optionally halogenated $C_{1-6}$ alkyl group (e.g., methyl, trifluoromethyl), and
    (c) a $C_{1-6}$ alkoxy group (e.g., methoxy),
  (iii) a pyridyl group optionally substituted by 1 to 3 substituents selected from
    (a) a halogen atom (e.g., a fluorine atom, a chlorine atom), and
    (b) an optionally halogenated $C_{1-6}$ alkyl group (e.g., methyl, trifluoromethyl),
  (iv) a pyrimidinyl group optionally substituted by 1 to 3 substituents selected from
    (a) a halogen atom (e.g., a fluorine atom, a chlorine atom),
    (b) an optionally halogenated $C_{1-6}$ alkyl group (e.g., methyl, trifluoromethyl), and
    (c) a $C_{1-6}$ alkoxy group (e.g., methoxy),
  (v) a pyridazinyl group optionally substituted by 1 to 3 optionally halogenated $C_{1-6}$ alkyl groups (e.g., trifluoromethyl),
  (vi) a pyrazinyl group optionally substituted by 1 to 3 optionally halogenated $C_{1-6}$ alkyl groups (e.g., trifluoromethyl),
  (vii) a $C_{1-6}$ alkyl group (e.g., methyl) optionally substituted by 1 to 3 phenyl groups optionally substituted by 1 to 3 halogen atoms (e.g., a fluorine atom),
  (viii) a $C_{1-6}$ alkyl-carbonyl group (e.g., acetyl, ethylcarbonyl, isobutylcarbonyl, neopentylcarbonyl) optionally substituted by 1 to 3 substituents selected from
    (a) a halogen atom (e.g., a fluorine atom),
    (b) a phenyl group optionally substituted by 1 to 3 halogen atoms (e.g., a fluorine atom, a chlorine atom),
    (c) a $C_{3-10}$ cycloalkyl group (e.g., cyclopropyl),
    (d) a pyridyl group optionally substituted by 1 to 3 substituents selected from a halogen atom (e.g., a chlorine atom) and a $C_{1-6}$ alkoxy group (e.g., methoxy), and
    (e) a tetrahydropyranyl group,
  (ix) a $C_{1-6}$ alkoxy-carbonyl group (e.g., tert-butoxycarbonyl),
  (x) a benzoyl group,
  (xi) a tetrahydropyranylcarbonyl group, and
  (xii) a $C_{3-10}$ cycloalkyl group (e.g., cyclopropyl); and
$R^2$ is
(1) a thiazolylcarbonyl group, a thienylcarbonyl group, a furylcarbonyl group or an oxazolylcarbonyl group, each of which is optionally substituted by 1 to 3 halogen atoms (e.g., a chlorine atom),
(2) a pyrrolidinylcarbonyl group, or
(3) a pyridyl group or a pyrimidinyl group, each of which is optionally substituted by 1 to 3 cyano groups.

[Compound G]
Compound (I) wherein
ring A is a pyrrolidin-2-one ring optionally substituted by 1 or 2 additional substituents selected from a halogen atom (e.g., a fluorine atom), a hydroxy group and a $C_{1-6}$ alkyl group (e.g., methyl);
ring B is a piperazine ring not substituted by the additional substituents;
$R^1$ is
(1) a phenyl group optionally substituted by 1 to 3 substituents selected from
  (i) a phenoxy group optionally substituted by 1 to 3 halogen atoms (e.g., a fluorine atom),
  (ii) a halogen atom (e.g., a fluorine atom, a bromine atom),
  (iii) a $C_{1-6}$ alkoxy group (e.g., methoxy),
  (iv) an optionally halogenated $C_{1-6}$ alkyl group (e.g., trifluoromethyl),
  (v) a benzyloxy group,
  (vi) a $C_{3-10}$ cycloalkyl group (e.g., cyclopropyl),
  (vii) a phenyl group optionally substituted by 1 to 5 halogen atoms (e.g., a fluorine atom, a chlorine atom),
  (viii) a pyridyl group optionally substituted by 1 to 3 $C_{1-6}$ alkyl groups (e.g., methyl),
  (ix) a monophenylamino group optionally substituted by 1 to 3 halogen atoms (e.g., a fluorine atom),
  (x) a pyrimidinyl group optionally substituted by 1 to 3 $C_{1-6}$ alkyl groups (e.g., methyl), and
  (xi) a dihydroindolyl group optionally substituted by 1 to 3 substituents selected from
    (a) a $C_{1-6}$ alkoxy group (e.g., methoxy), and
    (b) an oxo group,
(2) an indolyl group, an indazolyl group, a dibenzofuranyl group, a dihydroindolyl group or a benzothiophenyl group, each of which is optionally substituted by 1 to 3 substituents selected from
  (i) a halogen atom (e.g., a fluorine atom, a chlorine atom),
  (ii) a phenyl group optionally substituted by 1 to 3 substituents selected from
    (a) a halogen atom (e.g., a fluorine atom, a chlorine atom), and
    (b) an optionally halogenated $C_{1-6}$ alkyl group (e.g., trifluoromethyl),
  (iii) a pyridyl group optionally substituted by 1 to 3 optionally halogenated $C_{1-6}$ alkyl groups (e.g., trifluoromethyl),
  (iv) a pyrimidinyl group optionally substituted by 1 to 3 optionally halogenated $C_{1-6}$ alkyl groups (e.g., trifluoromethyl), (v) a $C_{1-6}$ alkyl group (e.g., methyl) optionally substituted by 1 to 3 phenyl groups optionally substituted by 1 to 3 halogen atoms (e.g., a fluorine atom), (vi) a $C_{1-6}$ alkyl-carbonyl group (e.g., acetyl, neopentylcarbonyl) optionally substituted by 1 to 3 substituents selected from
  (a) a halogen atom (e.g., a fluorine atom), and
  (b) a phenyl group optionally substituted by 1 to 3 halogen atoms (e.g., a chlorine atom), (vii) a $C_{1-6}$ alkoxy-carbonyl group (e.g., tert-butoxycarbonyl), and (viii) a $C_{3-10}$ cycloalkyl group (e.g., cyclopropyl), or (3) a $C_{1-6}$ alkyl group (e.g., methyl) optionally substituted by 1 to 3 phenyl groups; and $R^2$ is (1) a thiazolylcarbonyl group or an oxazolylcarbonyl group, (2) a pyrrolidinylcarbonyl group, or (3) a pyridyl group or a pyrimidinyl group, each of which is optionally substituted by 1 to 3 cyano groups.

[Compound H]

Compound (I) wherein ring A is a pyrrolidin-2-one ring not substituted by the additional substituents;

ring B is a piperazine ring not substituted by the additional substituents;

$R^1$ is (1) a phenyl group substituted by 1 to 3 substituents selected from
  (i) a halogen atom (e.g., a fluorine atom), and
  (ii) a pyridyl group substituted by 1 to 3 $C_{1-6}$ alkyl groups (e.g., methyl), or (2) an indolyl group or an indazolyl group, each of which is substituted by 1 to 3 substituents selected from
  (i) a phenyl group substituted by 1 to 3 substituents selected from
    (a) a halogen atom (e.g., a fluorine atom), and
    (b) a halogenated $C_{1-6}$ alkyl group (e.g., trifluoromethyl), and
  (ii) a pyrimidinyl group substituted by 1 to 3 halogenated $C_{1-6}$ alkyl groups (e.g., trifluoromethyl); and $R^2$ is a thiazolylcarbonyl group or a pyrimidinyl group.

Specific examples of compound (I) include the compounds of Examples 1-434. Of these, (4R)-4-(4-(1,3-thiazol-2-ylcarbonyl)piperazin-1-yl)-1-(1-(5-(trifluoromethyl)pyrimidin-2-yl)-1H-indol-5-yl)pyrrolidin-2-one, (4R)-4-(4-(1,3-thiazol-4-ylcarbonyl)piperazin-1-yl)-1-(1-(4-(trifluoromethyl)phenyl)-1H-indol-5-yl)pyrrolidin-2-one, and (4R)-1-(3-fluoro-5-(2-methylpyridin-3-yl)phenyl)-4-(4-(pyrimidin-2-yl)piperazin-1-yl)pyrrolidin-2-one, and a salt thereof are preferable.

When the compound (I) is a salt, for example, metal salts, ammonium salts, salts with organic bases, salts with inorganic acids, salts with organic acids, salts with basic or acidic amino acids can be included. Preferable examples of metal salts, for example, include alkali metal salts such as sodium salts, potassium salts and the like; alkali earth metal salts such as calcium salts, magnesium salts, barium salts and the like; and aluminum salts. Preferable examples of salts with organic bases include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of salts with inorganic acids include salts with hydrochloric acid, hydrobromic acid, nitric acid, sulfuric acid, phosphoric acid and the like. Preferable examples of salts with organic acids include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of salts with basic amino acids include salts with arginine, lysine, ornithine and the like. Preferable examples of salts with acidic amino acids include salts with aspartic acid, glutamic acid and the like. Among them, salts that are pharmaceutically acceptable are preferable. For example, in the case when acidic functional group are present in the compound, for example, inorganic salts including alkali metal salts (e.g., sodium salts, potassium salt, etc.) and alkali earth metal salts (e.g., calcium salts, magnesium salts, barium salts, etc.) and ammonium salts are preferable. In the case when basic functional group are present in the compound, for example, salts with inorganic acids such as hydrochloric acid, hydrobromic acid, nitric acid, sulfuric acid, phosphoric acid, etc. or salts with organic acid such as acetic acid, phthalic acid, fumaric acid, oxalic acid, tartaric acid, maleic acid, citric acid, succinic acid, methanesulfonic acid, p-toluenesulfonic acid, etc. are preferable.

If the compound (I) includes isomers such as tautomers, optical isomers, stereoisomers, position isomers and rotational isomers, one of the other isomers or mixture are also included in the compound of the present invention. Further, if the compound (I) has an optical isomer, the optical isomer separated from the racemate is included in the compound (I).

The compound (I) can be obtained in the crystal form. Either single crystalline form or crystalline mixture can be included in the compound (I).

The compound (I) can be a pharmaceutically acceptable co-crystal or a co-crystal salt. The co-crystal or co-crystal salt as used herein means a crystalline material composed of two or more unique solids at room temperature, each of which has distinctive physical characteristics such as structure, melting point, and heats of fusion, hygroscopicity, solubility, and stability. A co-crystal or a co-crystal salt can be produced according to a per se known co-crystallization method.

The compound (I) may be a solvate (e.g., hydrate) or a non-solvate and both are included in the compound (I).

Compounds labeled with or substituted by isotopes (e.g., $^2$H, $^3$H, $^{11}$C, $^{14}$C, $^{18}$F, $^{35}$S, $^{125}$I, etc.) are also included in compound (I). Compound (I) labeled with or substituted by isotopes can be used as, for example, a tracer used for Positron Emission Tomography (PET) (PET tracer), and are useful in the field of medical diagnosis and the like.

The production method of the compound of the present invention is explained below.

The raw material compound and reagent used and the compound obtained in each step in the following production method may be each in a form of a salt, and examples of such salt include those similar to the salts of the compound of the present invention and the like.

When the compound obtained in each step is a free form, it can be converted to the objective salt according to a method known per se. When the compound obtained in each step is a salt, it can be converted to the objective free form or the other salt according to a method known per se.

The compound obtained in each step can be used directly as the reaction mixture or as a crude product for the next reaction. Alternatively, the compound obtained in each step can be isolated and purified from a reaction mixture according to a method known per se, for example, a separation means such as concentration, crystallization, recrystallization, distillation, solvent extraction, fractional distillation, column chromatography and the like.

When the raw material compound and reagent used in each step are commercially available, the commercially available product can also be used directly.

In the reaction in each step, while the reaction time varies depending on the kind of the reagent and solvent to be used, it is generally 1 min-48 hr, preferably 10 min-8 hr, unless otherwise specified.

In the reaction in each step, while the reaction temperature varies depending on the kind of the reagent and solvent to be used, it is generally −78° C.-300° C., preferably −78° C.-150° C., unless otherwise specified.

In the reaction in each step, while the pressure varies depending on the kind of the reagent and solvent to be used, it is generally 1 atm-20 atm, preferably 1 atm-3 atm, unless otherwise specified.

Microwave synthesizer such as Initiator manufactured by Biotage and the like may be used for the reaction in each step. While the reaction temperature varies depending on the kind of the reagent and solvent to be used, it is generally room temperature—300° C., preferably 50° C.-250° C., unless otherwise specified. While the reaction time varies depending on the kind of the reagent and solvent to be used, it is generally 1 min-48 hr, preferably 1 min-8 hr, unless otherwise specified.

In the reaction in each step, the reagent is used in an amount of 0.5 equivalents-20 equivalents, preferably 0.8 equivalents-5 equivalents, relative to the substrate, unless otherwise specified. When the reagent is used as a catalyst, the reagent is used in an amount of 0.001 equivalent-1 equivalent, preferably 0.01 equivalent-0.2 equivalent, relative to the substrate. When the reagent is used as a reaction solvent, the reagent is used in a solvent amount.

Unless otherwise specified, the reaction in each step is carried out without solvent, or by dissolving or suspending the raw material compound in a suitable solvent. Examples of the solvent include those described in Examples and the following solvents.
alcohols: methanol, ethanol, tert-butyl alcohol, 2-methoxyethanol and the like;
ethers: diethyl ether, diphenyl ether, tetrahydrofuran, 1,2-dimethoxyethane and the like;
aromatic hydrocarbons: chlorobenzene, toluene, xylene and the like;
saturated hydrocarbons: cyclohexane, hexane and the like;
amides: N,N-dimethylformamide, N-methylpyrrolidone and the like;
halogenated hydrocarbons: dichloromethane, carbon tetrachloride and the like;
nitriles: acetonitrile and the like;
sulfoxides: dimethyl sulfoxide and the like;
aromatic organic bases: pyridine and the like;
anhydrides: acetic anhydride and the like;
organic acids: formic acid, acetic acid, trifluoroacetic acid and the like;
inorganic acids: hydrochloric acid, sulfuric acid and the like;
esters: ethyl acetate and the like;
ketones: acetone, methyl ethyl ketone and the like;
water.

The above-mentioned solvent can be used in a mixture of two or more kinds thereof in an appropriate ratio.

When a base is used for the reaction in each step, examples thereof include those described in Examples and the following bases.
inorganic bases: sodium hydroxide, magnesium hydroxide and the like;
basic salts: sodium carbonate, calcium carbonate, sodium hydrogen carbonate and the like;
organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine and the like;
metal alkoxides: sodium ethoxide, potassium tert-butoxide and the like;
alkali metal hydrides: sodium hydride and the like;
metal amides: sodium amide, lithium diisopropylamide, lithium hexamethyldisilazide and the like;
organic lithiums: n-butyllithium and the like.

When an acid or an acid catalyst is used for the reaction in each step, examples thereof include those described in Examples and the following acids and acid catalysts.
inorganic acids: hydrochloric acid, sulfuric acid, nitric acid, hydrobromic acid, phosphoric acid and the like;
organic acids: acetic acid, trifluoroacetic acid, citric acid, p-toluenesulfonic acid, 10-camphorsulfonic acid and the like; Lewis acid: boron trifluoride diethyl ether complex, zinc iodide, anhydrous aluminum chloride, anhydrous zinc chloride, anhydrous iron chloride and the like.

Unless otherwise specified, the reaction in each step is carried out according to a method known per se, for example, the method described in Jikken Kagaku Kouza, 5th Edition, vol. 13-19 (the Chemical Society of Japan ed.); Shin Jikken Kagaku Kouza, vol. 14-15 (the Chemical Society of Japan ed.); Fine Organic Chemistry, Revised 2nd Edition (L. F. Tietze, Th. Eicher, Nankodo); Organic Name Reactions, the Reaction Mechanism and Essence, Revised Edition (Hideo Togo, Kodansha); ORGANIC SYNTHESES Collective Volume I-VII (John Wiley & Sons Inc); Modern Organic Synthesis in the Laboratory A Collection of Standard Experimental Procedures (Jie Jack Li, OXFORD UNIVERSITY); Comprehensive Heterocyclic Chemistry III, Vol. 1-Vol. 14 (Elsevier Japan); Strategic Applications of Named Reactions in Organic Synthesis (translated by Kiyoshi Tomioka, Kagakudojin); Comprehensive Organic Transformations (VCH Publishers Inc.), 1989, or the like, or the method described in Examples.

In each step, the protection or deprotection reaction of an functional group is carried out according to a method known per se, for example, the method described in "Protective Groups in Organic Synthesis, 4th Ed", Wiley-Interscience, Inc., 2007 (Theodora W. Greene, Peter G. M. Wuts); "Protecting Groups 3rd Ed." Thieme, 2004 (P. J. Kocienski), or the like, or the method described in Examples.

Examples of the protected hydroxy group of an alcohol and a phenol include ether groups such as methoxymethyl ether, benzyl ether, t-butyldimethylsilyl ether, tetrahydropyranyl ether and the like; carboxylate groups such as acetate and the like; sulfonate groups such as methanesulfonate and the like; carbonate groups such as t-butyl carbonate and the like, and the like.

Examples of the protected carbonyl group of an aldehyde include acetal groups such as dimethyl acetal and the like; cyclic acetal groups such as cyclic 1,3-dioxane and the like, and the like.

Examples of the protected carbonyl group of a ketone include ketal groups such as dimethyl ketal and the like; cyclic ketal groups such as cyclic 1,3-dioxane and the like; oxime groups such as O-methyloxime and the like; hydrazone groups such as N,N-dimethylhydrazone and the like, and the like.

Examples of the protected carboxyl group include ester groups such as methyl ester and the like; amide groups such as N,N-dimethylamide and the like, and the like.

Examples of the protected thiol group include ether groups such as benzylthio ether and the like; ester groups such as thioacetate, thiocarbonate, thiocarbamate and the like, and the like.

Examples of the protected amino group and aromatic heterocycle (e.g., imidazole, pyrrole, indole etc.) include carbamate groups such as benzyl carbamate and the like; amide groups such as acetamide and the like; alkyl amine groups such as N-triphenylmethylamine and the like; sulfonamide groups such as methanesulfonamide and the like, and the like.

The protecting groups can be removed according to a method known per se, for example, by employing a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide) and the like, a reduction method, and the like.

When reduction reaction is carried out in each step, examples of the reducing agent to be used include metal hydrides such as lithium aluminum hydride, sodium triacetoxyborohydride, sodium cyanoborohydride, diisobutylaluminum hydride (DIBAL-H), sodium borohydride, tetramethylammonium triacetoxyborohydride and the like; boranes such as borane tetrahydrofuran complex and the like; Raney nickel; Raney cobalt; hydrogen; formic acid and the like. When carbon-carbon double bond or triple bond is reduced, a method using a catalyst such as palladium-carbon, Lindlar's catalyst and the like may be employed.

When oxidation reaction is carried out in each step, examples of the oxidizing agent to be used include peroxides such as m-chloroperbenzoic acid (MCPBA), hydrogen peroxide, t-butylhydroperoxide and the like; perchlorates such as tetrabutylammonium perchlorate and the like; chlorates such as sodium chlorate and the like; chlorites such as sodium chlorite and the like; periodic acids such as sodium periodate and the like; hypervalent iodine reagents such as iodosylbenzene and the like; reagents containing manganese such as manganese dioxide, potassium permanganate and the like; leads such as lead tetraacetate and the like; reagents containing chromium such as pyridinium chlorochromate (PCC), pyridinium dichromate (PDC), Jones reagent and the like; halogen compounds such as N-bromosuccinimide (NBS) and the like; oxygen; ozone; sulfur trioxide-pyridine complex; osmium tetroxide; selenium dioxide; 2,3-dichloro-5,6-dicyano-1,4-benzoquinone (DDQ) and the like.

When radical cyclization reaction is carried out in each step, examples of the radical initiator to be used include azo compounds such as azobisisobutyronitrile (AIBN) and the like; water-soluble radical initiators such as 4-4'-azobis-4-cyanopentanoic acid (ACPA) and the like; triethylboron in the presence of air or oxygen; benzoyl peroxide and the like. Examples of the radical reagent to be used include tributylstannane, tristrimethylsilylsilane, 1,1,2,2-tetraphenyldisilane, diphenylsilane, samarium iodide and the like.

When Wittig reaction is carried out in each step, examples of the Wittig reagent to be used include alkylidene phosphoranes and the like. The alkylidene phosphoranes can be prepared according to a method known per se, for example, by reacting a phosphonium salt with a strong base.

When Horner-Emmons reaction is carried out in each step, examples of the reagent to be used include phosphonoacetates such as methyl dimethylphosphonoacetate, ethyl diethylphosphonoacetate and the like; and bases such as alkali metal hydrides, organic lithiums and the like.

When Friedel-Crafts reaction is carried out in each step, a combination of a Lewis acid and an acid chloride or a combination of a Lewis acid and an alkylating agent (e.g., an alkyl halide, an alcohol, an olefin etc.) is used as a reagent. Alternatively, an organic acid or an inorganic acid can also be used instead of a Lewis acid, and an anhydride such as acetic anhydride and the like can also be used instead of an acid chloride.

When aromatic nucleophilic substitution reaction is carried out in each step, a nucleophile (e.g., an amine, imidazole etc.) and a base (e.g., a basic salt, an organic base etc.) are used as a reagent.

When nucleophilic addition reaction by a carbo anion, nucleophilic 1,4-addition reaction (Michael addition reaction) by a carbo anion or nucleophilic displacement reaction by a carbo anion is carried out in each step, examples of the base to be used for generation of the carbo anion include organic lithiums, metal alkoxides, inorganic bases, organic bases and the like.

When Grignard reagent is carried out in each step, examples of the Grignard reagent to be used include arylmagnesium halides such as phenylmagnesium bromide and the like; and alkylmagnesium halides such as methylmagnesium bromide and the like. The Grignard reagent can be prepared according to a method known per se, for example, by reacting an alkyl halide or an aryl halide with a metal magnesium in an ether or tetrahydrofuran as a solvent.

When Knoevenagel condensation reaction is carried out in each step, a compound having an activated methylene group with two electron withdrawing groups (e.g., malonic acid, diethyl malonate, malononitrile etc.) and a base (e.g., an organic base, a metal alkoxide, an inorganic base) are used as a reagent.

When Vilsmeier-Haack reaction is carried out in each step, phosphoryl chloride and an amide derivative (e.g., N,N-dimethylformamide etc.) are used as a reagent.

When azidation reaction of an alcohol, an alkyl halide or a sulfonate is carried out in each step, examples of the azidating agent to be used include diphenylphosphorylazide (DPPA), trimethylsilylazide, sodium azide and the like. For example, for the azidation reaction of an alcohol, a method using diphenylphosphorylazide and 1,8-diazabicyclo[5.4.0]undec-7-ene (DBU), a method using trimethylsilylazide and a Lewis acid, and the like are employed.

When reductive amination reaction is carried out in each step, examples of the reducing agent to be used include sodium triacetoxyborohydride, sodium cyanoborohydride, hydrogen, formic acid and the like. When the substrate is an amine compound, examples of the carbonyl compound to be used include paraformaldehyde, aldehydes such as acetaldehyde and the like, and ketones such as cyclohexanone and the like. When the substrate is a carbonyl compound, examples of the amine to be used include ammonia, primary amines such as methylamine and the like; secondary amines such as dimethylamine and the like, and the like.

When Mitsunobu reaction is carried out in each step, an azodicarboxylate (e.g., diethyl azodicarboxylate (DEAD), diisopropyl azodicarboxylate (DIAD) etc.) and triphenylphosphine are used as a reagent.

When esterification reaction, amidation reaction or urea formation reaction is carried out in each step, examples of the reagent to be used include acyl halides such as acid chlorides, acid bromides and the like; activated carboxylic acids such as anhydrides, activated esters, sulfates and the like. Examples of the activating agent of the carboxylic acid include carbodiimide condensing agents such as 1-ethyl-3-(3-dimethylaminopropyl)carbodiimide hydrochloride (WSCD) and the like; triazine condensing agents such as 4-(4,6-dimethoxy-1,3,5-triazin-2-yl)-4-methylmorpholinium chloride n-hydrate (DMT-MM) and the like; carbonate condensing agents such as 1,1-carbonyldiimidazole (CDI) and the like; diphenylphosphoryl azide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformates such as ethyl chloroformate and the like; O-(7-azabenzotriazol-1-yl)-N,N,N',N'-tetramethyluronium hexafluorophosphorate (HATU); sulfuric acid; combinations thereof and the like. When carbodiimide condensing agent is used, an additive such as 1-hydroxybenzotriazole (HOBt), N-hydroxysuccinimide (HOSu), dimethylaminopyridine (DMAP) and the like may be added to the reaction system.

When coupling reaction is carried out in each step, examples of the metal catalyst to be used include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocene palladium(II) chloride, palladium (II) acetate and the like; nickel compounds such as tetrakis (triphenylphosphine)nickel(0) and the like; rhodium compounds such as tris(triphenylphosphine)rhodium(III) chloride and the like; cobalt compounds; copper compounds such as copper oxide, copper(I) iodide and the like; platinum compounds and the like. In addition, a base can be added to the reaction system, and examples thereof include inorganic bases, basic salts and the like.

When thiocarbonylation reaction is carried out in each step, phosphorus pentasulfide is typically used as the thiocarbonylating agent. Alternatively, a reagent having a 1,3,2,4-dithiadiphosphetane-2,4-disulfide structure (e.g., 2,4-bis (4-methoxyphenyl-1,3,2,4-dithiadiphosphetane-2,4-disulfide (Lawesson reagent) etc.) can also be used instead of phosphorus pentasulfide.

When Wohl-Ziegler reaction is carried out in each step, examples of the halogenating agent to be used include N-iodosuccinimide, N-bromosuccinimide (NBS), N-chlorosuccinimide (NCS), bromine, sulfuryl chloride and the like. In addition, the reaction can be accelerated by subjecting a radical initiator such as heat, light, benzoyl peroxide, azobisisobutyronitrile and the like to the reaction system reaction.

When halogenation reaction of a hydroxy group is carried out in each step, examples of the halogenating agent to be used include hydrohalic acids and acid halides of inorganic acids, specifically, hydrochloric acid, thionyl chloride, phosphorus oxychloride and the like for chlorination, 48% hydrobromic acid and the like for bromination. In addition, a method of producing an alkyl halide by reacting an alcohol with triphenylphosphine and carbon tetrachloride or carbon tetrabromide or the like can be employed. Alternatively, a method of producing an alkyl halide via two step comprising converting an alcohol to the corresponding sulfonate, and then reacting the sulfonate with lithium bromide, lithium chloride or sodium iodide can also be employed.

When Arbuzov reaction is carried out in each step, examples of the reagent to be used include alkyl halides such as ethyl bromoacetate and the like; and phosphites such as triethyl phosphite, tri(isopropyl) phosphite and the like.

When sulfonate esterification reaction is carried out in each step, examples of the sulfonating agent to be used include methanesulfonyl chloride, p-toluenesulfonyl chloride, methanesulfonic anhydride, p-toluenesulfonic anhydride and the like.

When hydrolysis reaction is carried out in each step, an acid or a base is used as a reagent. For acid hydrolysis reaction of t-butyl ester, formic acid, triethylsilane and the like may be added to reductively-trap t-butyl cation which is by-produced.

When dehydration reaction is carried out in each step, examples of the dehydrating agent to be used include sulfuric acid, diphosphorus pentaoxide, phosphorus oxychloride, N,N'-dicyclohexylcarbodiimide, alumina, polyphosphoric acid and the like.

Compound (I) can be produced from compound (2) by the following production step A.

[Production Step A]

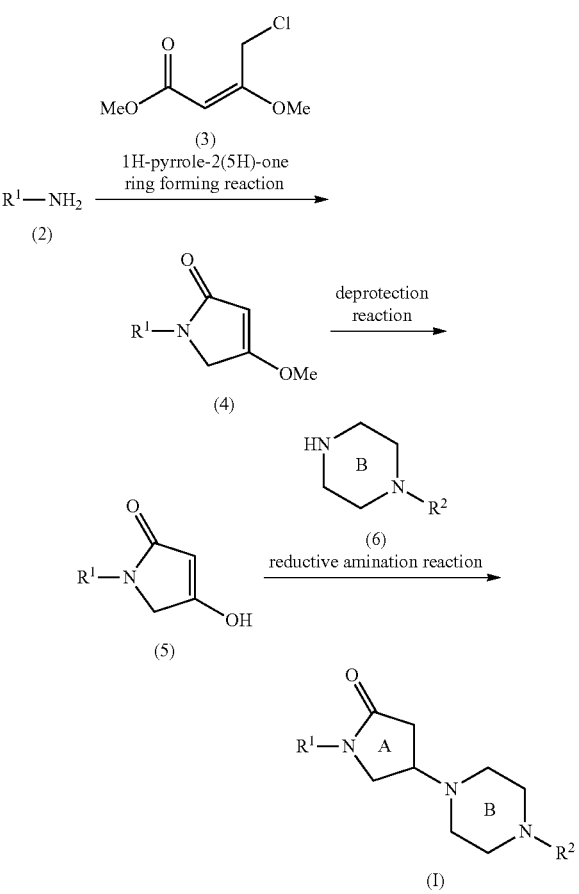

Compound (4) can be produced by reacting compound (2) with compound (3) to form a 1H-pyrrole-2(5H)-one ring. In this reaction, compound (2) and compound (3) are reacted first. In this case, a base may be added. Examples of such base include organic bases and the like. Then, the obtained intermediate is treated with organic acids, inorganic acids and the like, whereby compound (4) can be produced.

Compound (5) can be produced by a deprotection reaction of compound (4).

Compound (I) can be produced by a reductive amination reaction of compound (5) and compound (6). Examples of the reagent to be used for the reductive amination reaction include the reagents recited above as examples, 2-picoline borane and the like.

Compound (I) can also be produced from compound (5) according to the following production step B.

[Production Step B]

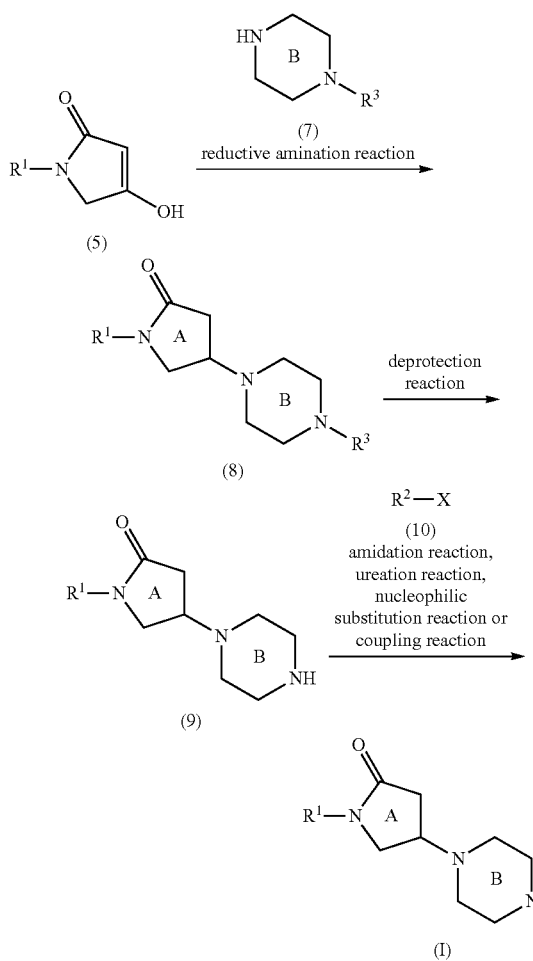

wherein R³ is an amino-protecting group, X is a leaving group, and the other symbols are as defined above. Examples of the "amino-protecting group" for R³ include the amino-protecting groups recited above as examples, a tert-butoxycarbonyl group and the like. Examples of the "leaving group" for X include a hydrogen atom, a halogen atom (e.g., fluorine, chlorine, bromine, iodine etc.), a hydroxy group, an optionally substituted acyloxy group (e.g., acetyloxy, benzoyloxy etc.), an optionally substituted $C_{1-6}$ alkoxysulfonyloxy group (e.g., methoxysulfonyloxy etc.), an optionally halogenated $C_{1-6}$ alkylsulfonyloxy group [e.g., methanesulfonyloxy, trifluoromethanesulfonyloxy(triflate) and the like], an optionally substituted $C_{6-14}$ arylsulfonyloxy group [e.g., a $C_{6-14}$ arylsulfonyloxy group optionally having 1 to 3 substituents selected from a $C_{1-6}$ alkyl group (e.g., methyl etc.), a $C_{1-6}$ alkoxy group (e.g., methoxy etc.) and a nitro group, and the like, and specific examples include benzenesulfonyloxy, m-nitrobenzenesulfonyloxy, p-toluenesulfonyloxy, naphthylsulfonyloxy and the like] and the like.

Compound (8) can be produced by a reductive amination reaction of compound (5) and compound (7). Examples of the reagent to be used for the reductive amination reaction include the reagents recited above as examples, 2-picoline borane and the like.

Compound (9) can be produced by a deprotection reaction of compound (8).

Compound (I) can be produced by an amidation reaction, an urea formation reaction, a nucleophilic substitution reaction, or a coupling reaction of compound (9) and compound (10). When it is produced by a nucleophilic substitution reaction, a base (e.g., basic salts, organic bases and the like) can also be used.

Compound (I) can also be produced from compound (11) according to the following production step C.

[Production Step C]

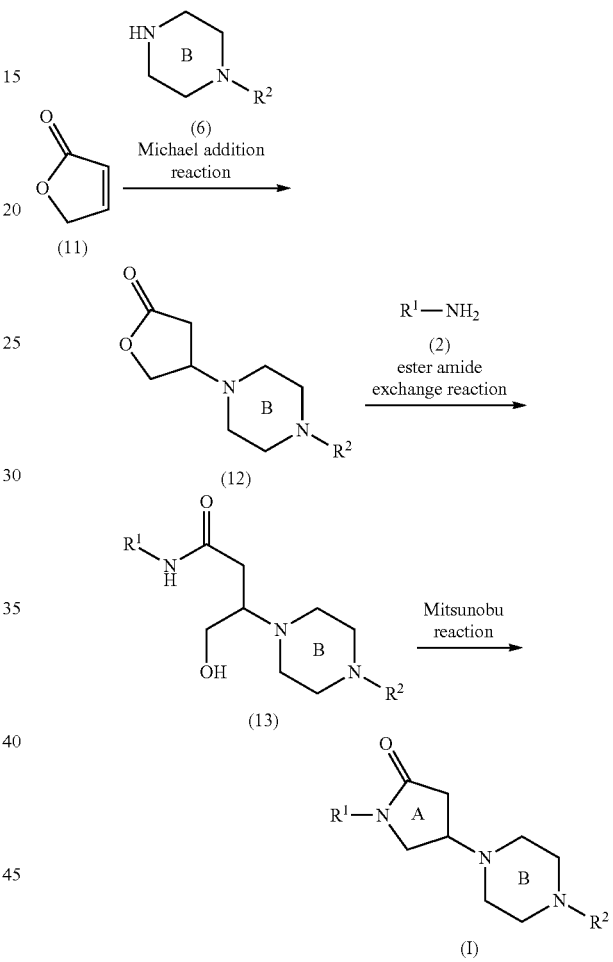

Compound (12) can be produced by the Michael addition reaction of compound (11) and compound (6).

Compound (13) can be produced by an ester amide exchange reaction of compound (12) and compound (2). Examples of the reagent to be used for the ester amide exchange reaction include trimethylaluminum, bis(trimethylaluminum)-1,4-diazabicyclo[2.2.2]octane adduct and the like.

Compound (I) can be produced by subjecting compound (13) to the Mitsunobu reaction. Examples of the reagent to be used for the Mitsunobu reaction include the reagents recited above as examples, tri-n-butylphosphine, (cyanomethylene)trimethylphosphorane, (cyanomethylene)tributylphosphorane and the like.

Compound (I) can also be produced from compound (14) according to the following production step D.

[Production Step D]

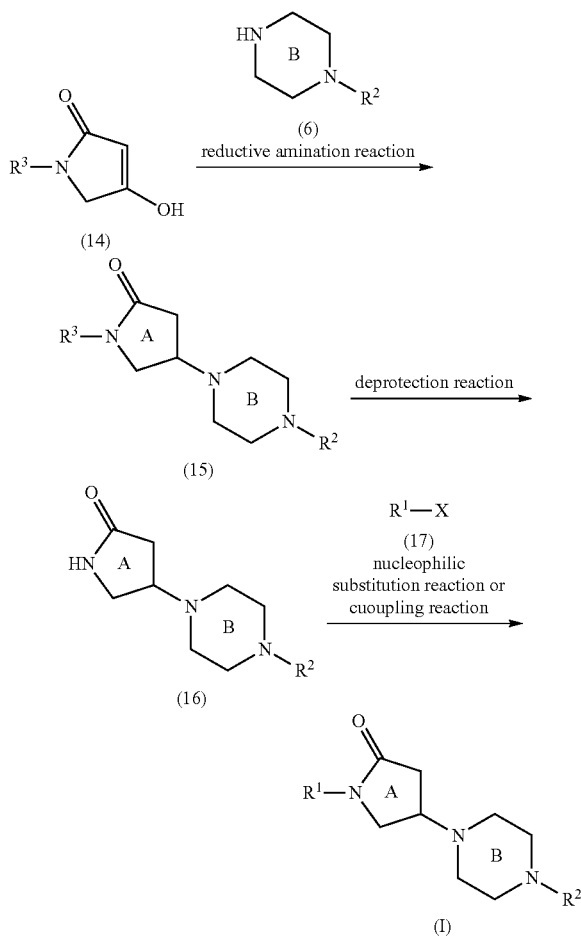

Compound (15) can be produced by a reductive amination reaction of compound (14) and compound (6). Examples of the reagent to be used for the reductive amination reaction include the reagents recited above as examples, 2-picoline borane and the like.

Compound (16) can be produced by a deprotection reaction of compound (15).

Compound (I) can be produced by a nucleophilic substitution reaction or a coupling reaction of compound (16) and compound (17). When it is produced by a nucleophilic substitution reaction, a base (e.g., basic salts, organic bases and the like) can also be used.

Compound (I) can also be produced from compound (12) according to the following production step E. [Production step E]

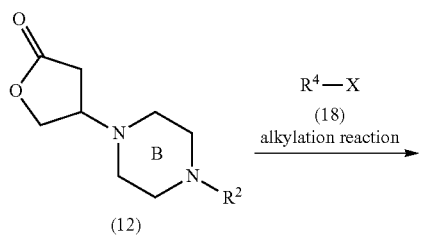

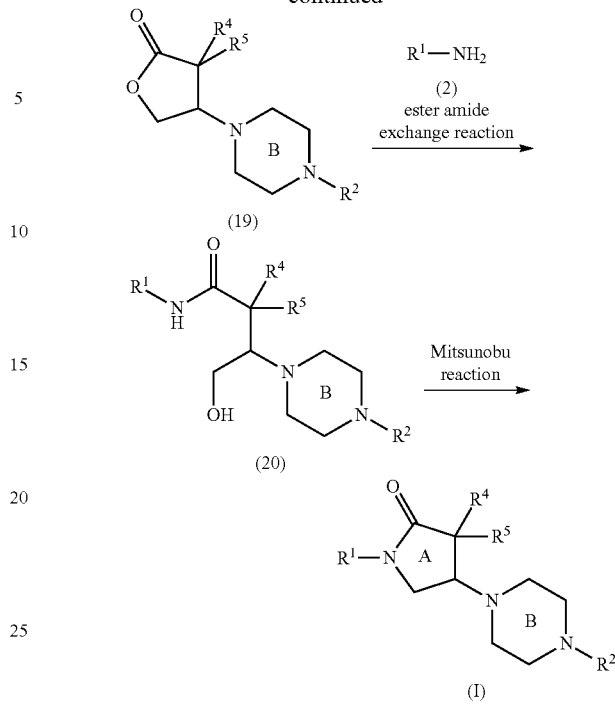

wherein $R^4$ is a $C_{1-3}$ alkyl group, $R^5$ is $R^4$ or a hydrogen atom, and the other symbols are as defined above.

Compound (19) can be produced by an alkylation reaction of compound (12) and compound (18). This reaction can be performed by a reaction known per se, and can be generally performed by using a base and reacting compound (18). As the base, the aforementioned bases, potassium hexamethyldisilazide and the like can be used.

Compound (20) can be produced by an ester amide exchange reaction of compound (19) and compound (2). Examples of the reagent to be used for the ester amide exchange reaction include trimethylaluminum, bis(trimethylaluminum)-1,4-diazabicyclo[2.2.2]octane adduct and the like.

Compound (I) can be produced by the Mitsunobu reaction of compound (20). Examples of the reagent to be used for the Mitsunobu reaction include the reagents recited above as examples, tri-n-butylphosphine, (cyanomethylene)trimethylphosphorane, (cyanomethylene)tributylphosphorane and the like.

Compound (I) can also be produced from compound (21) according to the following production step F. [Production step F]

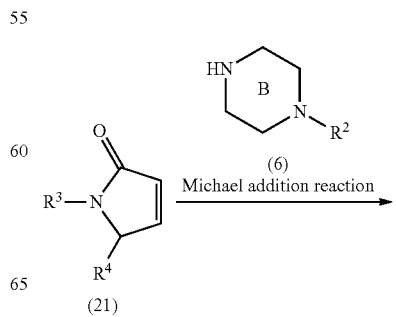

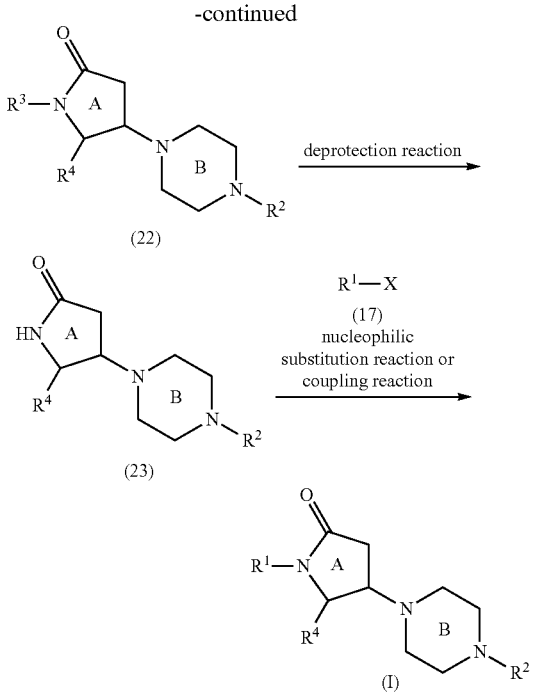

Compound (22) can be produced by the Michael addition reaction of compound (21) and compound (6).

Compound (23) can be produced by a deprotection reaction of compound (22).

Compound (I) can be produced by a nucleophilic substitution reaction or a coupling reaction of compound (23) and compound (17). When it is produced by a nucleophilic substitution reaction, a base (e.g., basic salts, organic bases and the like) can also be used.

The starting compound and/or the production intermediate for the compound (I) may form a salt. While the salt is not particularly limited as long as the reaction can be performed, examples thereof include those similar to the salts optionally formed by the compound (I) and the like, and the like.

As for the configuration isomers (E, Z forms) of compound (I), they can be isolated and purified when isomerization occurs, for example, according to a conventional separation means such as extraction, recrystallization, distillation, chromatography and the like to obtain a pure compound. In addition, the corresponding pure isomer can be obtained by isomerizing a double bond using heating, an acid catalyst, a transition metal complex, a metal catalyst, a radical catalyst, light irradiation or a strong base catalyst and the like, according to the method described in Jikken Kagaku Kouza (Courses in Experimental Chemistry) 14 (The Chemical Society of Japan ed.), pages 251 to 253, 4th Edition Jikken Kagaku Kouza 19 (The Chemical Society of Japan ed.), pages 273 to 274 or a method analogous thereto.

Compound (I) contains a stereoisomer depending to the kind of a substituent, and each stereoisomer and a mixture thereof are encompassed in the present invention.

Compound (I) may be a hydrate or a non-hydrate.

When desired, compound (I) can be synthesized by performing deprotection reaction, acylation reaction, alkylation reaction, hydrogenation reaction, oxidation reaction, reduction reaction, reaction of carbon chain extension, halogenation reaction, hydroxylation reaction, coupling reaction, substituent exchange reaction singly or two or more thereof in combination.

When the objective product is obtained as a free form by the above-mentioned reaction, it can be converted to a salt according to a conventional method, or when the objective product is obtained as a salt, it can be converted to a free form or other salt according to a conventional method. The thus-obtained compound (I) can also be isolated and purified from a reaction mixture according to a known method such as phase transfer, concentration, solvent extraction, distillation, crystallization, recrystallization, chromatography and the like.

When compound (I) contains a configurational isomer, a diastereomer, a conformer and the like, each can be isolated according to the above-mentioned separation and purification methods, if desired. In addition, when compound (I) is racemic, d-form and l-form can be isolated according to a conventional optical resolution.

The thus-obtained compound (I), other reaction intermediate therefor and starting compounds thereof can be isolated and purified from a reaction mixture according to a method known per se, for example, extraction, concentration, neutralization, filtration, distillation, recrystallization, column chromatography, thin layer chromatography, preparative high performance liquid chromatography (preparative HPLC), moderate-pressure preparative liquid chromatography (moderate-pressure preparative LC) and the like.

A salt of compound (I) can be produced according to a method known per se. For example, when compound (I) is a basic compound, it can be produced by adding an inorganic acid or organic acid, or when compound (I) is an acidic compound, by adding an organic base or inorganic base.

When compound (I) contains an optical isomer, each optical isomer and a mixture thereof are encompassed in the scope of the present invention, and these isomers can be subjected to optical resolution or can be produced respectively, according to a method known per se, if desired.

When compound (I) contains a configurational isomer, a diastereomer, a conformer and the like, each can be isolated according to the above-mentioned separation and purification methods, if desired. In addition, when compound (I) is racemic, S-form and R-form can be isolated according to a conventional optical resolution.

When compound (I) contains a stereoisomer, each isomer and a mixture thereof are encompassed in the present invention.

The compound of the present invention is useful for mammals (e.g., mouse, rat, hamster, rabbit, cat, dog, bovine, sheep, monkey, human etc.) as an agent for the prophylaxis or treatment of diseases, for example, (1) psychiatric diseases [e.g., depression, major depression, bipolar depression, dysthymic disorder, emotional disorder (seasonal affective disorder and the like), recurrent depression, postpartum depression, stress disorder, depression symptom, mania, anxiety, generalized anxiety disorder, anxiety syndrome, panic disorder, phobia, social phobia, social anxiety disorder, obsessive disorder, post-traumatic stress syndrome, post-traumatic stress disorder, Tourette syndrome, autism, fragile X syndrome, Rett syndrome, adjustment disorder, bipolar disorder, neurosis, schizophrenia (e.g., positive symptom, negative symptom, cognitive impairment), chronic fatigue syndrome, anxiety neurosis, compulsive neurosis, panic disorder, epilepsy, anxiety, anxious mental state, emotional abnormality, cyclothymia, nervous erethism, faint, addiction, low sex drive, attention deficit hyperactivity disorder (ADHD), psychotic major depression, refractory major depression, treatment-resistant depression], (2) neurodegenerative diseases [e.g., Alzheimer's disease, Alzheimer-type senile dementia, Parkinson's disease, Huntington's disease, multi-infarct dementia, frontotemporal dementia, frontotemporal dementia Parkinson's Type, progressive supranuclear palsy, Pick's syndrome, Niemann-Pick syndrome, corticobasal degeneration, Down's disease, vascular dementia, postencephalitic parkinsonism, Lewy body dementia, HIV dementia, amyotrophic lateral sclerosis (ALS), motor neurogenesis disease (MND), Creutzfeldt-Jakob disease or prion disease, cerebral palsy, progressive supranuclear palsy, traumatic brain injury, glaucoma, multiple sclerosis], (3) age-related cognition memory disorders [e.g., age-related memory disorders, senile dementia], (4) sleep disorders [e.g., intrinsic sleep disorders (e.g., psychophysiological insomnia and the like), extrinsic sleep disorder, circadian rhythm disorders (e.g., time zone change syndrome (jet lag), shift work sleep disorder, irregular sleep-wake pattern, delayed sleep phase syndrome, advanced sleep phase syndrome, non-24-hour sleep-wake and the like), parasomnia, sleep disorders associated with internal medical or psychiatric disorder (e.g., chronic obstructive pulmonary diseases, Alzheimer's disease, Parkinson's disease, cerebrovascular dementia, schizophrenia, depression, anxiety neurosis), stress insomnia, insomnia, insomniac neurosis, sleep apnea syndrome], (5) respiratory depression caused by anesthetics, traumatic disease, or neurodegenerative disease and the like, (6) traumatic brain injury, cerebral apoplexy, neurotic anorexia, eating disorder, anorexia nervosa, hyperorexia, other eating disorder, alcohol dependence, alcohol abuse, alcoholic amnesia, alcohol paranoia, alcohol preference, alcohol withdrawal, alcoholic insanity, alcohol poisoning, alcoholic jealousy, alcoholic mania, alcohol-dependent psychiatric disorder, alcoholic insanity, pharmacophilia, pharmacophobia, pharmacomania, drug withdrawal, migraine, stress headache, catatonic headache, diabetic neuropathy, obesity, diabetes, muscular spasm, Meniere's disease, autonomic ataxia, alopecia, glaucoma, hypertension, cardiac disease, tachycardia, congestive cardiac failure, hyperventilation, bronchial asthma, apnea, sudden infant death syndrome, inflammatory disease, allergic disease, impotence, climacteric disorder, infertility, cancer, immunodeficiency syndrome caused by HIV infection, immunodeficiency syndrome caused by stress, cerebrospinal meningitis, acromegaly, incontinence, metabolic syndrome, osteoporosis, peptic ulcer, irritable bowel syndrome, inflammatory bowel disease, ulcerative colitis, Crohn's disease, stress gastrointestinal disorder, stress vomiting, diarrhea, constipation, postoperative ileus, (7) pain (e.g., inflammatory pain, cancer pain, neuropathic pain etc.), (8) migraine, (9) cerebral edema,

(10) cerebral ischemia, and the like.

Since the compound of the present invention has a superior MAGL inhibitory action, a superior prophylactic or therapeutic effect for the above-mentioned diseases can be expected.

Since the compound of the present invention has a superior MAGL inhibitory action, a superior prophylactic or therapeutic effect for neurodegenerative diseases (e.g., Alzheimer's disease, Parkinson's disease, Huntington's disease, amyotrophic lateral sclerosis, traumatic brain injury, glaucoma, multiple sclerosis etc.), anxiety disorder, pain (e.g., inflammatory pain, cancer pain, neuropathic pain etc.) or epilepsy (particularly Alzheimer's disease, Parkinson's disease, pain or epilepsy) can be expected.

A prodrug of compound (I) means a compound which is converted to the compound (I) with a reaction due to an enzyme, an gastric acid, etc. under the physiological condition in the living body, that is, a compound which is converted to the compound (I) with oxidation, reduction, hydrolysis, etc. according to an enzyme; a compound which is converted to the compound (I) by hydrolysis etc. due to gastric acid, etc.

A prodrug for compound (I) may be a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation, etc.); a compound obtained by subjecting a hydroxy group in compound (I) to an acylation, alkylation, phosphorylation or boration (e.g., a compound obtained by subjecting an hydroxy group in compound (I) to an acetylation, palmitoylation, propanoylation, pivaloylation, succinylation, fumarylation, alanylation, dimethylaminomethylcarbonylation, etc.); a compound obtained by subjecting a carboxyl group in compound (I) to an esterification or amidation (e.g., a compound obtained by subjecting a carboxyl group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification and methylamidation, etc.) and the like. Any of these compounds can be produced from compound (I) by a method known per se. The prodrug of compound (I) may be a compound that converts to compound (I) under physiological conditions as described in Development of Pharmaceutical Products, vol. 7, Molecule Design, 163-198, Hirokawa Shoten (1990).

The compound of the present invention is superior in in vivo kinetics (e.g., plasma drug half-life, intracerebral transferability, metabolic stability), shows low toxicity (e.g., more superior as a medicament in terms of acute toxicity, chronic toxicity, genetic toxicity, reproductive toxicity, cardiotoxicity, drug interaction, carcinogenicity and the like). The compound of the present invention is directly used as a medicament or a pharmaceutical composition mixed with a pharmaceutically acceptable carrier or the like to be orally or parenterally administered to mammals (e.g., humans, monkeys, cows, horses, pigs, mice, rats, hamsters, rabbits, cats, dogs, sheep and goats) in safety. Examples of the "parenteral" include intravenous, intramuscular, subcutaneous, intra-organ, intranasal, intradermal, instillation, intracerebral, intrarectal, intravaginal, intraperitoneal and intratumor administrations, administration to the vicinity of tumor etc. and direct administration to the lesion.

While the dose of the compound of the present invention varies depending on the administration route, symptom and the like, when, for example, the compound is orally administered to a patient with schizophrenia (adult, body weight 40-80 kg, for example, 60 kg), it is, for example, 0.001-1000 mg/kg body weight/day, preferably 0.01-100 mg/kg body weight/day, more preferably 0.1-10 mg/kg body weight/day. This amount can be administered in 1 to 3 portions per day.

A medicament containing the compound of the present invention can be used alone or as a pharmaceutical composition containing the compound of the present invention and a pharmaceutically acceptable carrier according to a method known per se as a production method of a pharmaceutical preparation (e.g., the method described in the Japanese Pharmacopoeia etc.). A medicament containing the compound of the present invention can be safely administered in the form of, for example, tablet (including sugar-coated tablet, film-coated tablet, sublingual tablet, orally disintegrating tablet, buccal and the like), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal administrations, and administration to the lesion).

As the aforementioned "pharmaceutically acceptable carrier", various organic or inorganic carriers conventionally used as preparation materials (starting materials) can be used. For example, excipient, lubricant, binder, disintegrant and the like are used for solid preparations, and solvent, solubilizing agent, suspending agent, isotonicity agent, buffer, soothing agent and the like are used for liquid preparations. Where necessary, preparation additives such as preservative, antioxidant, colorant, sweetening agent and the like can also be used.

Examples of the excipient include lactose, sucrose, D-mannitol, starch, corn starch, crystalline cellulose, light anhydrous silicic acid and the like.

Examples of the lubricant include magnesium stearate, calcium stearate, talc, colloidal silica and the like.

Examples of the binding agent include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, sodium carboxymethyl starch, L-hydroxypropylcellulose and the like.

Examples of the solvent include water for injection, alcohol, propylene glycol, Macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like. Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffering agent include buffer solutions such as phosphates, acetates, carbonates, citrates and the like.

Examples of the soothing agent include benzyl alcohol and the like.

Examples of the preservative include p-oxybenzoates, chlorobutanol, benzyl alcohol, phenylethyl alcohol, dehydroacetic acid, sorbic acid and the like.

Examples of the antioxidant include sulfite, ascorbic acid, α-tocopherol and the like.

While the pharmaceutical composition varies according to the dosage form, administration method, carrier and the like, it can be produced according to a conventional method by adding the compound of the present invention in a proportion of generally 0.01-100% (w/w), preferably 0.1-95% (w/w), of the total amount of the preparation.

The compound of the present invention can be used in combination with other active ingredients (hereinafter to be abbreviated as concomitant drug).

Examples of the concomitant drug include the following. benzodiazepine (chlordiazepoxide, diazepam, potassium clorazepate, lorazepam, clonazepam, alprazolam etc.), L-type calcium channel inhibitor (pregabalin etc.), tricyclic or tetracyclic antidepressant (imipramine hydrochloride, amitriptyline hydrochloride, desipramine hydrochloride, clomipramine hydrochloride etc.), selective serotonin reuptake inhibitor (fluvoxamine maleate, fluoxetine hydrochloride, citalopram hydrobromide, sertraline hydrochloride, paroxetine hydrochloride, escitalopram oxalate etc.), serotonin-noradrenaline reuptake inhibitor (venlafaxine hydrochloride, duloxetine hydrochloride, desvenlafaxine hydrochloride etc.), noradrenaline reuptake inhibitor (reboxetine mesylate etc.), noradrenaline-dopamine reuptake inhibitor (bupropion hydrochloride etc.), mirtazapine, trazodone hydrochloride, nefazodone hydrochloride, bupropion hydrochloride, setiptiline maleate, 5-$HT_{1A}$ agonist (buspirone hydrochloride, tandospirone citrate, osemozotan hydrocloride etc.), 5-$HT_3$ antagonist (Cyamemazine etc.), heart non-selective β inhibitor (propranolol hydrochloride, oxprenolol hydrochloride etc.), histamine $H_1$ antagonist (hydroxyzine hydrochloride etc.), therapeutic drug for schizophrenia (chlorpromazine, haloperidol, sulpiride, clozapine, trifluoperazine hydrochloride, fluphenazine hydrochloride, olanzapine, quetiapine fumarate, risperidone, aripiprazole etc.), CRF antagonist, other antianxiety drug (meprobamate etc.), tachykinin antagonist (MK-869, saredutant etc.), medicament that acts on metabotropic glutamate receptor, CCK antagonist, β3 adrenaline antagonist (amibegron hydrochloride etc.), GAT-1 inhibitor (tiagabine hydrochloride etc.), N-type calcium channel inhibitor, carbonic anhydrase II inhibitor, NMDA glycine moiety agonist, NMDA antagonist (memantine etc.), peripheral benzodiazepine receptor agonist, vasopressin antagonist, vasopressin Vib antagonist, vasopressin Via antagonist, phosphodiesterase inhibitor, opioid antagonist, opioid agonist, uridine, nicotinic acid receptor agonist, thyroid hormone (T3, T4), TSH, TRH, MAO inhibitor (phenelzine sulfate, tranylcypromine sulfate, moclobemide etc.), 5-$HT_{2A}$ antagonist, 5-$HT_{2A}$ inverse agonist, COMT inhibitor (entacapone etc.), therapeutic drug for bipolar disorder (lithium carbonate, sodium valproate, lamotrigine, riluzole, felbamate etc.), cannabinoid CB1 antagonist (rimonabant etc.), FAAH inhibitor, sodium channel inhibitor, anti-ADHD drug (methylphenidate hydrochloride, methamphetamine hydrochloride etc.), therapeutic drug for alcoholism, therapeutic drug for autism, therapeutic drug for chronic fatigue syndrome, therapeutic drug for spasm, therapeutic drug for fibromyalgia syndrome, therapeutic drug for headache, therapeutic drug for insomnia (etizolam, zopiclone, triazolam, zolpidem, ramelteon, indiplon etc.), therapeutic drug for quitting smoking, therapeutic drug for myasthenia gravis, therapeutic drug for cerebral infarction, therapeutic drug for mania, therapeutic drug for hypersomnia, therapeutic drug for pain, therapeutic drug for dysthymia, therapeutic drug for autonomic ataxia, therapeutic drug for male and female sexual dysfunction, therapeutic drug for migraine, therapeutic drug for pathological gambler, therapeutic drug for restless legs syndrome, therapeutic drug for substance addiction, therapeutic drug for alcohol-related syndrome, therapeutic drug for irritable bowel syndrome, therapeutic drug for Alzheimer's disease (donepezil, galanthamine, memantine etc.), therapeutic drug for Parkinson's disease, therapeutic drug for ALS (riluzole etc., neurotrophic factor etc.), therapeutic drug for lipid abnormality such as cholesterol-lowering drug (statin series (pravastatin sodium, atrovastatin, simvastatin, rosuvastatin etc.), fibrate (clofibrate etc.), squalene synthetase inhibitor), therapeutic drug for abnormal behavior or suppressant of dromomania due to dementia (sedatives, antianxiety drug etc.), apoptosis inhibitor, antiobesity drug, therapeutic drug for diabetes, therapeutic drug for hypertension, therapeutic drug for hypotension, therapeutic drug for rheumatism (DMARD), anticancer agent, therapeutic drug for parathyroid (PTH), calcium receptor antagonist, sex hormone or a derivative thereof (progesterone, estradiol, estradiol benzoate etc.), neuronal differentiation promoter, nerve regeneration promoter, non-steroidal anti-inflammatory drug (meloxicam, tenoxicam, indomethacin, ibuprofen, celecoxib, rofecoxib, aspirin etc.), steroid (dexamethasone, cortisone acetate etc.), anti-cytokine drug (TNF inhibitor, MAP kinase inhibitor etc.), antibody medicament, nucleic acid or nucleic acid derivative, aptamer drug and the like.

By combining the compound of the present invention and a concomitant drug, a superior effect such as (1) the dose can be reduced as compared to single administration of the compound of the present invention or a concomitant drug,
(2) the drug to be combined with the compound of the present invention can be selected according to the condition of patients (mild case, severe case and the like),
(3) the period of treatment can be set longer by selecting a concomitant drug having different action and mechanism from the compound of the present invention,
(4) a sustained treatment effect can be designed by selecting a concomitant drug having different action and mechanism from the compound of the present invention,
(5) a synergistic effect can be afforded by a combined use of the compound of the present invention and a concomitant drug, and the like, can be achieved.

Hereinafter the compound of the present invention and a concomitant drug used in combination are referred to as the "combination agent of the present invention".

When using the combination agent of the present invention, the administration time of the compound of the present invention and the concomitant drug is not restricted, and the compound of the present invention or a pharmaceutical composition thereof and the concomitant drug or a pharmaceutical composition thereof can be administered to an administration subject simultaneously, or may be administered at different times. The dosage of the concomitant drug may be determined according to the dose clinically used, and can be appropriately selected depending on an administration subject, administration route, disease, combination and the like.

The administration mode of the concomitant drug of the present invention is not particularly restricted, and it is sufficient that the compound of the present invention and the concomitant drug are combined in administration. Examples of such administration mode include the following methods: (1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (for example, administration in the order of the compound of the present invention and the concomitant drug, or in the reverse order) and the like.

The combination drug of the present invention exhibits low toxicity. For example, the compound of the present invention or(and) the aforementioned concomitant drug can be combined with a pharmacologically acceptable carrier according to the known method to prepare a pharmaceutical composition such as tablets (including sugar-coated tablet and film-coated tablet), powders, granules, capsules (including soft capsule), liquids, injections, suppositories, sustained-release agents, etc. These compositions can be administered safely orally or non-orally (e.g., topical, rectal, intravenous administration etc.). Injection can be administered intravenously, intramuscularly, subcutaneously, or by intraorgan administration or directly to the lesion.

Examples of the pharmacologically acceptable carriers usable for the production of a combination agent of the present invention, various organic or inorganic carrier substances conventionally used as preparation materials can be mentioned. For solid preparations, for example, excipient, lubricant, binder and disintegrant can be used. For liquid preparations, for example, solvent, solubilizing agent, suspending agent, isotonic agent, buffering agent, soothing agent and the like can be used. Where necessary, an appropriate amount of conventional preservative, antioxidant, colorant, sweetening agent, adsorbent, wetting agent and the like can be used as appropriate.

Examples of the excipient include lactose, sucrose, D-mannitol, starch, corn starch, crystalline cellulose, light anhydrous silicic acid and the like.

Examples of the lubricant include magnesium stearate, calcium stearate, talc, colloidal silica and the like.

Examples of the binding agent include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, sodium carboxymethyl starch, L-hydroxypropylcellulose and the like.

Examples of the solvent include water for injection, alcohol, propylene glycol, Macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffering agent include buffer solutions such as phosphates, acetates, carbonates, citrates and the like.

Examples of the soothing agent include benzyl alcohol and the like.

Examples of the preservative include p-oxybenzoates, chlorobutanol, benzyl alcohol, phenylethyl alcohol, dehydroacetic acid, sorbic acid and the like.

Examples of the antioxidant include sulfite, ascorbic acid, α-tocopherol and the like.

The mixing ratio of the compound of the present invention to the concomitant drug in the combination agent of the present invention can be appropriately selected depending on an administration subject, administration route, diseases and the like.

For example, the content of the compound of the present invention in the combination agent of the present invention differs depending on the form of a preparation, and usually from about 0.01 to about 100 wt %, preferably from about 0.1 to about 50 wt %, further preferably from about 0.5 to about 20 wt %, based on the preparation.

The content of the concomitant drug in the combination agent of the present invention differs depending on the form of a preparation, and usually from about 0.01 to about 100 wt %, preferably from about 0.1 to about 50 wt %, further preferably from about 0.5 to about 20 wt %, based on the preparation.

The content of additives such as a carrier and the like in the combination agent of the present invention differs depending on the form of a preparation, and usually from about 1 to about 99.99 wt %, preferably from about 10 to about 90 wt %, based on the preparation.

When the compound of the present invention and a concomitant drug are separately formulated into preparations, the contents thereof are similar to the above.

EXAMPLES

The present invention is explained in detail in the following by referring to Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

In silica gel column chromatography, NH means use of aminopropylsilane-bound silica gel. In HPLC (high performance liquid chromatography), C18 means use of octadecyl-bound silica gel.

The ratios of elution solvents are volume mixing ratios, unless otherwise specified.

In Examples, the following abbreviations are used.
mp: melting point
MS: mass spectrum
M: mol concentration
CDCl$_3$: deuterochloroform
DMSO-d$_6$: deuterodimethyl sulfoxide
$^1$H NMR: proton nuclear magnetic resonance
LC/MS: liquid chromatograph mass spectrometer
ESI: Electron Spray Ionization
APCI: atmospheric pressure chemical ionization
SFC: supercritical fluid chromatography
DMF: N,N-dimethylformamide
DMA: N,N-dimethylacetamide
THF: tetrahydrofuran
HATU: 2-(7-azabenzotriazol-1-yl)-1,1,3,3-tetramethyluronium hexafluorophosphate $^1$H NMR was measured by Fourier-transform type NMR. For the analysis, ACD/SpecManager (trade name) and the like were used. Peaks with very mild protons such as a hydroxy group, an amino group and the like are not described.

MS was measured by LC/MS. As ionization method, ESI method or APCI method was used. The data indicates those actual measured value (found). Generally, molecular ion peaks ([M+H]$^+$, [M−H]$_-$ and the like) are observed. For example, in the case of a compound having a tert-butoxycarbonyl group, a peak after elimination of a tert-butoxycarbonyl group or tert-butyl group may be observed as a fragment ion. In the case of a compound having a hydroxy group, a peak after elimination of H$_2$O may be observed as a fragment ion. In the case of a salt, a molecular ion peak or fragment ion peak of free form is generally observed.

The unit of sample concentration (c) for optical rotation ($[\alpha]_D$) is g/100 mL.

Elemental analysis value (Anal.) was described as calculated value (Calcd) and actual measured value (Found).

Example 1

1-(4-Phenoxyphenyl)-4-(4-(1,3-thiazol-2-ylcarbonyl) piperazin-1-yl)pyrrolidin-2-one A) 4-Methoxy-1-(4-phenoxyphenyl)-1H-pyrrole-2 (5H)-one To a mixture of 4-phenoxyaniline (10 g) and acetonitrile (40 mL) was added a mixture of methyl 4-chloro-3-methoxy-2-(E)-butenoate (9.18 mL) and acetonitrile (40 mL) at 0° C. To the reaction mixture was added a mixture of triethylamine (8.28 mL) and acetonitrile (20 mL) at 0° C. The reaction mixture was heated under reflux for 4 hr and cooled to room temperature. The precipitate was removed by filtration. To the filtrate was added water (80 mL), and the mixture was adjusted to pH 3 with concentrated hydrochloric acid. The reaction mixture was extracted with ethyl acetate. The organic layer was dried over sodium sulfate and concentrated under reduced pressure. To the residue were added toluene (80 mL) and acetic acid (2.0 mL) at room temperature. The reaction mixture was heated at 50° C. for 1.5 hr. The reaction mixture was diluted at room temperature with water, saturated brine and saturated aqueous sodium hydrogen carbonate solution, and extracted with ethyl acetate. The organic layer was dried over sodium sulfate, and concentrated under reduced pressure. The residue was purified by silica gel column chromatography (ethyl acetate/hexane) to give the title compound (7.43 g).

MS: [M+H]$^+$ 281.8.

B) 4-Hydroxy-1-(4-phenoxyphenyl)-1H-pyrrole-2 (5H)-one

A mixture of 4-methoxy-1-(4-phenoxyphenyl)-1H-pyrrole-2(5H)-one (7.43 g), concentrated hydrochloric acid (46.4 mL) and toluene (91.2 mL) was heated at 50° C. for 21 hr. The reaction mixture was concentrated and diluted with saturated aqueous sodium hydrogen carbonate solution, water and saturated brine, and the mixture was extracted with ethyl acetate. The organic layer was dried over sodium sulfate, and concentrated under reduced pressure. The residue was triturated with ethyl acetate/hexane to give the title compound (6.89 g).

MS: [M+H]$^+$ 268.2.

C) tert-Butyl 4-(5-oxo-1-(4-phenoxyphenyl)pyrrolidin-3-yl)piperazine-1-carboxylate To a mixture of 4-hydroxy-1-(4-phenoxyphenyl)-1H-pyrrole-2(5H)-one (2.65 g) and THF (99 mL) was added tert-butyl piperazine-1-carboxylate (2.22 g) at room temperature. The reaction mixture was stirred at room temperature for 6.5 hr. To the reaction mixture were added acetic acid (1.70 mL) and sodium cyanoborohydride (1.87 g) at room temperature, and the reaction mixture was stirred at room temperature for 18 hr. To the reaction mixture was added sodium cyanoborohydride (0.62 g) at room temperature. The reaction mixture was stirred at room temperature for 5 hr. To the reaction mixture was added 2M aqueous sodium hydroxide solution (19.1 mL) at 0° C. The reaction mixture was diluted with water and saturated brine, and extracted with ethyl acetate. The organic layer was dried over sodium sulfate, and concentrated under reduced pressure. The residue was purified by silica gel column chromatography (NH, ethyl acetate/hexane) to give the title compound (2.86 g).

MS: [M+H]$^+$ 438.1.

D) 1-(4-Phenoxyphenyl)-4-(piperazin-1-yl)pyrrolidin-2-one hydrochloride

To a mixture of tert-butyl 4-(5-oxo-1-(4-phenoxyphenyl)pyrrolidin-3-yl)piperazine-1-carboxylate (2.90 g) and ethyl acetate (88 mL) was added 4M hydrogen chloride ethyl acetate solution (16.6 mL) at room temperature. The reaction mixture was stirred at room temperature for 30 min and at 60° C. for 30 min. To the reaction mixture was added 4 M hydrogen chloride ethyl acetate solution (16.6 mL) at 60° C. The reaction mixture was stirred at 60° C. for 14 hr. The reaction mixture was heated under reflux for 6 hr. To the reaction mixture was added 2 M hydrogen chloride methanol solution (66.3 mL) at room temperature. The reaction mixture was heated under reflux for 2 hr. The reaction mixture was concentrated under reduced pressure and triturated with ethyl acetate/hexane to give the title compound (2.46 g).

MS, found: 338.2.

E) 1-(4-Phenoxyphenyl)-4-(4-(1,3-thiazol-2-ylcarbonyl)piperazin-1-yl)pyrrolidin-2-one To a mixture of 1-(4-phenoxyphenyl)-4-(piperazin-1-yl)pyrrolidin-2-one hydrochloride (200 mg) and thiazole-2-carboxylic acid (83 mg) in DMF (3 mL) were added HATU (305 mg) and triethylamine (0.373 mL) at room temperature. The reaction mixture was stirred at room temperature overnight. To the reaction mixture was added water, and the mixture was extracted with ethyl acetate. The organic layer was washed with water and brine, dried over sodium sulfate, and concentrated under reduced pressure. The residue was purified by silica gel column chromatography (NH, ethyl acetate/hexane) and crystallized from 2-propanol/diisopropyl ether/hexane to give the title compound (170 mg).

$^1$H NMR (300 MHz, CDCl$_3$) δ 2.54-2.71 (5H, m), 2.72-2.85 (1H, m), 3.22-3.36 (1H, m), 3.74-3.87 (2H, m), 3.87-3.99 (2H, m), 4.35-4.49 (1H, m), 4.49-4.63 (1H, m), 6.96-7.06 (4H, m), 7.06-7.13 (1H, m), 7.30-7.37 (2H, m), 7.49-7.56 (3H, m), 7.88 (1H, d, J=3.4 Hz).

Example 7

2-(4-(5-Oxo-1-(4-phenoxyphenyl)pyrrolidin-3-yl)piperazin-1-yl)nicotinonitrile

To a mixture of 1-(4-phenoxyphenyl)-4-(piperazin-1-yl)pyrrolidin-2-one hydrochloride (50 mg) and 2-chloro-3-cyanopyridine (55.6 mg) in DMA (1 mL) was added triethylamine (0.093 mL) at room temperature. The reaction mixture was stirred under microwave irradiation at 170° C. for 1 hr. To the reaction mixture was added water, and the mixture was extracted with ethyl acetate. The organic layer was washed with water and brine, dried over sodium sulfate, and concentrated under reduced pressure. The residue was purified by silica gel column chromatography (NH, ethyl acetate/hexane) to give the title compound (25.6 mg).

$^1$H NMR (300 MHz, CDCl$_3$) δ 2.61-2.84 (6H, m), 3.22-3.35 (1H, m), 3.72-3.87 (5H, m), 3.89-3.98 (1H, m), 6.78 (1H, dd, J=7.8, 4.7 Hz), 6.96-7.06 (4H, m), 7.06-7.14 (1H, m), 7.28-7.38 (2H, m), 7.49-7.57 (2H, m), 7.78 (1H, dd, J=7.6, 1.9 Hz), 8.36 (1H, dd, J=4.7, 2.1 Hz).

Example 13

1-(2-Methoxy-4-phenoxyphenyl)-4-(4-(1,3-thiazol-2-ylcarbonyl)piperazin-1-yl)pyrrolidin-2-one A) tert-Butyl 4-(thiazole-2-carbonyl)piperazine-1-carboxylate To a mixture of tert-butyl piperazine-1-carboxylate (15.87 g) and THF (310 mL) were added thiazole-2-carboxylic acid (10 g), triethylamine (16.19 mL), 1-hydroxybenzotriazole monohydrate (14.23 g) and 1-ethyl-3-(3-dimethylaminopropyl)carbodiimide hydrochloride (17.81 g) at room temperature. The reaction mixture was stirred at room temperature for 22 hr. To the reaction mixture were added tert-butyl piperazine-1-carboxylate (2.88 g), 1-hydroxybenzotriazole monohydrate (2.372 g), 1-ethyl-3-(3-dimethylaminopropyl)carbodiimide hydrochloride (2.97 g) and THF (100 mL) at room temperature. The reaction mixture was stirred at room temperature for 6 hr. The reaction mixture was diluted with water, saturated brine and saturated aqueous sodium hydrogen carbonate solution, and extracted with ethyl acetate. The organic layer was dried over magnesium sulfate and concentrated under reduced pressure. The residue was purified by silica gel column chromatography (ethyl acetate/hexane) to give the title compound (20.10 g).

MS, found: 242.1.

B) Piperazin-1-yl(thiazol-2-yl)methanone

To a mixture of tert-butyl 4-(thiazole-2-carbonyl)piperazine-1-carboxylate (20.1 g) and ethyl acetate (451 mL) was added 4 M hydrogen chloride ethyl acetate solution (169 mL) at room temperature. The reaction mixture was stirred at room temperature for 16 hr. To the reaction mixture was added hexane. The precipitate was collected by filtration, washed with hexane, purified by silica gel column chromatography (NH, methanol/ethyl acetate) and triturated with hexane to give the title compound (12.78 g).
MS: [M+H]⁺ 198.1.

C) 4-(4-(1,3-Thiazol-2-yl-carbonyl)piperazin-1-yl) dihydrofuran-2(3H)-one

To a mixture of piperazin-1-yl(thiazol-2-yl)methanone (2.0 g) and methanol (4 mL) was added 2(5H)-furanone (0.852 mL) at 0° C. The reaction mixture was stirred at room temperature overnight. To the reaction mixture were added 2-propanol (4 mL) and diisopropyl ether (2 mL). The reaction mixture was stirred at room temperature for 1 hr. The precipitate was collected by filtration and washed with a 1:1 mixture of 2-propanol/diisopropylether to give the title compound (2.11 g).
MS: [M+H]⁺ 282.1.

D) 2-Methoxy-1-nitro-4-phenoxybenzene

To a mixture of phenol (1.13 mL) and 4-fluoro-2-methoxy-1-nitrobenzene (2 g) in DMF (15 mL) was added potassium carbonate (3.23 g) at room temperature. The reaction mixture was stirred under a nitrogen atmosphere at 80° C. overnight. To the reaction mixture was added water, and the mixture was extracted with ethyl acetate. The organic layer was washed with water and brine, dried over sodium sulfate, and concentrated under reduced pressure. The residue was triturated with diisopropyl ether, filtrated, and washed with diisopropyl ether to give the title compound (2.80 g).
MS: [M+H]⁺ 246.1.

E) 2-Methoxy-4-phenoxyaniline

A mixture of 2-methoxy-1-nitro-4-phenoxybenzene (1.0 g) and palladium carbon (10% Pd, 0.1 g) in ethanol (10 mL) was stirred at room temperature under a hydrogen atmosphere overnight. The reaction mixture was filtered, and the filtrate was concentrated to give the title compound (882 mg).
MS: [M+H]⁺ 216.2.

F) 4-Hydroxy-N-(2-methoxy-4-phenoxyphenyl)-3-(4-(1,3-thiazol-2-ylcarbonyl)piperazin-1-yl)butanamide To a mixture of 2-methoxy-4-phenoxyaniline (53.4 mg) and toluene (1 mL) was added trimethylaluminum (15% toluene solution, 0.197 mL) at room temperature, and the mixture was stirred for 1 hr. To the reaction mixture was added a mixture of 4-(4-(1,3-thiazol-2-ylcarbonyl)piperazin-1-yl)dihydrofuran-2(3H)-one (50 mg) and toluene (1 mL). The reaction mixture was stirred at 70° C. for 3 hr. The reaction mixture was purified by silica gel column chromatography (NH, ethyl acetate/hexane and methanol/ethyl acetate) to give the title compound (29.3 mg).
MS: [M+H]⁺ 497.2.

G) 1-(2-Methoxy-4-phenoxyphenyl)-4-(4-(1,3-thiazol-2-ylcarbonyl)piperazin-1-yl)pyrrolidin-2-one To a mixture of di-tert-butylazodicarboxylate (37.6 mg) and THF (1 mL) was added tri-n-butylphosphine (0.040 mL) at 0° C. The reaction mixture was stirred at room temperature for 30 min. To the reaction mixture was added a mixture of 4-hydroxy-N-(2-methoxy-4-phenoxyphenyl)-3-(4-(1,3-thiazol-2-ylcarbonyl)piperazin-1-yl)butanamide (27 mg) and THF (1 mL) at 0° C. The reaction mixture was stirred at room temperature overnight. The reaction mixture was concentrated under reduced pressure. To the reaction mixture were added THF (1 mL), and a mixture of di-tert-butylazodicarboxylate (37.6 mg), tri-n-butylphosphine (0.040 mL) and THF (1 mL) at 0° C. The reaction mixture was concentrated under reduced pressure. The residue was purified by silica gel column chromatography (ethyl acetate/hexane and methanol/ethyl acetate) and crystallized from 2-propanol/diisopropyl ether/hexane to give the title compound (9.8 mg).
¹H NMR (300 MHz, CDCl₃) δ 2.52-2.79 (6H, m), 3.26-3.41 (1H, m), 3.67-3.86 (6H, m), 3.86-3.98 (1H, m), 4.37-4.49 (1H, m), 4.49-4.60 (1H, m), 6.54 (1H, dd, J=8.5, 2.5 Hz), 6.65 (1H, d, J=2.7 Hz), 6.99-7.09 (2H, m, J=7.6 Hz), 7.09-7.19 (2H, m), 7.31-7.40 (2H, m), 7.54 (1H, d, J=3.0 Hz), 7.88 (1H, d, J=3.0 Hz).

Example 14

1-(1-(4-Fluorophenyl)-1H-indol-5-yl)-4-(4-(1,3-thiazol-2-ylcarbonyl)piperazin-1-yl)pyrrolidin-2-one A) 1-(4-Fluorophenyl)-5-nitro-1H-indole To a mixture of 5-nitro-1H-indole (2 g) and 1-fluoro-4-iodobenzene (4.27 mL) in toluene (17.2 mL) were added tripotassium phosphate (9.16 g), N,N'-dimethylethylenediamine (0.397 mL) and copper iodide (I) (0.235 g) at room temperature. The reaction mixture was heated under reflux under a nitrogen atmosphere for 1 day. The reaction mixture was filtered through Celite. The filtrate was concentrated under reduced pressure. The residue was purified by silica gel column chromatography (NH, ethyl acetate/hexane) and further purified by silica gel column chromatography (ethyl acetate/hexane) to give the title compound (1.666 g).
MS: [M+H]⁺ 257.2.

B) 1-(4-Fluorophenyl)-1H-indole-5-amine

To a mixture of 1-(4-fluorophenyl)-5-nitro-1H-indole (410 mg) and acetic acid (5 mL) was added zinc (523 mg) at room temperature. The reaction mixture was stirred at 70° C. for 3 hr. The reaction mixture was filtered, and the filtrate was concentrated. To the residue was added saturated aqueous sodium hydrogen carbonate solution, and the mixture was extracted with ethyl acetate. The organic layer was washed with water and brine, dried over sodium sulfate, and concentrated under reduced pressure. The residue was purified by silica gel column chromatography (ethyl acetate/hexane) to give the title compound (188 mg).
¹H NMR (300 MHz, CDCl₃) δ 3.56 (2H, brs), 6.49 (1H, dd, J=3.4, 0.8 Hz), 6.68 (1H, dd, J=8.7, 2.3 Hz), 6.97 (1H, d, J=1.5 Hz), 7.12-7.22 (3H, m), 7.28 (1H, d, J=8.7 Hz), 7.38-7.46 (2H, m).

C) N-(1-(4-Fluorophenyl)-1H-indol-5-yl)-4-hydroxy-3-(4-(1,3-thiazol-2-ylcarbonyl)piperazin-1-yl)butanamide To a mixture of 1-(4-fluorophenyl)-1H-indole-5-amine (55 mg) and toluene (1 mL) was added trimethylaluminum (15% toluene solution, 0.197 mL) at room temperature, and the mixture was stirred for 30 min. To the reaction mixture was added a mixture of 4-(4-(1,3-thiazol-2-ylcarbonyl)piperazin-1-yl)dihydrofuran-2(3H)-one (50 mg) and toluene (1 mL) and the mixture was stirred at 70° C. for 1 hr. To the reaction mixture were added water (0.013 mL), 4 M aqueous sodium hydroxide solution (0.013 mL) and water (0.038 mL). The reaction mixture was filtered, and the filtrate was purified by silica gel column chromatography (ethyl acetate/hexane and methanol/ethyl acetate) to give the title compound (81 mg).

MS: [M+H]$^+$ 508.2.

D) 1-(1-(4-Fluorophenyl)-1H-indol-5-yl)-4-(4-(1,3-thiazol-2-ylcarbonyl)piperazin-1-yl)pyrrolidin-2-one To a mixture of di-tert-butylazodicarboxylate (110 mg) and THF (2 mL) was added tri-n-butylphosphine (0.118 mL) at 0° C. The reaction mixture was stirred at room temperature for 30 min. To the reaction mixture was added a mixture of N-(1-(4-fluorophenyl)-1H-indol-5-yl)-4-hydroxy-3-(4-(1,3-thiazol-2-ylcarbonyl)piperazin-1-yl)butanamide (81 mg) and THF (1 mL) and the reaction mixture was stirred at room temperature overnight. The reaction mixture was concentrated under reduced pressure. The residue was purified by silica gel column chromatography (NH, ethyl acetate/hexane), crystallized from 2-propanol/diisopropyl ether/hexane and recrystallized from 2-propanol/methanol to give the title compound (40 mg).

$^1$H NMR (300 MHz, CDCl$_3$) δ 2.58-2.73 (5H, m), 2.75-2.86 (1H, m), 3.24-3.38 (1H, m), 3.79-3.97 (3H, m), 3.97-4.05 (1H, m), 4.37-4.50 (1H, m), 4.50-4.62 (1H, m), 6.66 (1H, d, J=3.4 Hz), 7.17-7.25 (2H, m), 7.29 (1H, d, J=3.4 Hz), 7.39-7.48 (4H, m), 7.54 (1H, d, J=3.4 Hz), 7.70-7.75 (1H, m), 7.88 (1H, d, J=3.0 Hz).

Example 15

(4R)-1-(4-Phenoxyphenyl)-4-(4-(1,3-thiazol-2-ylcarbonyl)piperazin-1-yl)pyrrolidin-2-one A racemate (190 mg) of 1-(4-phenoxyphenyl)-4-(4-(1,3-thiazol-2-ylcarbonyl)piperazin-1-yl)pyrrolidin-2-one was optically separated by SFC (column: CHIRALPAK AS-H (trade name), 20 mmID×250 mmL, manufactured by Daicel Chemical Industries Ltd., mobile phase: carbon dioxide/methanol=600/400), and the material with a shorter retention time was crystallized from 2-propanol/diisopropyl ether/hexane and recrystallized from isopropyl acetate/heptane to give the title compound (42.4 mg). The absolute configuration was determined by X-ray crystal structure analysis.

$^1$H NMR (300 MHz, CDCl$_3$) δ 2.54-2.71 (5H, m), 2.72-2.84 (1H, m), 3.22-3.34 (1H, m), 3.75-3.86 (2H, m), 3.86-4.00 (2H, m), 4.36-4.48 (1H, ms), 4.48-4.63 (1H, m), 6.95-7.06 (4H, m), 7.06-7.14 (1H, m), 7.28-7.38 (2H, m), 7.48-7.58 (3H, m), 7.88 (1H, d, J=3.0 Hz).

Example 21

1-(4-Phenoxyphenyl)-4-(4-(pyrrolidin-1-ylcarbonyl)piperazin-1-yl)pyrrolidin-2-one To a mixture of 1-(4-phenoxyphenyl)-4-(piperazin-1-yl)pyrrolidin-2-one hydrochloride (50 mg) and THF (1.34 mL) were added triethylamine (0.093 mL), 1-pyrrolidinecarbonyl chloride (0.027 g) and N,N-dimethyl-4-aminopyridine (1.63 mg) at room temperature. The reaction mixture was stirred at room temperature for 3 days. The reaction mixture was diluted with water, saturated brine and saturated aqueous sodium hydrogen carbonate solution, and extracted with ethyl acetate. The organic layer was dried over sodium sulfate, and concentrated under reduced pressure. The residue was purified by silica gel column chromatography (NH, ethyl acetate/hexane and methanol/ethyl acetate) and triturated with ethyl acetate/hexane to give the title compound (0.027 g).

$^1$H NMR (300 MHz, CDCl$_3$) δ 1.83 (4H, dt, J=6.3, 3.5 Hz), 2.51 (4H, t, J=4.9 Hz), 2.58-2.68 (1H, m), 2.70-2.80 (1H, m), 3.18-3.28 (1H, m), 3.30-3.40 (8H, m), 3.74-3.82 (1H, m), 3.86-3.95 (1H, m), 6.95-7.06 (4H, m), 7.06-7.13 (1H, m), 7.29-7.37 (2H, m), 7.49-7.56 (2H, m).

Example 23

1-(1-(4-Fluorophenyl)-1H-indol-5-yl)-4-(4-(1,3-thiazol-2-ylcarbonyl)piperazin-1-yl)pyrrolidin-2-one (optical isomer)

A racemate (20 mg) of 1-(1-(4-fluorophenyl)-1H-indol-5-yl)-4-(4-(1,3-thiazol-2-ylcarbonyl)piperazin-1-yl)pyrrolidin-2-one was optically separated by SFC (column: CHIRALPAK AS-H (trade name), 20 mmID×250 mmL, manufactured by Daicel Chemical Industries Ltd., mobile phase: carbon dioxide/methanol/acetonitrile=600/200/200), and the material with a shorter retention time was crystallized from isopropyl acetate/heptane to give the title compound (7 mg).

$^1$H NMR (300 MHz, CDCl$_3$) δ 2.58-2.73 (5H, m), 2.74-2.86 (1H, m), 3.25-3.38 (1H, m), 3.80-3.96 (3H, m), 3.97-4.05 (1H, m), 4.38-4.50 (1H, m), 4.50-4.61 (1H, m), 6.66 (1H, d, J=3.4 Hz), 7.17-7.25 (2H, m), 7.29 (1H, d, J=3.0 Hz), 7.38-7.49 (4H, m), 7.54 (1H, d, J=3.4 Hz), 7.69-7.75 (1H, m), 7.88 (1H, d, J=3.4 Hz).

Example 52

4-(4-(1,3-Thiazol-2-ylcarbonyl)piperazin-1-yl)-1-(1-(5-(trifluoromethyl)pyrimidin-2-yl)-1H-indol-5-yl)pyrrolidin-2-one A) tert-Butyl 5-(4-hydroxy-3-(4-(1,3-thiazol-2-ylcarbonyl)piperazin-1-yl)butanamide)-1H-indole-1-carboxylate To a mixture of 4-(4-(1,3-thiazol-2-ylcarbonyl)piperazin-1-yl)dihydrofuran-2(3H)-one (300 mg) and tert-butyl 5-amino-1H-indole-1-carboxylate (372 mg) in toluene (7 mL) was added bis(trimethylaluminum)-1,4-diazabicyclo[2.2.2]octane adduct (219 mg) at room temperature. The reaction mixture was stirred at 70° C. for 1 hr. To the reaction mixture were added ethyl acetate, THF and sodium sulfate decahydrate (1.65 g). The reaction mixture was stirred at room temperature for 1 hr. The reaction mixture was filtered, and the filtrate was concentrated under reduced pressure. The residue was purified by silica gel column chromatography (methanol/ethyl acetate) to give the title compound (461 mg).

MS: [M+H]$^+$ 514.2.

B) tert-Butyl 5-(2-oxo-4-(4-(1,3-thiazol-2-ylcarbonyl)piperazin-1-yl)pyrrolidin-1-yl)-1H-indole-1-carboxylate To a mixture of tert-butyl 5-(4-hydroxy-3-(4-(1,3-thiazol-2-ylcarbonyl)piperazin-1-yl)butanamide)-1H-indole-1-carboxylate (524 mg) and tri-n-butylphosphine (0.757 mL) in THF (10 mL) was added di-tert-butylazodicarboxylate (705 mg) at room temperature. The reaction mixture was stirred at room temperature for 3 hr and concentrated. The residue was purified by silica gel column chromatography (NH, ethyl acetate/hexane) to give the title compound (423 mg).
MS: [M+H]$^+$ 496.2.

C) 1-(1H-Indol-5-yl)-4-(4-(1,3-thiazol-2-ylcarbonyl)piperazin-1-yl)pyrrolidin-2-one To a mixture of tert-butyl 5-(2-oxo-4-(4-(1,3-thiazol-2-ylcarbonyl)piperazin-1-yl)pyrrolidin-1-yl)-1H-indole-1-carboxylate (550 mg) and acetonitrile (11 mL) was added trifluoroacetic acid (1.03 mL) at room temperature. The reaction mixture was stirred at room temperature overnight and further stirred at 50° C. for 3 hr. The reaction mixture was concentrated under reduced pressure, diluted with ethyl acetate/THF, neutralized with saturated aqueous sodium hydrogen carbonate solution, and extracted with ethyl acetate/THF. The organic layer was washed with brine, dried over sodium sulfate, and concentrated under reduced pressure. The residue was purified by silica gel column chromatography (NH, methanol/ethyl acetate) to give the title compound (64 mg).
MS: [M+H]$^+$ 396.1.

D) 4-(4-(1,3-Thiazol-2-ylcarbonyl)piperazin-1-yl)-1-(1-(5-(trifluoromethyl)pyrimidin-2-yl)-1H-indol-5-yl)pyrrolidin-2-one To a mixture of 1-(1H-indol-5-yl)-4-(4-(1,3-thiazol-2-ylcarbonyl)piperazin-1-yl)pyrrolidin-2-one (32 mg) and 2-chloro-5-(trifluoromethyl)pyrimidine (44.3 mg) in DMA (1 mL) was added cesium carbonate (52.7 mg) at room temperature. The reaction mixture was heated by microwave irradiation at 150° C. for 30 min. To the reaction mixture was added water, and the mixture was extracted with ethyl acetate. The organic layer was washed with brine, dried over sodium sulfate, and concentrated under reduced pressure. The residue was purified by silica gel column chromatography (hexane/ethyl acetate and methanol/ethyl acetate) to give the title compound (8 mg).
$^1$H NMR (300 MHz, CDCl$_3$) δ 2.58-2.76 (5H, m), 2.77-2.88 (1H, m), 3.26-3.39 (1H, m), 3.78-3.98 (3H, m), 3.99-4.10 (1H, m), 4.38-4.50 (1H, m), 4.52-4.65 (1H, m), 6.74 (1H, d, J=3.4 Hz), 7.49-7.57 (2H, m), 7.81-7.91 (2H, m), 8.28 (1H, d, J=3.8 Hz), 8.75 (1H, d, J=9.0 Hz), 8.92 (2H, d, J=0.8 Hz).

Example 53

4-(4-(1,3-Thiazol-2-ylcarbonyl)piperazin-1-yl)-1-(1-(5-(trifluoromethyl)pyridin-2-yl)-1H-indol-5-yl)pyrrolidin-2-one A mixture of 1-(1H-indol-5-yl)-4-(4-(1,3-thiazol-2-ylcarbonyl)piperazin-1-yl)pyrrolidin-2-one (32 mg), 2-fluoro-5-trifluoromethylpyridine (0.049 mL), cesium carbonate (52.7 mg) and DMA (1 mL) was heated by microwave irradiation at 150° C. for 30 min. The reaction mixture was diluted with water, and extracted with ethyl acetate. The organic layer was washed with brine, dried over sodium sulfate, and concentrated under reduced pressure. The residue was purified by silica gel column chromatography (hexane/ethyl acetate and methanol/ethyl acetate) to give the title compound (25.5 mg).
$^1$H NMR (300 MHz, CDCl$_3$) δ 2.58-2.75 (5H, m), 2.77-2.89 (1H, m), 3.24-3.39 (1H, m), 3.76-3.98 (3H, m), 3.99-4.08 (1H, m), 4.37-4.50 (1H, m), 4.50-4.64 (1H, m), 6.75 (1H, d, J=3.8 Hz), 7.45-7.63 (3H, m), 7.76 (1H, d, J=3.8 Hz), 7.83 (1H, d, J=2.3 Hz), 7.89 (1H, d, J=3.0 Hz), 8.03 (1H, dd, J=8.7, 2.3 Hz), 8.38 (1H, d, J=9.0 Hz), 8.81 (1H, s).

Example 54

4-(4-(1,3-Oxazol-2-ylcarbonyl)piperazin-1-yl)-1-(4-phenoxyphenyl)pyrrolidin-2-one To a mixture of 1-(4-phenoxyphenyl)-4-(piperazin-1-yl)pyrrolidin-2-one hydrochloride (50 mg) and THF (1.3 mL) were added oxazole-2-carboxylic acid (0.023 g), triethylamine (0.130 mL), 1-hydroxybenzotriazole monohydrate (0.031 g) and 1-ethyl-3-(3-dimethylaminopropyl)carbodiimide hydrochloride (0.038 g) at room temperature. The reaction mixture was stirred at room temperature for 17 hr, diluted with water, saturated brine and saturated aqueous sodium hydrogen carbonate solution, and extracted with ethyl acetate. The organic layer was dried over sodium sulfate, and concentrated under reduced pressure. The residue was purified by silica gel column chromatography (NH, ethyl acetate/hexane) to give the title compound (0.038 g).
$^1$H NMR (300 MHz, CDCl$_3$) δ 2.50-2.70 (5H, m), 2.72-2.86 (1H, m), 3.29 (1H, quin, J=7.4 Hz), 3.72-3.86 (2H, m), 3.85-3.99 (2H, m), 4.14-4.26 (1H, m), 4.26-4.41 (1H, m), 6.95-7.05 (4H, m), 7.06-7.14 (1H, m), 7.25 (1H, s), 7.29-7.38 (2H, m), 7.49-7.57 (2H, m), 7.78 (1H, s).

Example 57

1-(4-Cyclopropylphenyl)-4-(4-(1,3-thiazol-2-ylcarbonyl)piperazin-1-yl)pyrrolidin-2-one To a mixture of 4-cyclopropylaniline (16.0 mg) and 4-(4-(1,3-thiazol-2-ylcarbonyl)piperazin-1-yl)dihydrofuran-2(3H)-one (33.8 mg) and THF (1 mL) was added bis(trimethylaluminum)-1,4-diazabicyclo[2.2.2]octane adduct (24.6 mg) at room temperature, and the mixture was stirred by using microwave at 100° C. for 20 min. To the reaction mixture was added sodium sulfate decahydrate (200 mg), and the mixture was stirred at room temperature for 60 min. To the reaction mixture was added THF (2 mL), and the mixture was filtered through Celite, and the organic solvent was vaporized by an air spraying apparatus. The residue was purified by HPLC (C18, mobile phase: water/acetonitrile (10 mM NH$_4$HCO$_3$-containing system)), and the solvent was vaporized by an air spraying apparatus. The residue was dissolved in THF (1 mL), di-tert-butylazodicarboxylate (29.1 mg) and a triphenylphosphine polymer support (3.2 mmol/g, 39.5 mg) were added, and the mixture was stirred at room temperature overnight. The insoluble material was filtered, and the organic solvent was vaporized by an air spraying apparatus. The residue was purified by HPLC (C18, mobile phase: water/acetonitrile (10 mM NH$_4$HCO$_3$-containing system)) to give the title compound (7.7 mg).
MS: [M+H]$^+$ 397.1.

Example 60

1-(4-(Benzyloxy)phenyl)-4-(4-(1,3-thiazol-2-ylcarbonyl)piperazin-1-yl)pyrrolidin-2-one To a mixture of 4-(benzyloxy)aniline (23.9 mg) and 4-(4-(1,3-thiazol-2-ylcarbonyl)piperazin-1-yl)dihydrofuran-2(3H)-one (33.8 mg) in THF (1 mL) was added bis(trimethylaluminum)-1,4-diazabicyclo[2.2.2]octane adduct (24.6 mg) at room temperature, and the mixture was stirred by using microwave at 100° C. for 20 min. To the reaction mixture was added sodium sulfate decahydrate (200 mg), and the mixture was stirred at room temperature for 60 min. To the reaction mixture was added THF (2 mL), and the mixture was filtered through Celite. The organic solvent was vaporized by an air spraying apparatus. The residue was purified by HPLC (C18, mobile phase: water/acetonitrile (10 mM $NH_4HCO_3$-containing system)), and the solvent was vaporized by an air spraying apparatus. The residue was dissolved in THF (1 mL), di-tert-butylazodicarboxylate (16.2 mg) and a triphenylphosphine polymer support (3.2 mmol/g, 50.2 mg) were added, and the mixture was stirred at room temperature overnight. The insoluble material was filtered, and the organic solvent was vaporized by an air spraying apparatus. The residue was purified by HPLC (C18, mobile phase: water/acetonitrile (10 mM $NH_4HCO_3$-containing system)) to give the title compound (2.8 mg).
MS: $[M+H]^+$ 463.0.

Example 62

1-(Biphenyl-3-yl)-4-(4-(1,3-thiazol-2-ylcarbonyl)piperazin-1-yl)pyrrolidin-2-one To a mixture of 3-aminobiphenyl (20.9 mg) and 4-(4-(1,3-thiazol-2-ylcarbonyl)piperazin-1-yl)dihydrofuran-2(3H)-one (33.8 mg) in THF (1 mL) was added bis(trimethylaluminum)-1,4-diazabicyclo[2.2.2]octane adduct (24.6 mg) at room temperature, and the mixture was stirred by using microwave at 100° C. for 20 min. To the reaction mixture was added sodium sulfate decahydrate (200 mg), and the mixture was stirred at room temperature for 60 min. To the reaction mixture was added THF (2 mL), and the mixture was filtered through Celite. The organic solvent was vaporized by an air spraying apparatus. The residue was purified by HPLC (C18, mobile phase: water/acetonitrile (10 mM $NH_4HCO_3$-containing system)) and the solvent was vaporized by an air spraying apparatus. The residue was dissolved in THF (1 mL), di-tert-butylazodicarboxylate (26.0 mg) and a triphenylphosphine polymer support (3.2 mmol/g, 35.3 mg) were added, and the mixture was stirred at room temperature overnight. The insoluble material was filtrated, and the organic solvent was vaporized by an air spraying apparatus. The residue was purified by HPLC (C18, mobile phase: water/acetonitrile (10 mM $NH_4HCO_3$-containing system)) to give the title compound (4.9 mg).
MS: $[M+H]^+$ 433.0.

Example 72

1-(Dibenzo[b,d]furan-3-yl)-4-(4-(1,3-thiazol-2-ylcarbonyl)piperazin-1-yl)pyrrolidin-2-one To a mixture of dibenzo[b,d]furan-3-amine (22.0 mg) and 4-(4-(1,3-thiazol-2-ylcarbonyl)piperazin-1-yl)dihydrofuran-2(3H)-one (33.8 mg) in THF (1 mL) was added bis(trimethylaluminum)-1,4-diazabicyclo[2.2.2]octane adduct (24.6 mg) at room temperature, and the mixture was stirred by using microwave at 100° C. for 20 min. To the reaction mixture was added sodium sulfate decahydrate (200 mg), and the mixture was stirred at room temperature for 60 min. To the reaction mixture was added THF (2 mL), and the mixture was filtered through Celite. The organic solvent was vaporized by an air spraying apparatus. The residue was purified by HPLC (C18, mobile phase: water/acetonitrile (10 mM $NH_4HCO_3$-containing system)), and the solvent was vaporized by an air spraying apparatus. The residue was dissolved in THF (1 mL), di-tert-butylazodicarboxylate (18.9 mg) and triphenylphosphine polymer support (3.2 mmol/g, 25.7 mg) were added, and the mixture was stirred at room temperature overnight. The insoluble material was filtered, and the organic solvent was vaporized by an air spraying apparatus. The residue was purified by HPLC (C18, mobile phase: water/acetonitrile (10 mM $NH_4HCO_3$-containing system)) to give the title compound (3.3 mg).
MS: $[M+H]^+$ 447.0.

Example 79

1-(3-(4-Fluorophenoxy)phenyl)-4-(4-(1,3-thiazol-2-ylcarbonyl)piperazin-1-yl)pyrrolidin-2-one A) 1-(3-Iodophenyl)-4-methoxy-1H-pyrrole-2(5H)-one To a mixture of 3-iodoaniline (5.32 g) and tetrabutylammonium iodide (0.897 g) in acetonitrile (20 mL) was added a mixture of methyl 4-chloro-3-methoxy-2-(E)-butenoate (4.13 mL) and acetonitrile (20 mL). To the reaction mixture was added a mixture of triethylamine (3.72 mL) and acetonitrile (10 mL). The reaction mixture was stirred overnight at 50° C. To the reaction mixture were added methyl 4-chloro-3-methoxy-2-(E)-butenoate (1.65 mL) and triethylamine (1.69 mL). The reaction mixture was stirred at 50° C. for 5 hr and cooled to room temperature. The reaction mixture was adjusted to pH 3 with concentrated hydrochloric acid and extracted with ethyl acetate. The organic layer was dried over sodium sulfate, and concentrated under reduced pressure. To the residue were added toluene (40 mL) and acetic acid (1.0 mL) at room temperature. The reaction mixture was heated at 50° C. for 1.5 hr. The reaction mixture was concentrated under reduced pressure and crystallized from methanol/diisopropylether to give the title compound (3.41 g).
MS: $[M+H]^+$ 316.0.

B) 4-Hydroxy-1-(3-iodophenyl)-1H-pyrrole-2(5H)-one

A mixture of 1-(3-iodophenyl)-4-methoxy-1H-pyrrole-2(5H)-one (3.41 g) and concentrated hydrochloric acid (15 mL) was stirred at 50° C. for 3 hr. The precipitate was collected by filtration, and washed with water to give the title compound (3.09 g).
MS: $[M-H]^-$ 300.1.

C) 1-(3-Iodophenyl)-4-(4-(1,3-thiazol-2-ylcarbonyl)piperazin-1-yl)pyrrolidin-2-one To a mixture of 4-hydroxy-1-(3-iodophenyl)-1H-pyrrole-2(5H)-one (2 g), piperazin-1-yl(thiazol-2-yl)methanone (1.31 g) and acetic acid (1.14 mL) in THF (30 mL) was added sodium cyanoborohydride (1.25 g) at room temperature. The reaction mixture was stirred under a nitrogen atmosphere at 50° C. for 2 hr. The reaction mixture was poured into aqueous potassium carbonate solution, and the mixture was extracted with ethyl acetate. The organic layer was washed with brine, dried over sodium sulfate, and concentrated under reduced pressure. The residue was purified by silica gel column chromatography (NH, ethyl acetate/hexane) to give the title compound (2.14 g).
MS: $[M+H]^+$ 483.1.

D) 1-(3-(4-Fluorophenoxy)phenyl)-4-(4-(1,3-thiazol-2-ylcarbonyl)piperazin-1-yl)pyrrolidin-2-one A mixture of 1-(3-iodophenyl)-4-(4-(1,3-thiazol-2-ylcarbonyl)piperazin-1-yl)pyrrolidin-2-one (50 mg), 4-fluorophenol (17.4 mg), copper iodide (I) (3.95 mg), picolinic acid (5.10 mg) and tripotassium phosphate (66.0 mg) in dimethyl sulfoxide (3 mL) was heated by microwave irradiation at 120° C. for 1 hr. The reaction mixture was poured into water and extracted with ethyl acetate. The organic layer was washed with brine, dried over sodium sulfate, and concentrated under reduced pressure. The residue was purified by silica gel column chromatography (NH, ethyl acetate/hexane) and further collected by HPLC (C18, mobile phase: water/acetonitrile (0.1% trifluoroacetic acid-containing system)). To the obtained fraction was added saturated aqueous sodium hydrogen carbonate solution, and the mixture was extracted with ethyl acetate. The organic layer was dried over sodium sulfate, and concentrated under reduced pressure to give the title compound (16.3 mg).
$^1$H NMR (300 MHz, CDCl$_3$) δ 2.54-2.69 (5H, m), 2.71-2.88 (1H, m), 3.26 (1H, quin, J=7.5 Hz), 3.72-3.98 (4H, m), 4.34-4.64 (2H, m), 6.71-6.77 (1H, m), 6.96-7.09 (4H, m), 7.28-7.33 (3H, m), 7.55 (1H, d, J=3.4 Hz), 7.88 (1H, d, J=3.0 Hz).

Example 80

(4R)-4-(4-(1,3-Thiazol-2-ylcarbonyl)piperazin-1-yl)-1-(1-(5-(trifluoromethyl)pyrimidin-2-yl)-1H-indol-5-yl)pyrrolidin-2-one

A) 5-Nitro-1-(5-(trifluoromethyl)pyrimidin-2-yl)-1H-indole

To a mixture of 5-nitroindole (250 mg) and 2-chloro-5-(trifluoromethyl)pyrimidine (310 mg) in DMA (10 mL) was added cesium carbonate (754 mg) at room temperature. The reaction mixture was stirred at 100° C. for 2 hr. The reaction mixture was diluted with water, and extracted with ethyl acetate. The organic layer was washed with brine, dried over sodium sulfate, and concentrated under reduced pressure. The residue was triturated with hexane to give the title compound (390 mg).
MS: [M+H]$^+$ 309.1.

B) 1-(5-(Trifluoromethyl)pyrimidin-2-yl)-1H-indole-5-amine

A mixture of 5-nitro-1-(5-(trifluoromethyl)pyrimidin-2-yl)-1H-indole (390 mg) and palladium carbon (10% Pd, 50% water-moistened, 80 mg) in THF (4 mL)/ethanol (4 mL) was stirred at room temperature under a hydrogen atmosphere for 3 hr. The reaction mixture was filtered, and the filtrate was concentrated under reduced pressure to give the title compound (315 mg).
MS: [M+H]$^+$ 279.0.

C) (4R)-4-(4-(1,3-Thiazol-2-ylcarbonyl)piperazin-1-yl)dihydrofuran-2(3H)-one A racemate (400 mg) of 4-(4-(1,3-thiazol-2-ylcarbonyl)piperazin-1-yl)dihydrofuran-2(3H)-one was optically separated by SFC (column: CHIRALPAK AD-H (trade name), 50 mmID×500 mmL, Daicel Chemical Industries Ltd., mobile phase: carbon dioxide/methanol/acetonitrile=600/200/200) to give the title compound (190 mg) with a shorter retention time. The absolute configuration was determined by X-ray crystal structure analysis.
MS: [M+H]$^+$ 282.0.

D) (R)-4-Hydroxy-3-(4-(1,3-thiazol-2-ylcarbonyl)piperazin-1-yl)-N-(1-(5-(trifluoromethyl)pyrimidin-2-yl)-1H-indol-5-yl)butanamide To a mixture of (4R)-4-(4-(1,3-thiazol-2-ylcarbonyl)piperazin-1-yl)dihydrofuran-2(3H)-one (150 mg) and 1-(5-(trifluoromethyl)pyrimidin-2-yl)-1H-indole-5-amine (223 mg) in toluene (3 mL) was added bis(trimethylaluminum)-1,4-diazabicyclo[2.2.2]octane adduct (103 mg) at room temperature, and the mixture was stirred at 70° C. for 2 hr. To the reaction mixture was added ethyl acetate and sodium sulfate decahydrate, and the mixture was stirred at room temperature for 2 hr. The reaction mixture was filtered, and the filtrate was concentrated under reduced pressure. The residue was purified by silica gel column chromatography (methanol/ethyl acetate) to give the title compound (217 mg).
MS: [M+H]$^+$ 560.3.

E) (4R)-4-(4-(1,3-Thiazol-2-ylcarbonyl)piperazin-1-yl)-1-(1-(5-(trifluoromethyl)pyrimidin-2-yl)-1H-indol-5-yl)pyrrolidin-2-one To a mixture of (R)-4-hydroxy-3-(4-(1,3-thiazol-2-ylcarbonyl)piperazin-1-yl)-N-(1-(5-(trifluoromethyl)pyrimidin-2-yl)-1H-indol-5-yl)butanamide (200 mg) and tri-n-butylphosphine (0.177 mL) in THF (3 mL) was added di-tert-butylazodicarboxylate (165 mg) at room temperature. The reaction mixture was stirred at room temperature for 3 hr and concentrated. The residue was purified by silica gel column chromatography (NH, ethyl acetate/hexane), triturated with diisopropylether, and recrystallized from THF/methanol/ethanol/water to give the title compound (75 mg).
$^1$H NMR (300 MHz, CDCl$_3$) δ 2.56-2.76 (5H, m), 2.77-2.88 (1H, m), 3.25-3.39 (1H, m), 3.77-3.99 (3H, m), 4.00-4.09 (1H, m), 4.38-4.50 (1H, m), 4.52-4.64 (1H, m), 6.74 (1H, d, J=3.8 Hz), 7.50-7.59 (2H, m), 7.86 (2H, dd, J=14.3, 2.6 Hz), 8.28 (1H, d, J=3.8 Hz), 8.75 (1H, d, J=9.0 Hz), 8.92 (2H, s).

Example 85

1-(1-(4-Fluorophenyl)-1H-indazol-5-yl)-4-(4-(1,3-thiazol-2-ylcarbonyl)piperazin-1-yl)pyrrolidin-2-one

A) 1-(4-Fluorophenyl)-5-nitro-1H-indazole

A mixture of copper acetate (II) (730 mg), 5-nitro-1H-indazole (500 mg) and 4-fluorophenylboronic acid (643 mg) in THF (5 mL)/triethylamine (0.5 mL)/pyridine (1 mL) was stirred at room temperature over the weekend. To the reaction mixture was added aqueous ammonia, and the precipitate was collected by filtration. The obtained solid was successively washed with water and diisopropyl ether, purified by silica gel column chromatography (NH, ethyl acetate/hexane) and recrystallized from toluene/hexane/THF to give the title compound (400 mg).
MS: [M+H]$^+$ 258.0.

B) 1-(4-Fluorophenyl)-1H-indazole-5-amine

A mixture of 1-(4-fluorophenyl)-5-nitro-1H-indazole (390 mg) and palladium carbon (10% Pd, 50% water-moistened, 80 mg) in THF (4 mL)/ethanol (4 mL) was stirred at room temperature under a hydrogen atmosphere for 3 hr. The reaction mixture was filtered, and the filtrate was concentrated under reduced pressure to give the title compound (317 mg).

MS: [M+H]$^+$ 228.1.

C) N-(1-(4-Fluorophenyl)-1H-indazol-5-yl)-4-hydroxy-3-(4-(1,3-thiazol-2-ylcarbonyl)piperazin-1-yl) butanamide To a mixture of 4-(4-(1,3-thiazol-2-ylcarbonyl)piperazin-1-yl)dihydrofuran-2(3H)-one (50 mg) and 1-(4-fluorophenyl)-1H-indazole-5-amine (64.6 mg) in toluene (1 mL) was added bis(trimethylaluminum)-1,4-diazabicyclo[2.2.2]octane adduct (36.4 mg) at room temperature, and the mixture was stirred at 80° C. for 1 hr. To the reaction mixture were added ethyl acetate, THF and sodium sulfate decahydrate (275 mg), and the mixture was stirred at room temperature for 1 hr. The reaction mixture was filtered, and the filtrate was concentrated under reduced pressure. The residue was purified by silica gel column chromatography (methanol/ethyl acetate) to give the title compound (55.6 mg).

MS: [M+H]$^+$ 509.2.

D) 1-(1-(4-Fluorophenyl)-1H-indazol-5-yl)-4-(4-(1,3-thiazol-2-ylcarbonyl)piperazin-1-yl)pyrrolidin-2-one To a mixture of N-(1-(4-fluorophenyl)-1H-indazol-5-yl)-4-hydroxy-3-(4-(1,3-thiazol-2-ylcarbonyl)piperazin-1-yl) butanamide (75 mg) and tri-n-butylphosphine (0.054 mL) in THF (1.1 mL) was added di-tert-butylazodicarboxylate (50.3 mg) at room temperature. The reaction mixture was stirred at room temperature for 3 hr and concentrated. The residue was purified by silica gel column chromatography (NH, ethyl acetate/hexane) to give the title compound (31 mg).

$^1$H NMR (300 MHz, CDCl$_3$) δ 2.57-2.76 (5H, m), 2.77-2.89 (1H, m), 3.27-3.40 (1H, m), 3.78-3.97 (3H, m), 3.99-4.07 (1H, m), 4.37-4.50 (1H, m), 4.52-4.66 (1H, m), 7.20-7.25 (2H, m), 7.55 (1H, d, J=3.4 Hz), 7.63-7.71 (3H, m), 7.74-7.80 (1H, m), 7.84 (1H, d, J=1.5 Hz), 7.89 (1H, d, J=3.0 Hz), 8.17 (1H, d, J=0.8 Hz).

Example 77

1-(3-((4-Fluorophenyl)amino)phenyl)-4-(4-(1,3-thiazol-2-ylcarbonyl)piperazin-1-yl)pyrrolidin-2-one A mixture of 1-(3-iodophenyl)-4-(4-(1,3-thiazol-2-ylcarbonyl)piperazin-1-yl)pyrrolidin-2-one (50 mg), 4-fluoroaniline (14.91 μl), dicyclohexyl-(3,6-dimethoxy-2-(2,4,6-tri (propan-2-yl)phenyl)phenyl)phosphane (2.78 mg), chloro[2-(dicyclohexylphosphino)-3,6-dimethoxy-2',4',6'-tri-i-propyl-1,1'-biphenyl][2-(2-aminoethyl)phenyl]palladium (II) (4.14 mg), cesium carbonate (101 mg) and 2-methyl-2-butanol (3 mL) was heated at 120° C. for 1 hr under microwave irradiation. The mixture was poured into water and extracted with ethyl acetate. The organic layer was separated, washed with brine, dried over sodium sulfate and concentrated in vacuo. The residue was purified by column chromatography (NH silica gel, ethyl acetate/hexane) to give the title compound (41.1 mg).

MS: [M+H]$^+$ 466.0.

Example 88

4-(4-(1,3-Thiazol-2-ylcarbonyl)piperazin-1-yl)-1-(4-(trifluoromethyl)phenyl)pyrrolidin-2-one A) 4-(4-(1,3-Thiazol-2-ylcarbonyl)piperazin-1-yl) pyrrolidin-2-one To a mixture of tert-butyl 4-hydroxy-2-oxo-2,5-dihydro-1H-pyrrole-1-carboxylate (0.87 g) in ethyl acetate (10.95 mL) was added 4 M hydrogen chloride in ethyl acetate (10.92 mL) at room temperature. The mixture was stirred at room temperature for 1 hr. The mixture was concentrated in vacuo. To the residue were added 2-propanol (19.70 mL), piperazin-1-yl(1,3-thiazol-2-yl)methanone (0.861 g), and acetic acid (2.189 mL) at room temperature. The mixture was heated at 50° C. for 5.5 hr. To the mixture was added sodium cyanoborohydride (0.823 g) at room temperature. The mixture was stirred at room temperature for 15 hr. The mixture was diluted with 2 M aqueous sodium hydroxide solution (19.7 mL), water, and brine at 0° C., extracted with ethyl acetate/THF, dried over magnesium sulfate, filtered, concentrated in vacuo, and purified by column chromatography (NH silica gel, ethyl acetate/hexane and then methanol/ethyl acetate) to yield the title compound (0.375 g) after triturating with ethyl acetate/hexane.

MS: [M+H]$^+$ 281.1.

B) 4-(4-(1,3-Thiazol-2-ylcarbonyl)piperazin-1-yl)-1-(4-(trifluoromethyl)phenyl)pyrrolidin-2-one To a mixture of 4-(4-(1,3-thiazol-2-ylcarbonyl)piperazin-1-yl)pyrrolidin-2-one (0.03 g) in 2-methyl-2-butanol (1.070 mL) were added 4-bromobenzotrifluoride (0.030 mL), 2-(di-t-butylphosphino)-3,6-dimethoxy-2'-4'-6'-tri-i-propyl-1,1'-biphenyl (5.19 mg), tris(dibenzylideneacetone)dipalladium (4.90 mg), and cesium carbonate (0.087 g) at room temperature. The mixture was heated at 130° C. for 1 day in a sealed tube under nitrogen atmosphere. The mixture was diluted with water, brine, and saturated aqueous sodium hydrogen carbonate solution at room temperature, extracted with ethyl acetate, dried over magnesium sulfate, filtered, concentrated in vacuo, and purified by column chromatography (NH silica gel, ethyl acetate/hexane) to yield a crude material. The crude material was purified by preparative HPLC (C18, mobile phase: water in acetonitrile containing 0.1% trifluoroacetic acid), concentrated in vacuo, diluted with water, brine, and saturated aqueous sodium hydrogen carbonate solution, extracted with ethyl acetate, dried over sodium sulfate, filtered, and concentrated in vacuo to yield the title compound (3.40 mg).

$^1$H NMR (300 MHz, CDCl$_3$) δ 2.53-2.91 (6H, m), 3.23-3.39 (1H, m), 3.76-4.05 (4H, m), 4.38-4.65 (2H, m), 7.55 (1H, d, J=3.2 Hz), 7.59-7.68 (2H, m), 7.70-7.78 (2H, m), 7.88 (1H, d, J=3.2 Hz).

Example 109

4-(4-(1,3-Thiazol-2-ylcarbonyl)piperazin-1-yl)-1-(1-(2-(trifluoromethyl)pyridin-4-yl)-1H-indol-5-yl)pyrrolidin-2-one A mixture of 1-(1H-indol-5-yl)-4-(4-(1,3-thiazol-2-ylcarbonyl)piperazin-1-yl)pyrrolidin-2-one (30 mg), 4-iodo-2-(trifluoromethyl)pyridine (31.1 mg), potassium carbonate (20.97 mg), N,N'-dimethylethane-1,2-diamine (8.14 μl), copper(I) iodide (14.45 mg) and dimethyl sulfoxide (1 mL)

was heated at 120° C. for 1 hr under microwave irradiation. The reaction mixture was quenched with water and extracted with ethyl acetate. The organic layer was separated, washed with water and brine successively, dried over sodium sulfate and concentrated in vacuo. The residue was triturated with ethyl acetate to give the title compound (20.10 mg).

$^1$H NMR (300 MHz, CDCl$_3$) δ 2.56-2.76 (5H, m), 2.76-2.88 (1H, m), 3.28-3.40 (1H, m), 3.76-3.97 (3H, m), 3.98-4.08 (1H, m), 4.37-4.49 (1H, m), 4.51-4.65 (1H, m), 6.79 (1H, d, J=3.4 Hz), 7.44 (1H, d, J=3.4 Hz), 7.53-7.59 (2H, m), 7.63-7.72 (2H, m), 7.84 (2H, dd, J=5.3, 2.3 Hz), 7.89 (1H, d, J=3.0 Hz), 8.83 (1H, d, J=5.7 Hz).

Example 114

1-(1-(4-Fluorobenzyl)-1H-indazol-5-yl)-4-(4-(1,3-thiazol-2-ylcarbonyl)piperazin-1-yl)pyrrolidin-2-one A) tert-Butyl 5-((4-hydroxy-3-(4-(1,3-thiazol-2-ylcarbonyl)piperazin-1-yl)butanoyl)amino)-1H-indazole-1-carboxylate To a mixture of 4-(4-(1,3-thiazol-2-ylcarbonyl)piperazin-1-yl)dihydrofuran-2(3H)-one (300 mg) and tert-butyl 5-amino-1H-indazole-1-carboxylate (373 mg) in toluene (7 mL) was added bis(trimethylaluminum)-1,4-diazabicyclo[2.2.2]octane adduct (219 mg) at room temperature and the mixture was stirred at 70° C. for 2 hr. To the mixture were added ethyl acetate and sodium sulfate decahydrate (1649 mg) and the mixture was stirred at room temperature for 2 hr. The insoluble material was removed by filtration, and the filtrate was concentrated in vacuo. The residue was purified by column chromatography (silica gel, methanol/ethyl acetate) to give the title compound (482 mg).

MS: [M+H]$^+$ 515.2.

B) tert-Butyl 5-(2-oxo-4-(4-(1,3-thiazol-2-ylcarbonyl)piperazin-1-yl)pyrrolidin-1-yl)-1H-indazole-1-carboxylate To a solution of tert-butyl 5-((4-hydroxy-3-(4-(1,3-thiazol-2-ylcarbonyl)piperazin-1-yl)butanoyl)amino)-1H-indazole-1-carboxylate (482 mg) and tri-n-butyl phosphine (0.463 mL) in THF (9 mL) was added di-tert-butylazodicarboxylate (431 mg) at ambient temperature (water bath). The mixture was stirred at ambient temperature for 3 h. The mixture was concentrated and purified by column chromatography (NH silica gel, ethyl acetate/hexane) to give the title compound (372 mg).

MS: [M+H]$^+$ 497.2.

C) 1-(1H-Indazol-5-yl)-4-(4-(1,3-thiazol-2-ylcarbonyl)piperazin-1-yl)pyrrolidin-2-one To a solution of tert-butyl 5-(2-oxo-4-(4-(1,3-thiazol-2-ylcarbonyl)piperazin-1-yl)pyrrolidin-1-yl)-1H-indazole-1-carboxylate (759 mg) in acetonitrile (8 mL) was added trifluoroacetic acid (0.577 mL) at ambient temperature. The mixture was stirred at 60° C. for 5 hr. The mixture was diluted with ethyl acetate, neutralized with saturated aqueous sodium hydrogen carbonate solution at 0° C. and extracted with ethyl acetate. The organic layer was separated, washed with brine, dried over sodium sulfate and concentrated in vacuo. The residue was triturated with toluene to give the title compound (176 mg).

MS: [M+H]$^+$ 397.1.

D) 1-(1-(4-Fluorobenzyl)-1H-indazol-5-yl)-4-(4-(1,3-thiazol-2-ylcarbonyl)piperazin-1-yl)pyrrolidin-2-one To a solution of 1-(1H-indazol-5-yl)-4-(4-(1,3-thiazol-2-ylcarbonyl)piperazin-1-yl)pyrrolidin-2-one (30 mg) and 4-fluorobenzyl bromide (0.019 mL) in DMF (1 mL) was added cesium carbonate (37.0 mg, 0.11 mmol) at ambient temperature. The mixture was stirred at 80° C. for 3 hr. The reaction mixture was quenched with water and extracted with ethyl acetate. The organic layer was separated, washed with water and brine successively, dried over sodium sulfate and concentrated in vacuo. The residue was purified by column chromatography (silica gel, methanol/ethyl acetate). The residue was purified by preparative HPLC (C18, mobile phase: water in acetonitrile containing 0.1% trifluoroacetic acid). The desired fraction was neutralized with saturated aqueous sodium hydrogen carbonate solution and extracted with ethyl acetate. The organic layer was separated, dried over magnesium sulfate and concentrated in vacuo to give the title compound (2.1 mg).

$^1$H NMR (300 MHz, CDCl$_3$) δ 2.52-2.73 (5H, m), 2.75-2.88 (1H, m), 3.25-3.37 (1H, m), 3.76-3.94 (3H, m), 3.94-4.02 (1H, m), 4.34-4.49 (1H, m), 4.49-4.64 (1H, m), 5.56 (2H, s), 6.93-7.02 (2H, m), 7.15 (2H, dd, J=8.4, 5.4 Hz), 7.30-7.35 (1H, m), 7.55 (1H, d, J=3.2 Hz), 7.66 (1H, dd, J=9.0, 1.9 Hz), 7.75 (1H, d, J=1.9 Hz), 7.88 (1H, d, J=3.2 Hz), 8.02 (1H, s).

Example 139

1-(3-(2-Methylpyridin-3-yl)phenyl)-4-(4-(1,3-thiazol-2-ylcarbonyl)piperazin-1-yl)pyrrolidin-2-one A mixture of 1-(3-iodophenyl)-4-(4-(1,3-thiazol-2-ylcarbonyl)piperazin-1-yl)pyrrolidin-2-one (50 mg), 2-methyl-3-(4,4,5,5-tetramethyl-1,3,2-dioxaborolan-2-yl)pyridine (34.1 mg), bis(di-tert-butyl(4-dimethylaminophenyl)phosphine)dichloropalladium(II) (7.34 mg), cesium carbonate (67.6 mg) and toluene (3 mL)/water (1 mL) was heated at 100° C. for 15 min under microwave irradiation. The organic layer was separated, purified by column chromatography (NH silica gel, methanol/ethyl acetate) and recrystallized from ethyl acetate/hexane to give the title compound (32.7 mg).

$^1$H NMR (300 MHz, CDCl$_3$) δ 2.52 (3H, s), 2.57-2.72 (5H, m), 2.74-2.85 (1H, m), 3.29 (1H, t, J=7.2 Hz), 3.77-4.04 (4H, m), 4.36-4.61 (2H, m), 7.08-7.15 (1H, m), 7.19 (1H, dd, J=7.7, 4.9 Hz), 7.45 (1H, t, J=7.9 Hz), 7.50-7.55 (2H, m), 7.57-7.65 (2H, m), 7.88 (1H, d, J=3.2 Hz), 8.51 (1H, dd, J=4.8, 1.8 Hz).

Example 141

4-(4-(1,3-Thiazol-2-ylcarbonyl)piperazin-1-yl)-1-(1-(5-(trifluoromethyl)pyrimidin-2-yl)-2,3-dihydro-1H-indol-5-yl)pyrrolidin-2-one A) 1-(5-(Trifluoromethyl)pyrimidin-2-yl)indolin-5-amine A mixture of 5-nitro-1-(5-(trifluoromethyl)pyrimidin-2-yl)-1H-indole (2.88 g) and palladium on carbon (10% Pd, 50% wet, 576 mg) in THF (15 mL)/ethyl acetate (25 mL)/ethanol (15 mL) was hydrogenated under balloon pressure at ambient temperature for 5 hr. The catalyst was removed by filtration and the filtrate was concentrated in vacuo. The residue was purified by column chromatography (NH silica gel, ethyl acetate/hexane) to give the title compound (500 mg).

MS: [M+H]$^+$ 281.1.

B) 4-Hydroxy-3-(4-(1,3-thiazol-2-ylcarbonyl)piperazin-1-yl)-N-(1-(5-(trifluoromethyl)pyrimidin-2-yl)-2,3-dihydro-1H-indol-5-yl)butanamide To a mixture of 4-(4-(1,3-thiazol-2-ylcarbonyl)piperazin-1-yl)dihydrofuran-2(3H)-one (50 mg) and 1-(5-(trifluoromethyl)pyrimidin-2-yl)indolin-5-amine (69.7 mg) in toluene (1 mL) was added bis(trimethylaluminum)-1,4-diazabicyclo[2.2.2]octane adduct (31.9 mg) at room temperature and the mixture was stirred at 70° C. for 2 hr. To the mixture were added ethyl acetate and sodium sulfate decahydrate (223 mg) and the mixture was stirred at room temperature for 2 hr. The insoluble material was removed by filtration, and the filtrate was concentrated in vacuo. The residue was purified by column chromatography (silica gel, methanol/ethyl acetate) to give the title compound (64.0 mg).

MS: [M+H]$^+$ 562.2.

C) 4-(4-(1,3-Thiazol-2-ylcarbonyl)piperazin-1-yl)-1-(1-(5-(trifluoromethyl)pyrimidin-2-yl)-2,3-dihydro-1H-indol-5-yl)pyrrolidin-2-one To a solution of 4-hydroxy-3-(4-(1,3-thiazol-2-ylcarbonyl)piperazin-1-yl)-N-(1-(5-(trifluoromethyl)pyrimidin-2-yl)-2,3-dihydro-1H-indol-5-yl)butanamide (64 mg) and tri-n-butyl phosphine (0.051 mL) in THF (1 mL) was added di-tert-butylazodicarboxylate (47.2 mg) at ambient temperature (water bath). The mixture was stirred at ambient temperature for 3 hr. The mixture was concentrated and purified by column chromatography (NH silica gel, ethyl acetate/hexane) to give the title compound (31.0 mg) after triturating with diisopropyl ether/2-propanol.

$^1$H NMR (300 MHz, CDCl$_3$) δ 2.57-2.72 (5H, m), 2.73-2.85 (1H, m), 3.19-3.35 (3H, m), 3.76-3.87 (2H, m), 3.88-4.01 (2H, m), 4.30 (2H, t, J=8.5 Hz), 4.37-4.49 (1H, m), 4.50-4.62 (1H, m), 7.23 (1H, dd, J=8.9, 2.4 Hz), 7.55 (1H, d, J=3.0 Hz), 7.68 (1H, s), 7.88 (1H, d, J=3.4 Hz), 8.38 (1H, d, J=9.0 Hz), 8.68 (2H, s).

Example 145

1-(2',6'-Difluorobiphenyl-3-yl)-4-(4-(1,3-thiazol-2-ylcarbonyl)piperazin-1-yl)pyrrolidin-2-one A mixture of 1-(3-iodophenyl)-4-(4-(1,3-thiazol-2-ylcarbonyl)piperazin-1-yl)pyrrolidin-2-one (50 mg), (2,6-difluorophenyl)boronic acid (65.5 mg), sodium hydrogen carbonate (34.8 mg), 2-dicyclohexylphosphino-2',6'-dimethoxybiphenyl (8.51 mg) and chloro(2-dicyclohexylphosphino-2',6'-dimethoxy-1,1'-biphenyl)(2'-amino-1,1'-biphenyl-2-yl) palladium(II) (14.94 mg) in 1,2-dimethoxyethane (2 mL) and water (0.2 mL) was heated at 100° C. for 10 min under microwave irradiation. The mixture was purified by column chromatography (NH silica gel, methanol/ethyl acetate) to give the title compound (30.0 mg).

$^1$H NMR (300 MHz, CDCl$_3$) δ 2.52-2.71 (5H, m), 2.73-2.86 (1H, m), 3.28 (1H, quin, J=7.6 Hz), 3.76-4.04 (4H, m), 4.36-4.61 (2H, m), 6.98 (2H, t, J=7.9 Hz), 7.27-7.35 (2H, m), 7.46 (1H, t, J=7.9 Hz), 7.54 (1H, d, J=3.2 Hz), 7.62 (1H, s), 7.72 (1H, ddd, J=8.3, 2.3, 0.9 Hz), 7.88 (1H, d, J=3.2 Hz).

Example 147

1-Benzyl-4-(4-(1,3-thiazol-2-ylcarbonyl)piperazin-1-yl)pyrrolidin-2-one

To a solution of 4-(4-(1,3-thiazol-2-ylcarbonyl)piperazin-1-yl)pyrrolidin-2-one (50 mg) in DMF (1 mL) was added sodium hydride (60% dispersion in oil, 10.27 mg) at 0° C. The mixture was stirred at 0° C. for 20 min. To a mixture was added alpha-bromotoluene (0.025 mL) at 0° C. The mixture was stirred at room temperature for 2 h. The reaction mixture was diluted with ethyl acetate, quenched with water and extracted with ethyl acetate. The organic layer was separated, washed with water and brine successively, dried over sodium sulfate and concentrated in vacuo. The residue was purified by column chromatography (NH silica gel, ethyl acetate/hexane) to give the title compound (20.00 mg) after triturating with hexane/2-propyl acetate.

$^1$H NMR (300 MHz, CDCl$_3$) δ 2.41-2.55 (5H, m), 2.56-2.69 (1H, m), 3.03-3.14 (1H, m), 3.15-3.23 (1H, m), 3.35 (1H, dd, J=9.3, 7.4 Hz), 3.68-3.78 (1H, m), 3.78-3.90 (1H, m), 4.29-4.41 (1H, m), 4.41-4.54 (3H, m), 7.21-7.25 (2H, m), 7.28-7.39 (3H, m), 7.53 (1H, d, J=3.2 Hz), 7.86 (1H, d, J=3.2 Hz).

Example 149

1-(3-(5-Methylpyridin-2-yl)phenyl)-4-(4-(1,3-thiazol-2-ylcarbonyl)piperazin-1-yl)pyrrolidin-2-one A) 1-(3-(4,4,5,5-Tetramethyl-1,3,2-dioxaborolan-2-yl)phenyl)-4-(4-(1,3-thiazol-2-ylcarbonyl)piperazin-1-yl)pyrrolidin-2-one A mixture of 1-(3-iodophenyl)-4-(4-(1,3-thiazol-2-ylcarbonyl)piperazin-1-yl)pyrrolidin-2-one (50 mg), 4,4,4',4',5,5,5',5'-octamethyl-2,2'-bi-1,3,2-dioxaborolane (39.5 mg), dichloro(1,1'-bis(diphenylphosphino)ferrocene)palladium dichloromethane adduct (8.47 mg) and potassium acetate (30.5 mg) in DMF (1 mL) was stirred at 80° C. under nitrogen atmosphere for 1 hr. The reaction mixture was quenched with water and extracted with ethyl acetate. The organic layer was separated, washed with water and brine successively, dried over sodium sulfate and concentrated in vacuo to give the title compound (19 mg) after triturating with diisopropyl ether.

MS: [M+H]$^+$ 483.2.

B) 1-(3-(5-Methylpyridin-2-yl)phenyl)-4-(4-(1,3-thiazol-2-ylcarbonyl)piperazin-1-yl)pyrrolidin-2-one To a mixture of 1-(3-(4,4,5,5-tetramethyl-1,3,2-dioxaborolan-2-yl)phenyl)-4-(4-(1,3-thiazol-2-ylcarbonyl)piperazin-1-yl)pyrrolidin-2-one (33 mg), 2-bromo-5-methylpyridine (17.65 mg), cesium carbonate (44.6 mg) in toluene (1 mL) were added bis(di-tert-butyl(4-dimethylaminophenyl)phosphine)dichloropalladium(II) (4.60 mg) and water (0.1 mL) successively. The mixture was stirred at 120° C. for 2 hr. The residue was purified by column chromatography (silica gel, ethyl acetate/hexane and then methanol/ethyl acetate). The residue was purified by column chromatography (NH silica gel, ethyl acetate/hexane) to give the title compound (7.80 mg) after triturating diisopropyl ether/2-propyl acetate.

¹H NMR (300 MHz, CDCl₃) δ 2.38 (3H, s), 2.57-2.73 (5H, m), 2.75-2.86 (1H, m), 3.22-3.36 (1H, m), 3.77-3.97 (3H, m), 4.02-4.10 (1H, m), 4.37-4.49 (1H, m), 4.50-4.60 (1H, m), 7.41-7.50 (1H, m), 7.52-7.59 (2H, m), 7.61-7.67 (1H, m), 7.71-7.79 (2H, m), 7.88 (1H, d, J=3.2 Hz), 8.11 (1H, t, J=1.9 Hz), 8.51 (1H, d, J=2.1 Hz).

Example 150

1-(3-(6-Methylpyridin-2-yl)phenyl)-4-(4-(1,3-thiazol-2-ylcarbonyl)piperazin-1-yl)pyrrolidin-2-one To a mixture of 4,4,4',4',5,5,5',5'-octamethyl-2,2'-bi-1,3,2-dioxaborolane (39.5 mg), 1-(3-iodophenyl)-4-(4-(1,3-thiazol-2-ylcarbonyl)piperazin-1-yl)pyrrolidin-2-one (50 mg) and potassium acetate (30.5 mg) in DMF (1 mL) was added 1,1'-bis(diphenylphosphino)ferrocene palladium dichloride (7.58 mg) at ambient temperature. The mixture was stirred at 120° C. under nitrogen atmosphere for 1 hr. To the mixture were added 2-bromo-6-methylpyridine (0.035 mL), cesium carbonate (67.6 mg), bis(di-tert-butyl(4-dimethylaminophenyl)phosphine)dichloropalladium(II) (6.97 mg) and water (0.1 mL) successively. The mixture was stirred at 120° C. for 2 hr. The residue was purified by column chromatography (silica gel, ethyl acetate/hexane and then methanol/ethyl acetate). The residue was purified by column chromatography (NH silica gel, ethyl acetate/hexane) to give the title compound (5.20 mg) after triturating diisopropyl ether/2-propyl acetate.

¹H NMR (300 MHz, CDCl₃) δ 2.56-2.73 (8H, m), 2.74-2.87 (1H, m), 3.24-3.37 (1H, m), 3.76-3.98 (3H, m), 4.01-4.10 (1H, m), 4.37-4.50 (1H, m), 4.50-4.61 (1H, m), 7.11 (1H, d, J=7.4 Hz), 7.41-7.50 (1H, m), 7.50-7.56 (2H, m), 7.60-7.68 (1H, m), 7.70-7.78 (2H, m), 7.88 (1H, d, J=3.2 Hz), 8.13 (1H, t, J=1.8 Hz).

Example 172

1-(3-(2-Methylpyridin-3-yl)phenyl)-4-(4-(1,3-thiazol-2-ylcarbonyl)piperazin-1-yl)pyrrolidin-2-one (optical isomer)

A) 1-(3-Iodophenyl)-4-(4-(1,3-thiazol-2-ylcarbonyl)piperazin-1-yl)pyrrolidin-2-one (optical isomer)

A racemate of 1-(3-iodophenyl)-4-(4-(1,3-thiazol-2-ylcarbonyl)piperazin-1-yl)pyrrolidin-2-one (1 g) was optically separated by preparative SFC (CHIRALPAK AS (Trade name), 30 mmID×250 mmL, Daicel Corporation, mobile phase: carbon dioxide/methanol/acetonitrile=600/200/200) to give the title compound (0.356 g) which showed shorter retention time.

MS: [M+H]⁺ 483.0.

B) 1-(3-(2-Methylpyridin-3-yl)phenyl)-4-(4-(1,3-thiazol-2-ylcarbonyl)piperazin-1-yl)pyrrolidin-2-one (optical isomer)

To a mixture of 1-(3-iodophenyl)-4-(4-(1,3-thiazol-2-ylcarbonyl)piperazin-1-yl)pyrrolidin-2-one (optical isomer) (50 mg), 2-methyl-3-(4,4,5,5-tetramethyl-1,3,2-dioxaborolan-2-yl)pyridine (45.4 mg) and cesium carbonate (67.6 mg) in DMF (1 mL) were added bis(di-tert-butyl(4-dimethylaminophenyl)phosphine)dichloropalladium(II) (6.97 mg) and water (0.1 mL) successively. The mixture was stirred at 100° C. for 1 hr. The reaction mixture was diluted with ethyl acetate, quenched with water and extracted with ethyl acetate. The organic layer was separated, washed with water and brine successively, dried over sodium sulfate and concentrated in vacuo. The residue was purified by column chromatography (NH silica gel, ethyl acetate/hexane) to give the title compound (34.0 mg) after recrystallizing with ethyl acetate/hexane.

¹H NMR (300 MHz, CDCl₃) δ 2.52 (3H, s), 2.56-2.73 (5H, m), 2.75-2.87 (1H, m), 3.23-3.36 (1H, m), 3.74-4.02 (4H, m), 4.36-4.49 (1H, m), 4.49-4.63 (1H, m), 7.10-7.15 (1H, m), 7.19 (1H, dd, J=7.7, 4.9 Hz), 7.45 (1H, t, J=7.8 Hz), 7.50-7.55 (2H, m), 7.56-7.64 (2H, m), 7.88 (1H, d, J=3.0 Hz), 8.51 (1H, dd, J=4.9, 1.7 Hz).

Example 225

1-(2'-Chlorobiphenyl-3-yl)-3-methyl-4-(4-(1,3-thiazol-2-ylcarbonyl)piperazin-1-yl)pyrrolidin-2-one A) 3-Methyl-4-(4-(1,3-thiazol-2-ylcarbonyl)piperazin-1-yl)dihydrofuran-2(3H)-one To a solution of 4-(4-(1,3-thiazol-2-ylcarbonyl)piperazin-1-yl)dihydrofuran-2(3H)-one (1.0 g) in THF (20 mL) was added potassium bis(trimethylsilyl)amide (1.0 M in THF, 4.3 mL) at −78° C. The yellow solution was stirred for 90 min before it was treated with methyl iodide (1.0 g). The mixture was allowed to warm to room temperature and stirred overnight. The reaction mixture was quenched with saturated aqueous ammonium chloride solution. The solvent was evaporated in vacuo and the crude product was purified by column chromatography (dichloromethane/methanol) to give the title compound (320 mg).

MS: [M+H]⁺ 296.2.

B) 4-Hydroxy-N-(3-iodophenyl)-2-methyl-3-(4-(1,3-thiazol-2-ylcarbonyl)piperazin-1-yl)butanamide To a mixture of 3-methyl-4-(4-(1,3-thiazol-2-ylcarbonyl)piperazin-1-yl)dihydrofuran-2(3H)-one (100 mg) and 3-iodoaniline (0.065 mL) in toluene (2 mL) was added bis(trimethylaluminum)-1,4-diazabicyclo[2.2.2]octane adduct (69.4 mg) at room temperature and the mixture was stirred at 80° C. for 3 hr. To the mixture were added ethyl acetate, THF and sodium sulfate decahydrate (524 mg) and the mixture was stirred at room temperature for 1 hr. The insoluble material was removed by filtration, and the filtrate was concentrated in vacuo. The residue was purified by column chromatography (silica gel, ethyl acetate/hexane) to give the title compound (66.5 mg).

MS: [M+H]⁺ 515.1.

C) 1-(3-Iodophenyl)-3-methyl-4-(4-(1,3-thiazol-2-ylcarbonyl)piperazin-1-yl)pyrrolidin-2-one To a solution of 4-hydroxy-N-(3-iodophenyl)-2-methyl-3-(4-(1,3-thiazol-2-ylcarbonyl)piperazin-1-yl)butanamide (66.5 mg) and tri-n-butyl phosphine (0.058 mL) in THF (3 mL) was added di-tert-butylazodicarboxylate (53.6 mg) at ambient temperature. The mixture was stirred at ambient temperature for 3 hr. The mixture was concentrated and purified by column chromatography (NH silica gel, ethyl acetate/hexane) to give the title compound (39.6 mg).

MS: [M+H]⁺ 497.1.

D) 1-(2'-Chlorobiphenyl-3-yl)-3-methyl-4-(4-(1,3-thiazol-2-ylcarbonyl)piperazin-1-yl)pyrrolidin-2-one A mixture of 1-(3-iodophenyl)-3-methyl-4-(4-(1,3-thiazol-2-ylcarbonyl)piperazin-1-yl)pyrrolidin-2-one (19.8 mg), (2-chlorophenyl)boronic acid (9.36 mg), bis(di-tert-butyl(4-dimethylaminophenyl)phosphine)dichloropalladium(II) (2.82 mg), cesium carbonate (26.0 mg) and toluene (3 mL)/water (1.000 mL) was heated at 100° C. for 10 min under microwave irradiation. The organic layer was purified by column chromatography (NH silica gel, ethyl acetate/hexane) and recrystallized from ethyl acetate/hexane to give the title compound (16.00 mg).

$^1$H NMR (300 MHz, CDCl$_3$) δ 1.40 (3H, d, J=7.2 Hz), 2.50-2.82 (5H, m), 3.03 (1H, q, J=7.3 Hz), 3.56-3.98 (4H, m), 4.47 (2H, d, J=17.2 Hz), 7.21-7.25 (1H, m), 7.27-7.38 (3H, m), 7.40-7.49 (2H, m), 7.54 (1H, d, J=3.2 Hz), 7.64 (1H, t, J=1.8 Hz), 7.72 (1H, ddd, J=8.2, 2.2, 0.9 Hz), 7.88 (1H, d, J=3.2 Hz).

Example 226

1-(2'-Chlorobiphenyl-3-yl)-3,3-dimethyl-4-(4-(1,3-thiazol-2-ylcarbonyl)piperazin-1-yl)pyrrolidin-2-one A) 3,3-Dimethyl-4-(4-(1,3-thiazol-2-ylcarbonyl)piperazin-1-yl)dihydrofuran-2(3H)-one To a solution of 4-(4-(1,3-thiazol-2-ylcarbonyl)piperazin-1-yl)dihydrofuran-2(3H)-one (1.0 g) in THF (20 mL) was added potassium bis(trimethylsilyl)amide (1.0 M in THF, 4.3 mL) at −78° C. The yellow solution was stirred for 90 min before it was treated with methyl iodide (1.0 g). The mixture was allowed to warm to room temperature and stirred overnight. The reaction mixture was quenched with saturated aqueous ammonium chloride solution. The solvent was evaporated and the crude product was purified by column chromatography (dichloromethane/methanol) to give the title compound (250 mg).

MS: [M+H]$^+$ 310.2.

B) 4-Hydroxy-N-(3-iodophenyl)-2,2-dimethyl-3-(4-(1,3-thiazol-2-ylcarbonyl)piperazin-1-yl)butanamide To a mixture of 3,3-dimethyl-4-(4-(1,3-thiazol-2-ylcarbonyl)piperazin-1-yl)dihydrofuran-2(3H)-one (100 mg) and 3-iodoaniline (0.062 mL) in toluene (2 mL) was added bis(trimethylaluminum)-1,4-diazabicyclo[2.2.2]octane adduct (66.3 mg) at room temperature and the mixture was stirred at 80° C. for 3 hr. To the mixture were added ethyl acetate, THF and sodium sulfate decahydrate (500 mg) and the mixture was stirred at room temperature for 1 hr. The insoluble material was removed by filtration and the filtrate was concentrated in vacuo. The residue was purified by column chromatography (silica gel, ethyl acetate/hexane) to give the title compound (72.1 mg).

MS: [M+H]$^+$ 529.1.

C) 1-(3-Iodophenyl)-3,3-dimethyl-4-(4-(1,3-thiazol-2-ylcarbonyl)piperazin-1-yl)pyrrolidin-2-one To a solution of 4-hydroxy-N-(3-iodophenyl)-2,2-dimethyl-3-(4-(1,3-thiazol-2-ylcarbonyl)piperazin-1-yl)butanamide (72.1 mg) and tri-n-butyl phosphine (0.061 mL) in THF (3 mL) was added di-tert-butylazodicarboxylate (56.6 mg) at ambient temperature. The mixture was stirred at ambient temperature for 3 hr. The mixture was concentrated and purified by column chromatography (NH silica gel, ethyl acetate/hexane) to give the title compound (47.1 mg).

MS: [M+H]$^+$ 511.1.

D) 1-(2'-Chlorobiphenyl-3-yl)-3,3-dimethyl-4-(4-(1,3-thiazol-2-ylcarbonyl)piperazin-1-yl)pyrrolidin-2-one A mixture of 1-(3-iodophenyl)-3,3-dimethyl-4-(4-(1,3-thiazol-2-ylcarbonyl)piperazin-1-yl)pyrrolidin-2-one (23.5 mg), (2-chlorophenyl)boronic acid (10.80 mg), bis(di-tert-butyl(4-dimethylaminophenyl)phosphine)dichloropalladium(II) (3.26 mg), cesium carbonate (30.0 mg) and toluene (3 mL)/water (1.000 mL) was heated at 100° C. for 10 min under microwave irradiation. The mixture was poured into water and extracted with ethyl acetate. The organic layer was separated, washed with brine, dried over sodium sulfate and concentrated in vacuo. The residue was purified by column chromatography (NH silica gel, ethyl acetate/hexane) and preparative HPLC (C18, mobile phase: water/acetonitrile containing 0.1% trifluoroacetic acid). The desired fraction was neutralized with saturated aqueous sodium hydrogen carbonate solution and extracted with ethyl acetate. The organic layer was separated, dried over sodium sulfate and concentrated in vacuo. The residue was purified by column chromatography (NH silica gel, ethyl acetate/hexane) to give the title compound (12.50 mg).

$^1$H NMR (300 MHz, CDCl$_3$) δ 1.25 (3H, s), 1.38 (3H, s), 2.62 (4H, brs), 2.90 (1H, t, J=6.4 Hz), 3.72 (1H, dd, J=9.6, 6.2 Hz), 3.78-3.94 (3H, m), 4.45 (2H, brs), 7.20-7.26 (1H, m), 7.27-7.38 (3H, m), 7.39-7.49 (2H, m), 7.53 (1H, d, J=3.2 Hz), 7.64-7.73 (2H, m), 7.87 (1H, d, J=3.2 Hz).

Example 228

5-Methyl-1-(4-phenoxyphenyl)-4-(4-(1,3-thiazol-2-ylcarbonyl)piperazin-1-yl)pyrrolidin-2-one A) tert-Butyl 2-methyl-5-oxo-3-(4-(1,3-thiazol-2-ylcarbonyl)piperazin-1-yl)pyrrolidine-1-carboxylate To a solution of piperazin-1-yl(1,3-thiazol-2-yl)methanone (743 mg) in methanol (5 mL) was added a solution of tert-butyl 2-methyl-5-oxo-2,5-dihydro-1H-pyrrole-1-carboxylate (620 mg) in methanol (5 mL) over 30 min at 0° C. The mixture was then stirred at room temperature overnight. The solvent was evaporated in vacuo and the crude product was purified by preparative HPLC (C18, mobile phase: water/acetonitrile containing 10 mM ammonium hydrogen carbonate) to give the title compound (587 mg).

MS, found: 295.4.

B) 5-Methyl-4-(4-(1,3-thiazol-2-ylcarbonyl)piperazin-1-yl)pyrrolidin-2-one

To a solution of tert-butyl 2-methyl-5-oxo-3-(4-(1,3-thiazol-2-ylcarbonyl)piperazin-1-yl)pyrrolidine-1-carboxylate (600 mg) in dichloromethane (15 mL) was added trifluoroacetic acid (6 mL). After being stirred at room temperature for 20 min, the reaction mixture was concentrated. The residue was purified by preparative HPLC (C18, mobile phase: water/acetonitrile containing 10 mM ammonium hydrogen carbonate) to give the title compound (371 mg).

MS: [M+H]$^+$ 295.2.

C) 5-Methyl-1-(4-phenoxyphenyl)-4-(4-(1,3-thiazol-2-ylcarbonyl)piperazin-1-yl)pyrrolidin-2-one To a solution of 5-methyl-4-(4-(1,3-thiazol-2-ylcarbonyl)piperazin-1-yl)pyrrolidin-2-one (300 mg) in DMF (5 mL) was added copper(I) iodide (95 mg), 4-phenoxyaniline (355 mg), potassium phosphate (432 mg) and trans-N,N'-dimethylcyclohexane-1,2-diamine (29 mg) under nitrogen atmosphere. The reaction was stirred at 110° C. overnight. After cooling to room temperature, water (15 mL) was added and the solution was extracted with ethyl acetate three times. The combined organic layers were washed with brine, dried over anhydrous sodium sulfate and concentrated. The residue was purified by preparative HPLC (C18, mobile phase: water/acetonitrile containing 10 mM ammonium hydrogen carbonate) to give the title compound (34 mg).

$^1$H NMR (400 MHz, CD$_3$OD) δ 1.26 (3H, d, J=6.4 Hz), 2.60-2.66 (1H, m), 2.75 (4H, brs), 2.85-2.91 (1H, m), 3.16-3.20 (1H, m), 3.85 (2H, brs), 4.33-4.42 (3H, m), 7.02-7.05 (4H, m), 7.12-7.16 (1H, m), 7.36-7.42 (4H, m), 7.84 (1H, d, J=3.2 Hz), 7.96 (1H, d, J=2.8 Hz).

Example 232

1-(2'-Chlorobiphenyl-3-yl)-4-(4-(1,3-thiazol-4-ylcarbonyl)piperazin-1-yl)pyrrolidin-2-one (optical isomer)

A) 1-(3-Iodophenyl)-4-(4-(1,3-thiazol-4-ylcarbonyl)piperazin-1-yl)pyrrolidin-2-one A mixture of 4-hydroxy-1-(3-iodophenyl)-1,5-dihydro-2H-pyrrol-2-one (534 mg), piperazin-1-yl(1,3-thiazol-4-yl)methanone (350 mg), sodium cyanoborohydride (335 mg) and acetic acid (0.305 mL) in anhydrous THF (10 mL) was stirred at 50° C. overnight. The mixture was neutralized with saturated sodium hydrogen carbonate aqueous solution and extracted with ethyl acetate. The organic layer was separated, washed with water and brine successively, dried over anhydrous sodium sulfate and concentrated in vacuo. The residue was purified by column chromatography (NH silica gel, ethyl acetate/hexane) to give the title compound (436 mg).

MS: [M+H]$^+$ 483.1.

B) 1-(3-Iodophenyl)-4-(4-(1,3-thiazol-4-ylcarbonyl)piperazin-1-yl)pyrrolidin-2-one (optical isomer)

A racemate of 1-(3-iodophenyl)-4-(4-(1,3-thiazol-4-ylcarbonyl)piperazin-1-yl)pyrrolidin-2-one (430 mg) was optically separated by preparative HPLC (CHIRALPAK AS (Trade name), 20 mm ID×250 mmL, Daicel Corporation, mobile phase: methanol) to give the title compound (184.7 mg) which showed shorter retention time.

MS: [M+H]$^+$ 483.1.

C) 1-(2'-Chlorobiphenyl-3-yl)-4-(4-(1,3-thiazol-4-ylcarbonyl)piperazin-1-yl)pyrrolidin-2-one (optical isomer)

A mixture of 1-(3-iodophenyl)-4-(4-(1,3-thiazol-4-ylcarbonyl)piperazin-1-yl)pyrrolidin-2-one (optical isomer) (50 mg), (2-chlorophenyl)boronic acid (24.32 mg), bis(di-tert-butyl(4-dimethylaminophenyl)phosphine)dichloropalladium(II) (7.34 mg), cesium carbonate (67.6 mg) and toluene (3 mL)/water (1.000 mL) was heated at 100° C. for 15 min under microwave irradiation. The organic layer was purified by column chromatography (NH silica gel, ethyl acetate/hexane) and recrystallized from ethyl acetate-hexane to give the title compound (31.2 mg).

$^1$H NMR (300 MHz, CDCl$_3$) δ 2.53-2.74 (5H, m), 2.74-2.85 (1H, m), 3.28 (1H, t, J=7.4 Hz), 3.76-4.11 (6H, m), 7.20-7.25 (1H, m), 7.27-7.38 (3H, m), 7.41-7.50 (2H, m), 7.58 (1H, t, J=1.9 Hz), 7.70 (1H, ddd, J=8.2, 2.2, 0.9 Hz), 8.03 (1H, d, J=2.3 Hz), 8.78 (1H, d, J=2.1 Hz).

Example 256

1-(3-(2-Methylpyridin-3-yl)phenyl)-4-(4-(pyrimidin-2-yl)piperazin-1-yl)pyrrolidin-2-one A) 4-(4-(Pyrimidin-2-yl)piperazin-1-yl)dihydrofuran-2(3H)-one To a solution of 2-(piperazin-1-yl)pyrimidine (10 g) in methanol (20 mL) was added 2(5H)-furanone (5.12 mL) at room temperature. The mixture was stirred at ambient temperature overnight. To the mixture was added 2-propanol (4 mL). The mixture was stirred at room temperature for 1 hr. The precipitate was collected by filtration and washed with 2-propanol to give the title compound (12.84 g).

MS: [M+H]$^+$ 249.1.

B) 4-Hydroxy-N-(3-iodophenyl)-3-(4-(pyrimidin-2-yl)piperazin-1-yl)butanamide

To a mixture of 3-iodoaniline (0.204 mL) and 4-(4-(pyrimidin-2-yl)piperazin-1-yl)dihydrofuran-2(3H)-one (300 mg) in toluene (5 mL) was added bis(trimethylaluminum)-1,4-diazabicyclo[2.2.2]octane adduct (217 mg) at room temperature and the mixture was stirred at 80° C. for 1 hr. The reaction mixture was diluted with ethyl acetate and quenched with sodium sulfate decahydrate (1635 mg) at room temperature. The insoluble material was removed by filtration and the filtrate was concentrated in vacuo. The residue was purified by column chromatography (silica gel, methanol/ethyl acetate) to give the title compound (486 mg).

MS: [M+H]$^+$ 468.1.

C) 1-(3-Iodophenyl)-4-(4-(pyrimidin-2-yl)piperazin-1-yl)pyrrolidin-2-one

To a solution of 4-hydroxy-N-(3-iodophenyl)-3-(4-(pyrimidin-2-yl)piperazin-1-yl)butanamide (486 mg) and tri-n-butyl phosphine (0.463 mL) in THF (5 mL) was added di-tert-butylazodicarboxylate (431 mg) at ambient temperature. The mixture was stirred at ambient temperature for 3 hr. The precipitate was collected by filtration and washed with 2-propyl acetate/diisopropyl ether to give the title compound (315 mg).

MS: [M+H]$^+$ 450.1

D) 1-(3-(2-Methylpyridin-3-yl)phenyl)-4-(4-(pyrimidin-2-yl)piperazin-1-yl)pyrrolidin-2-one To a solution of 1-(3-iodophenyl)-4-(4-(pyrimidin-2-yl)piperazin-1-yl)pyrrolidin-2-one (50 mg), 2-methyl-3-(4,4,5,5-tetramethyl-1,3,2-dioxaborolan-2-yl)pyridine (48.8 mg) and cesium carbonate (72.5 mg) in DMF (1 mL) was added bis(di-tert-butyl(4-dimethylaminophenyl)phosphine)dichloropalladium(II) (7.49 mg) and water (0.1 mL) at ambient temperature. The mixture was stirred at 80° C. under nitrogen atmosphere for 1 hr. The reaction mixture was diluted with ethyl acetate, quenched with water and extracted with ethyl acetate. The organic layer was separated, washed with water and brine successively, dried over sodium sulfate and concentrated in vacuo. The residue was triturated with 2-propyl acetate/diisopropyl ether to give the title compound (34.3 mg).

¹H NMR (300 MHz, CDCl₃) δ 2.52 (3H, s), 2.54-2.62 (4H, m), 2.64-2.75 (1H, m), 2.76-2.86 (1H, m), 3.20-3.33 (1H, m), 3.84-3.92 (5H, m), 3.94-4.03 (1H, m), 6.51 (1H, t, J=4.7 Hz), 7.09-7.15 (1H, m), 7.19 (1H, dd, J=7.5, 4.9 Hz), 7.45 (1H, t, J=7.9 Hz), 7.53 (1H, dd, J=7.6, 1.8 Hz), 7.57-7.65 (2H, m), 8.31 (2H, d, J=4.7 Hz), 8.51 (1H, dd, J=4.9, 1.7 Hz).

Example 257

(4R)-4-(4-(1,3-Thiazol-2-ylcarbonyl)piperazin-1-yl)-1-(1-(5-(trifluoromethyl)pyrimidin-2-yl)-1H-indol-5-yl)pyrrolidin-2-one hydrochloride To a suspension of (4R)-4-(4-(1,3-thiazol-2-ylcarbonyl)piperazin-1-yl)-1-(1-(5-(trifluoromethyl)pyrimidin-2-yl)-1H-indol-5-yl)pyrrolidin-2-one (920 mg) in ethyl acetate (10 mL) was added hydrogen chloride (2 M in ethyl acetate, 1.019 mL) at ambient temperature. The mixture was stirred at ambient temperature under nitrogen atmosphere for 3 hr. The insoluble material was collected by filtration and washed with ethyl acetate to give a crude material. The solid was recrystallized by dimethyl sulfoxide/ethyl acetate to give the title compound (640 mg) after triturating with diethyl ether.

¹H NMR (300 MHz, DMSO-d₆) δ 3.05 (2H, brs), 3.69 (6H, brs), 4.29 (3H, brs), 4.60 (1H, brs), 5.67 (1H, brs), 6.92 (1H, d, J=3.8 Hz), 7.69 (1H, dd, J=9.0, 2.3 Hz), 7.94 (1H, d, J=1.9 Hz), 8.03-8.07 (1H, m), 8.07-8.13 (1H, m), 8.33 (1H, d, J=3.8 Hz), 8.72 (1H, d, J=9.4 Hz), 9.29 (2H, d, J=0.8 Hz), 11.70 (1H, brs).

Example 259

3,3-Difluoro-1-(4-phenoxyphenyl)-4-(4-(1,3-thiazol-2-ylcarbonyl)piperazin-1-yl)pyrrolidin-2-one To a solution of diisopropylamine (505 mg) in THF (10 mL) was added dropwise a solution of N-butyllithium (2.0 M in hexane, 2.5 mL) at −78° C. and the resulting solution was stirred at −78° C. for 1 hr. A solution of 1-(4-phenoxyphenyl)-4-(4-(1,3-thiazol-2-ylcarbonyl)piperazin-1-yl)pyrrolidin-2-one (448 mg) in THF (5 mL) was then added slowly to the freshly prepared lithium diisopropylamide solution. The resulting light yellow solution was stirred at −78° C. for 45 min. A solution of N-fluorobenzenesulfonimide (946 mg) in THF (15 mL) was then added and the reaction mixture was allowed to stir at −78° C. for 35 min. The reaction mixture was allowed to warm to room temperature and stirred overnight. The reaction mixture was quenched with saturated aqueous ammonium chloride solution and concentrated in vacuo. The residue was partitioned between ethyl acetate (20 mL) and water (20 mL). The aqueous layer was extracted with ethyl acetate twice. The combined organic layers were dried over sodium sulfate, filtered and evaporated to leave an orange residue which was purified by preparative HPLC (C18, mobile phase: water/acetonitrile containing 10 mM ammonium hydrogen carbonate) to give the title compound (6 mg).

¹H NMR (400 MHz, DMSO-d₆) δ 2.67-2.74 (4H, m), 3.51-3.62 (1H, m), 3.74 (2H, brs), 3.93 (1H, t, J=8.8 Hz), 4.11 (1H, t, J=8.8 Hz), 4.36 (2H, brs), 7.02 (2H, d, J=8.0 Hz), 7.11 (2H, d, J=8.0 Hz), 7.16 (1H, t, J=7.2 Hz), 7.41 (2H, t, J=8.0 Hz), 7.75 (2H, d, J=9.2 Hz), 8.04 (2H, dd, J=10.0, 3.2 Hz).

Example 260

3-Hydroxy-1-(4-phenoxyphenyl)-4-(4-(1,3-thiazol-2-ylcarbonyl)piperazin-1-yl)pyrrolidin-2-one A solution of N-butyllithium (2.0 M in hexane, 0.68 mL) was slowly added to a solution of diisopropylamine (136 mg) in THF (10 mL) at −78° C. The resulting solution was stirred at −78° C. for 1 hr. A solution of 1-(4-phenoxyphenyl)-4-(4-(1,3-thiazol-2-ylcarbonyl)piperazin-1-yl)pyrrolidin-2-one (120 mg) in THF (10 mL) was then added slowly to the above freshly prepared lithium diisopropylamide solution. The resulting light yellow mixture was stirred at −78° C. for 45 min. A solution of 2-(phenylsulfonyl)-3-phenyloxaziridine (84 mg) in THF (10 mL) was then added and the final reaction mixture was allowed to stir at room temperature overnight. The reaction mixture was quenched with saturated aqueous ammonium chloride solution and concentrated in vacuo to leave an orange residue which was purified by preparative HPLC (C18, mobile phase: water/acetonitrile containing 10 mM ammonium hydrogen carbonate) to give the title compound (27 mg).

¹H NMR (400 MHz, DMSO-d₆) δ 2.60-2.64 (2H, m), 2.78 (2H, brs), 2.94-2.97 (1H, m), 3.59 (1H, t, J=8.8 Hz), 3.71 (2H, brs), 3.88 (1H, t, J=8.8 Hz), 4.27-4.32 (3H, m), 5.93 (1H, d, J=6.4 Hz), 6.98 (2H, d, J=8.0 Hz), 7.06 (2H, d, J=8.8 Hz), 7.12 (1H, t, J=7.2 Hz), 7.38 (2H, t, J=8.0 Hz), 7.71 (2H, d, J=8.8 Hz), 8.03 (2H, dd, J=8.4, 3.2 Hz).

Example 261

3-Fluoro-1-(4-phenoxyphenyl)-4-(4-(1,3-thiazol-2-ylcarbonyl)piperazin-1-yl)pyrrolidin-2-one To a solution of diisopropylamine (182 mg) in THF (10 mL) at −78° C. was added dropwise a solution of N-butyllithium (2.0 M in hexane, 0.9 mL) and the resulting solution was stirred at −78° C. for 1 hr. A solution of 1-(4-phenoxyphenyl)-4-(4-(1,3-thiazol-2-ylcarbonyl)piperazin-1-yl)pyrrolidin-2-one (161 mg) in THF (5 mL) was added slowly to the freshly prepared lithium diisopropylamide solution. The resulting light yellow solution was stirred at −78° C. for 45 min. A solution of N-fluorobenzenesulfonimide (113 mg) in THF (5 mL) was then added and the reaction was allowed to stir at −78° C. for 35 min. The reaction mixture was allowed to warm to room temperature and stirred overnight. The reaction mixture was quenched with saturated aqueous ammonium chloride solution and concentrated in vacuo. The residue was partitioned between ethyl acetate (10 mL) and water (10 mL). The aqueous layer was extracted with ethyl acetate twice. The combined organic layers were dried by sodium sulfate, filtered and evaporated to leave an orange residue which was purified by preparative HPLC (C18, mobile phase: water/acetonitrile containing 10 mM ammonium hydrogen carbonate) to give the title compound (21 mg).

¹H NMR (300 MHz, DMSO-d₆) δ 2.65-2.73 (4H, m), 3.31-3.38 (1H, m), 3.66-3.73 (3H, m), 3.99 (1H, t, J=8.8 Hz), 4.35 (2H, brs), 5.46 (1H, dd, J=52.8, 8.4 Hz), 6.98-7.16 (5H, m), 7.37-7.41 (2H, m), 7.70-7.73 (2H, m), 8.04 (2H, dd, J=8.8, 3.2 Hz).

Example 273

1-(3-(4,6-Dimethylpyrimidin-5-yl)phenyl)-4-(4-(1,3-thiazol-2-ylcarbonyl)piperazin-1-yl)pyrrolidin-2-one A mixture of potassium acetate (122 mg), 1,1'-bis(diphenylphosphino)ferrocene palladium dichloride (30.3 mg), 5-bromo-4,6-dimethylpyrimidine (78 mg) and 4,4,4',4',5,5,5',5'-octamethyl-2,2'-bi-1,3,2-dioxaborolane (116 mg) in anhydrous DMF (3 mL) was stirred at 100° C. under argon atmosphere overnight. The mixture was poured into water and extracted with ethyl acetate. The organic layer was separated, washed with brine, dried over sodium sulfate and concentrated in vacuo. To the residue were added chloro(2-dicyclohexylphosphino-2',6'-dimethoxy-1,1'-biphenyl)(2'-amino-1,1'-biphenyl-2-yl) palladium(II) (29.9 mg), 2-dicyclohexylphosphino-2',6'-dimethoxybiphenyl (17.02 mg), 1-(3-iodophenyl)-4-(4-(1,3-thiazol-2-ylcarbonyl)piperazin-1-yl)pyrrolidin-2-one (100 mg), 1,2-dimethoxyethane (3.00 mL), water (0.300 mL) and sodium hydrogen carbonate (69.7 mg), and the mixture was stirred at 100° C. for 15 min under microwave irradiation. The organic phase was purified by column chromatography (NH silica gel, ethyl acetate/hexane) to give the title compound (9.10 mg).
$^1$H NMR (300 MHz, CDCl$_3$) δ 2.29 (6H, s), 2.53-2.74 (5H, m), 2.75-2.87 (1H, m), 3.29 (1H, quin, J=7.6 Hz), 3.75-4.04 (4H, m), 4.32-4.66 (2H, m), 6.95-7.04 (1H, m), 7.43-7.52 (2H, m), 7.54 (1H, d, J=3.2 Hz), 7.59-7.65 (1H, m), 7.88 (1H, d, J=3.2 Hz), 8.95 (1H, s).

Example 351

7-Methoxy-6-(3-(2-oxo-4-(4-(1,3-thiazol-2-ylcarbonyl)piperazin-1-yl)pyrrolidin-1-yl)phenyl)-1,3-dihydro-2H-indol-2-one A) 7-Methoxy-2-oxo-2,3-dihydro-1H-indol-6-yl trifluoromethanesulfonate To a mixture of 6-hydroxy-7-methoxy-1,3-dihydro-2H-indol-2-one (20.6 mg) in anhydrous THF (3 mL) was added sodium hydride (60% dispersion in oil, 5.06 mg) at room temperature. After being stirred at room temperature for 10 min, N-phenyltrifluoromethanesulfonimide (53.4 mg) was added to the reaction mixture. The mixture was stirred at room temperature under nitrogen atmosphere for 2 hr. The mixture was poured into water and extracted with ethyl acetate. The organic layer was separated, washed with brine, dried over sodium sulfate and concentrated in vacuo. The residue was purified by column chromatography (NH silica gel, ethyl acetate/hexane) to give the title compound (25.3 mg).
MS: [M−H]$^-$ 309.9.

B) 7-Methoxy-6-(3-(2-oxo-4-(4-(1,3-thiazol-2-ylcarbonyl)piperazin-1-yl)pyrrolidin-1-yl)phenyl)-1,3-dihydro-2H-indol-2-one To a solution of 1-(3-iodophenyl)-4-(4-(1,3-thiazol-2-ylcarbonyl)piperazin-1-yl)pyrrolidin-2-one (50 mg), 4,4,4',4',5,5,5',5'-octamethyl-2,2'-bi-1,3,2-dioxaborolane (31.6 mg) and potassium acetate (30.5 mg) in DMF (1 mL) was added 1,1'-bis(diphenylphosphino)ferrocene palladium dichloride (7.58 mg) at ambient temperature. The mixture was stirred at 100° C. under nitrogen atmosphere for 1 hr. The mixture was poured into water and extracted with ethyl acetate. The organic layer was separated, washed with brine, dried over sodium sulfate and concentrated in vacuo. To the residue were added 7-methoxy-2-oxo-2,3-dihydro-1H-indol-6-yl trifluoromethanesulfonate (35.5 mg), chloro(2-dicyclohexylphosphino-2',6'-dimethoxy-1,1'-biphenyl) (2'-amino-1,1'-biphenyl-2-yl) palladium(II) (7.47 mg), 2-dicyclohexylphosphino-2',6'-dimethoxybiphenyl (4.26 mg), sodium hydrogen carbonate (17.42 mg), 1,2-dimethoxyethane (2.000 mL) and water (0.200 mL) successively. The mixture was stirred at 80° C. overnight. The organic phase was purified by column chromatography (NH silica gel, methanol/ethyl acetate). The residue was purified by preparative HPLC (C18, mobile phase: water/acetonitrile containing 0.1% trifluoroacetic acid). The desired fraction was neutralized with saturated aqueous sodium hydrogen carbonate solution and extracted with ethyl acetate. The organic layer was separated, dried over sodium sulfate and concentrated in vacuo. The residue was purified by column chromatography (NH silica gel, methanol/ethyl acetate) to give the title compound (2.500 mg).
$^1$H NMR (300 MHz, CDCl$_3$) δ 2.51-2.72 (5H, m), 2.75-2.87 (1H, m), 3.30 (1H, t, J=7.4 Hz), 3.47 (3H, s), 3.61 (2H, s), 3.77-4.05 (4H, m), 4.33-4.64 (2H, m), 6.94-7.10 (2H, m), 7.32-7.38 (1H, m), 7.41-7.47 (1H, m), 7.51-7.60 (2H, m), 7.65 (1H, d, J=8.1 Hz), 7.74 (1H, s), 7.88 (1H, d, J=3.2 Hz).

Example 353

1-(7-(2-Fluorophenyl)-1H-indol-5-yl)-4-(4-(1,3-thiazol-2-ylcarbonyl)piperazin-1-yl)pyrrolidin-2-one A) 7-(2-Fluorophenyl)-5-nitro-1H-indole A mixture of 7-bromo-5-nitro-1H-indole (300 mg), (2-fluorophenyl)boronic acid (261 mg), bis(di-tert-butyl(4-dimethylaminophenyl)phosphine)dichloropalladium(II) (44.1 mg), cesium carbonate (811 mg) and toluene (10 mL)/water (3.33 mL) was heated at 100° C. overnight. The organic layer was separated, and purified by column chromatography (NH silica gel, ethyl acetate/hexane) to give the title compound (133 mg).
MS: [M+H]$^+$ 257.0.

B) 7-(2-Fluorophenyl)-1H-indol-5-amine

A mixture of 7-(2-fluorophenyl)-5-nitro-1H-indole (132.8 mg) and 4.2% palladium-activated carbon ethylenediamine complex (20 mg) in ethyl acetate (3.00 mL)/THF (3 mL) was hydrogenated under balloon pressure at 50° C. overnight. The catalyst was removed by filtration. The residue was purified by column chromatography (NH silica gel, ethyl acetate/hexane) to give the title compound (78 mg).
MS: [M+H]$^+$ 268.2.

C) N-(7-(2-Fluorophenyl)-1H-indol-5-yl)-4-hydroxy-3-(4-(1,3-thiazol-2-ylcarbonyl)piperazin-1-yl) butanamide To a mixture of 4-(4-(1,3-thiazol-2-ylcarbonyl)piperazin-1-yl)dihydrofuran-2(3H)-one (81 mg) and 7-(2-fluorophenyl)-1H-indol-5-amine (78.0 mg) in toluene (4 mL) was added bis(trimethylaluminum)-1,4-diazabicyclo[2.2.2]octane adduct (44.2 mg) at room temperature and the mixture was stirred at 80° C. for 3 hr. To the mixture were added ethyl acetate, THF and sodium sulfate decahydrate (333 mg) and the mixture was stirred at room temperature overnight. The insoluble material was removed by filtration and the filtrate was concentrated in vacuo. The residue was purified by column chromatography (silica gel, methanol/ethyl acetate) to give the title compound (127 mg).
MS: [M+H]$^+$ 508.3.

D) 1-(7-(2-Fluorophenyl)-1H-indol-5-yl)-4-(4-(1,3-thiazol-2-ylcarbonyl)piperazin-1-yl)pyrrolidin-2-one To a solution of N-(7-(2-fluorophenyl)-1H-indol-5-yl)-4-hydroxy-3-(4-(1,3-thiazol-2-ylcarbonyl)piperazin-1-yl)butanamide (127.2 mg) and tri-n-butyl phosphine (0.093 mL) in THF (5 mL) was added di-tert-butylazodicarboxylate (87 mg) at ambient temperature. The mixture was stirred at ambient temperature overnight. Tri-n-butyl phosphine (0.062 mL) and di-tert-butylazodicarboxylate (57.7 mg) were added again, the mixture was stirred at 50° C. for 6 hr. The mixture was concentrated and purified by column chromatography (NH silica gel, ethyl acetate/hexane). The residue was purified by preparative HPLC (C18, mobile phase: water/acetonitrile containing 0.1% trifluoroacetic acid). The desired fraction was neutralized with saturated aqueous sodium hydrogen carbonate solution and extracted with ethyl acetate. The organic layer was separated, dried over sodium sulfate and concentrated in vacuo. The residue was purified by column chromatography (NH silica gel, ethyl acetate/hexane) and recrystallized from ethyl acetate/hexane to give the title compound (10.30 mg).

$^1$H NMR (300 MHz, CDCl$_3$) δ 2.55-2.74 (5H, m), 2.76-2.87 (1H, m), 3.32 (1H, t, J=7.3 Hz), 3.78-3.97 (3H, m), 3.99-4.07 (1H, m), 4.39-4.63 (2H, m), 6.60 (1H, dd, J=3.1, 2.0 Hz), 7.18-7.25 (2H, m), 7.27-7.32 (1H, m), 7.35-7.43 (1H, m), 7.45 (1H, d, J=1.9 Hz), 7.52-7.59 (2H, m), 7.76 (1H, d, J=1.7 Hz), 7.88 (1H, d, J=3.2 Hz), 8.21 (1H, brs).

Example 366

1-(3-Chloro-6-fluoro-1-benzothiophen-2-yl)-4-(4-(1,3-thiazol-2-ylcarbonyl)piperazin-1-yl)pyrrolidin-2-one A) tert-Butyl (3-chloro-6-fluoro-1-benzothiophen-2-yl)carbamate To a solution of 3-chloro-6-fluoro-1-benzothiophene-2-carboxylic acid (500 mg) in tert-butyl alcohol (10 mL) was added diphenylphosphorazidate (716 mg) and triethylamine (0.363 mL) at ambient temperature. The mixture was stirred at 90° C. for 5 hr. The reaction mixture was quenched with water and extracted with ethyl acetate. The organic layer was separated, washed with water and brine successively, dried over sodium sulfate and concentrated in vacuo. The residue was purified by column chromatography (silica gel, ethyl acetate/hexane) to give the title compound (610 mg).

MS: [M−H]⁻ 300.1.

B) 3-Chloro-6-fluoro-1-benzothiophen-2-amine hydrochloride

To a solution of tert-butyl (3-chloro-6-fluoro-1-benzothiophen-2-yl)carbamate (610 mg) in THF (2.5 mL) were added hydrogen chloride (4 M in ethyl acetate, 2.53 mL) and the mixture was stirred at ambient temperature for 3 hr. The volatile material was removed by evaporation and the residue was triturated with diisopropyl ether. The precipitate was collected by filtration and washed with diisopropyl ether to give the title compound (440 mg).

MS, found: 202.0.

C) N-(3-Chloro-6-fluoro-1-benzothiophen-2-yl)-4-hydroxy-3-(4-(1,3-thiazol-2-ylcarbonyl)piperazin-1-yl)butanamide 3-Chloro-6-fluoro-1-benzothiophen-2-amine hydrochloride (85 mg) was dissolved with ethyl acetate/water, desalted with saturated aqueous sodium hydrogen carbonate solution and extracted with ethyl acetate. The organic layer was separated, washed with water and brine successively, dried over sodium sulfate and concentrated in vacuo. The residue was azeotroped with toluene. The resulting amine and 4-(4-(1,3-thiazol-2-ylcarbonyl)piperazin-1-yl)dihydrofuran-2(3H)-one (84 mg) were dissolved with toluene (1 mL). To a solution was added bis(trimethylaluminum)-1,4-diazabicyclo[2.2.2]octane adduct (45.8 mg) at room temperature and the mixture was stirred at 80° C. for 30 min. The reaction mixture was diluted with THF and quenched with sodium sulfate decahydrate (431 mg) at room temperature. The insoluble material was removed by filtration, and the filtrate was concentrated in vacuo. The residue was purified by column chromatography (silica gel, methanol/ethyl acetate) to give the title compound (60.0 mg).

MS: [M+H]⁺ 483.1.

D) 1-(3-Chloro-6-fluoro-1-benzothiophen-2-yl)-4-(4-(1,3-thiazol-2-ylcarbonyl)piperazin-1-yl)pyrrolidin-2-one To a mixture of N-(3-chloro-6-fluoro-1-benzothiophen-2-yl)-4-hydroxy-3-(4-(1,3-thiazol-2-ylcarbonyl)piperazin-1-yl)butanamide (60 mg) and tri-n-butyl phosphine (0.055 mL) in THF (1.5 mL) was added di-tert-butylazodicarboxylate (51.5 mg) at room temperature and the mixture was stirred at room temperature overnight. The mixture was concentrated in vacuo and the residue was purified by column chromatography (NH silica gel, ethyl acetate/hexane and then methanol/ethyl acetate) to give the title compound (45.0 mg) after triturating with diisopropyl ether.

$^1$H NMR (300 MHz, CDCl$_3$) δ 2.55-2.72 (5H, m), 2.72-2.86 (1H, m), 3.33-3.48 (1H, m), 3.77-3.97 (2H, m), 4.02 (1H, dd, J=9.7, 6.6 Hz), 4.13-4.24 (1H, m), 4.38-4.63 (2H, m), 7.19 (1H, td, J=8.9, 2.3 Hz), 7.43 (1H, dd, J=8.4, 2.3 Hz), 7.55 (1H, d, J=3.2 Hz), 7.72 (1H, dd, J=8.8, 5.0 Hz), 7.88 (1H, d, J=3.2 Hz).

Example 372 tert-Butyl 5-(2-oxo-4-(4-(1,3-thiazol-2-ylcarbonyl)piperazin-1-yl)pyrrolidin-1-yl)indoline-1-carboxylate A) tert-Butyl 5-((4-hydroxy-3-(4-(1,3-thiazol-2-ylcarbonyl)piperazin-1-yl)butanoyl)amino)indoline-1-carboxylate To a mixture of 4-(4-(1,3-thiazol-2-ylcarbonyl)piperazin-1-yl)dihydrofuran-2(3H)-one (2000 mg) and tert-butyl 5-aminoindoline-1-carboxylate (1.999 g) in toluene (40 mL) was added bis(trimethylaluminum)-1,4-diazabicyclo[2.2.2]octane adduct (1.093 g) at room temperature and the mixture was stirred at 70° C. for 1 hr. To the mixture were added THF and sodium sulfate decahydrate (10.994 g) and the mixture was stirred at room temperature overnight. The insoluble material was removed by filtration and the filtrate was concentrated in vacuo. The residue was purified by column chromatography (silica gel, methanol/ethyl acetate) to give the title compound (3.67 g).

MS: [M+H]⁺ 516.2.

B) tert-Butyl 5-(2-oxo-4-(4-(1,3-thiazol-2-ylcarbonyl)piperazin-1-yl)pyrrolidin-1-yl)indoline-1-carboxylate To a mixture of tert-butyl 5-((4-hydroxy-3-(4-(1,3-thiazol-2-ylcarbonyl)piperazin-1-yl)butanoyl)amino)indoline-1-carboxylate (3.67 g) and tri-n-butyl phosphine (3.00 mL)

in THF (37 mL) was added di-tert-butylazodicarboxylate (2.79 g) at room temperature. The mixture was stirred at room temperature overnight. The precipitate was collected by filtration and washed with diisopropyl ether to give the title compound (2.330 g).

$^1$H NMR (300 MHz, CDCl$_3$) δ 1.47-1.64 (9H, m), 2.53-2.69 (5H, m), 2.70-2.83 (1H, m), 3.09 (2H, t, J=8.6 Hz), 3.19-3.34 (1H, m), 3.73-4.06 (6H, m), 4.33-4.63 (2H, m), 7.12 (1H, brs), 7.42-7.65 (2H, m), 7.80 (1H, brs), 7.88 (1H, d, J=3.2 Hz).

Example 373

4-(4-(1,3-Thiazol-2-ylcarbonyl)piperazin-1-yl)-1-(1-(trifluoroacetyl)-2,3-dihydro-1H-indol-5-yl)pyrrolidin-2-one A mixture of tert-butyl 5-(2-oxo-4-(4-(1,3-thiazol-2-ylcarbonyl)piperazin-1-yl)pyrrolidin-1-yl)indoline-1-carboxylate (500 mg) and trifluoroacetic acid (1.548 mL) in acetonitrile (5 mL) was stirred at ambient temperature for 1 h and then at 60° C. for 1 hr. The mixture was concentrated in vacuo. The residue was neutralized with saturated aqueous sodium hydrogen carbonate solution at room temperature and extracted with ethyl acetate. The organic layer was separated, washed with water and brine successively, dried over sodium sulfate and concentrated in vacuo. The residue was triturated with diisopropyl ether to give the title compound (386 mg).

$^1$H NMR (300 MHz, CDCl$_3$) δ 2.52-2.71 (5H, m), 2.74-2.84 (1H, m), 3.21-3.34 (3H, m), 3.71-4.00 (4H, m), 4.30 (2H, t, J=8.2 Hz), 4.36-4.62 (2H, m), 7.20 (1H, dd, J=8.8, 2.3 Hz), 7.51-7.57 (1H, m), 7.83 (1H, d, J=1.9 Hz), 7.88 (1H, d, J=3.2 Hz), 8.19 (1H, d, J=8.8 Hz).

Example 374

1-(2,3-Dihydro-1H-indol-5-yl)-4-(4-(1,3-thiazol-2-ylcarbonyl)piperazin-1-yl)pyrrolidin-2-one To a suspension of tert-butyl 5-(2-oxo-4-(4-(1,3-thiazol-2-ylcarbonyl)piperazin-1-yl)pyrrolidin-1-yl)indoline-1-carboxylate (300 mg) in ethyl acetate (0.9 mL) was added hydrogen chloride (4 M in ethyl acetate, 3.01 mL) at 80° C. for 1 hr. The volatile component was removed by evaporation. The residue was diluted with saturated aqueous sodium hydrogen carbonate solution and ethyl acetate and extracted with ethyl acetate. The organic layer was separated, washed with water and brine successively, dried over sodium sulfate and concentrated in vacuo. The residue was triturated with ethyl acetate to give the title compound (124 mg).

$^1$H NMR (300 MHz, CDCl$_3$) δ 2.50-2.66 (5H, m), 2.68-2.82 (1H, m), 3.04 (2H, t, J=8.4 Hz), 3.18-3.31 (1H, m), 3.57 (2H, t, J=8.4 Hz), 3.67-3.96 (5H, m), 4.30-4.62 (2H, m), 6.61 (1H, d, J=8.3 Hz), 7.03 (1H, dd, J=8.3, 2.3 Hz), 7.31-7.36 (1H, m), 7.54 (1H, d, J=3.2 Hz), 7.88 (1H, d, J=3.2 Hz).

Example 375

1-(1-Cyclopropyl-2,3-dihydro-1H-indol-5-yl)-4-(4-(1,3-thiazol-2-ylcarbonyl)piperazin-1-yl)pyrrolidin-2-one A mixture of 1-(2,3-dihydro-1H-indol-5-yl)-4-(4-(1,3-thiazol-2-ylcarbonyl)piperazin-1-yl)pyrrolidin-2-one (30 mg), cyclopropylboronic acid (12.97 mg), copper(II) acetate (13.71 mg), sodium carbonate (16.00 mg) and 2,2'-bipyridine (11.79 mg) in THF (1 mL) was stirred at 70° C. overnight. The insoluble material was removed by filtration with celite and the filtrate was concentrated in vacuo. The mixture was diluted with water and extracted with ethyl acetate. The organic layer was separated, washed with water and brine successively, dried over sodium sulfate and concentrated in vacuo. The residue was purified by column chromatography (NH silica gel, ethyl acetate/hexane) to give the title compound (13.00 mg) after crystallizing with ethyl acetate/hexane.

$^1$H NMR (300 MHz, CDCl$_3$) δ 0.54-0.75 (4H, m), 2.04-2.15 (1H, m), 2.53-2.68 (5H, m), 2.69-2.80 (1H, m), 2.85-2.95 (2H, m), 3.19-3.31 (1H, m), 3.33-3.41 (2H, m), 3.69-3.97 (4H, m), 4.34-4.61 (2H, m), 6.77 (1H, d, J=8.4 Hz), 7.07 (1H, dd, J=8.4, 2.2 Hz), 7.27-7.30 (1H, m), 7.54 (1H, d, J=3.2 Hz), 7.88 (1H, d, J=3.2 Hz).

Example 378

4-(4-(Pyrimidin-2-yl)piperazin-1-yl)-1-(1-(5-(trifluoromethyl)pyrimidin-2-yl)-2,3-dihydro-1H-indol-5-yl)pyrrolidin-2-one A) 4-Hydroxy-3-(4-(pyrimidin-2-yl)piperazin-1-yl)-N-(1-(5-(trifluoromethyl)pyrimidin-2-yl)-2,3-dihydro-1H-indol-5-yl)butanamide To a mixture of 4-(4-(pyrimidin-2-yl)piperazin-1-yl)dihydrofuran-2(3H)-one (50 mg) and 1-(5-(trifluoromethyl)pyrimidin-2-yl)indolin-5-amine (67.7 mg) in toluene (1 mL) was added bis(trimethylaluminum)-1,4-diazabicyclo[2.2.2]octane adduct (31.0 mg) at room temperature, and the mixture was stirred at 80° C. for 1 hr. The reaction mixture was diluted with THF and quenched with sodium sulfate decahydrate (273 mg) at room temperature. The insoluble material was removed by filtration, and the filtrate was concentrated in vacuo. The residue was purified by column chromatography (silica gel, methanol/ethyl acetate) to give the title compound (83 mg).

MS: [M+H]$^+$ 529.3.

B) 4-(4-(Pyrimidin-2-yl)piperazin-1-yl)-1-(1-(5-(trifluoromethyl)pyrimidin-2-yl)-2,3-dihydro-1H-indol-5-yl)pyrrolidin-2-one To a mixture of 4-hydroxy-3-(4-(pyrimidin-2-yl)piperazin-1-yl)-N-(1-(5-(trifluoromethyl)pyrimidin-2-yl)-2,3-dihydro-1H-indol-5-yl)butanamide (83 mg) and tri-n-butyl phosphine (0.070 mL) in DMF (1 mL) was added di-tert-butylazodicarboxylate (65.1 mg) at room temperature, and the mixture was stirred at room temperature for 1 hr. The precipitate was collected by filtration and washed with ethyl acetate to give the title compound (56.0 mg).

$^1$H NMR (300 MHz, CDCl$_3$) δ 2.58 (4H, t, J=5.1 Hz), 2.62-2.73 (1H, m), 2.74-2.85 (1H, m), 3.19-3.31 (3H, m), 3.79-3.91 (5H, m), 3.92-4.00 (1H, m), 4.30 (2H, t, J=8.6 Hz), 6.51 (1H, t, J=4.7 Hz), 7.23 (1H, d, J=2.4 Hz), 7.68 (1H, d, J=2.0 Hz), 8.32 (2H, d, J=4.7 Hz), 8.38 (1H, d, J=8.8 Hz), 8.68 (2H, s).

Example 380

1-(3-(2-Methylpyridin-3-yl)phenyl)-4-(4-(pyrimidin-2-yl)piperazin-1-yl)pyrrolidin-2-one (optical isomer)

A racemate of 1-(3-(2-methylpyridin-3-yl)phenyl)-4-(4-(pyrimidin-2-yl)piperazin-1-yl)pyrrolidin-2-one (24.4 mg)

was optically separated by preparative SFC (CHIRALPAK AS (Trade name), 20 mmID×250 mmL, Daicel Corporation, mobile phase: carbon dioxide/methanol=770/230). The material which showed shorter retention time was triturated with diisopropyl ether to give the title compound (7.5 mg).

$^1$H NMR (300 MHz, CDCl$_3$) δ 2.52 (3H, s), 2.54-2.63 (4H, m), 2.64-2.75 (1H, m), 2.76-2.86 (1H, m), 3.20-3.35 (1H, m), 3.82-3.93 (5H, m), 3.95-4.05 (1H, m), 6.51 (1H, t, J=4.8 Hz), 7.12 (1H, dt, J=7.7, 1.2 Hz), 7.19 (1H, dd, J=7.3, 4.9 Hz), 7.45 (1H, t, J=7.9 Hz), 7.53 (1H, dd, J=7.6, 1.7 Hz), 7.56-7.66 (2H, m), 8.31 (2H, d, J=4.8 Hz), 8.51 (1H, dd, J=4.9, 1.7 Hz).

Example 382

1-(1-(3,3-Dimethylbutanoyl)-2,3-dihydro-1H-indol-5-yl)-4-(4-(1,3-thiazol-2-ylcarbonyl)piperazin-1-yl) pyrrolidin-2-one To a solution of 1-(2,3-dihydro-1H-indol-5-yl)-4-(4-(1,3-thiazol-2-ylcarbonyl)piperazin-1-yl)pyrrolidin-2-one (30 mg) in THF (1 mL) were added triethylamine (0.021 mL) and tert-butylacetyl chloride (0.016 mL) at ambient temperature. The mixture was stirred at ambient temperature under nitrogen atmosphere for 1 hr. The reaction mixture was diluted with ethyl acetate, quenched with water and extracted with ethyl acetate. The organic layer was separated, washed with water and brine successively, dried over sodium sulfate and concentrated in vacuo. The residue was purified by column chromatography (NH silica gel, ethyl acetate/hexane) to give the title compound (11.00 mg) after triturating with diisopropyl ether.

$^1$H NMR (300 MHz, CDCl$_3$) δ 1.09-1.15 (9H, m), 2.33 (2H, s), 2.54-2.70 (5H, m), 2.71-2.82 (1H, m), 3.10-3.33 (3H, m), 3.74-3.97 (4H, m), 4.09 (2H, t, J=8.5 Hz), 4.34-4.61 (2H, m), 7.07 (1H, d, J=7.2 Hz), 7.54 (1H, d, J=3.2 Hz), 7.70 (1H, s), 7.88 (1H, d, J=3.2 Hz), 8.25 (1H, d, J=8.7 Hz).

Example 394

1-(1-((3-Chlorophenyl)acetyl)-2,3-dihydro-1H-indol-5-yl)-4-(4-(1,3-thiazol-2-ylcarbonyl)piperazin-1-yl)pyrrolidin-2-one To a solution of 1-(2,3-dihydro-1H-indol-5-yl)-4-(4-(1,3-thiazol-2-ylcarbonyl)piperazin-1-yl)pyrrolidin-2-one (50 mg), triethylamine (0.053 mL) and 2-(3-chlorophenyl)acetic acid (32.2 mg) in DMF (2 mL) was added HATU (71.7 mg) at room temperature. The mixture was stirred at room temperature for 4 hr. The reaction mixture was diluted with saturated aqueous sodium hydrogen carbonate solution, water and diethyl ether. The mixture was stirred for 10 min at room temperature. The resulted precipitate was collected by filtration and washed with water ant diethyl ether give the title compound (55.0 mg).

$^1$H NMR (300 MHz, CDCl$_3$) δ 2.53-2.83 (6H, m), 3.15-3.32 (3H, m), 3.70-3.96 (6H, m), 4.09 (2H, t, J=8.5 Hz), 4.34-4.65 (2H, m), 7.09 (1H, dd, J=8.8, 2.2 Hz), 7.16-7.22 (1H, m), 7.23-7.29 (2H, m), 7.31 (1H, s), 7.54 (1H, d, J=3.1 Hz), 7.72 (1H, s), 7.88 (1H, d, J=3.1 Hz), 8.22 (1H, d, J=8.8 Hz).

Example 403

1-(3-Bromo-5-fluorophenyl)-4-(4-(pyrimidin-2-yl) piperazin-1-yl)pyrrolidin-2-one A) N-(3-Bromo-5-fluorophenyl)-4-hydroxy-3-(4-(pyrimidin-2-yl)piperazin-1-yl)butanamide To a mixture of 4-(4-(pyrimidin-2-yl)piperazin-1-yl)dihydrofuran-2(3H)-one (100 mg) and 3-bromo-5-fluoroaniline (92 mg) in toluene (1 mL) was added bis(trimethylaluminum)-1,4-diazabicyclo[2.2.2]octane adduct (61.9 mg) at room temperature and the mixture was stirred at 80° C. for 30 min. The reaction mixture was diluted with THF and quenched with sodium sulfate decahydrate (545 mg) at room temperature. The insoluble material was removed by filtration, and the filtrate was concentrated in vacuo. The residue was purified by column chromatography (silica gel, methanol/ethyl acetate) to give the title compound (80 mg).

MS: [M+H]$^+$ 438.1.

B) 1-(3-Bromo-5-fluorophenyl)-4-(4-(pyrimidin-2-yl)piperazin-1-yl)pyrrolidin-2-one To a mixture of N-(3-bromo-5-fluorophenyl)-4-hydroxy-3-(4-(pyrimidin-2-yl)piperazin-1-yl)butanamide (80 mg) and tri-n-butyl phosphine (0.068 mL) in THF (1 mL) was added di-tert-butylazodicarboxylate (63.0 mg) at room temperature. The mixture was stirred at room temperature overnight. The precipitate was collected by filtration and washed with diisopropyl ether to give the title compound (40.0 mg).

$^1$H NMR (300 MHz, CDCl$_3$) δ 2.47-2.63 (4H, m), 2.63-2.73 (1H, m), 2.74-2.86 (1H, m), 3.18-3.31 (1H, m), 3.71-3.80 (1H, m), 3.81-3.97 (5H, m), 6.49-6.54 (1H, m), 7.00-7.08 (1H, m), 7.47-7.57 (2H, m), 8.32 (2H, d, J=4.8 Hz).

Example 405

(4R)-4-(4-(1,3-Thiazol-4-ylcarbonyl)piperazin-1-yl)-1-(1-(4-(trifluoromethyl)phenyl)-2,3-dihydro-1H-indol-5-yl)pyrrolidin-2-one A) 1-(4-(Trifluoromethyl)phenyl)indolin-5-amine A mixture of 5-nitro-1-(4-(trifluoromethyl)phenyl)-1H-indole (150 mg) and 10% palladium on carbon (10% Pd, 50% wet, 30 mg) in methanol (2 mL) was hydrogenated under balloon pressure at ambient temperature overnight. The catalyst was removed by filtration, and the filtrate was concentrated in vacuo. The residue was purified by column chromatography (silica gel, ethyl acetate/hexane) to give the title compound (17 mg).

MS: [M+H]$^+$ 279.2.

B) (3R)-4-Hydroxy-3-(4-(1,3-thiazol-4-ylcarbonyl) piperazin-1-yl)-N-(1-(4-(trifluoromethyl)phenyl)-2,3-dihydro-1H-indol-5-yl)butanamide To a mixture of (4R)-4-(4-(1,3-thiazol-4-ylcarbonyl)piperazin-1-yl)dihydrofuran-2(3H)-one (14.32 mg) and 1-(4-(trifluoromethyl)phenyl)indolin-5-amine (17 mg) in toluene (0.5 mL) was added bis(trimethylaluminum)-1,4-diazabicyclo[2.2.2]octane adduct (7.83 mg) at room temperature, and the mixture was stirred at 80° C. for 30 min. To the mixture were added THF and sodium sulfate decahydrate (79 mg), and the mixture was stirred at room temperature overnight. The insoluble material was removed by filtration, and the filtrate was concentrated in vacuo. The residue was purified by column chromatography (silica gel, methanol/ethyl acetate) to give the title compound (19.00 mg).

MS: [M+H]$^+$ 560.1.

C) (4R)-4-(4-(1,3-Thiazol-4-ylcarbonyl)piperazin-1-yl)-1-(1-(4-(trifluoromethyl)phenyl)-2,3-dihydro-1H-indol-5-yl)pyrrolidin-2-one To a mixture of (3R)-4-hydroxy-3-(4-(1,3-thiazol-4-ylcarbonyl)piperazin-1-yl)-N-(1-(4-(trifluoromethyl)phenyl)-2, 3-dihydro-1H-indol-5-yl)butanamide (15 mg) and tri-n-butyl phosphine (9.94 μl) in THF (0.5 mL) was added di-tert-butylazodicarboxylate (9.26 mg) at room temperature. The mixture was stirred at room temperature overnight and the mixture was concentrated in vacuo. The residue was purified by column chromatography (NH silica gel, ethyl acetate/hexane and then methanol/ethyl acetate) to give the title compound (9.50 mg) after crystallizing with diisopropyl ether/toluene.

$^1$H NMR (300 MHz, CDCl$_3$) δ 2.49-2.89 (6H, m), 3.10-3.38 (3H, m), 3.72-4.19 (8H, m), 7.09-7.25 (4H, m), 7.48-7.70 (3H, m), 8.03 (1H, d, J=2.1 Hz), 8.79 (1H, d, J=2.1 Hz).

Example 406

1-(3-Fluoro-5-(2-methylpyridin-3-yl)phenyl)-4-(4-(pyrimidin-2-yl)piperazin-1-yl)pyrrolidin-2-one A mixture of 1-(3-bromo-5-fluorophenyl)-4-(4-(pyrimidin-2-yl)piperazin-1-yl)pyrrolidin-2-one (35 mg), 2-methyl-3-(4,4,5,5-tetramethyl-1,3,2-dioxaborolan-2-yl)pyridine (27.4 mg), bis(di-tert-butyl(4-dimethylaminophenyl)phosphine)dichloropalladium(II) (5.90 mg), cesium carbonate (54.3 mg) and toluene (1 mL)/water (0.333 mL) was heated at 100° C. for 15 min under microwave irradiation. The reaction mixture was quenched with water and extracted with ethyl acetate. The organic layer was separated, washed with water and brine successively, dried over sodium sulfate and concentrated in vacuo. The residue was purified by column chromatography (NH silica gel, ethyl acetate/hexane and then methanol/ethyl acetate) to give the title compound (28.0 mg) after triturating with ethyl acetate.

$^1$H NMR (300 MHz, CDCl$_3$) δ 2.52 (3H, s), 2.54-2.62 (4H, m), 2.65-2.76 (1H, m), 2.76-2.89 (1H, m), 3.20-3.34 (1H, m), 3.75-4.02 (6H, m), 6.47-6.55 (1H, m), 6.78-6.88 (1H, m), 7.15-7.24 (1H, m), 7.31 (1H, s), 7.48-7.56 (2H, m), 8.32 (2H, d, J=4.7 Hz), 8.53 (1H, dd, J=4.8, 1.8 Hz).

Example 418

(4R)-4-(4-(1,3-Thiazol-4-ylcarbonyl)piperazin-1-yl)-1-(1-(4-(trifluoromethyl)phenyl)-1H-indol-5-yl)pyrrolidin-2-one A) Piperazin-1-yl(1,3-thiazol-4-yl)methanone To a mixture of tert-butyl piperazine-1-carboxylate (31.7 g), 1,3-thiazole-4-carboxylic acid (20 g) and 1-hydroxybenzotriazole hydrate (28.5 g) in anhydrous DMF (500 mL) was added 1-ethyl-3-(3-dimethylaminopropyl)carbodiimide hydrochloride (35.6 g) at room temperature. The mixture was stirred at room temperature for 22 hr. The mixture was poured into water and extracted with ethyl acetate. The organic layer was separated, washed with brine, dried over sodium sulfate and concentrated in vacuo. The solid was washed with diisopropyl ether. The solid was suspended with ethyl acetate (100 mL) and added hydrogen chloride (4 M in ethyl acetate, 171 mL). The mixture was stirred at 50° C. for 2 hr. The solid was collected by filtration. The residue was purified by column chromatography (NH silica gel, methanol/ethyl acetate) to give the title compound (16.00 g).
MS: [M+H]$^+$ 198.0.

B) (4R)-4-(4-(1,3-Thiazol-4-ylcarbonyl)piperazin-1-yl)dihydrofuran-2(3H)-one

A mixture of piperazin-1-yl(1,3-thiazol-4-yl)methanone (8000 mg) and furan-2(5H)-one (3.41 mL) in methanol (8 mL) was stirred at ambient temperature overnight. The mixture was concentrated and purified by column chromatography (NH silica gel, methanol/ethyl acetate). The residue was optically separated by preparative HPLC (CHIRALPAK AD (Trade name), 50 mm ID×500 mmL, Daicel Corporation, mobile phase: ethanol). The material which showed shorter retention time was triturated with diisopropyl ether/2-propyl acetate to give the title compound (3.48 g). The absolute configuration was assigned as R from the result of X-ray crystallographic analysis of another isomer.
MS: [M+H]$^+$ 282.0.

C) 5-Nitro-1-(4-(trifluoromethyl)phenyl)-1H-indole

To a mixture of 5-nitro-1H-indole (1000 mg), potassium carbonate (1705 mg), copper(I) iodide (1175 mg) in dimethyl sulfoxide (10 mL) were added 4-iodobenzotrifluoride (1.071 mL) and N,N'-dimethylethane-1,2-diamine (0.662 mL) at room temperature. The mixture was stirred at 140° C. for 3 hr and then partitioned between ethyl acetate and 14% aqueous NH$_3$ solution. The mixture was extracted with ethyl acetate. The organic layer was separated, washed with water and brine successively, dried over sodium sulfate and concentrated in vacuo. The residue was purified by column chromatography (silica gel, ethyl acetate/hexane) to give the title compound (1040 mg).

$^1$H NMR (300 MHz, CDCl$_3$) δ 6.91 (1H, dd, J=3.4, 0.7 Hz), 7.50 (1H, d, J=3.4 Hz), 7.57 (1H, d, J=9.2 Hz), 7.65 (2H, d, J=8.2 Hz), 7.86 (2H, d, J=8.4 Hz), 8.16 (1H, dd, J=9.2, 2.3 Hz), 8.66 (1H, d, J=2.2 Hz).

D) 1-(4-(Trifluoromethyl)phenyl)-1H-indol-5-amine

A mixture of 5-nitro-1-(4-(trifluoromethyl)phenyl)-1H-indole (300 mg) and 4.2% palladium-activated carbon ethylenediamine complex (60 mg) in ethyl acetate (3 mL) was hydrogenated under balloon pressure at ambient temperature overnight. The catalyst was removed by filtration and the filtrate was concentrated in vacuo. The residue was purified by column chromatography (silica gel, ethyl acetate/hexane) to give the title compound (264 mg).
MS: [M+H]$^+$ 277.0.

E) (3R)-4-Hydroxy-3-(4-(1,3-thiazol-4-ylcarbonyl)piperazin-1-yl)-N-(1-(4-(trifluoromethyl)phenyl)-1H-indol-5-yl)butanamide To a mixture of (4R)-4-(4-(1,3-thiazol-4-ylcarbonyl)piperazin-1-yl)dihydrofuran-2(3H)-one (200 mg) and 1-(4-(trifluoromethyl)phenyl)-1H-indol-5-amine (236 mg) in toluene (2 mL) was added bis(trimethylaluminum)-1,4-diazabicyclo[2.2.2]octane adduct (109 mg) at room temperature, and the mixture was stirred at 80° C. for 30 min. To the mixture were added THF and sodium sulfate decahydrate (1099 mg), and the mixture was stirred at room temperature overnight. The insoluble material was removed by filtration, and the filtrate was concentrated in vacuo. The residue was purified by column chromatography (silica gel, methanol/ethyl acetate) to give the title compound (380 mg).
MS: [M+H]$^+$ 558.2.

F) (4R)-4-(4-(1,3-Thiazol-4-ylcarbonyl)piperazin-1-yl)-1-(1-(4-(trifluoromethyl)phenyl)-1H-indol-5-yl)pyrrolidin-2-one To a mixture of (3R)-4-hydroxy-3-(4-(1,3-thiazol-4-ylcarbonyl)piperazin-1-yl)-N-(1-(4-(trifluoromethyl)phenyl)-

1H-indol-5-yl)butanamide (370 mg) and tri-n-butyl phosphine (0.246 mL) in THF (4 mL) was added di-tert-butylazodicarboxylate (229 mg) at room temperature. The mixture was stirred at room temperature overnight. The mixture was purified by column chromatography (NH silica gel, ethyl acetate/hexane and then methanol/ethyl acetate) to give the title compound (200 mg) after recrystallizing from ethanol/heptane.

$^1$H NMR (300 MHz, CDCl$_3$) δ 2.51-2.74 (5H, m), 2.75-2.86 (1H, m), 3.26-3.38 (1H, m), 3.68-4.10 (6H, m), 6.71 (1H, d, J=3.3 Hz), 7.37 (1H, d, J=3.3 Hz), 7.45-7.50 (1H, m), 7.54-7.59 (1H, m), 7.62 (2H, d, J=8.7 Hz), 7.75-7.83 (3H, m), 8.03 (1H, d, J=2.2 Hz), 8.79 (1H, d, J=2.2 Hz).

Example 419

(4R)-4-(4-(1,3-Thiazol-4-ylcarbonyl)piperazin-1-yl)-1-(1-(5-(trifluoromethyl)pyridin-2-yl)-1H-indol-5-yl)pyrrolidin-2-one A) 5-Nitro-1-(5-(trifluoromethyl)pyridin-2-yl)-1H-indole To a solution of 5-nitroindole (500 mg) and 2-fluoro-5-trifluoromethylpyridine (0.447 mL) in DMA (5 mL) was added cesium carbonate (1507 mg) at ambient temperature. The mixture was stirred at 130° C. for 3 hr. The reaction mixture was quenched with water and extracted with ethyl acetate. The organic layer was separated, washed with brine, dried over sodium sulfate and concentrated in vacuo. The residue was triturated, collected by filtration and washed with diisopropyl ether to give the title compound (260 mg).

MS: [M+H]$^+$ 308.0.

B) 1-(5-(Trifluoromethyl)pyridin-2-yl)-1H-indol-5-amine

A mixture of 5-nitro-1-(5-(trifluoromethyl)pyridin-2-yl)-1H-indole (260 mg) and 4.2% palladium-activated carbon ethylenediamine complex (52 mg) in ethyl acetate (3 mL) was hydrogenated under balloon pressure at ambient temperature for 3 hr. The catalyst was removed by filtration and the filtrate was concentrated in vacuo. The residue was purified by column chromatography (silica gel, ethyl acetate/hexane) to give the title compound (211 mg).

MS: [M+H]$^+$ 278.0.

C) (3R)-4-Hydroxy-3-(4-(1,3-thiazol-4-ylcarbonyl)piperazin-1-yl)-N-(1-(5-(trifluoromethyl)pyridin-2-yl)-1H-indol-5-yl)butanamide To a mixture of (4R)-4-(4-(1,3-thiazol-4-ylcarbonyl)piperazin-1-yl)dihydrofuran-2(3H)-one (50 mg) and 1-(5-(trifluoromethyl)pyridin-2-yl)-1H-indol-5-amine (59.1 mg) in toluene (1 mL) was added bis(trimethylaluminum)-1,4-diazabicyclo[2.2.2]octane adduct (27.3 mg) at room temperature and the mixture was stirred at 80° C. for 30 min. To the mixture were added THF and sodium sulfate decahydrate (275 mg) and the mixture was stirred at room temperature overnight. The insoluble material was removed by filtration, and the filtrate was concentrated in vacuo. The residue was purified by column chromatography (silica gel, methanol/ethyl acetate) to give the title compound (81 mg).

MS: [M+H]$^+$ 559.1.

D) (4R)-4-(4-(1,3-Thiazol-4-ylcarbonyl)piperazin-1-yl)-1-(1-(5-(trifluoromethyl)pyridin-2-yl)-1H-indol-5-yl)pyrrolidin-2-one To a mixture of (3R)-4-hydroxy-3-(4-(1,3-thiazol-4-ylcarbonyl)piperazin-1-yl)-N-(1-(5-(trifluoromethyl)pyridin-2-yl)-1H-indol-5-yl)butanamide (81 mg) and tri-n-butyl phosphine (0.054 mL) in THF (1 mL) was added di-tert-butylazodicarboxylate (50.1 mg) at room temperature. The mixture was stirred at room temperature overnight. The mixture was purified by column chromatography (NH silica gel, ethyl acetate/hexane and then methanol/ethyl acetate) to give the title compound (44.5 mg).

$^1$H NMR (300 MHz, CDCl$_3$) δ 2.49-2.74 (5H, m), 2.75-2.87 (1H, m), 3.25-3.40 (1H, m), 3.69-4.13 (6H, m), 6.75 (1H, d, J=3.2 Hz), 7.48-7.60 (2H, m), 7.75 (1H, d, J=3.6 Hz), 7.83 (1H, d, J=2.0 Hz), 7.97-8.10 (2H, m), 8.38 (1H, d, J=9.0 Hz), 8.74-8.88 (2H, m).

Example 420

(4R)-4-(4-(1,3-Thiazol-4-ylcarbonyl)piperazin-1-yl)-1-(1-(5-(trifluoromethyl)pyridin-2-yl)-2,3-dihydro-1H-indol-5-yl)pyrrolidin-2-one A) 5-Nitro-1-(5-(trifluoromethyl)pyridin-2-yl)indoline To a solution of 5-nitroindoline (500 mg) and 2-fluoro-5-trifluoromethylpyridine (0.441 mL) in DMA (5 mL) was added cesium carbonate (1489 mg) at ambient temperature. The mixture was stirred at 130° C. for 3 hr. The reaction mixture was quenched with water and extracted with ethyl acetate. The organic layer was separated, washed with brine, dried over sodium sulfate and concentrated in vacuo. The residue was purified by column chromatography (silica gel, ethyl acetate/hexane) to give the title compound (830 mg) after triturating with diisopropyl ether.

MS: [M+H]$^+$ 310.0.

B) 1-(5-(Trifluoromethyl)pyridin-2-yl)indolin-5-amine

A mixture of 5-nitro-1-(5-(trifluoromethyl)pyridin-2-yl)indoline (100 mg) and 4.2% palladium-activated carbon ethylenediamine complex (20 mg) in ethyl acetate (2 mL) was hydrogenated under balloon pressure at ambient temperature for 5 hr. The catalyst was removed by filtration and the filtrate was concentrated in vacuo. The residue was purified by column chromatography (silica gel, ethyl acetate/hexane) to give the title compound (90 mg).

MS: [M+H]$^+$ 280.0.

C) (3R)-4-Hydroxy-3-(4-(1,3-thiazol-4-ylcarbonyl)piperazin-1-yl)-N-(1-(5-(trifluoromethyl)pyridin-2-yl)-2,3-dihydro-1H-indol-5-yl)butanamide To a mixture of (4R)-4-(4-(1,3-thiazol-4-ylcarbonyl)piperazin-1-yl)dihydrofuran-2(3H)-one (50 mg) and 1-(5-(trifluoromethyl)pyridin-2-yl)indolin-5-amine (59.6 mg) in toluene (1 mL) was added bis(trimethylaluminum)-1,4-diazabicyclo[2.2.2]octane adduct (27.3 mg, 0.11 mmol) at room temperature and the mixture was stirred at 80° C. for 30 min. To the mixture were added THF and sodium sulfate decahydrate (275 mg) and the mixture was stirred at room temperature for 3 hr. The insoluble material was removed by filtration, and the filtrate was concentrated in vacuo. The residue was purified by column chromatography (silica gel, methanol/ethyl acetate) to give the title compound (72.0 mg).

MS: [M+H]+ 561.2.

D) (4R)-4-(4-(1,3-Thiazol-4-ylcarbonyl)piperazin-1-yl)-1-(1-(5-(trifluoromethyl)pyridin-2-yl)-2,3-dihydro-1H-indol-5-yl)pyrrolidin-2-one To a mixture of (3R)-4-hydroxy-3-(4-(1,3-thiazol-4-ylcarbonyl)piperazin-1-yl)-N-(1-(5-(trifluoromethyl)pyridin-2-yl)-2,3-dihydro-1H-indol-5-yl)butanamide (75 mg) and tri-n-butyl phosphine (0.050 mL) in THF (1 mL) was added di-tert-butylazodicarboxylate (46.2 mg) at room temperature. The mixture was stirred at room temperature overnight. The precipitate was collected by filtration and washed with diisopropyl ether to give the title compound (47.0 mg).

$^1$H NMR (300 MHz, CDCl$_3$) δ 2.53-2.71 (5H, m), 2.71-2.83 (1H, m), 3.19-3.37 (3H, m), 3.71-3.85 (2H, m), 3.86-4.12 (6H, m), 6.72 (1H, d, J=8.9 Hz), 7.16 (1H, dd, J=8.8, 2.4 Hz), 7.65 (1H, s), 7.76 (1H, dd, J=8.9, 2.2 Hz), 8.03 (1H, d, J=2.2 Hz), 8.33 (1H, d, J=8.8 Hz), 8.57 (1H, s), 8.79 (1H, d, J=2.2 Hz).

Example 423

(4R)-1-(1-(4-Chlorophenyl)-1H-indol-5-yl)-4-(4-(1,3-thiazol-4-ylcarbonyl)piperazin-1-yl)pyrrolidin-2-one A) 1-(4-Chlorophenyl)-1H-indol-5-amine A mixture of 1H-indol-5-amine (400 mg), potassium carbonate (837 mg), copper(I) iodide (144 mg), 1-chloro-4-iodobenzene (0.461 mL), N,N'-dimethylethane-1,2-diamine (0.162 mL), and toluene (10 mL) was heated at 120° C. for 1 hr under microwave irradiation. The mixture was diluted with ethyl acetate, filtered through the short pad of silica gel eluting with ethyl acetate. The filtrate was concentrated in vacuo, and the residue was purified by column chromatography (silica gel, ethyl acetate/hexane) to give the title compound (63.0 mg).

MS: [M+H]+ 243.1.

B) (3R)—N-(1-(4-Chlorophenyl)-1H-indol-5-yl)-4-hydroxy-3-(4-(1,3-thiazol-4-ylcarbonyl)piperazin-1-yl)butanamide To a mixture of (4R)-4-(4-(1,3-thiazol-4-ylcarbonyl)piperazin-1-yl)dihydrofuran-2(3H)-one (58.0 mg) and 1-(4-chlorophenyl)-1H-indol-5-amine (55 mg) in toluene (2 mL) was added bis(trimethylaluminum)-1,4-diazabicyclo[2.2.2]octane adduct (31.7 mg) at room temperature and the mixture was stirred at 80° C. for 2 hr. The mixture was cooled to 0° C., and then THF (2 mL) and sodium sulfate decahydrate (478 mg) were added thereto. After the mixture was stirred at room temperature for overnight, the insoluble material was removed by filtration, and the filtrate was concentrated in vacuo. The residue was purified by column chromatography (silica gel, methanol/ethyl acetate) to give a crude of the title compound (73.0 mg).

MS: [M+H]+ 524.2.

C) (4R)-1-(1-(4-Chlorophenyl)-1H-indol-5-yl)-4-(4-(1,3-thiazol-4-ylcarbonyl)piperazin-1-yl)pyrrolidin-2-one To a stirred solution of (3R)—N-(1-(4-Chlorophenyl)-1H-indol-5-yl)-4-hydroxy-3-(4-(1,3-thiazol-4-ylcarbonyl)piperazin-1-yl)butanamide (73 mg) in anhydrous THF (2.5 mL) were successively added tri-n-butyl phosphine (0.045 mL) and di-tert-butylazodicarboxylate (41.7 mg) at room temperature, and the mixture was stirred for 2 hr. The mixture was concentrated in vacuo, and the residue was dissolved in anhydrous THF (2.5 mL). To this solution were re-added tri-n-butyl phosphine (0.045 mL) and di-tert-butylazodicarboxylate (41.7 mg), and the mixture was stirred for 2 hr. The mixture was heated at 60° C. for 1 hr. The mixture was concentrated in vacuo, and the residue was purified by column chromatography (NH-silica gel, ethyl acetate/hexane) to give a crude brown oil. The residue was purified by preparative HPLC (C18, mobile phase: water/acetonitrile containing 0.1% trifluoroacetic acid). The desired fraction was neutralized with saturated aqueous sodium hydrogen carbonate solution and extracted with ethyl acetate. The organic layer was separated, dried over magnesium sulfate and concentrated in vacuo, and the residue was crystallized from methanol/water to give the title compound (26.0 mg).

$^1$H NMR (300 MHz, CDCl$_3$) δ 2.38-2.98 (6H, m), 3.19-3.44 (1H, m), 3.65-4.39 (6H, m), 6.67 (1H, d, J=3.4 Hz), 7.31 (1H, d, J=3.4 Hz), 7.38-7.54 (6H, m), 7.73 (1H, d, J=1.3 Hz), 8.03 (1H, d, J=2.1 Hz), 8.79 (1H, d, J=2.1 Hz).

Example 424

(4R)-1-(3-Fluoro-5-(2-methylpyridin-3-yl)phenyl)-4-(4-(1,3-thiazol-2-ylcarbonyl)piperazin-1-yl)pyrrolidin-2-one A) 3-(3-Fluoro-5-nitrophenyl)-2-methylpyridine A mixture of 1-nitro-3-fluoro-5-bromobenzene (274 mg), 2-methyl-3-(4,4,5,5-tetramethyl-1,3,2-dioxaborolan-2-yl)pyridine (300 mg) and toluene (3 mL) was added 1,1'-bis(diphenylphosphino)ferrocene palladium dichloride (45.5 mg) and 2 M aqueous sodium carbonate solution (1.245 mL). The mixture was heated at 150° C. for 30 min under microwave irradiation. The reaction mixture was quenched with water and extracted with ethyl acetate. The organic layer was separated, washed with water and brine successively, dried over sodium sulfate and concentrated in vacuo. The residue was purified by column chromatography (NH silica gel, ethyl acetate/hexane) to give the title compound (235 mg).

MS: [M+H]+ 233.2.

B) 3-Fluoro-5-(2-methylpyridin-3-yl)aniline

A mixture of 3-(3-fluoro-5-nitrophenyl)-2-methylpyridine (235 mg) and 4.2% palladium-activated carbon ethylenediamine complex (47 mg) in methanol (2 mL) was hydrogenated under balloon pressure at room temperature overnight. The catalyst was removed by filtration and the filtrate was concentrated in vacuo. The residue was purified by column chromatography (silica gel, ethyl acetate/hexane) to give the title compound (107 mg).
MS: [M+H]⁺ 203.2.

C) (3R)—N-(3-Fluoro-5-(2-methylpyridin-3-yl)phenyl)-4-hydroxy-3-(4-(1,3-thiazol-2-ylcarbonyl)piperazin-1-yl)butanamide To a mixture of (4R)-4-(4-(1,3-thiazol-2-ylcarbonyl)piperazin-1-yl)dihydrofuran-2(3H)-one (58.0 mg) and 3-fluoro-5-(2-methylpyridin-3-yl)aniline (50 mg) in toluene (1 mL) was added bis(trimethylaluminum)-1,4-diazabicyclo[2.2.2]octane adduct (31.7 mg) at room temperature and the mixture was stirred at 80° C. for 30 min. The reaction mixture was diluted with THF and quenched with sodium sulfate decahydrate (279 mg) at room temperature. The insoluble material was removed by filtration, and the filtrate was concentrated in vacuo. The residue was purified by column chromatography (silica gel, methanol/ethyl acetate) to give the title compound (71.0 mg).
MS: [M+H]⁺ 484.3.

D) (4R)-1-(3-Fluoro-5-(2-methylpyridin-3-yl)phenyl)-4-(4-(1,3-thiazol-2-ylcarbonyl)piperazin-1-yl)pyrrolidin-2-one To a mixture of (3R)—N-(3-fluoro-5-(2-methylpyridin-3-yl)phenyl)-4-hydroxy-3-(4-(1,3-thiazol-2-ylcarbonyl)piperazin-1-yl)butanamide (71 mg) and tri-n-butyl phosphine (0.054 mL) in THF (1 mL) was added di-tert-butylazodicarboxylate (50.7 mg) at room temperature. The mixture was stirred at room temperature overnight. The mixture was purified by column chromatography (NH silica gel, ethyl acetate/hexane and then methanol/ethyl acetate) to give the title compound (26.0 mg) after triturating with diisopropyl ether.
¹H NMR (300 MHz, CDCl₃) δ 2.52 (3H, s), 2.56-2.73 (5H, m), 2.76-2.86 (1H, m), 3.24-3.35 (1H, m), 3.76-4.01 (4H, m), 4.36-4.61 (2H, m), 6.81-6.87 (1H, m), 7.19 (1H, dd, J=7.9, 4.9 Hz), 7.30 (1H, s), 7.48-7.57 (3H, m), 7.88 (1H, d, J=3.2 Hz), 8.53 (1H, dd, J=4.9, 1.7 Hz).

Example 425

(4R)-4-(4-(1,3-Thiazol-4-ylcarbonyl)piperazin-1-yl)-1-(1-(4-(trifluoromethyl)pyridin-2-yl)-1H-indol-5-yl)pyrrolidin-2-one

A) 5-Nitro-1-(4-(trifluoromethyl)pyridin-2-yl)-1H-indole

To a solution of 5-nitroindole (300 mg) and 2-chloro-4-(trifluoromethyl)pyridine (0.476 mL) in DMA (3 mL) was added potassium carbonate (384 mg) at ambient temperature. The mixture was stirred at 170° C. for 30 min under microwave irradiation. The reaction mixture was quenched with water and extracted with ethyl acetate. The organic layer was separated, washed with brine, dried over sodium sulfate and concentrated in vacuo. The residue was purified by column chromatography (NH silica gel, ethyl acetate/hexane) to give the title compound (563 mg) after triturating with diisopropyl ether.
¹H NMR (300 MHz, CDCl₃) δ 6.94 (1H, dd, J=3.6, 0.7 Hz), 7.49 (1H, dd, J=5.1, 0.8 Hz), 7.68 (1H, s), 7.85 (1H, d, J=3.6 Hz), 8.23 (1H, dd, J=9.2, 2.3 Hz), 8.45 (1H, d, J=9.3 Hz), 8.61 (1H, d, J=2.2 Hz), 8.80 (1H, d, J=5.1 Hz).

B) 1-(4-(Trifluoromethyl)pyridin-2-yl)-1H-indol-5-amine

A mixture of 5-nitro-1-(4-(trifluoromethyl)pyridin-2-yl)-1H-indole (563 mg) and 4.2% palladium-activated carbon ethylenediamine complex (112 mg) in ethyl acetate (3 mL) was hydrogenated under balloon pressure at ambient temperature overnight. The catalyst was removed by filtration and the filtrate was concentrated in vacuo. The residue was purified by column chromatography (silica gel, ethyl acetate/hexane) to give the title compound (479 mg).
MS: [M+H]⁺ 278.2.

C) (3R)-4-Hydroxy-3-(4-(1,3-thiazol-4-ylcarbonyl)piperazin-1-yl)-N-(1-(4-(trifluoromethyl)pyridin-2-yl)-1H-indol-5-yl)butanamide To a mixture of (4R)-4-(4-(1,3-thiazol-4-ylcarbonyl)piperazin-1-yl)dihydrofuran-2(3H)-one (50 mg) and 1-(4-(trifluoromethyl)pyridin-2-yl)-1H-indol-5-amine (59.1 mg) in toluene (1 mL) was added bis(trimethylaluminum)-1,4-diazabicyclo[2.2.2]octane adduct (27.3 mg) at room temperature and the mixture was stirred at 80° C. for 30 min. To the mixture were added THF and sodium sulfate decahydrate (275 mg) and the mixture was stirred at room temperature overnight. The insoluble material was removed by filtration, and the filtrate was concentrated in vacuo. The residue was purified by column chromatography (silica gel, methanol/ethyl acetate) to give the title compound (78 mg).
MS: [M+H]⁺ 559.1.

D) (4R)-4-(4-(1,3-Thiazol-4-ylcarbonyl)piperazin-1-yl)-1-(1-(4-(trifluoromethyl)pyridin-2-yl)-1H-indol-5-yl)pyrrolidin-2-one To a mixture of (3R)-4-hydroxy-3-(4-(1,3-thiazol-4-ylcarbonyl)piperazin-1-yl)-N-(1-(4-(trifluoromethyl)pyridin-2-yl)-1H-indol-5-yl)butanamide (78 mg) and tri-n-butyl phosphine (0.052 mL) in THF (1 mL) was added di-tert-butylazodicarboxylate (48.2 mg) at room temperature. The mixture was stirred at the same temperature overnight. The mixture was purified by column chromatography (silica gel, ethyl acetate/hexane and then methanol/ethyl acetate) to give the title compound (27.0 mg) after triturating with diisopropyl ether/toluene.
¹H NMR (300 MHz, CDCl₃) δ 2.51-2.74 (5H, m), 2.75-2.88 (1H, m), 3.25-3.41 (1H, m), 3.73-4.12 (6H, m), 6.75 (1H, d, J=3.8 Hz), 7.36 (1H, d, J=5.1 Hz), 7.52 (1H, dd, J=9.0, 2.1 Hz), 7.65 (1H, s), 7.75 (1H, d, J=3.6 Hz), 7.82 (1H, d, J=2.1 Hz), 8.03 (1H, d, J=2.1 Hz), 8.32 (1H, d, J=9.1 Hz), 8.73 (1H, d, J=5.2 Hz), 8.79 (1H, d, J=2.1 Hz).

Example 426

(4R)-1-(3-Fluoro-5-(2-methylpyridin-3-yl)phenyl)-4-(4-(pyrimidin-2-yl)piperazin-1-yl)pyrrolidin-2-one A racemate of 1-(3-fluoro-5-(2-methylpyridin-3-yl)phenyl)-4-(4-(pyrimidin-2-yl)piperazin-1-yl)pyrrolidin-2-one (4.40 g) was separated by preparative HPLC (CHIRALCEL OD (Trade name), 50 mmID×500 mmL, Daicel Corporation, mobile phase: ethanol/hexane=500/500). The material which showed shorter retention time was recrystallized from ethyl acetate/heptane to give the title compound (1.66 g). The absolute configuration was assigned as R from the result of X-ray crystallographic analysis of another isomer.

¹H NMR (300 MHz, CDCl₃) δ 2.52 (3H, s), 2.54-2.62 (4H, m), 2.64-2.75 (1H, m), 2.77-2.88 (1H, m), 3.16-3.34 (1H, m), 3.81 (1H, dd, J=9.3, 6.9 Hz), 3.85-3.92 (4H, m), 3.93-4.02 (1H, m), 6.46-6.55 (1H, m), 6.80-6.88 (1H, m), 7.19 (1H, dd, J=7.6, 5.0 Hz), 7.29-7.33 (1H, m), 7.47-7.57 (2H, m), 8.31 (2H, d, J=4.7 Hz), 8.53 (1H, dd, J=4.9, 1.7 Hz).

Example 430

4-(4-(Pyrimidin-2-yl)piperazin-1-yl)-1-(1-(5-(trifluoromethyl)pyrimidin-2-yl)-2,3-dihydro-1H-indol-5-yl)pyrrolidin-2-one (optical isomer)

A racemate of 4-(4-(pyrimidin-2-yl)piperazin-1-yl)-1-(1-(5-(trifluoromethyl)pyrimidin-2-yl)-2,3-dihydro-1H-indol-5-yl)pyrrolidin-2-one (20 mg) was optically separated by preparative SFC (CHIRALPAK AS-H (Trade name), 20 mmID×250 mmL, Daicel Corporation, mobile phase: carbon dioxide/methanol=700/300). The material which showed shorter retention time was collected by filtration to give the title compound (6.10 mg) after triturating with diisopropyl ether.

¹H NMR (300 MHz, CDCl₃) δ 2.53-2.61 (4H, m), 2.63-2.89 (2H, m), 3.18-3.34 (3H, m), 3.78-4.03 (6H, m), 4.25-4.35 (2H, m), 6.45-6.57 (1H, m), 7.21-7.25 (1H, m), 7.68 (1H, d, J=2.0 Hz), 8.32 (2H, d, J=4.7 Hz), 8.38 (1H, d, J=8.8 Hz), 8.68 (2H, s).

Example 432

(4R)-4-(4-(1,3-Thiazol-4-ylcarbonyl)piperazin-1-yl)-1-(1-(5-(trifluoromethyl)pyrimidin-2-yl)-1H-indol-5-yl)pyrrolidin-2-one A) (3R)-4-Hydroxy-3-(4-(1,3-thiazol-4-ylcarbonyl)piperazin-1-yl)-N-(1-(5-(trifluoromethyl)pyrimidin-2-yl)-1H-indol-5-yl)butanamide To a mixture of (4R)-4-(4-(1,3-thiazol-4-ylcarbonyl)piperazin-1-yl)dihydrofuran-2(3H)-one (16.85 mg) and 1-(5-(trifluoromethyl)pyrimidin-2-yl)-1H-indol-5-amine (20 mg) in toluene (0.5 mL) was added bis(trimethylaluminum)-1,4-diazabicyclo[2.2.2]octane adduct (9.21 mg) at room temperature, and the mixture was stirred at 80° C. for 30 min. To the mixture were added THF and sodium sulfate decahydrate (93 mg), and the mixture was stirred at room temperature overnight. The insoluble material was removed by filtration, and the filtrate was concentrated in vacuo. The residue was purified by column chromatography (silica gel, methanol/ethyl acetate) to give the title compound (16.00 mg).

MS: [M+H]⁺ 560.2.

B) (4R)-4-(4-(1,3-Thiazol-4-ylcarbonyl)piperazin-1-yl)-1-(1-(5-(trifluoromethyl)pyrimidin-2-yl)-1H-indol-5-yl)pyrrolidin-2-one To a mixture of (3R)-4-hydroxy-3-(4-(1,3-thiazol-4-ylcarbonyl)piperazin-1-yl)-N-(1-(5-(trifluoromethyl)pyrimidin-2-yl)-1H-indol-5-yl)butanamide (16 mg) and tri-n-butyl phosphine (10.61 μl) in THF (0.5 mL) was added di-tert-butylazodicarboxylate (9.88 mg) at room temperature. The mixture was stirred at room temperature overnight and the mixture was concentrated in vacuo. The residue was purified by column chromatography (NH silica gel, ethyl acetate/hexane and then methanol/ethyl acetate) to give the title compound (5.00 mg) after triturating with ethyl acetate.

¹H NMR (300 MHz, CDCl₃) δ 2.53-2.74 (5H, m), 2.76-2.87 (1H, m), 3.26-3.39 (1H, m), 3.74-4.07 (6H, m), 6.73 (1H, d, J=3.8 Hz), 7.53 (1H, dd, J=9.1, 2.3 Hz), 7.84 (1H, d, J=2.1 Hz), 8.04 (1H, d, J=2.1 Hz), 8.28 (1H, d, J=3.8 Hz), 8.75 (1H, d, J=9.1 Hz), 8.80 (1H, d, J=2.1 Hz), 8.92 (2H, s).

Example 433

4-(4-(Pyrimidin-2-yl)piperazin-1-yl)-1-(1-(5-(trifluoromethyl)pyrimidin-2-yl)-1H-indol-5-yl)pyrrolidin-2-one A) 4-Hydroxy-3-(4-(pyrimidin-2-yl)piperazin-1-yl)-N-(1-(5-(trifluoromethyl)pyrimidin-2-yl)-1H-indol-5-yl)butanamide To a mixture of 4-(4-(pyrimidin-2-yl)piperazin-1-yl)dihydrofuran-2(3H)-one (19.33 mg) and 1-(5-(trifluoromethyl)pyrimidin-2-yl)-1H-indol-5-amine (26 mg) in toluene (1 mL) was added bis(trimethylaluminum)-1,4-diazabicyclo[2.2.2]octane adduct (11.98 mg) at room temperature, and the mixture was stirred at 80° C. for 1 hr. The reaction mixture was diluted with THF and quenched with sodium sulfate decahydrate (105 mg) at room temperature. The insoluble material was removed by filtration, and the filtrate was concentrated in vacuo. The residue was purified by column chromatography (silica gel, methanol/ethyl acetate) to give the title compound (26.1 mg).

MS: [M+H]⁺ 527.2.

B) 4-(4-(Pyrimidin-2-yl)piperazin-1-yl)-1-(1-(5-(trifluoromethyl)pyrimidin-2-yl)-1H-indol-5-yl)pyrrolidin-2-one To a mixture of 4-hydroxy-3-(4-(pyrimidin-2-yl)piperazin-1-yl)-N-(1-(5-(trifluoromethyl)pyrimidin-2-yl)-1H-indol-5-yl)butanamide (30 mg) and tri-n-butyl phosphine (0.021 mL) in DMF (1 mL) was added di-tert-butylazodicarboxylate (19.68 mg) at room temperature. The mixture was stirred at room temperature overnight. The precipitate was collected by filtration and washed with diisopropyl ether to give the title compound (18.00 mg).

¹H NMR (300 MHz, CDCl₃) δ 2.55-2.66 (4H, m), 2.67-2.77 (1H, m), 2.78-2.88 (1H, m), 3.22-3.37 (1H, m), 3.84-3.97 (5H, m), 4.01-4.10 (1H, m), 6.47-6.55 (1H, m), 6.74 (1H, d, J=3.2 Hz), 7.55 (1H, dd, J=9.1, 2.2 Hz), 7.84 (1H, d, J=2.1 Hz), 8.28 (1H, d, J=3.7 Hz), 8.32 (2H, d, J=4.7 Hz), 8.75 (1H, d, J=9.1 Hz), 8.92 (2H, d, J=0.8 Hz).

All Example compounds are shown in the following Tables 1-1 to 1-48. The compounds of Example 2 to 6, 8 to 12, 16 to 20, 22, 24 to 51, 55, 56, 58, 59, 61, 63 to 71, 73 to 76, 78, 81 to 84, 86, 87, 89 to 108, 110 to 113, 115 to 138, 140, 142 to 144, 146, 148, 151 to 171, 173 to 224, 227, 229 to 231, 233 to 255, 258, 262 to 272, 274 to 350, 352, 354 to 365, 368 to 371, 377, 379, 381, 383, 385 to 393, 395 to 402, 404, 407 to 417, 421, 422, 427 to 429, 431, and 434 were produced according to the above-mentioned production methods, Examples or a method analogous thereto. MS in the tables means actual measured value.

TABLE 1-1

| EX-AMPLE | IUPAC NAME | STRUCTURE | ADDITIVE | MS |
|---|---|---|---|---|
| 1 | 1-(4-phenoxyphenyl)-4-(4-(1,3-thiazol-2-ylcarbonyl)piperazin-1-yl)pyrrolidin-2-one | 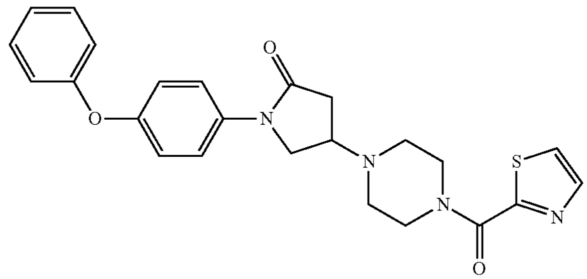 [SMILES: O=C(c1nccs1)N1CCN(C2CC(=O)N(c3ccc(Oc4ccccc4)cc3)C2)CC1] | | 449.0 |
| 2 | 1-(4-phenoxyphenyl)-4-(4-(pyrimidin-2-yl)piperazin-1-yl)pyrrolidin-2-one | 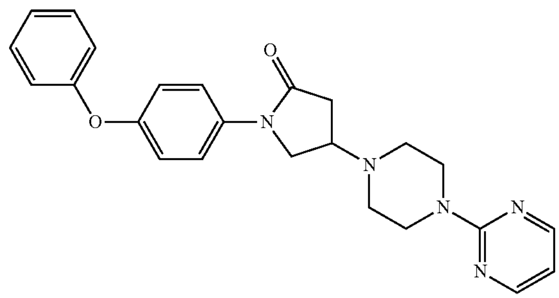 [SMILES: O=C1CC(N2CCN(c3ncccn3)CC2)CN1c1ccc(Oc2ccccc2)cc1] | | 416.2 |
| 3 | tert-butyl 4-(5-oxo-1-(4-phenoxyphenyl)pyrrolidin-3-yl)piperazine-1-carboxylate | 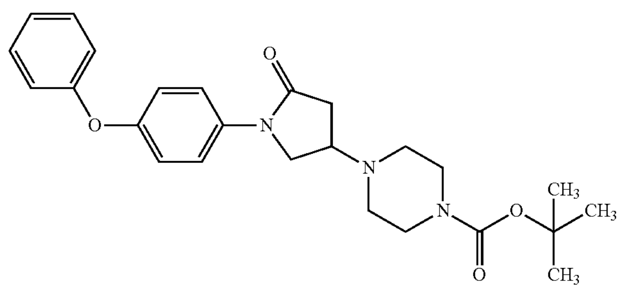 [SMILES: CC(C)(C)OC(=O)N1CCN(C2CC(=O)N(c3ccc(Oc4ccccc4)cc3)C2)CC1] | | 438.1 |
| 4 | 1-(4-phenoxyphenyl)-4-(4-(2-thienylcarbonyl)piperazin-1-yl)pyrrolidin-2-one | 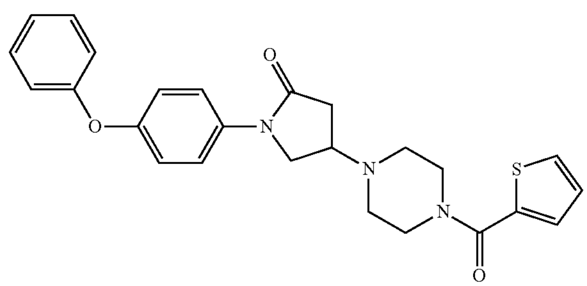 [SMILES: O=C(c1cccs1)N1CCN(C2CC(=O)N(c3ccc(Oc4ccccc4)cc3)C2)CC1] | | 448.1 |
| 5 | 4-(4-benzoylpiperazin-1-yl)-1-(4-phenoxyphenyl)pyrrolidin-2-one | 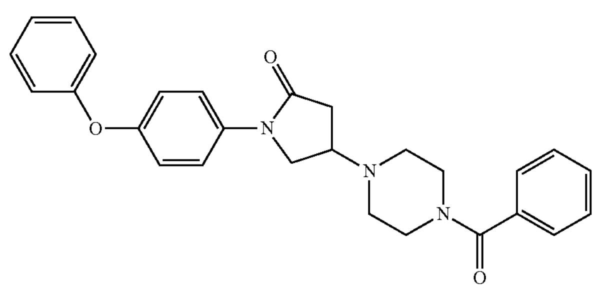 [SMILES: O=C(c1ccccc1)N1CCN(C2CC(=O)N(c3ccc(Oc4ccccc4)cc3)C2)CC1] | | 442.2 |

TABLE 1-1-continued

| EXAMPLE | IUPAC NAME | STRUCTURE | ADDITIVE | MS |
|---|---|---|---|---|
| 6 | 1-(4-phenoxyphenyl)-4-(4-(1,3-thiazol-4-ylcarbonyl)piperazin-1-yl)pyrrolidin-2-one | 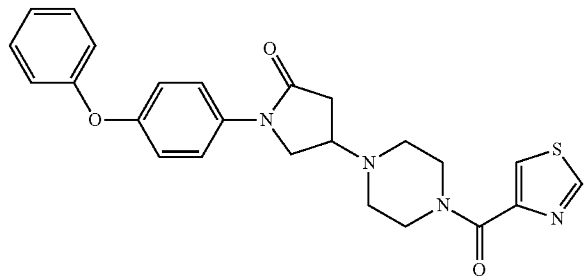 [SMILES: O=C(c1cscn1)N1CCN(C2CC(=O)N(c3ccc(Oc4ccccc4)cc3)C2)CC1] | | 449.0 |
| 7 | 2-(4-(5-oxo-1-(4-phenoxyphenyl)pyrrolidin-3-yl)piperazin-1-yl)nicotinonitrile | 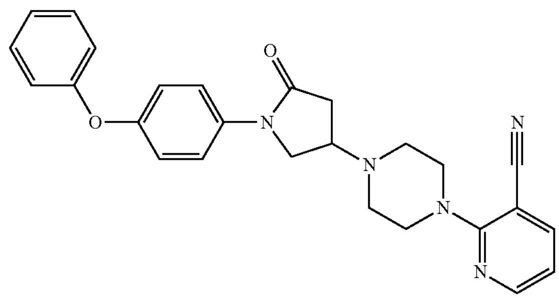 [SMILES: N#Cc1cccnc1N1CCN(C2CC(=O)N(c3ccc(Oc4ccccc4)cc3)C2)CC1] | | 440.1 |
| 8 | 4-(4-(5-chloro-2-furoyl)piperazin-1-yl)-1-(4-phenoxyphenyl)pyrrolidin-2-one | 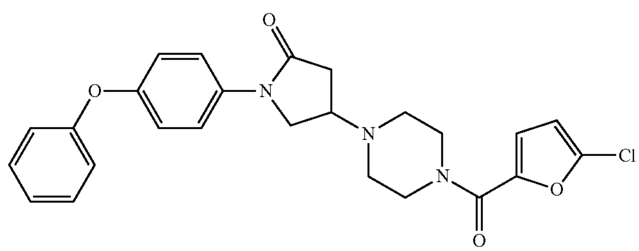 [SMILES: O=C(c1ccc(Cl)o1)N1CCN(C2CC(=O)N(c3ccc(Oc4ccccc4)cc3)C2)CC1] | | 466.1 |
| 9 | 1-(4-phenoxyphenyl)-4-(4-(1H-pyrrol-2-ylcarbonyl)piperazin-1-yl)pyrrolidin-2-one | 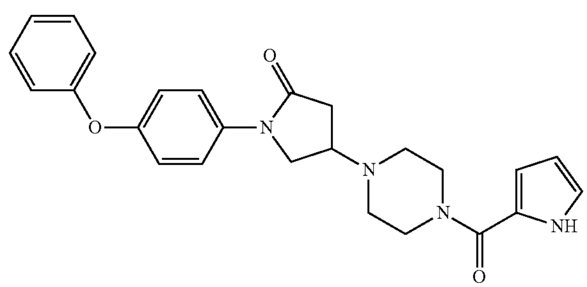 [SMILES: O=C(c1ccc[nH]1)N1CCN(C2CC(=O)N(c3ccc(Oc4ccccc4)cc3)C2)CC1] | | 431.1 |

TABLE 1-2

| | | | | |
|---|---|---|---|---|
| 10 | 1-(4-phenoxyphenyl)-4-(4-(pyridin-2-yl)piperazin-1-yl)pyrrolidin-2-one | | | 415.2 |

TABLE 1-2-continued

| 11 | 1-(3-phenoxyphenyl)-4-(4-(1,3-thiazol-2-ylcarbonyl)piperazin-1-yl)pyrrolidin-2-one | 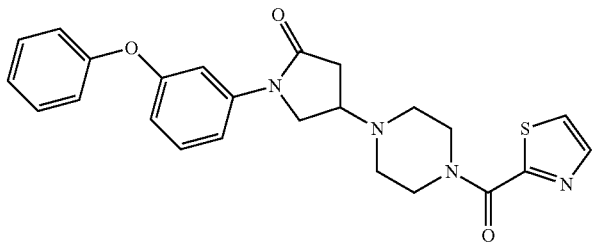 [SMILES: O=C(c1nccs1)N1CCN(C2CC(=O)N(c3cccc(Oc4ccccc4)c3)C2)CC1] | 448.9 |
| 12 | 1-(4-(3,4-difluorophenoxy)phenyl)-4-(4-(1,3-thiazol-2-ylcarbonyl)piperazin-1-yl)pyrrolidin-2-one | 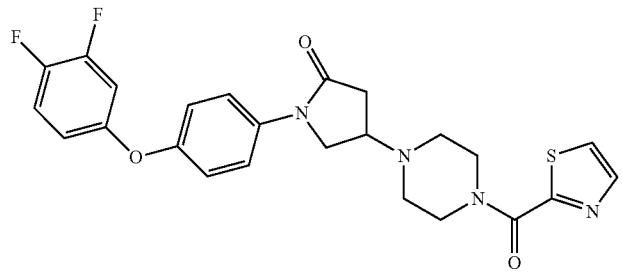 [SMILES: O=C(c1nccs1)N1CCN(C2CC(=O)N(c3ccc(Oc4ccc(F)c(F)c4)cc3)C2)CC1] | 485.0 |
| 13 | 1-(2-methoxy-4-phenoxyphenyl)-4-(4-(1,3-thiazol-2-ylcarbonyl)piperazin-1-yl)pyrrolidin-2-one | 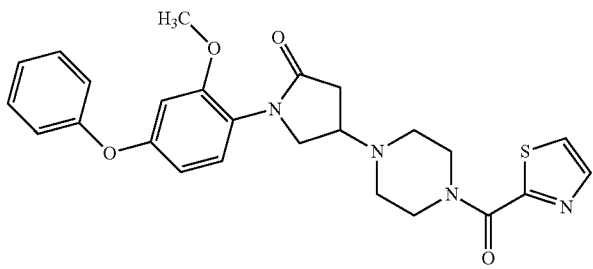 [SMILES: COc1cc(Oc2ccccc2)ccc1N1CC(N2CCN(C(=O)c3nccs3)CC2)CC1=O] | 479.0 |
| 14 | 1-(1-(4-fluorophenyl)-1H-indol-5-yl)-4-(4-(1,3-thiazol-2-ylcarbonyl)piperazin-1-yl)pyrrolidin-2-one | 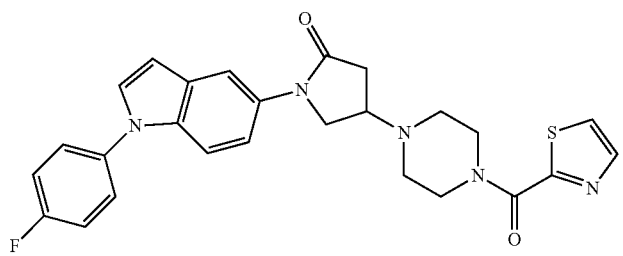 [SMILES: O=C(c1nccs1)N1CCN(C2CC(=O)N(c3ccc4c(ccn4-c4ccc(F)cc4)c3)C2)CC1] | 490.0 |
| 15 | (4R)-1-(4-phenoxyphenyl)-4-(4-(1,3-thiazol-2-ylcarbonyl)piperazin-1-yl)pyrrolidin-2-one | 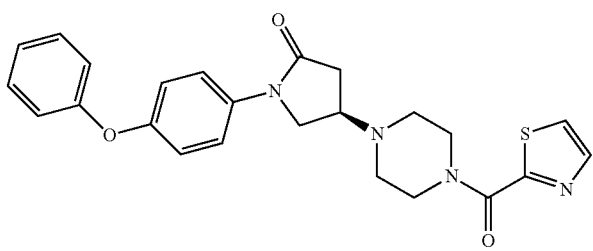 [SMILES: O=C(c1nccs1)N1CCN([C@@H]2CC(=O)N(c3ccc(Oc4ccccc4)cc3)C2)CC1] | 449.0 |
| 16 | (4S)-1-(4-phenoxyphenyl)-4-(4-(1,3-thiazol-2-ylcarbonyl)piperazin-1-yl)pyrrolidin-2-one | 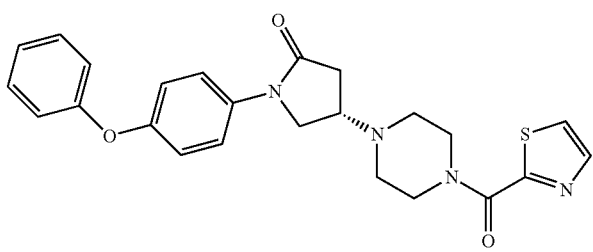 [SMILES: O=C(c1nccs1)N1CCN([C@H]2CC(=O)N(c3ccc(Oc4ccccc4)cc3)C2)CC1] | 449.0 |

TABLE 1-2-continued

| | | | |
|---|---|---|---|
| 17 | 4-(4-(1,3-thiazol-2-ylcarbonyl)piperazin-1-yl)-1-(4-(trifluoromethoxy)phenyl)pyrrolidin-2-one | 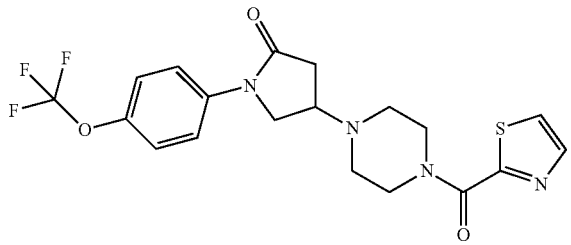 [SMILES: O=C(c1nccs1)N1CCN(C2CC(=O)N(c3ccc(OC(F)(F)F)cc3)C2)CC1] | 441.0 |
| 18 | 1-(5-phenoxypyridin-2-yl)-4-(4-(1,3-thiazol-2-ylcarbonyl)piperazin-1-yl)pyrrolidin-2-one | 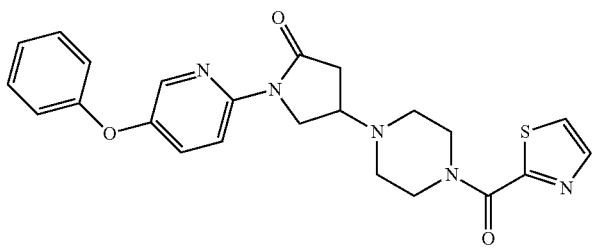 [SMILES: O=C(c1nccs1)N1CCN(C2CC(=O)N(c3ccc(Oc4ccccc4)cn3)C2)CC1] | 450.0 |

TABLE 1-3

| | | | |
|---|---|---|---|
| 19 | 1-(4-(pyridin-4-yloxy)phenyl)-4-(4-(1,3-thiazol-2-ylcarbonyl)piperazin-1-yl)pyrrolidin-2-one | 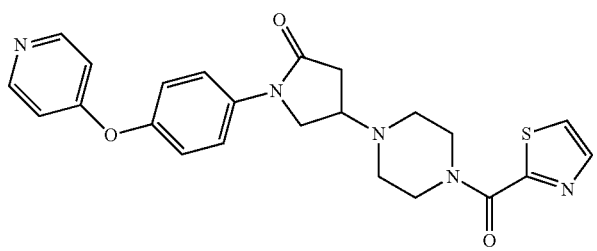 [SMILES: O=C(c1nccs1)N1CCN(C2CC(=O)N(c3ccc(Oc4ccncc4)cc3)C2)CC1] | 450.0 |
| 20 | 1-(1-(4-fluorophenyl)-1H-indol-6-yl)-4-(4-(1,3-thiazol-2-ylcarbonyl)piperazin-1-yl)pyrrolidin-2-one | 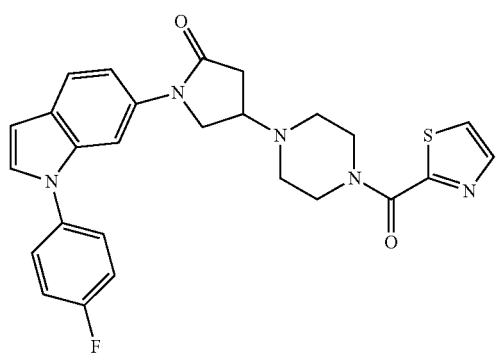 [SMILES: O=C(c1nccs1)N1CCN(C2CC(=O)N(c3ccc4ccn(-c5ccc(F)cc5)c4c3)C2)CC1] | 490.1 |
| 21 | 1-(4-phenoxyphenyl)-4-(4-(pyrrolidin-1-ylcarbonyl)piperazin-1-yl)pyrrolidin-2-one | 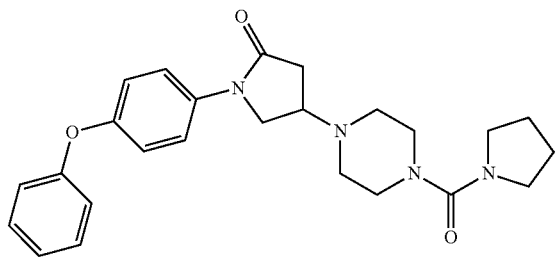 [SMILES: O=C(N1CCCC1)N1CCN(C2CC(=O)N(c3ccc(Oc4ccccc4)cc3)C2)CC1] | 435.1 |

TABLE 1-3-continued

| 22 | 1-(4-(4-methoxyphenoxy)phenyl)-4-(4-(1,3-thiazol-2-ylcarbonyl)piperazin-1-yl)pyrrolidin-2-one | 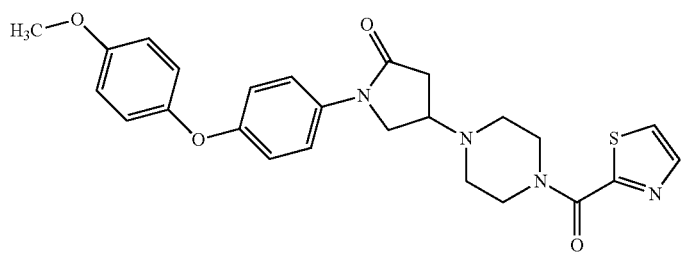 [SMILES: COc1ccc(Oc2ccc(N3CC(N4CCN(C(=O)c5nccs5)CC4)CC3=O)cc2)cc1] | 479.0 |
| 23 | 1-(1-(4-fluorophenyl)-1H-indol-5-yl)-4-(4-(1,3-thiazol-2-ylcarbonyl)piperazin-1-yl)pyrrolidin-2-one(optical isomer) | 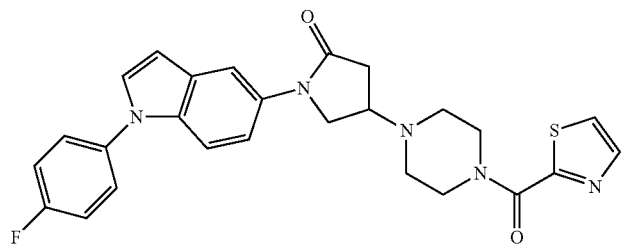 [SMILES: O=C(c1nccs1)N1CCN(C2CC(=O)N(c3ccc4c(ccn4-c4ccc(F)cc4)c3)C2)CC1] | 490.1 |
| 24 | 1-(1-(4-fluorophenyl)-1H-indol-5-yl)-4-(4-(1,3-thiazol-2-ylcarbonyl)piperazin-1-yl)pyrrolidin-2-one(optical isomer) | 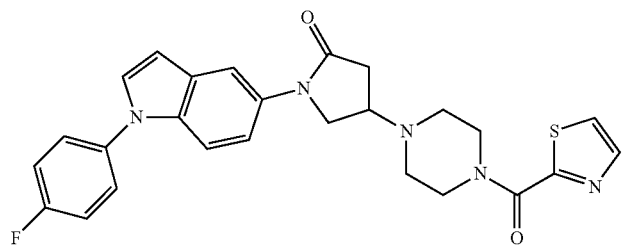 [SMILES: O=C(c1nccs1)N1CCN(C2CC(=O)N(c3ccc4c(ccn4-c4ccc(F)cc4)c3)C2)CC1] | 490.1 |
| 25 | 4-(4-((dimethylamino)acetyl)piperazin-1-yl)-1-(4-phenoxyphenyl)pyrrolidin-2-one | 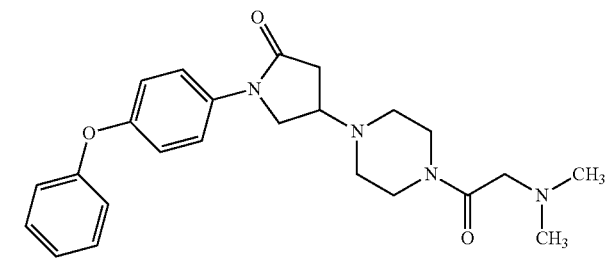 [SMILES: CN(C)CC(=O)N1CCN(C2CC(=O)N(c3ccc(Oc4ccccc4)cc3)C2)CC1] | 423.1 |
| 26 | 1-(4-phenoxyphenyl)-4-(4-(trifluoroacetyl)piperazin-1-yl)pyrrolidin-2-one | 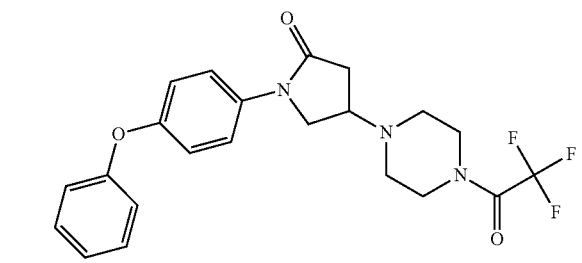 [SMILES: O=C1CC(N2CCN(C(=O)C(F)(F)F)CC2)CN1c1ccc(Oc2ccccc2)cc1] | 434.0 |
| 27 | 1-(4-(pyridin-3-yloxy)phenyl)-4-(4-(1,3-thiazol-2-ylcarbonyl)piperazin-1-yl)pyrrolidin-2-one | 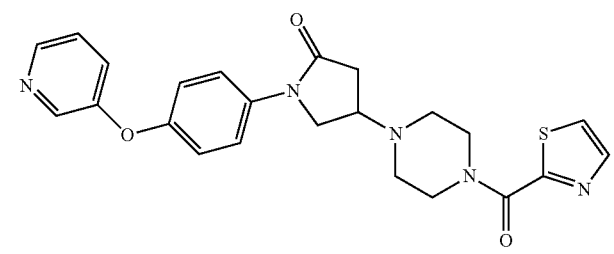 [SMILES: O=C(c1nccs1)N1CCN(C2CC(=O)N(c3ccc(Oc4cccnc4)cc3)C2)CC1] | 450.0 |

TABLE 1-4

| 28 | 4-(4-((1-methyl-1H-pyrazol-3-yl)carbonyl)piperazin-1-yl)-1-(4-phenoxyphenyl)pyrrolidin-2-one | 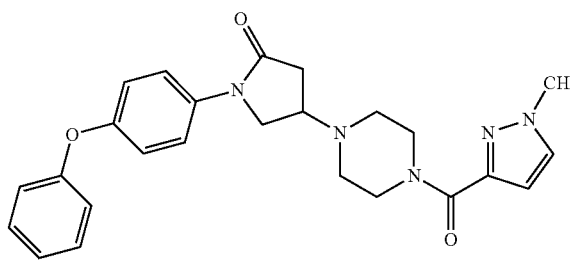 [SMILES: Cn1ccc(C(=O)N2CCN(C3CC(=O)N(c4ccc(Oc5ccccc5)cc4)C3)CC2)n1] | 446.2 |
| 29 | 4-(4-((2,2-difluorocyclopropyl)carbonyl)piperazin-1-yl)-1-(4-phenoxyphenyl)pyrrolidin-2-one | 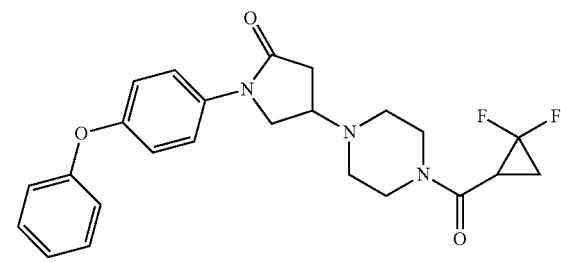 [SMILES: O=C(C1CC1(F)F)N1CCN(C2CC(=O)N(c3ccc(Oc4ccccc4)cc3)C2)CC1] | 442.1 |
| 30 | 1-(4-phenoxyphenyl)-4-(4-(pyridin-2-ylacetyl)piperazin-1-yl)pyrrolidin-2-one | 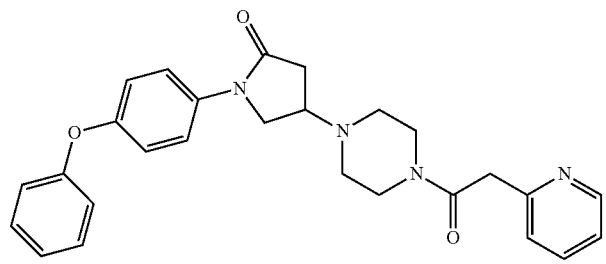 [SMILES: O=C(Cc1ccccn1)N1CCN(C2CC(=O)N(c3ccc(Oc4ccccc4)cc3)C2)CC1] | 457.1 |
| 31 | 4-(4-((1-methyl-1H-imidazol-2-yl)carbonyl)piperazin-1-yl)-1-(4-phenoxyphenyl)pyrrolidin-2-one | 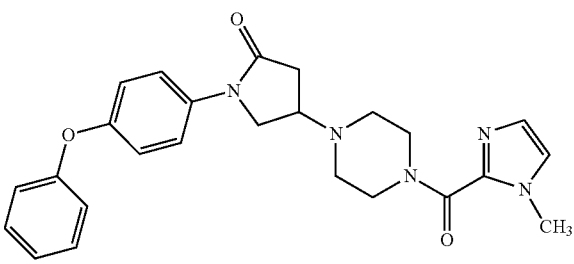 [SMILES: Cn1ccnc1C(=O)N1CCN(C2CC(=O)N(c3ccc(Oc4ccccc4)cc3)C2)CC1] | 446.1 |
| 32 | 1-(4-phenoxyphenyl)-4-(4-(quinolin-2-ylcarbonyl)piperazin-1-yl)pyrrolidin-2-one | 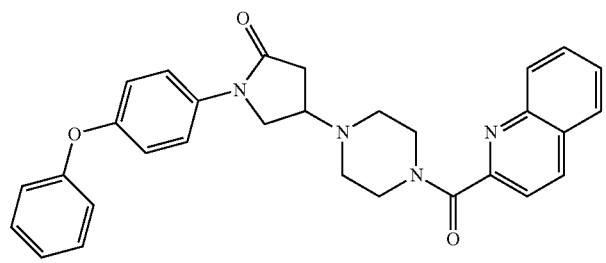 [SMILES: O=C(c1ccc2ccccc2n1)N1CCN(C2CC(=O)N(c3ccc(Oc4ccccc4)cc3)C2)CC1] | 493.2 |
| 33 | 1-(4-phenoxyphenyl)-4-(4-phenylpiperazin-1-yl)pyrrolidin-2-one | 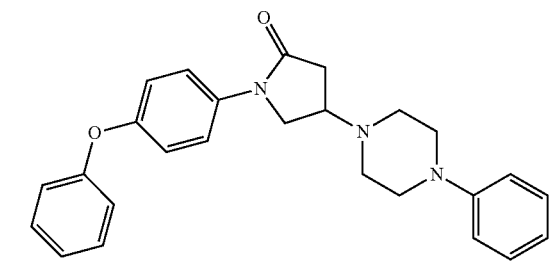 [SMILES: O=C1CC(N2CCN(c3ccccc3)CC2)CN1c1ccc(Oc2ccccc2)cc1] | 414.1 |

TABLE 1-4-continued

| | | | |
|---|---|---|---|
| 34 | 1-(4-phenoxyphenyl)-4-(4-(pyridin-2-ylsulfonyl)piperazin-1-yl)pyrrolidin-2-one | 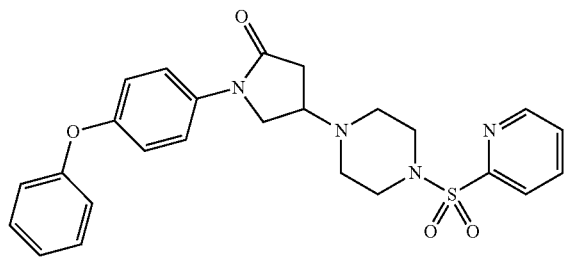 [SMILES: O=C1CC(N2CCN(S(=O)(=O)c3ccccn3)CC2)CN1c1ccc(Oc2ccccc2)cc1] | 479.0 |
| 35 | 1-(4-phenoxyphenyl)-4-(4-(1,3-thiazol-5-ylcarbonyl)piperazin-1-yl)pyrrolidin-2-one | 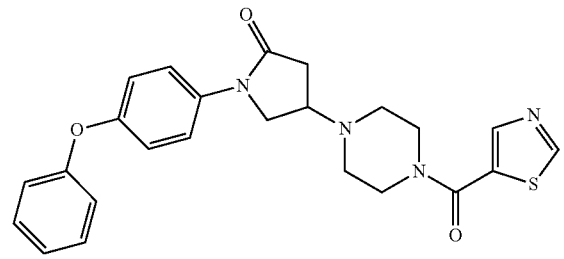 [SMILES: O=C(c1cncs1)N1CCN(C2CC(=O)N(c3ccc(Oc4ccccc4)cc3)C2)CC1] | 448.9 |
| 36 | 4-(4-(1,3-oxazol-4-ylcarbonyl)piperazin-1-yl)-1-(4-phenoxyphenyl)pyrrolidin-2-one | 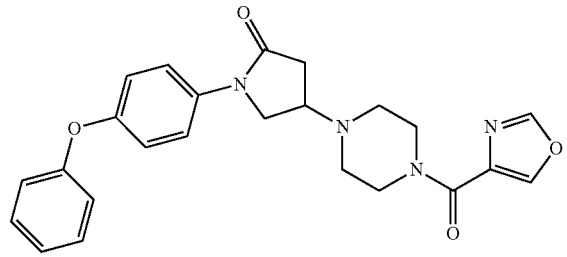 [SMILES: O=C(c1cocn1)N1CCN(C2CC(=O)N(c3ccc(Oc4ccccc4)cc3)C2)CC1] | 433.0 |

TABLE 1-5

| | | | |
|---|---|---|---|
| 37 | 4-(4-((4-methyl-1,3-thiazol-5-yl)carbonyl)piperazin-1-yl)-1-(4-phenoxyphenyl)pyrrolidin-2-one | 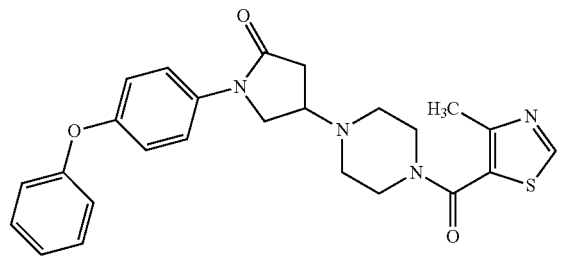 [SMILES: Cc1ncsc1C(=O)N1CCN(C2CC(=O)N(c3ccc(Oc4ccccc4)cc3)C2)CC1] | 463.0 |
| 38 | 1-(4-benzylphenyl)-4-(4-(1,3-thiazol-2-ylcarbonyl)piperazin-1-yl)pyrrolidin-2-one | 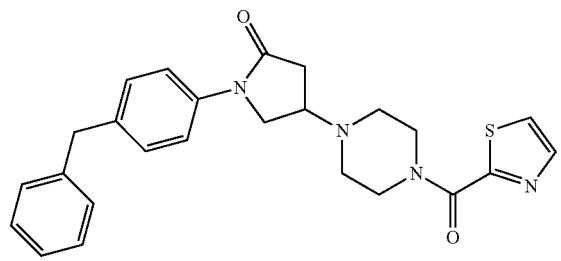 [SMILES: O=C(c1nccs1)N1CCN(C2CC(=O)N(c3ccc(Cc4ccccc4)cc3)C2)CC1] | 447.0 |
| 39 | 1-(4-(pyridin-2-yl)phenyl)-4-(4-(1,3-thiazol-2-ylcarbonyl)piperazin-1-yl)pyrrolidin-2-one | 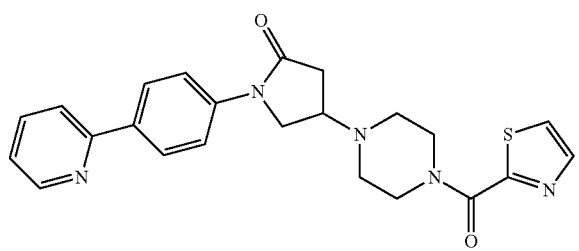 [SMILES: O=C(c1nccs1)N1CCN(C2CC(=O)N(c3ccc(-c4ccccn4)cc3)C2)CC1] | 434.0 |

TABLE 1-5-continued

| | | | |
|---|---|---|---|
| 40 | 1-(4-bromophenyl)-4-(4-(1,3-thiazol-2-ylcarbonyl)piperazin-1-yl)pyrrolidin-2-one | 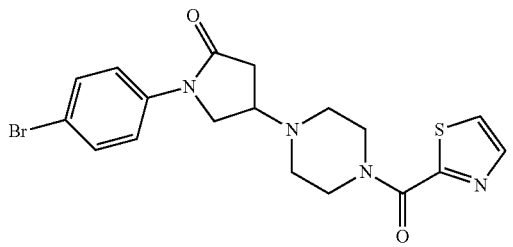 [SMILES: O=C(c1nccs1)N1CCN(C2CC(=O)N(c3ccc(Br)cc3)C2)CC1] | 434.9 |
| 41 | 4-(2-oxo-4-(4-(1,3-thiazol-2-ylcarbonyl)piperazin-1-yl)pyrrolidin-1-yl)benzonitrile | 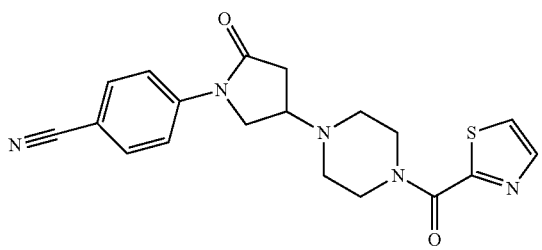 [SMILES: N#Cc1ccc(N2CC(N3CCN(C(=O)c4nccs4)CC3)CC2=O)cc1] | 382.0 |
| 42 | 4-(2-oxo-4-(4-(1,3-thiazol-2-ylcarbonyl)piperazin-1-yl)pyrrolidin-1-yl)-N-phenylbenzamide | 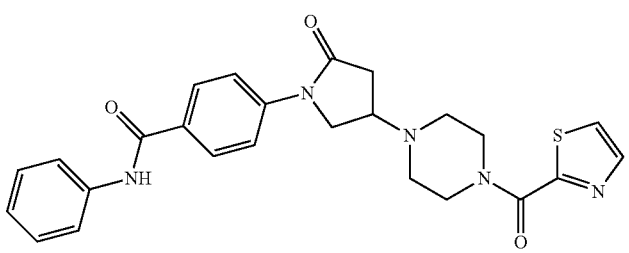 [SMILES: O=C(Nc1ccccc1)c1ccc(N2CC(N3CCN(C(=O)c4nccs4)CC3)CC2=O)cc1] | 476.1 |
| 43 | 4-(4-((5-methyl-1,3-thiazol-2-yl)carbonyl)piperazin-1-yl)-1-(4-phenoxyphenyl)pyrrolidin-2-one | 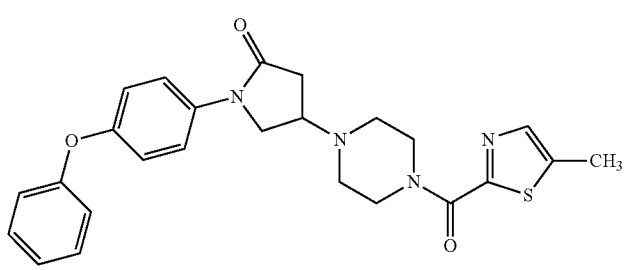 [SMILES: Cc1cnc(C(=O)N2CCN(C3CC(=O)N(c4ccc(Oc5ccccc5)cc4)C3)CC2)s1] | 463.0 |
| 44 | 1-(4-(3-methoxyphenoxy)phenyl)-4-(4-(1,3-thiazol-2-ylcarbonyl)piperazin-1-yl)pyrrolidin-2-one | 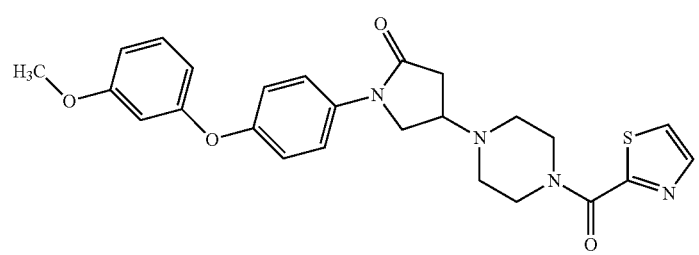 [SMILES: COc1cccc(Oc2ccc(N3CC(N4CCN(C(=O)c5nccs5)CC4)CC3=O)cc2)c1] | 479.0 |
| 45 | 1-(4-(2-methoxyphenoxy)phenyl)-4-(4-(1,3-thiazol-2-ylcarbonyl)piperazin-1-yl)pyrrolidin-2-one | 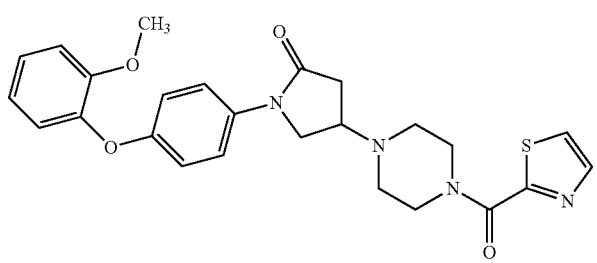 [SMILES: COc1ccccc1Oc1ccc(N2CC(N3CCN(C(=O)c4nccs4)CC3)CC2=O)cc1] | 479.0 |

TABLE 1-6

| | | | |
|---|---|---|---|
| 46 | 2-(4-(5-oxo-1-(4-phenoxyphenyl)pyrrolidin-3-yl)piperazin-1-yl)pyrimidine-4-carbonitrile | 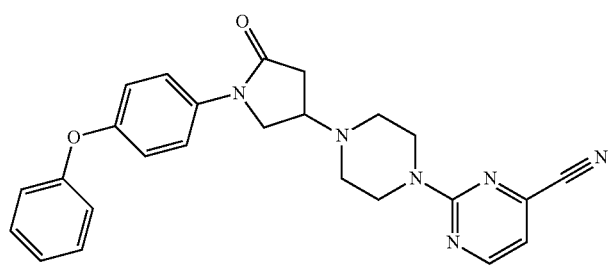 [SMILES: N#Cc1ccnc(N2CCN(C3CC(=O)N(c4ccc(Oc5ccccc5)cc4)C3)CC2)n1] | 441.0 |
| 47 | 1-(1H-indazol-5-yl)-4-(4-(1,3-thiazol-2-ylcarbonyl)piperazin-1-yl)pyrrolidin-2-one | 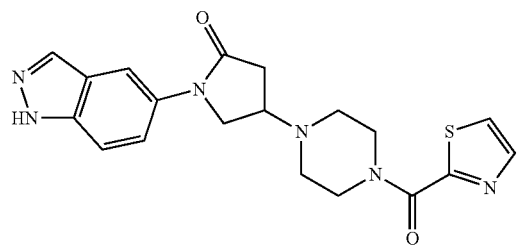 [SMILES: O=C(c1nccs1)N1CCN(C2CC(=O)N(c3ccc4[nH]ncc4c3)C2)CC1] | 397.1 |
| 48 | 4-(4-(1,3-oxazol-5-ylcarbonyl)piperazin-1-yl)-1-(4-phenoxyphenyl)pyrrolidin-2-one | 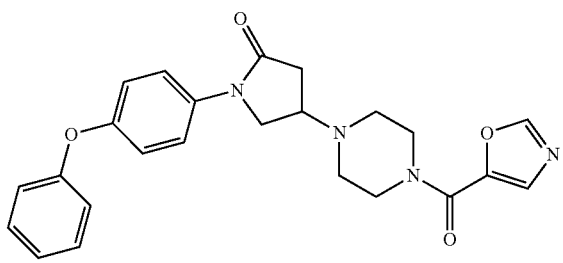 [SMILES: O=C(c1cnco1)N1CCN(C2CC(=O)N(c3ccc(Oc4ccccc4)cc3)C2)CC1] | 433.0 |
| 49 | 4-(4-((1-methyl-1H-imidazol-4-yl)carbonyl)piperazin-1-yl)-1-(4-phenoxyphenyl)pyrrolidin-2-one | 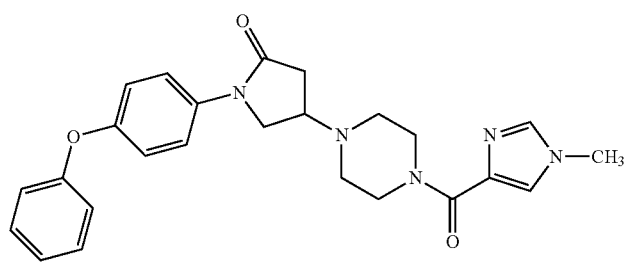 [SMILES: Cn1cnc(C(=O)N2CCN(C3CC(=O)N(c4ccc(Oc5ccccc5)cc4)C3)CC2)c1] | 446.1 |
| 50 | 4-(4-((2-methyl-1,3-oxazol-4-yl)carbonyl)piperazin-1-yl)-1-(4-phenoxyphenyl)pyrrolidin-2-one | 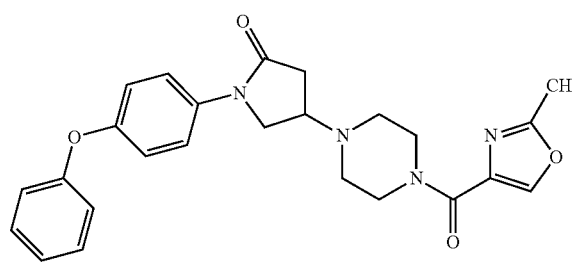 [SMILES: Cc1nc(C(=O)N2CCN(C3CC(=O)N(c4ccc(Oc5ccccc5)cc4)C3)CC2)co1] | 447.0 |
| 51 | 1-(1-(4-fluorophenyl)-1H-pyrrolo[2,3-b]pyridin-5-yl)-4-(4-(1,3-thiazol-2-ylcarbonyl)piperazin-1-yl)pyrrolidin-2-one | 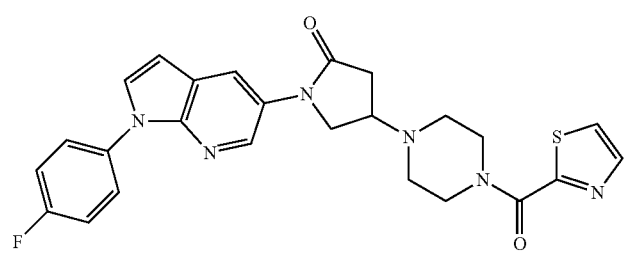 [SMILES: O=C(c1nccs1)N1CCN(C2CC(=O)N(c3cnc4c(ccn4-c4ccc(F)cc4)c3)C2)CC1] | 491.0 |

TABLE 1-6-continued

| | | | |
|---|---|---|---|
| 52 | 4-(4-(1,3-thiazol-2-ylcarbonyl)piperazin-1-yl)-1-(1-(5-(trifluoromethyl)pyrimidin-2-yl)-1H-indol-5-yl)pyrrolidin-2-one | 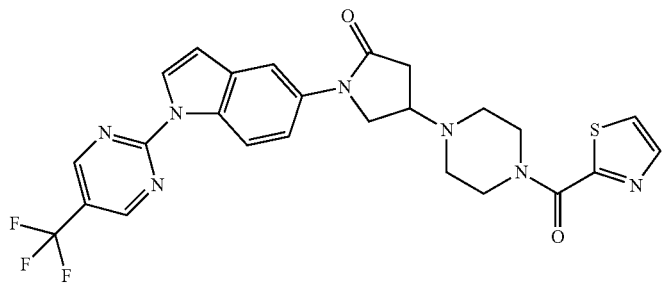 [SMILES: O=C(c1nccs1)N1CCN(C2CC(=O)N(c3ccc4c(ccn4-c4ncc(C(F)(F)F)cn4)c3)C2)CC1] | 542.0 |
| 53 | 4-(4-(1,3-thiazol-2-ylcarbonyl)piperazin-1-yl)-1-(1-(5-(trifluoromethyl)pyridin-2-yl)-1H-indol-5-yl)pyrrolidin-2-one | 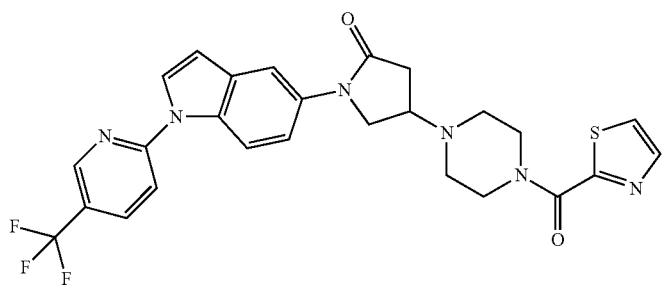 [SMILES: O=C(c1nccs1)N1CCN(C2CC(=O)N(c3ccc4c(ccn4-c4ccc(C(F)(F)F)cn4)c3)C2)CC1] | 541.3 |
| 54 | 4-(4-(1,3-oxazol-2-ylcarbonyl)piperazin-1-yl)-1-(4-phenoxyphenyl)pyrrolidin-2-one | 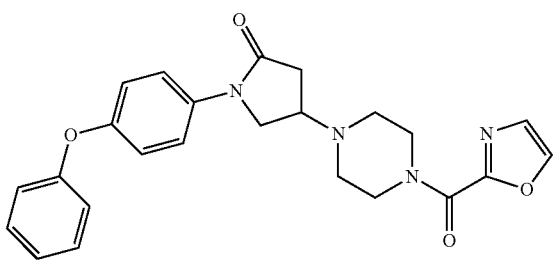 [SMILES: O=C(c1ncco1)N1CCN(C2CC(=O)N(c3ccc(Oc4ccccc4)cc3)C2)CC1] | 433.0 |

TABLE 1-7

| | | | |
|---|---|---|---|
| 55 | 1-(3-chloro-4-(morpholin-4-yl)phenyl)-4-(4-(1,3-thiazol-2-ylcarbonyl)piperazin-1-yl)pyrrolidin-2-one | 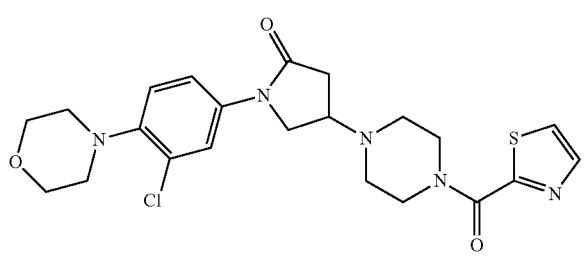 [SMILES: O=C(c1nccs1)N1CCN(C2CC(=O)N(c3ccc(N4CCOCC4)c(Cl)c3)C2)CC1] | 476.0 |
| 56 | 1-(4-((4-methylpiperazin-1-yl)methyl)phenyl)-4-(4-(1,3-thiazol-2-ylcarbonyl)piperazin-1-yl)pyrrolidin-2-one | 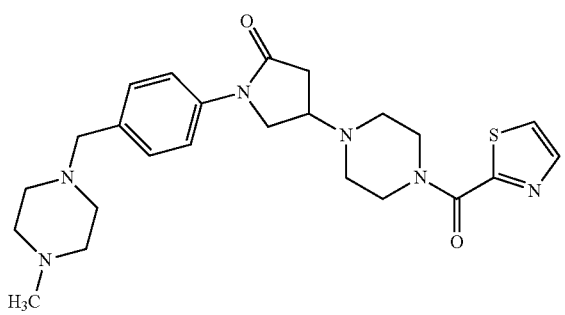 [SMILES: CN1CCN(Cc2ccc(N3CC(N4CCN(C(=O)c5nccs5)CC4)CC3=O)cc2)CC1] | 469.1 |

TABLE 1-7-continued

| 57 | 1-(4-cyclopropylphenyl)-4-(4-(1,3-thiazol-2-ylcarbonyl)piperazin-1-yl)pyrrolidin-2-one | 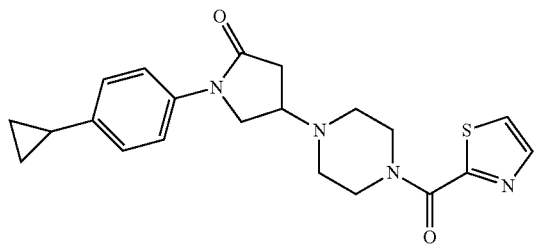 [SMILES: O=C(c1nccs1)N1CCN(C2CC(=O)N(c3ccc(C4CC4)cc3)C2)CC1] | 397.1 |
| 58 | 1-(2-(benzyloxy)phenyl)-4-(4-(1,3-thiazol-2-ylcarbonyl)piperazin-1-yl)pyrrolidin-2-one | 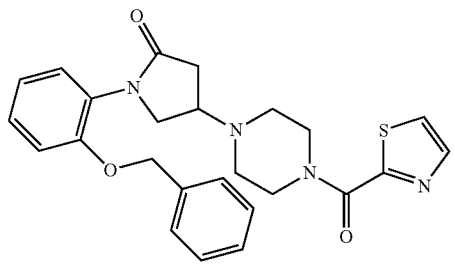 [SMILES: O=C(c1nccs1)N1CCN(C2CC(=O)N(c3ccccc3OCc3ccccc3)C2)CC1] | 463.0 |
| 59 | 1-(3-(benzyloxy)phenyl)-4-(4-(1,3-thiazol-2-ylcarbonyl)piperazin-1-yl)pyrrolidin-2-one | 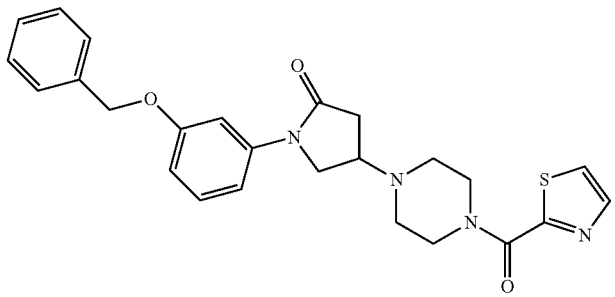 [SMILES: O=C(c1nccs1)N1CCN(C2CC(=O)N(c3cccc(OCc4ccccc4)c3)C2)CC1] | 463.0 |
| 60 | 1-(4-(benzyloxy)phenyl)-4-(4-(1,3-thiazol-2-ylcarbonyl)piperazin-1-yl)pyrrolidin-2-one | 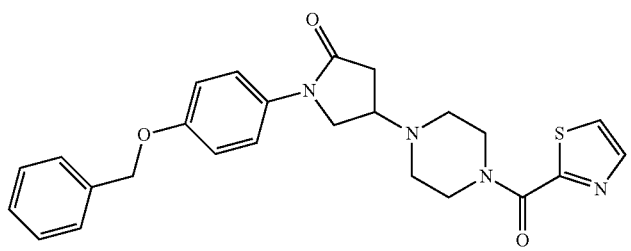 [SMILES: O=C(c1nccs1)N1CCN(C2CC(=O)N(c3ccc(OCc4ccccc4)cc3)C2)CC1] | 463.0 |
| 61 | 1-(biphenyl-2-yl)-4-(4-(1,3-thiazol-2-ylcarbonyl)piperazin-1-yl)pyrrolidin-2-one | 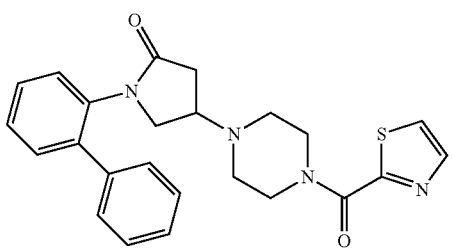 [SMILES: O=C(c1nccs1)N1CCN(C2CC(=O)N(c3ccccc3-c3ccccc3)C2)CC1] | 433.0 |
| 62 | 1-(biphenyl-3-yl)-4-(4-(1,3-thiazol-2-ylcarbonyl)piperazin-1-yl)pyrrolidin-2-one | 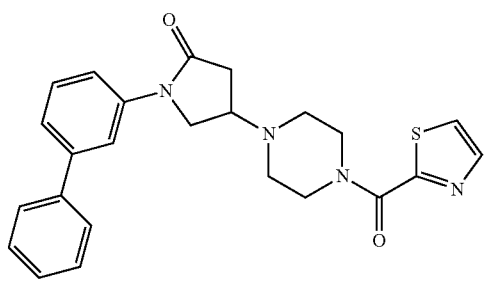 [SMILES: O=C(c1nccs1)N1CCN(C2CC(=O)N(c3cccc(-c4ccccc4)c3)C2)CC1] | 433.0 |

TABLE 1-7-continued

| 63 | 1-(4'-chlorobiphenyl-4-yl)-4-(4-(1,3-thiazol-2-ylcarbonyl)piperazin-1-yl)pyrrolidin-2-one | 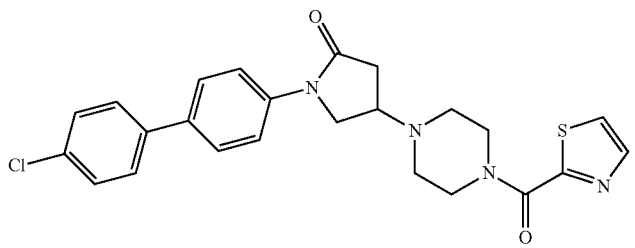 [SMILES: O=C(c1nccs1)N1CCN(C2CC(=O)N(c3ccc(-c4ccc(Cl)cc4)cc3)C2)CC1] | 466.9 |

TABLE 1-8

| 64 | 1-(3-(pyridin-2-yl)phenyl)-4-(4-(1,3-thiazol-2-ylcarbonyl)piperazin-1-yl)pyrrolidin-2-one | 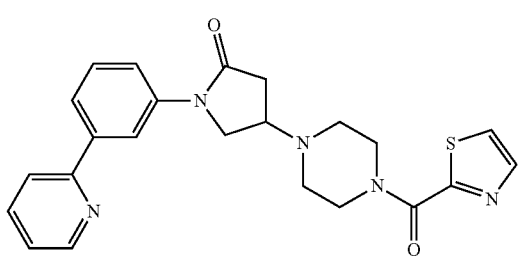 [SMILES: O=C(c1nccs1)N1CCN(C2CC(=O)N(c3cccc(-c4ccccn4)c3)C2)CC1] | 434.0 |
| 65 | 1-(3-(pyridin-3-yl)phenyl)-4-(4-(1,3-thiazol-2-ylcarbonyl)piperazin-1-yl)pyrrolidin-2-one | 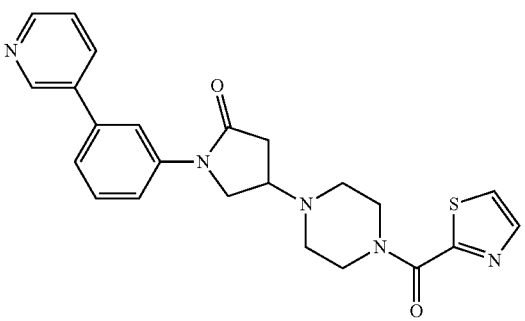 [SMILES: O=C(c1nccs1)N1CCN(C2CC(=O)N(c3cccc(-c4cccnc4)c3)C2)CC1] | 434.0 |
| 66 | 1-(3-(pyridin-4-yl)phenyl)-4-(4-(1,3-thiazol-2-ylcarbonyl)piperazin-1-yl)pyrrolidin-2-one | 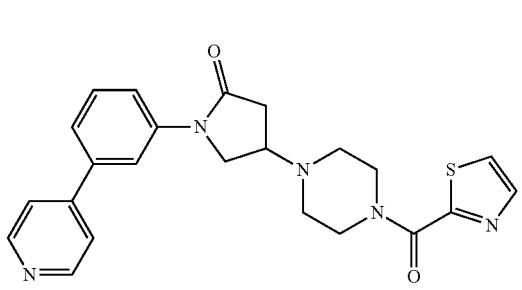 [SMILES: O=C(c1nccs1)N1CCN(C2CC(=O)N(c3cccc(-c4ccncc4)c3)C2)CC1] | 434.0 |
| 67 | 1-(3-(2-methyl-1,3-thiazol-4-yl)phenyl)-4-(4-(1,3-thiazol-2-ylcarbonyl)piperazin-1-yl)pyrrolidin-2-one | 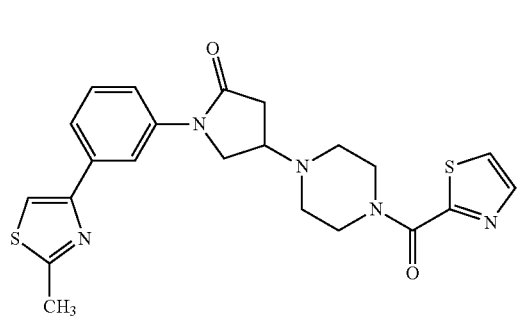 [SMILES: Cc1nc(-c2cccc(N3CC(N4CCN(C(=O)c5nccs5)CC4)CC3=O)c2)cs1] | 454.0 |

TABLE 1-8-continued
| | | | |
|---|---|---|---|
| 68 | 1-(1-phenyl-1H-imidazol-4-yl)-4-(4-(1,3-thiazol-2-ylcarbonyl)piperazin-1-yl)pyrrolidin-2-one | 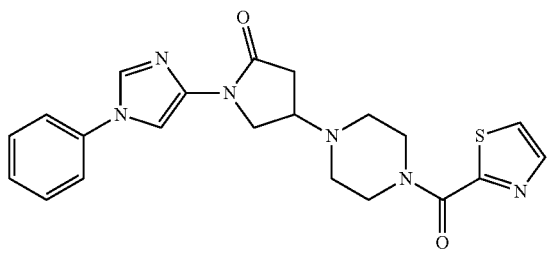 [SMILES: O=C(c1nccs1)N1CCN(C2CC(=O)N(c3cn(-c4ccccc4)cn3)C2)CC1] | 423.0 |
| 69 | 1-(1-phenyl-1H-pyrazol-3-yl)-4-(4-(1,3-thiazol-2-ylcarbonyl)piperazin-1-yl)pyrrolidin-2-one | 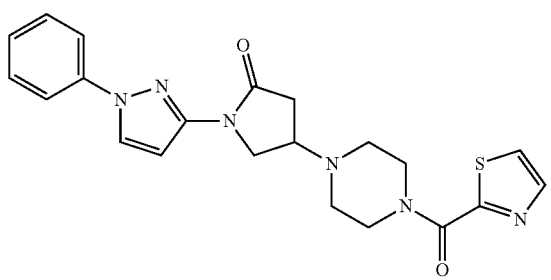 [SMILES: O=C(c1nccs1)N1CCN(C2CC(=O)N(c3ccn(-c4ccccc4)n3)C2)CC1] | 423.0 |
| 70 | 1-(1-naphthyl)-4-(4-(1,3-thiazol-2-ylcarbonyl)piperazin-1-yl)pyrrolidin-2-one | 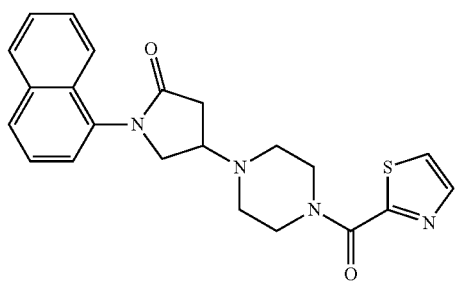 [SMILES: O=C(c1nccs1)N1CCN(C2CC(=O)N(c3cccc4ccccc34)C2)CC1] | 406.9 |
| 71 | 1-(6-bromo-2-naphthyl)-4-(4-(1,3-thiazol-2-ylcarbonyl)piperazin-1-yl)pyrrolidin-2-one | 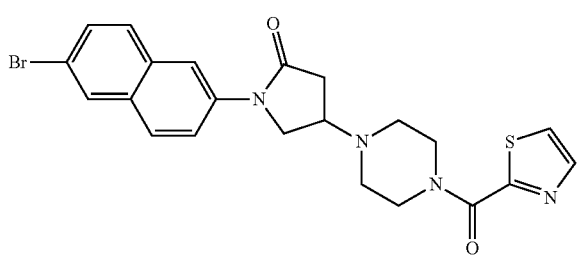 [SMILES: O=C(c1nccs1)N1CCN(C2CC(=O)N(c3ccc4cc(Br)ccc4c3)C2)CC1] | 485.0 |
| 72 | 1-(dibenzo[b,c]furan-3-yl)-4-(4-(1,3-thiazol-2-ylcarbonyl)piperazin-1-yl)pyrrolidin-2-one | 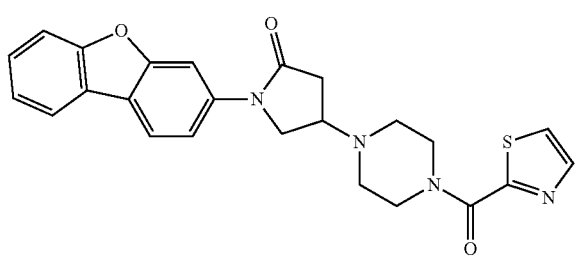 [SMILES: O=C(c1nccs1)N1CCN(C2CC(=O)N(c3ccc4c(c3)oc3ccccc34)C2)CC1] | 447.0 |

TABLE 1-9

| 73 | 1-(6-bromoimidazo[1,2-a]pyridin-2-yl)-4-(4-(1,3-thiazol-2-ylcarbonyl)piperazin-1-yl)pyrrolidin-2-one | | 474.9 |
|---|---|---|---|
| 74 | 1-(4-iodophenyl)-4-(4-(1,3-thiazol-2-ylcarbonyl)piperazin-1-yl)pyrrolidin-2-one | | 482.8 |
| 75 | 1-(3-iodophenyl)-4-(4-(1,3-thiazol-2-ylcarbonyl)piperazin-1-yl)pyrrolidin-2-one | | 482.8 |
| 76 | 1-(4'-fluorobiphenyl-3-yl)-4-(4-(1,3-thiazol-2-ylcarbonyl)piperazin-1-yl)pyrrolidin-2-one | | 450.9 |
| 77 | 1-(3-((4-fluorophenyl)amino)phenyl)-4-(4-(1,3-thiazol-2-ylcarbonyl)piperazin-1-yl)pyrrolidin-2-one | | 466.0 |
| 78 | 4-(4-((4-methyl-1,3-thiazol-2-yl)carbonyl)piperazin-1-yl)-1-(4-phenoxyphenyl)pyrrolidin-2-one | | 463.0 |

TABLE 1-9-continued

| 79 | 1-(3-(4-fluorophenoxy)phenyl)-4-(4-(1,3-thiazol-2-ylcarbonyl)piperazin-1-yl)pyrrolidin-2-one | 466.9 |
|---|---|---|
| 80 | (4R)-4-(4-(1,3-thiazol-2-ylcarbonyl)piperazin-1-yl)-1-(1-(5-(trifluoromethyl)pyrimidin-2-yl)-1H-indol-5-yl)pyrrolidin-2-one | 542.1 |
| 81 | 1-(1-(5-fluoropyridin-2-yl)-1H-indazol-5-yl)-4-(4-(1,3-thiazol-2-ylcarbonyl)piperazin-1-yl)pyrrolidin-2-one | 492.1 |

TABLE 1-10

| 82 | 1-(1-(5-fluoropyridin-2-yl)-1H-indol-5-yl)-4-(4-(1,3-thiazol-2-ylcarbonyl)piperazin-1-yl)pyrrolidin-2-one | 491.0 |
|---|---|---|
| 83 | 1-(1-(5-fluoropyrimidin-2-yl)-1H-indol-5-yl)-4-(4-(1,3-thiazol-2-ylcarbonyl)piperazin-1-yl)pyrrolidin-2-one | 492.0 |
| 84 | 1-(1-(5-chloropyrimidin-2-yl)-1H-indol-5-yl)-4-(4-(1,3-thiazol-2-ylcarbonyl)piperazin-1-yl)pyrrolidin-2-one | 508.0 |

TABLE 1-10-continued

| 85 | 1-(1-(4-fluorophenyl)-1H-indazol-5-yl)-4-(4-(1,3-thiazol-2-ylcarbonyl)piperazin-1-yl)pyrrolidin-2-one | | 490.9 |
|---|---|---|---|
| 86 | 1-(1-(5-chloropyridin-2-yl)-1H-indazol-5-yl)-4-(4-(1,3-thiazol-2-ylcarbonyl)piperazin-1-yl)pyrrolidin-2-one | | 508.0 |
| 87 | 1-(1-(5-chloropyridin-2-yl)-1H-indol-5-yl)-4-(4-(1,3-thiazol-2-ylcarbonyl)piperazin-1-yl)pyrrolidin-2-one | | 507.0 |
| 88 | 4-(4-(1,3-thiazol-2-ylcarbonyl)piperazin-1-yl)-1-(4-(trifluoromethyl)phenyl)pyrrolidin-2-one | | 425.1 |
| 89 | 1-(4'-chlorobiphenyl-3-yl)-4-(4-(1,3-thiazol-2-ylcarbonyl)piperazin-1-yl)pyrrolidin-2-one | | 467.1 |
| 90 | 1-(4'-methylbiphenyl-3-yl)-4-(4-(1,3-thiazol-2-ylcarbonyl)piperazin-1-yl)pyrrolidin-2-one | | 447.1 |

TABLE 1-11

| | | | |
|---|---|---|---|
| 91 | 1-(3'-methylbiphenyl-3-yl)-4-(4-(1,3-thiazol-2-ylcarbonyl)piperazin-1-yl)pyrrolidin-2-one | 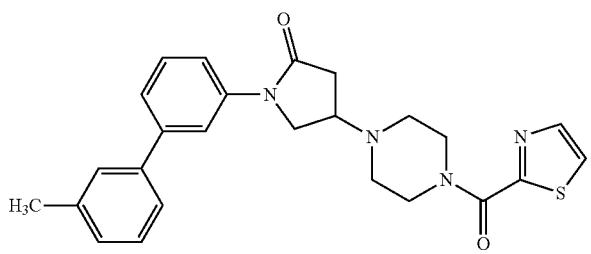 [SMILES: Cc1cccc(-c2cccc(N3CC(N4CCN(C(=O)c5nccs5)CC4)CC3=O)c2)c1] | 447.1 |
| 92 | 1-(2'-methylbiphenyl-3-yl)-4-(4-(1,3-thiazol-2-ylcarbonyl)piperazin-1-yl)pyrrolidin-2-one | 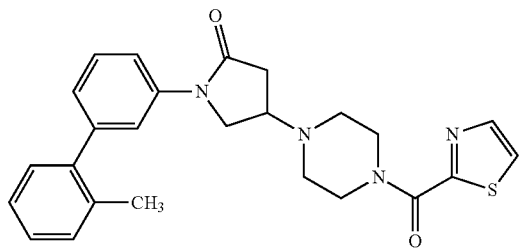 [SMILES: Cc1ccccc1-c1cccc(N2CC(N3CCN(C(=O)c4nccs4)CC3)CC2=O)c1] | 447.1 |
| 93 | 4-(4-(1,3-thiazol-2-ylcarbonyl)piperazin-1-yl)-1-(3-(2-thienyl)phenyl)pyrrolidin-2-one | 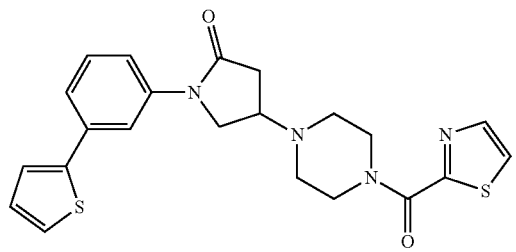 [SMILES: O=C(c1nccs1)N1CCN(C2CC(=O)N(c3cccc(-c4cccs4)c3)C2)CC1] | 439.1 |
| 94 | 4-(4-(1,3-thiazol-2-ylcarbonyl)piperazin-1-yl)-1-(3-(3-thienyl)phenyl)pyrrolidin-2-one | 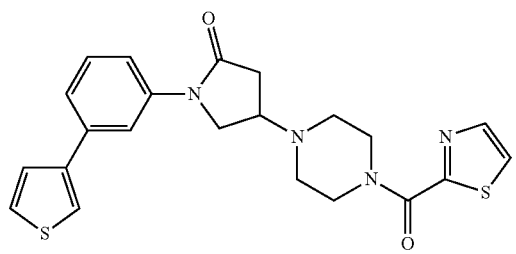 [SMILES: O=C(c1nccs1)N1CCN(C2CC(=O)N(c3cccc(-c4ccsc4)c3)C2)CC1] | 439.1 |
| 95 | N-(3'-(2-oxo-4-(4-(1,3-thiazol-2-ylcarbonyl)piperazin-1-yl)pyrrolidin-1-yl)biphenyl-3-yl)acetamide | 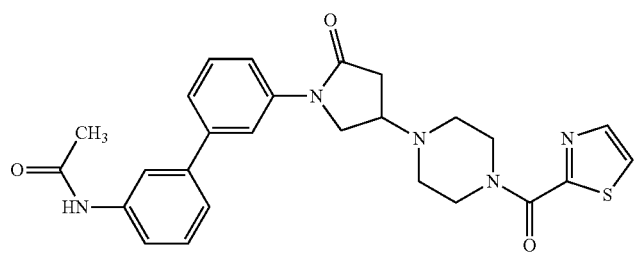 [SMILES: CC(=O)Nc1cccc(-c2cccc(N3CC(N4CCN(C(=O)c5nccs5)CC4)CC3=O)c2)c1] | 490.2 |
| 96 | 1-(3-(3-furyl)phenyl)-4-(4-(1,3-thiazol-2-ylcarbonyl)piperazin-1-yl)pyrrolidin-2-one | 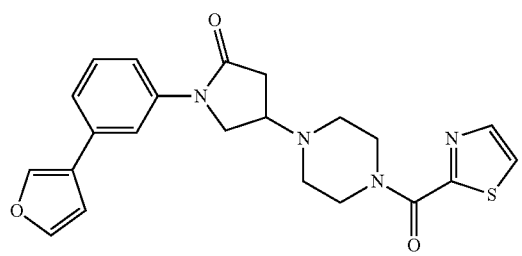 [SMILES: O=C(c1nccs1)N1CCN(C2CC(=O)N(c3cccc(-c4ccoc4)c3)C2)CC1] | 423.1 |

TABLE 1-11-continued

| 97 | N-(3'-(2-oxo-4-(4-(1,3-thiazol-2-ylcarbonyl)piperazin-1-yl)pyrrolidin-1-yl)biphenyl-4-yl)acetamide | 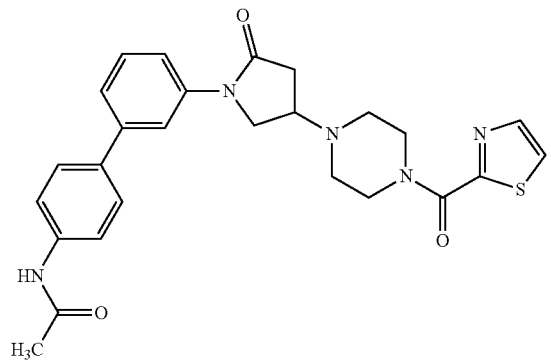 [SMILES: CC(=O)Nc1ccc(-c2cccc(N3CC(N4CCN(C(=O)c5nccs5)CC4)CC3=O)c2)cc1] | 490.2 |
| 98 | 3'-(2-oxo-4-(4-(1,3-thiazol-2-ylcarbonyl)piperazin-1-yl)pyrrolidin-1-yl)biphenyl-3-carboxamide | 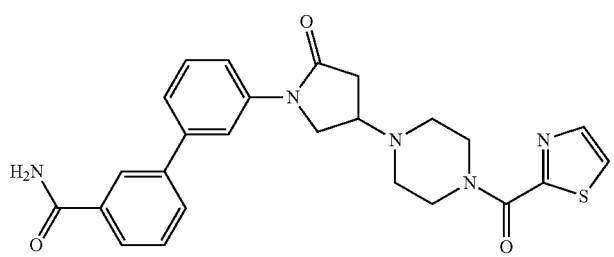 [SMILES: NC(=O)c1cccc(-c2cccc(N3CC(N4CCN(C(=O)c5nccs5)CC4)CC3=O)c2)c1] | 476.2 |
| 99 | 1-(3-benzylphenyl)-4-(4-(1,3-thiazol-2-ylcarbonyl)piperazin-1-yl)pyrrolidin-2-one | 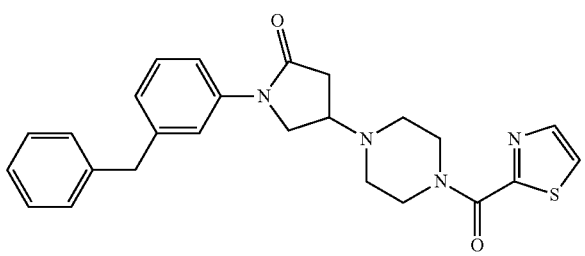 [SMILES: O=C(c1nccs1)N1CCN(C2CC(=O)N(c3cccc(Cc4ccccc4)c3)C2)CC1] | 447.1 |

TABLE 1-12

| 100 | N-(3'-(2-oxo-4-(4-(1,3-thiazol-2-ylcarbonyl)piperazin-1-yl)pyrrolidin-1-yl)biphenyl-3-yl)methanesulfonamide | 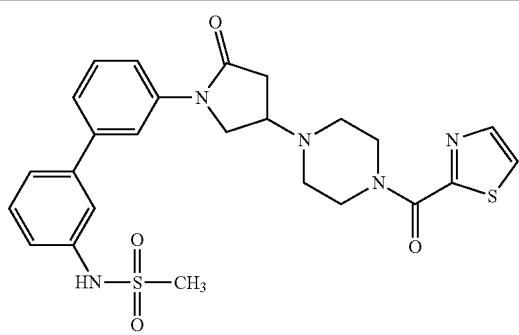 [SMILES: CS(=O)(=O)Nc1cccc(-c2cccc(N3CC(N4CCN(C(=O)c5nccs5)CC4)CC3=O)c2)c1] | 526.2 |
| 101 | 1-(3-(1-methyl-1H-pyrazol-5-yl)phenyl)-4-(4-(1,3-thiazol-2-ylcarbonyl)piperazin-1-yl)pyrrolidin-2-one | 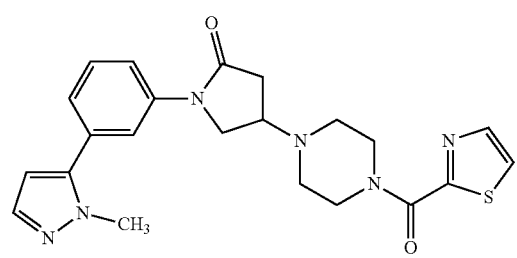 [SMILES: Cn1nccc1-c1cccc(N2CC(N3CCN(C(=O)c4nccs4)CC3)CC2=O)c1] | 437.1 |

TABLE 1-12-continued

| | | | |
|---|---|---|---|
| 102 | 3'-(2-oxo-4-(4-(1,3-thiazol-2-ylcarbonyl)piperazin-1-yl)pyrrolidin-1-yl)biphenyl-4-sulfonamide | | 512.1 |
| 103 | 3'-(2-oxo-4-(4-(1,3-thiazol-2-ylcarbonyl)piperazin-1-yl)pyrrolidin-1-yl)biphenyl-3-sulfonamide | | 512.1 |
| 104 | N-methyl-3'-(2-oxo-4-(4-(1,3-thiazol-2-ylcarbonyl)piperazin-1-yl)pyrrolidin-1-yl)biphenyl-4-carboxamide | | 490.3 |
| 105 | 5-(3-(2-oxo-4-(4-(1,3-thiazol-2-ylcarbonyl)piperazin-1-yl)pyrrolidin-1-yl)phenyl)-1,3-dihydro-2H-indol-2-one | | 488.1 |
| 106 | 1-(3-(pyrazolo[1,5-a]pyridin-3-yl)phenyl)-4-(4-(1,3-thiazol-2-ylcarbonyl)piperazin-1-yl)pyrrolidin-2-one | | 473.1 |

TABLE 1-12-continued

| 107 | 1-(3-(morpholin-4-ylmethyl)phenyl)-4-(4-(1,3-thiazol-2-ylcarbonyl)piperazin-1-yl)pyrrolidin-2-one | 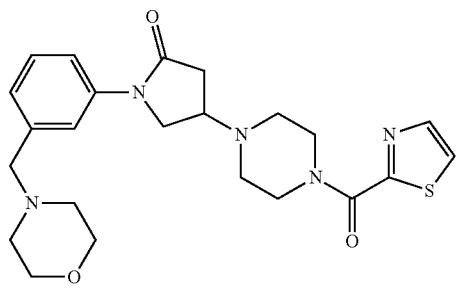 [SMILES: O=C(c1nccs1)N1CCN(C2CC(=O)N(c3cccc(CN4CCOCC4)c3)C2)CC1] | 456.1 |
| 108 | 4-(4-(1,3-thiazol-2-ylcarbonyl)piperazin-1-yl)-1-(1-(4-(trifluoromethyl)pyridin-2-yl)-1H-indol-5-yl)pyrrolidin-2-one | 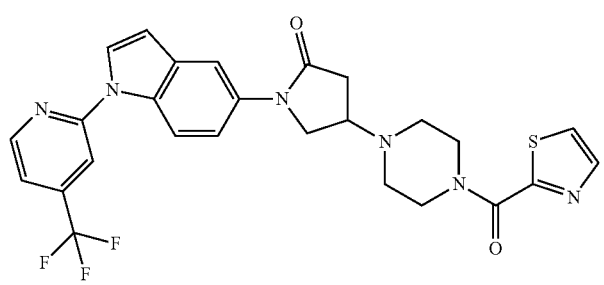 [SMILES: O=C(c1nccs1)N1CCN(C2CC(=O)N(c3ccc4c(ccn4-c4cc(C(F)(F)F)ccn4)c3)C2)CC1] | 541.2 |

TABLE 1-13

| 109 | 4-(4-(1,3-thiazol-2-ylcarbonyl)piperazin-1-yl)-1-(1-(2-(trifluoromethyl)pyridin-4-yl)-1H-indol-5-yl)pyrrolidin-2-one | 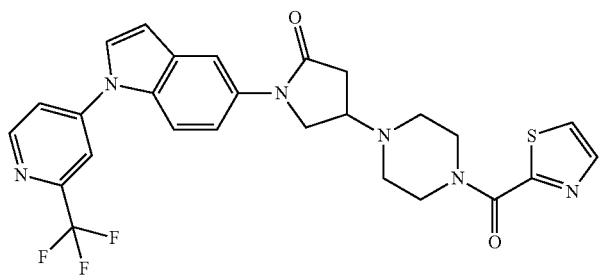 [SMILES: O=C(c1nccs1)N1CCN(C2CC(=O)N(c3ccc4c(ccn4-c4ccnc(C(F)(F)F)c4)c3)C2)CC1] | 541.2 |
| 110 | N-(3'-(2-oxo-4-(4-(1,3-thiazol-2-ylcarbonyl)piperazin-1-yl)pyrrolidin-1-yl)biphenyl-4-yl)methanesulfonamide | 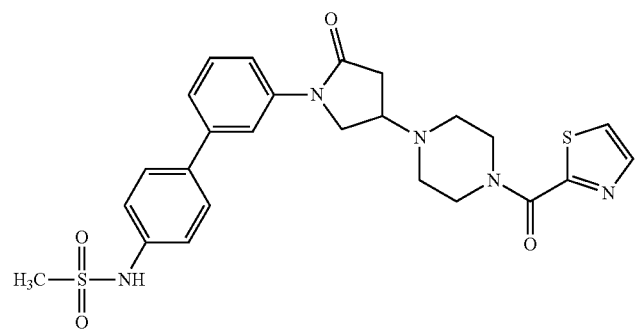 [SMILES: CS(=O)(=O)Nc1ccc(-c2cccc(N3CC(N4CCN(C(=O)c5nccs5)CC4)CC3=O)c2)cc1] | 526.2 |
| 111 | 4-(4-(1,3-thiazol-2-ylcarbonyl)piperazin-1-yl)-1-(1-(6-(trifluoromethyl)pyridin-3-yl)-1H-indol-5-yl)pyrrolidin-2-one | 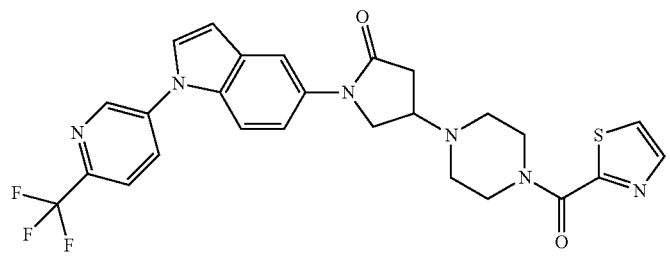 [SMILES: O=C(c1nccs1)N1CCN(C2CC(=O)N(c3ccc4c(ccn4-c4ccc(C(F)(F)F)nc4)c3)C2)CC1] | 541.2 |

TABLE 1-13-continued

| 112 | N-methyl-3'-(2-oxo-4-(4-(1,3-thiazol-2-ylcarbonyl)piperazin-1-yl)pyrrolidin-1-yl)biphenyl-4-sulfonamide | 526.2 |
| --- | --- | --- |
| 113 | 1-(1H-indol-5-yl)-4-(4-(1,3-thiazol-2-ylcarbonyl)piperazin-1-yl)pyrrolidin-2-one | 396.2 |
| 114 | 1-(1-(4-fluorobenzyl)-1H-indazol-5-yl)-4-(4-(1,3-thiazol-2-ylcarbonyl)piperazin-1-yl)pyrrolidin-2-one | 505.2 |
| 115 | 1-(3-(cyclohexylamino)phenyl)-4-(4-(1,3-thiazol-2-ylcarbonyl)piperazin-1-yl)pyrrolidin-2-one | 454.2 |
| 116 | N-(4-((3-(2-oxo-4-(4-(1,3-thiazol-2-ylcarbonyl)piperazin-1-yl)pyrrolidin-1-yl)phenyl)amino)phenyl)acetamide | 505.2 |
| 117 | N-methyl-N-(4-((3-(2-oxo-4-(4-(1,3-thiazol-2-ylcarbonyl)piperazin-1-yl)pyrrolidin-1-yl)phenyl)amino)phenyl)acetamide | 519.2 |

TABLE 1-14

| | | | |
|---|---|---|---|
| 118 | N-(3-((3-(2-oxo-4-(4-(1,3-thiazol-2-ylcarbonyl)piperazin-1-yl)pyrrolidin-1-yl)phenyl)amino)phenyl)acetamide | | 505.2 |
| 119 | 1-(3-((4-(2-oxopyrrolidin-1-yl)phenyl)amino)phenyl)-4-(4-(1,3-thiazol-2-ylcarbonyl)piperazin-1-yl)pyrrolidin-2-one | | 531.2 |
| 120 | 1-(3-((1-methylpiperidin-4-yl)amino)phenyl)-4-(4-(1,3-thiazol-2-ylcarbonyl)piperazin-1-yl)pyrrolidin-2-one | | 469.2 |
| 121 | 1-(3-(tetrahydro-2H-pyran-4-ylarnino)phenyl)-4-(4-(1,3-thiazol-2-ylcarbonyl)piperazin-1-yl)pyrrolidin-2-one | | 456.2 |
| 122 | 6-((3-(2-oxo-4-(4-(1,3-thiazol-2-ylcarbonyl)piperazin-1-yl)pyrrolidin-1-yl)phenyl)amino)-2H-1,4-benzoxazin-3(4H)-one | | 519.2 |
| 123 | 7-((3-(2-oxo-4-(4-(1,3-thiazol-2-ylcarbonyl)piperazin-1-yl)pyrrolidin-1-yl)phenyl)amino)-3,4-dihydroquinolin-2(1H)-one | | 517.2 |

TABLE 1-14-continued

| 124 | 1-(3-((1-methylpiperidin-3-yl)amino)phenyl)-4-(4-(1,3-thiazol-2-ylcarbonyl)piperazin-1-yl)pyrrolidin-2-one | 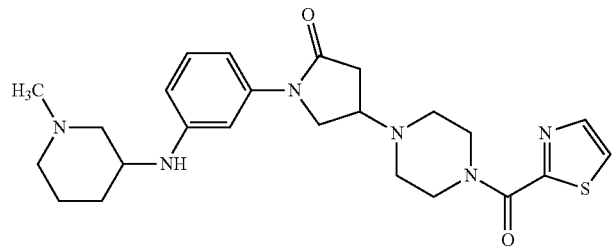 [SMILES: CN1CCCC(Nc2cccc(N3CC(N4CCN(C(=O)c5nccs5)CC4)CC3=O)c2)C1] | 469.1 |
| --- | --- | --- | --- |
| 125 | 5-((3-(2-oxo-4-(4-(1,3-thiazol-2-ylcarbonyl)piperazin-1-yl)pyrrolidin-1-yl)phenyl)amino)-3,4-dihydroquinolin-2(1H)-one | 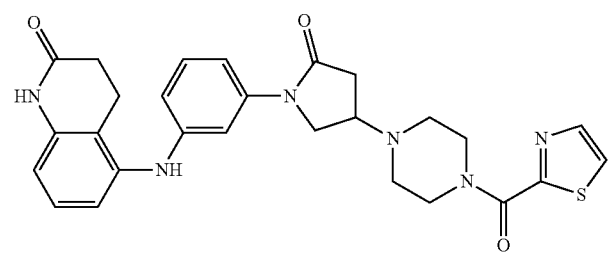 [SMILES: O=C1CCc2c(cccc2Nc2cccc(N3CC(N4CCN(C(=O)c5nccs5)CC4)CC3=O)c2)N1] | 517.2 |
| 126 | 1-(3-((1-acetylpiperidin-3-yl)amino)phenyl)-4-(4-(1,3-thiazol-2-ylcarbonyl)piperazin-1-yl)pyrrolidin-2-one | 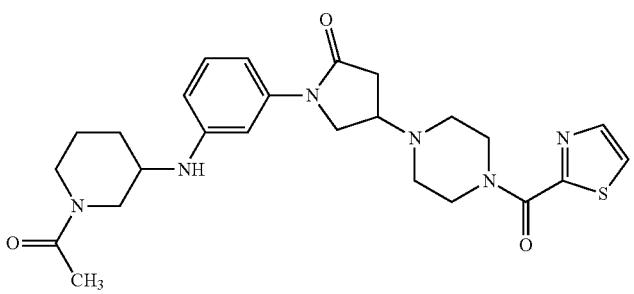 [SMILES: CC(=O)N1CCCC(Nc2cccc(N3CC(N4CCN(C(=O)c5nccs5)CC4)CC3=O)c2)C1] | 497.2 |

TABLE 1-15

| 127 | 1-methyl-5-((3-(2-oxo-4-(4-(1,3-thiazol-2-ylcarbonyl)piperazin-1-yl)pyrrolidin-1-yl)phenyl)amino)piperidin-2-one | 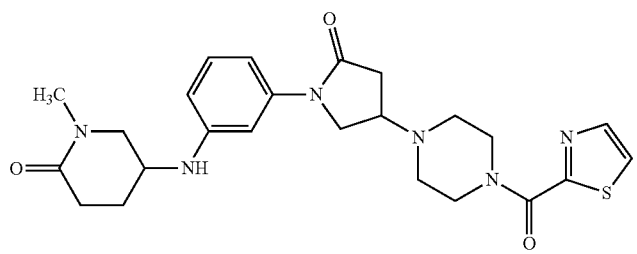 [SMILES: CN1CC(Nc2cccc(N3CC(N4CCN(C(=O)c5nccs5)CC4)CC3=O)c2)CCC1=O] | 483.0 |
| --- | --- | --- | --- |
| 128 | 4-(4-(1,3-thiazol-2-ylcarbonyl)piperazin-1-yl)-1-(1-(6-(trifluoromethyl)pyridazin-3-yl)-1H-indol-5-yl)pyrrolidin-2-one | 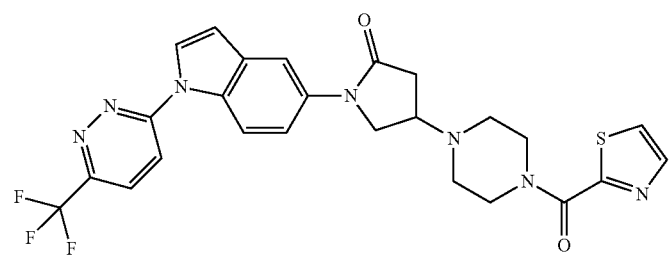 [SMILES: O=C(c1nccs1)N1CCN(C2CC(=O)N(c3ccc4c(ccn4-c4ccc(C(F)(F)F)nn4)c3)C2)CC1] | 542.2 |

TABLE 1-15-continued

| 129 | 4-(4-(1,3-thiazol-2-ylcarbonyl)piperazin-1-yl)-1-(1-(5-(trifluoromethyl)pyrazin-2-yl)-1H-indol-5-yl)pyrrolidin-2-one | 542.2 |
|---|---|---|
| 130 | 1-(4-phenylpyridin-2-yl)-4-(4-(1,3-thiazol-2-ylcarbonyl)piperazin-1-yl)pyrrolidin-2-one | 434.1 |
| 131 | 1-(5-phenylpyridin-3-yl)-4-(4-(1,3-thiazol-2-ylcarbonyl)piperazin-1-yl)pyrrolidin-2-one | 434.1 |
| 132 | 1-(2',6'-dimethylbiphenyl-3-yl)-4-(4-(1,3-thiazol-2-ylcarbonyl)piperazin-1-yl)pyrrolidin-2-one | 461.2 |
| 133 | 1-(3'-chlorobiphenyl-3-yl)-4-(4-(1,3-thiazol-2-ylcarbonyl)piperazin-1-yl)pyrrolidin-2-one | 467.1 |
| 134 | 1-(2'-methoxybiphenyl-3-yl)-4-(4-(1,3-thiazol-2-ylcarbonyl)piperazin-1-yl)pyrrolidin-2-one | 463.1 |

TABLE 1-15-continued

| | | | |
|---|---|---|---|
| 135 | 3'-(2-oxo-4-(4-(1,3-thiazol-2-ylcarbonyl)piperazin-1-yl)pyrrolidin-1-yl)biphenyl-2-carbonitrile | 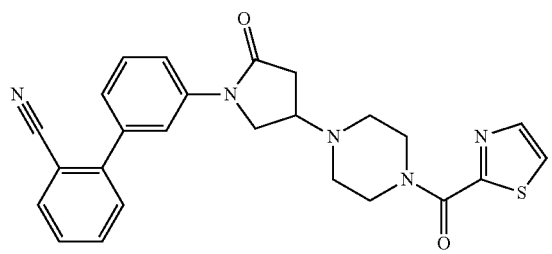 [SMILES: N#Cc1ccccc1-c1cccc(N2CC(N3CCN(C(=O)c4nccs4)CC3)CC2=O)c1] | 458.1 |

TABLE 1-16

| | | | |
|---|---|---|---|
| 136 | 1-(2'-fluorobiphenyl-3-yl)-4-(4-(1,3-thiazol-2-ylcarbonyl)piperazin-1-yl)pyrrolidin-2-one | 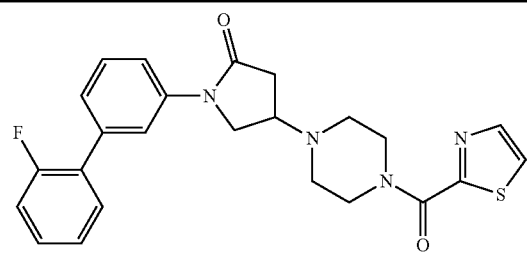 | 451.1 |
| 137 | 1-(2'-chlorobiphenyl-3-yl)-4-(4-(1,3-thiazol-2-ylcarbonyl)piperazin-1-yl)pyrrolidin-2-one | 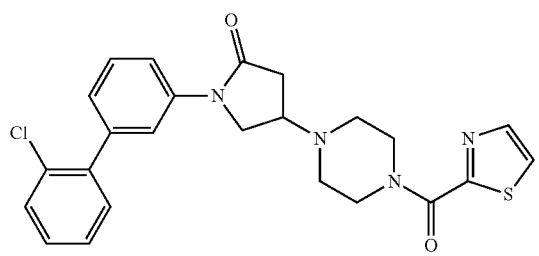 [SMILES: O=C(c1nccs1)N1CCN(C2CC(=O)N(c3cccc(-c4ccccc4Cl)c3)C2)CC1] | 467.0 |
| 138 | 4-(4-(1,3-thiazol-2-ylcarbonyl)piperazin-1-yl)-1-(2'-(trifluoromethyl)biphenyl-3-yl)pyrrolidin-2-one | 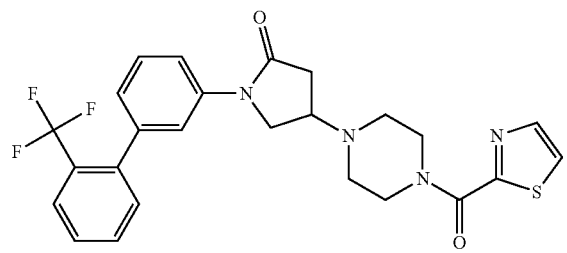 [SMILES: O=C(c1nccs1)N1CCN(C2CC(=O)N(c3cccc(-c4ccccc4C(F)(F)F)c3)C2)CC1] | 501.1 |
| 139 | 1-(3-(2-methylpyridin-3-yl)phenyl)-4-(4-(1,3-thiazol-2-ylcarbonyl)piperazin-1-yl)pyrrolidin-2-one | 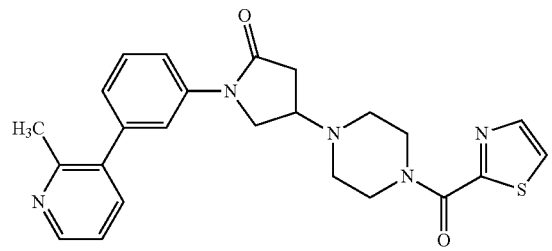 | 448.1 |
| 140 | 1-(6-phenylpyridin-2-yl)-4-(4-(1,3-thiazol-2-ylcarbonyl)piperazin-1-yl)pyrrolidin-2-one | 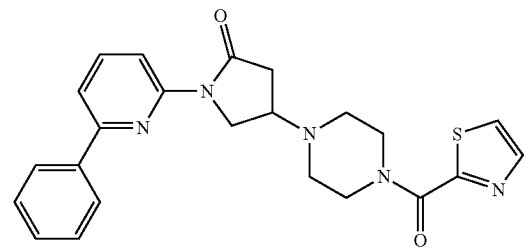 | 434.1 |

TABLE 1-16-continued

| | | | |
|---|---|---|---|
| 141 | 4-(4-(1,3-thiazol-2-ylcarbonyl)piperazin-1-yl)-1-(1-(5-(trifluoromethyl)pyrimidin-2-yl)-2,3-dihydro-1H-indol-5-yl)pyrrolidin-2-one | 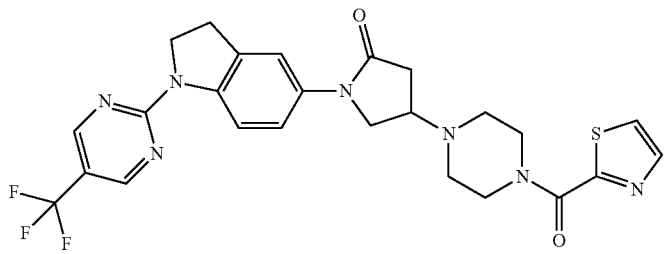 [SMILES: O=C(c1nccs1)N1CCN(C2CC(=O)N(c3ccc4c(c3)CCN4c3ncc(C(F)(F)F)cn3)C2)CC1] | 544.1 |
| 142 | 1-(2'-ethylbiphenyl-3-yl)-4-(4-(1,3-thiazol-2-ylcarbonyl)piperazin-1-yl)pyrrolidin-2-one | 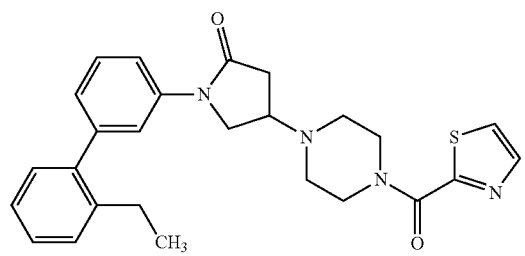 [SMILES: CCc1ccccc1-c1cccc(N2CC(N3CCN(C(=O)c4nccs4)CC3)CC2=O)c1] | 461.2 |
| 143 | 1-(2',3'-dimethylbiphenyl-3-yl)-4-(4-(1,3-thiazol-2-ylcarbonyl)piperazin-1-yl)pyrrolidin-2-one | 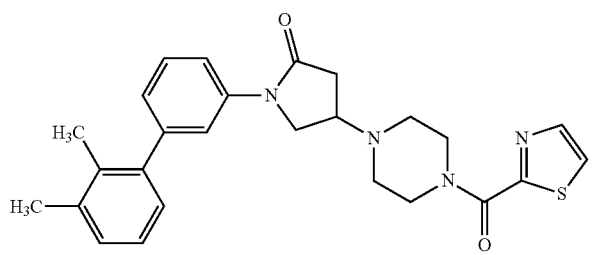 [SMILES: Cc1cccc(-c2cccc(N3CC(N4CCN(C(=O)c5nccs5)CC4)CC3=O)c2)c1C] | 461.2 |
| 144 | 1-(2',5'-dimethylbiphenyl-3-yl)-4-(4-(1,3-thiazol-2-ylcarbonyl)piperazin-1-yl)pyrrolidin-2-one | 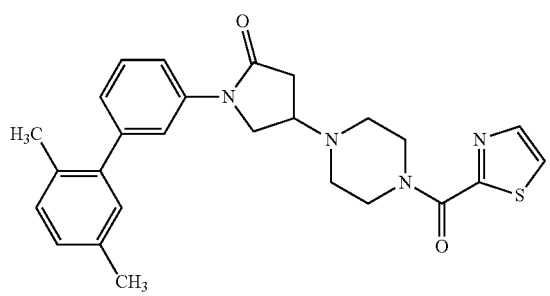 [SMILES: Cc1ccc(C)c(-c2cccc(N3CC(N4CCN(C(=O)c5nccs5)CC4)CC3=O)c2)c1] | 461.2 |

TABLE 1-17

| | | | |
|---|---|---|---|
| 145 | 1-(2',6'-difluorobiphenyl-3-yl)-4-(4-(1,3-thiazol-2-ylcarbonyl)piperazin-1-yl)pyrrolidin-2-one | 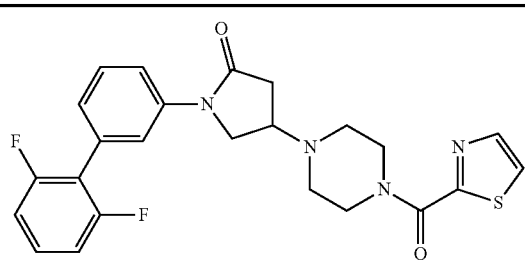 | 469.1 |

TABLE 1-17-continued

| | | | |
|---|---|---|---|
| 146 | 1-(2',6'-dichlorobiphenyl-3-yl)-4-(4-(1,3-thiazol-2-ylcarbonyl)piperazin-1-yl)pyrrolidin-2-one | 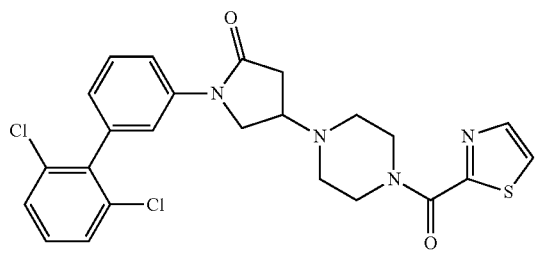 [SMILES: O=C(c1nccs1)N1CCN(C2CC(=O)N(c3cccc(-c4c(Cl)cccc4Cl)c3)C2)CC1] | 501.1 |
| 147 | 1-benzyl-4-(4-(1,3-thiazol-2-ylcarbonyl)piperazin-1-yl)pyrrolidin-2-one | 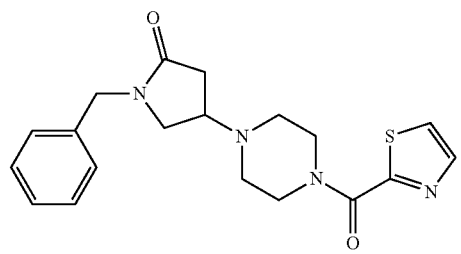 [SMILES: O=C1CC(N2CCN(C(=O)c3nccs3)CC2)CN1Cc1ccccc1] | 371.1 |
| 148 | 4-(4-(1,3-thiazol-2-ylcarbonyl)piperazin-1-yl)-1-(3-(trifluoromethoxy)phenyl)pyrrolidin-2-one | 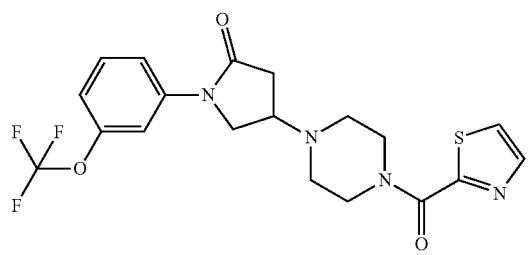 [SMILES: O=C(c1nccs1)N1CCN(C2CC(=O)N(c3cccc(OC(F)(F)F)c3)C2)CC1] | 441.1 |
| 149 | 1-(3-(5-methylpyridin-2-yl)phenyl)-4-(4-(1,3-thiazol-2-ylcarbonyl)piperazin-1-yl)pyrrolidin-2-one | 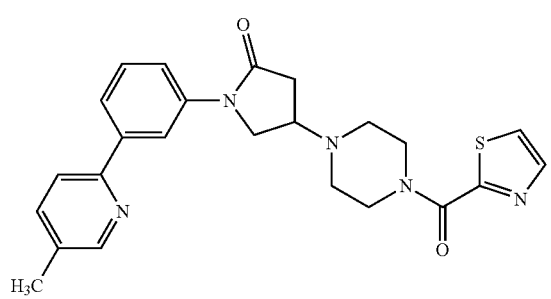 [SMILES: Cc1ccc(-c2cccc(N3CC(N4CCN(C(=O)c5nccs5)CC4)CC3=O)c2)nc1] | 448.2 |
| 150 | 1-(3-(6-methylpyridin-2-yl)phenyl)-4-(4-(1,3-thiazol-2-ylcarbonyl)piperazin-1-yl)pyrrolidin-2-one | 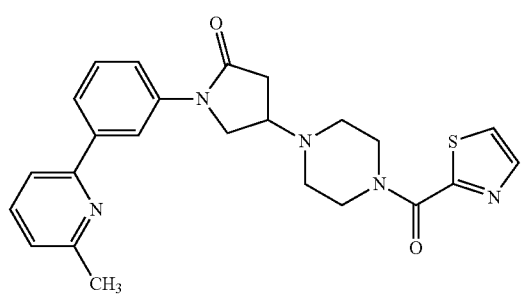 [SMILES: Cc1cccc(-c2cccc(N3CC(N4CCN(C(=O)c5nccs5)CC4)CC3=O)c2)n1] | 448.2 |
| 151 | 1-(3-(3-chloropyridin-2-yl)phenyl)-4-(4-(1,3-thiazol-2-ylcarbonyl)piperazin-1-yl)pyrrolidin-2-one | 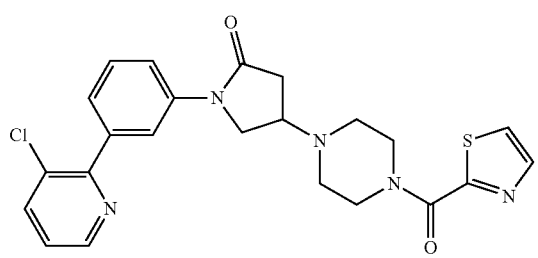 [SMILES: O=C(c1nccs1)N1CCN(C2CC(=O)N(c3cccc(-c4ncccc4Cl)c3)C2)CC1] | 468.1 |

TABLE 1-17-continued

| 152 | 1-(3-(4-rnethylpyridin-2-yl)phenyl)-4-(4-(1,3-thiazol-2-ylcarbonyl)piperazin-1-yl)pyrrolidin-2-one | 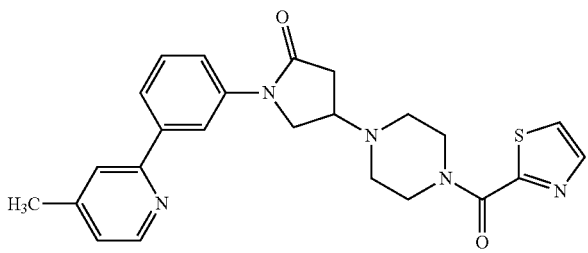 [SMILES: Cc1ccnc(-c2cccc(N3CC(N4CCN(C(=O)c5nccs5)CC4)CC3=O)c2)c1] | 448.2 |
| 153 | 1-(3-(3-rnethylpyridin-2-yl)phenyl)-4-(4-(1,3-thiazol-2-ylcarbonyl)piperazin-1-yl)pyrrolidin-2-one | 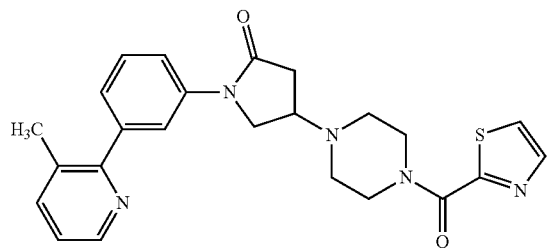 [SMILES: Cc1cccnc1-c1cccc(N2CC(N3CCN(C(=O)c4nccs4)CC3)CC2=O)c1] | 448.2 |

TABLE 1-18

| 154 | 6-methyl-3'-(2-oxo-4-(4-(1,3-thiazol-2-ylcarbonyl)piperazin-1-yl)pyrrolidin-1-yl)biphenyl-2-carbonitrile | 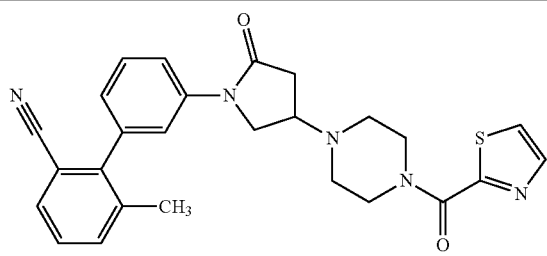 [SMILES: Cc1cccc(C#N)c1-c1cccc(N2CC(N3CCN(C(=O)c4nccs4)CC3)CC2=O)c1] | 472.0 |
| 155 | 1-(3-(3,5-dimethyl-1,2-oxazol-4-yl)phenyl)-4-(4-(1,3-thiazol-2-ylcarbonyl)piperazin-1-yl)pyrrolidin-2-one | 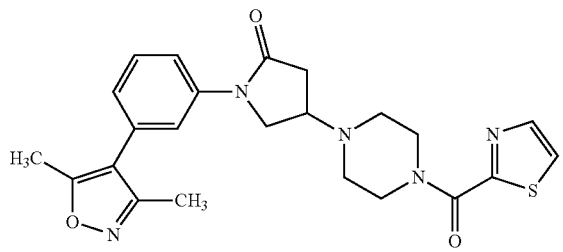 [SMILES: Cc1noc(C)c1-c1cccc(N2CC(N3CCN(C(=O)c4nccs4)CC3)CC2=O)c1] | 452.1 |
| 156 | 1-(3-(1-ethyl-1H-pyrazol-5-yl)phenyl)-4-(4-(1,3-thiazol-2-ylcarbonyl)piperazin-1-yl)pyrrolidin-2-one | 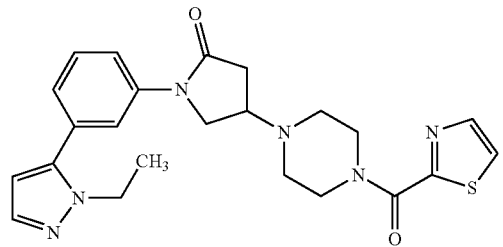 [SMILES: CCn1nccc1-c1cccc(N2CC(N3CCN(C(=O)c4nccs4)CC3)CC2=O)c1] | 451.1 |
| 157 | 1-(3-(1,3-dimethyl-1H-pyrazol-5-yl)phenyl)-4-(4-(1,3-thiazol-2-ylcarbonyl)piperazin-1-yl)pyrrolidin-2-one | 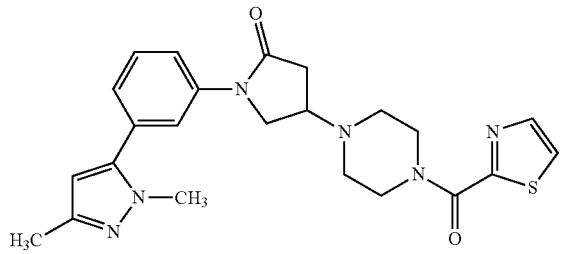 [SMILES: Cc1cc(-c2cccc(N3CC(N4CCN(C(=O)c5nccs5)CC4)CC3=O)c2)n(C)n1] | 451.1 |

TABLE 1-18-continued

| | | | |
|---|---|---|---|
| 158 | 1-(3-(1-methyl-3-(trifluoromethyl)-1H-pyrazol-5-yl)phenyl)-4-(4-(1,3-thiazol-2-ylcarbonyl)piperazin-1-yl)pyrrolidin-2-one | | 505.1 |
| 159 | 1-(6-bromopyridin-2-yl)-4-(4-(1,3-thiazol-2-ylcarbonyl)piperazin-1-yl)pyrrolidin-2-one | | 436.0 |
| 160 | 1-phenyl-4-(4-(1,3-thiazol-2-ylcarbonyl)piperazin-1-yl)pyrrolidin-2-one | | 357.1 |
| 161 | 1-(3-(2,4-dimethyl-1,3-thiazol-5-yl)phenyl)-4-(4-(1,3-thiazol-2-ylcarbonyl)piperazin-1-yl)pyrrolidin-2-one | | 468.1 |
| 162 | 1-(3-(3-methyl-2-thienyl)phenyl)-4-(4-(1,3-thiazol-2-ylcarbonyl)piperazin-1-yl)pyrrolidin-2-one | | 453.1 |

TABLE 1-19

| 163 | 1-(3-iodophenyl)-4-(4-(1,3-oxazol-2-ylcarbonyl)piperazin-1-yl)pyrrolidin-2-one | 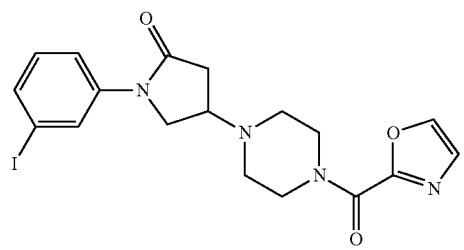 [SMILES: O=C(c1ncco1)N1CCN(C2CC(=O)N(c3cccc(I)c3)C2)CC1] | 467.0 |
| 164 | 1-(3-iodophenyl)-4-(4-(1,3-thiazol-4-ylcarbonyl)piperazin-1-yl)pyrrolidin-2-one | 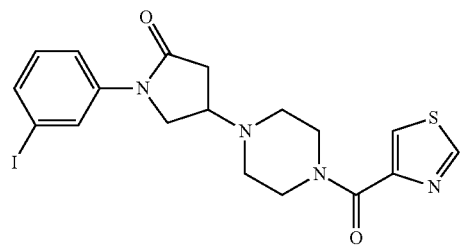 [SMILES: O=C(c1cscn1)N1CCN(C2CC(=O)N(c3cccc(I)c3)C2)CC1] | 482.8 |
| 165 | 4-(4-(1,3-thiazol-2-ylcarbonyl)piperazin-1-yl)-1-(3-(3-(trifluoromethyl)pyridin-2-yl)phenyl)pyrrolidin-2-one | 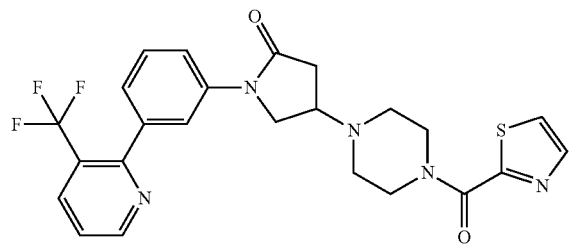 [SMILES: O=C(c1nccs1)N1CCN(C2CC(=O)N(c3cccc(-c4ncccc4C(F)(F)F)c3)C2)CC1] | 502.2 |
| 166 | 1-(2'-chlorobiphenyl-3-yl)-4-(4-(1,3-oxazol-2-ylcarbonyl)piperazin-1-yl)pyrrolidin-2-one | 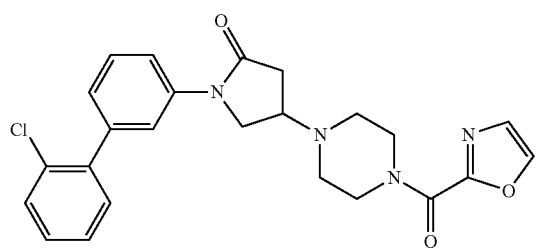 | 451.1 |
| 167 | 1-(3-(2-methylpyridin-3-yl)phenyl)-4-(4-(1,3-oxazol-2-ylcarbonyl)piperazin-1-yl)pyrrolidin-2-one | 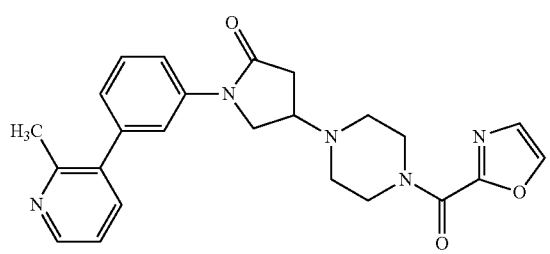 | 432.1 |
| 168 | 1-(2'-chlorobiphenyl-3-yl)-4-(4-(1,3-thiazol-4-ylcarbonyl)piperazin-1-yl)pyrrolidin-2-one | 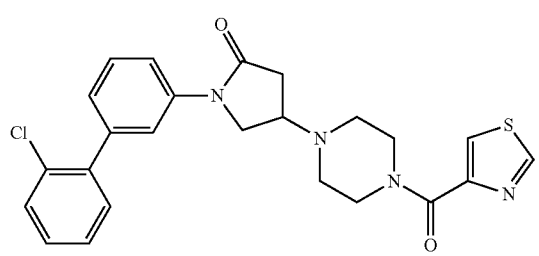 | 467.1 |

TABLE 1-19-continued

| | | | |
|---|---|---|---|
| 169 | 1-(3-(2-methylpyridin-3-yl)phenyl)-4-(4-(1,3-thiazol-4-ylcarbonyl)piperazin-1-yl)pyrrolidin-2-one | 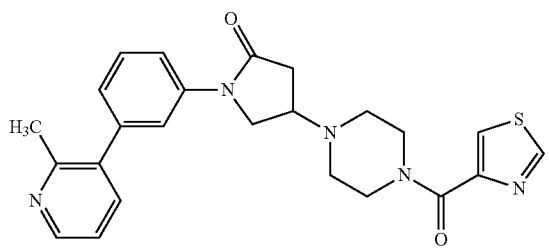 [SMILES: Cc1ncccc1-c1cccc(N2CC(N3CCN(C(=O)c4cscn4)CC3)CC2=O)c1] | 448.2 |
| 170 | 1-(3-bromo-4-fluorophenyl)-4-(4-(1,3-thiazol-2-ylcarbonyl)piperazin-1-yl)pyrrolidin-2-one | 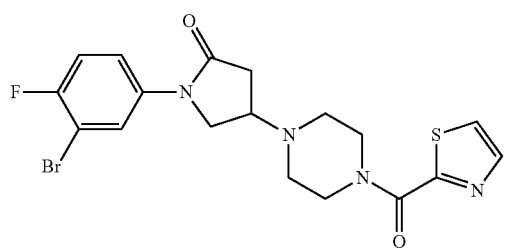 [SMILES: O=C(c1nccs1)N1CCN(C2CC(=O)N(c3ccc(F)c(Br)c3)C2)CC1] | 453.0 |
| 171 | 1-(3-(1-isopropyl-1H-pyrazol-5-yl)phenyl)-4-(4-(1,3-thiazol-2-ylcarbonyl)piperazin-1-yl)pyrrolidin-2-one | 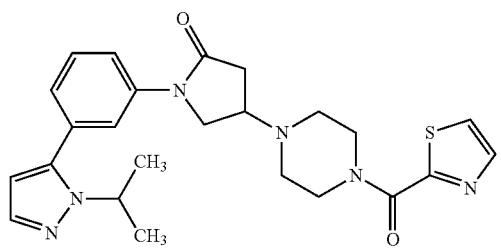 [SMILES: CC(C)n1nccc1-c1cccc(N2CC(N3CCN(C(=O)c4nccs4)CC3)CC2=O)c1] | 465.1 |

TABLE 1-20

| | | | |
|---|---|---|---|
| 172 | 1-(3-(2-methylpyridin-3-yl)phenyl)-4-(4-(1,3-thiazol-2-ylcarbonyl)piperazin-1-yl)pyrrolidin-2-one(optical isomer) | 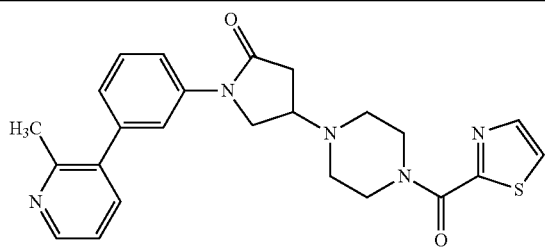 | 448.1 |
| 173 | 1-(3-(2-methylpyridin-3-yl)phenyl)-4-(4-(1,3-thiazol-2-ylcarbonyl)piperazin-1-yl)pyrrolidin-2-one(optical isomer) | 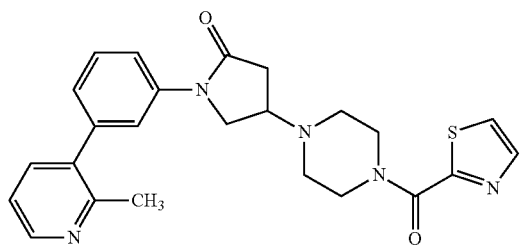 [SMILES: Cc1ncccc1-c1cccc(N2CC(N3CCN(C(=O)c4nccs4)CC3)CC2=O)c1] | 448.2 |
| 174 | 1-(2'-methyl-2,3'-bipyridin-6-yl)-4-(4-(1,3-thiazol-2-ylcarbonyl)piperazin-1-yl)pyrrolidin-2-one | 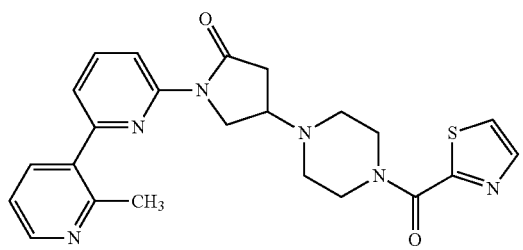 [SMILES: Cc1ncccc1-c1cccc(N2CC(N3CCN(C(=O)c4nccs4)CC3)CC2=O)n1] | 449.1 |

TABLE 1-20-continued

| | | | |
|---|---|---|---|
| 175 | 1-(4-fluoro-3-(2-methylpyridin-3-yl)phenyl)-4-(4-(1,3-thiazol-2-ylcarbonyl)piperazin-1-yl)pyrrolidin-2-one | 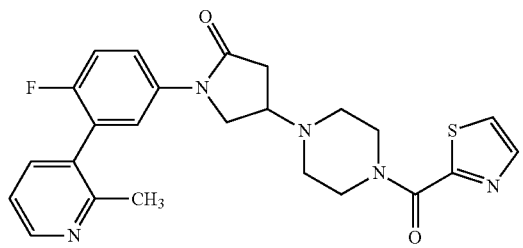 [SMILES: Cc1ncccc1-c1cc(N2CC(N3CCN(C(=O)c4nccs4)CC3)CC2=O)ccc1F] | 466.0 |
| 176 | 1-(2'-methylbiphenyl-4-yl)-4-(4-(1,3-thiazol-2-ylcarbonyl)piperazin-1-yl)pyrrolidin-2-one | 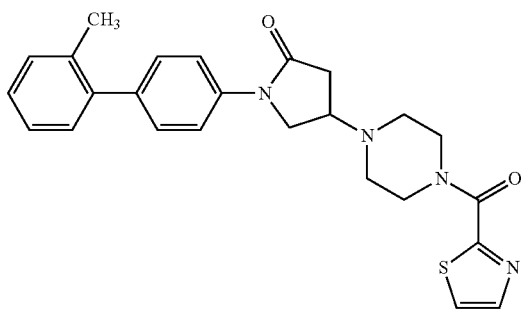 | 447.2 |
| 177 | 1-(4-(4-methylpyridin-3-yl)phenyl)-4-(4-(1,3-thiazol-2-ylcarbonyl)piperazin-1-yl)pyrrolidin-2-one | 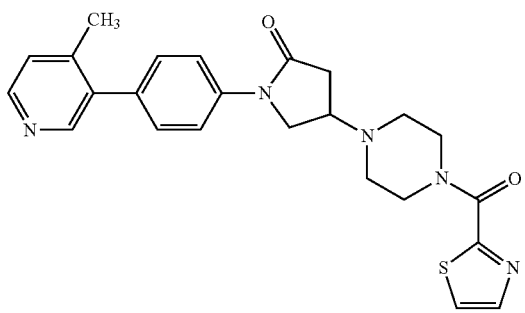 [SMILES: Cc1ccncc1-c1ccc(N2CC(N3CCN(C(=O)c4nccs4)CC3)CC2=O)cc1] | 448.2 |
| 178 | 1-(4-(3-methylpyridin-4-yl)phenyl)-4-(4-(1,3-thiazol-2-ylcarbonyl)piperazin-1-yl)pyrrolidin-2-one | 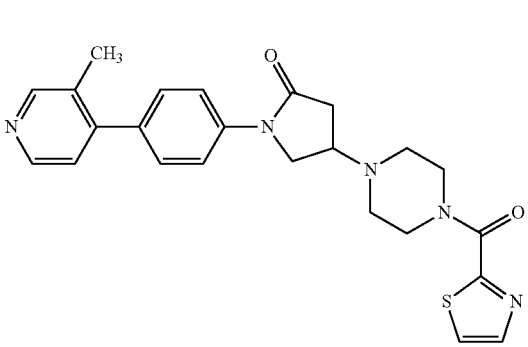 [SMILES: Cc1cnccc1-c1ccc(N2CC(N3CCN(C(=O)c4nccs4)CC3)CC2=O)cc1] | 448.2 |
| 179 | 1-(2'-fluorobiphenyl-4-yl)-4-(4-(1,3-thiazol-2-ylcarbonyl)piperazin-1-yl)pyrrolidin-2-one | 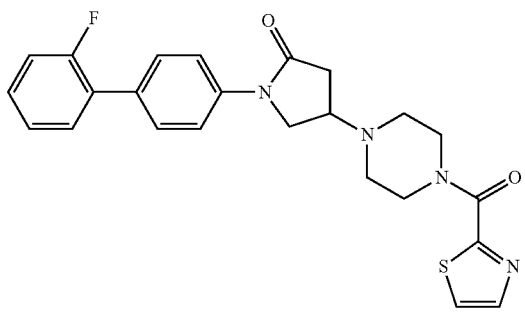 | 451.1 |

TABLE 1-20-continued

| | | | |
|---|---|---|---|
| 180 | 1-(4-(1,3-dimethyl-1H-pyrazol-5-yl)phenyl)-4-(4-(1,3-thiazol-2-ylcarbonyl)piperazin-1-yl)pyrrolidin-2-one | 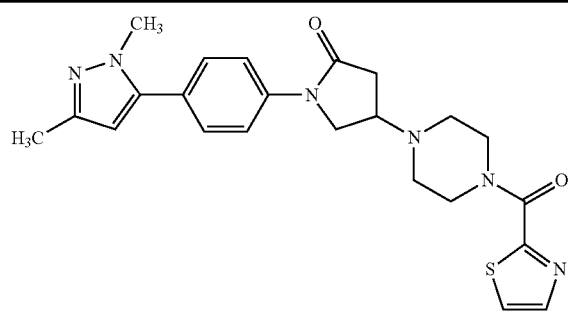 | 451.2 |

TABLE 1-21

| | | | |
|---|---|---|---|
| 181 | 1-(4-(1,3-dimethyl-1H-pyrazol-4-yl)phenyl)-4-(4-(1,3-thiazol-2-ylcarbonyl)piperazin-1-yl)pyrrolidin-2-one | 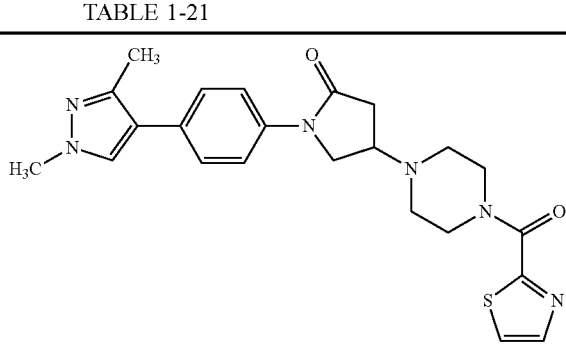 | 451.2 |
| 182 | 1-(4-(1,5-dimethyl-1H-pyrazol-4-yl)phenyl)-4-(4-(1,3-thiazol-2-ylcarbonyl)piperazin-1-yl)pyrrolidin-2-one | 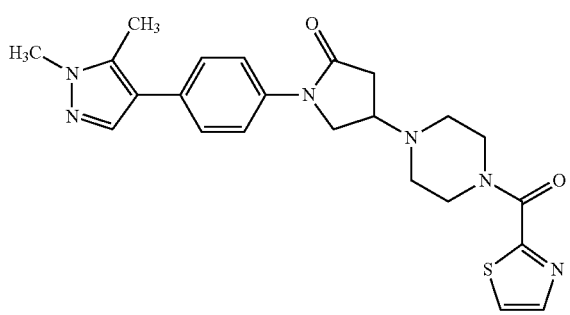 [SMILES: Cc1c(-c2ccc(N3CC(N4CCN(C(=O)c5nccs5)CC4)CC3=O)cc2)cnn1C] | 451.1 |
| 183 | 1-(4-(3,5-dimethyl-1,2-oxazol-4-yl)phenyl)-4-(4-(1,3-thiazol-2-ylcarbonyl)piperazin-1-yl)pyrrolidin-2-one | 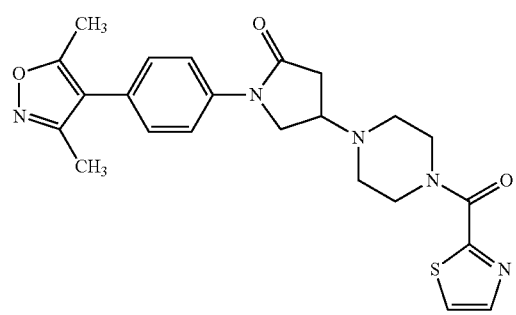 [SMILES: Cc1noc(C)c1-c1ccc(N2CC(N3CCN(C(=O)c4nccs4)CC3)CC2=O)cc1] | 452.1 |
| 184 | 1-(4-(3-furyl)phenyl)-4-(4-(1,3-thiazol-2-ylcarbonyl)piperazin-1-yl)pyrrolidin-2-one | 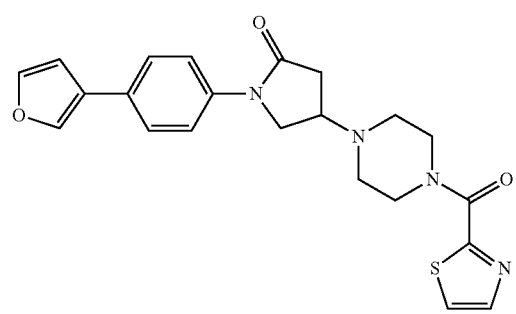 [SMILES: O=C(c1nccs1)N1CCN(C2CC(=O)N(c3ccc(-c4ccoc4)cc3)C2)CC1] | 423.1 |

TABLE 1-21-continued

| 185 | 4'-(2-oxo-4-(4-(1,3-thiazol-2-ylcarbonyl)piperazin-1-yl)pyrrolidin-1-yl)biphenyl-3-carbonitrile | | 458.2 |
|---|---|---|---|
| 186 | 1-(2,6'-dimethylbiphenyl-4-yl)-4-(4-(1,3-thiazol-2-ylcarbonyl)piperazin-1-yl)pyrrolidin-2-one | | 461.2 |
| 187 | 1-(3'-(hydroxymethyl)biphenyl-4-yl)-4-(4-(1,3-thiazol-2-ylcarbonyl)piperazin-1-yl)pyrrolidin-2-one | | 463.2 |
| 188 | 1-(2'-chlorobiphenyl-4-yl)-4-(4-(1,3-thiazol-2-ylcarbonyl)piperazin-1-yl)pyrrolidin-2-one | | 467.2 |
| 189 | 1-(4-(2,4-dimethyl-1,3-thiazol-5-yl)phenyl)-4-(4-(1,3-thiazol-2-ylcarbonyl)piperazin-1-yl)pyrrolidin-2-one | | 468.2 |

TABLE 1-22
| | | | |
|---|---|---|---|
| 190 | N-(4'-(2-oxo-4-(4-(1,3-thiazol-2-ylcarbonyl)piperazin-1-yl)pyrrolidin-1-yl)biphenyl-4-yl)acetamide | 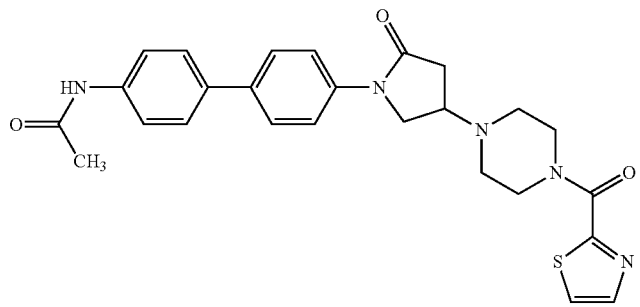 [SMILES: CC(=O)Nc1ccc(-c2ccc(N3CC(N4CCN(C(=O)c5nccs5)CC4)CC3=O)cc2)cc1] | 490.2 |
| 191 | N-(4'-(2-oxo-4-(4-(1,3-thiazol-2-ylcarbonyl)piperazin-1-yl)pyrrolidin-1-yl)biphenyl-3-yl)acetamide | 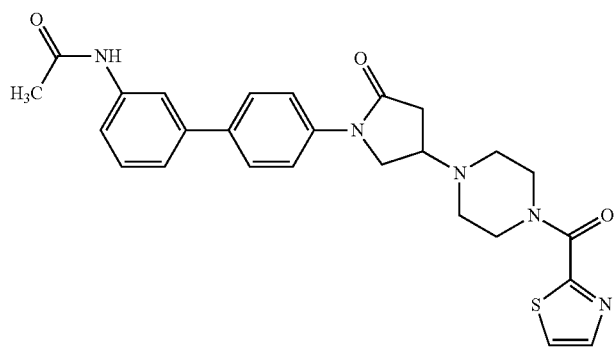 [SMILES: CC(=O)Nc1cccc(-c2ccc(N3CC(N4CCN(C(=O)c5nccs5)CC4)CC3=O)cc2)c1] | 490.2 |
| 192 | N-(4'-(2-oxo-4-(4-(1,3-thiazol-2-ylcarbonyl)piperazin-1-yl)pyrrolidin-1-yl)biphenyl-2-yl)acetamide | 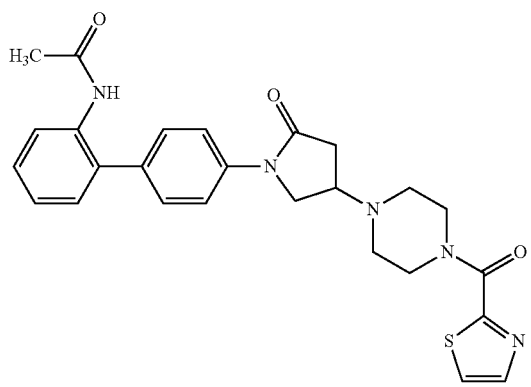 [SMILES: CC(=O)Nc1ccccc1-c1ccc(N2CC(N3CCN(C(=O)c4nccs4)CC3)CC2=O)cc1] | 490.2 |
| 193 | 4'-(2-oxo-4-(4-(1,3-thiazol-2-ylcarbonyl)piperazin-1-yl)pyrrolidin-1-yl)biphenyl-4-sulfonamide | 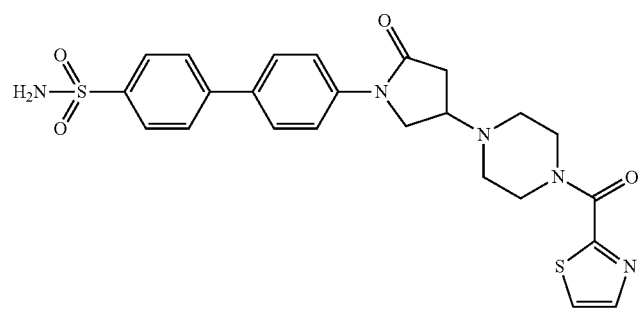 [SMILES: NS(=O)(=O)c1ccc(-c2ccc(N3CC(N4CCN(C(=O)c5nccs5)CC4)CC3=O)cc2)cc1] | 512.1 |

TABLE 1-22-continued

| # | Name | Structure | MS |
|---|------|-----------|-----|
| 194 | 4'-(2-oxo-4-(4-(1,3-thiazol-2-ylcarbonyl)piperazin-1-yl)pyrrolidin-1-yl)biphenyl-3-sulfonamide | 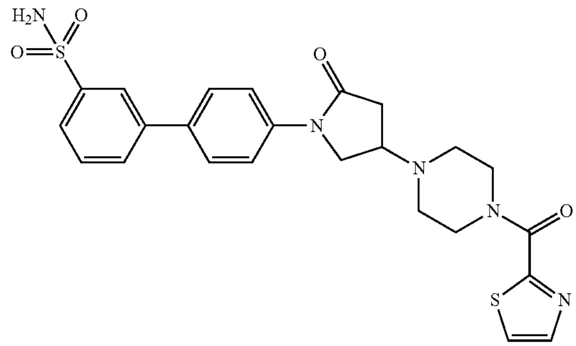 [SMILES: NS(=O)(=O)c1cccc(-c2ccc(N3CC(N4CCN(C(=O)c5nccs5)CC4)CC3=O)cc2)c1] | 512.1 |
| 195 | N-(4'-(2-oxo-4-(4-(1,3-thiazol-2-ylcarbonyl)piperazin-1-yl)pyrrolidin-1-yl)biphenyl-2-yl)methanesulfonamide | 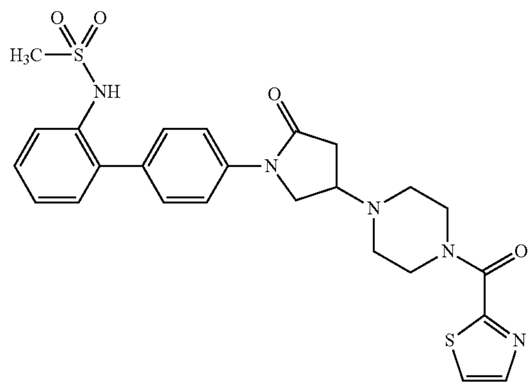 [SMILES: CS(=O)(=O)Nc1ccccc1-c1ccc(N2CC(N3CCN(C(=O)c4nccs4)CC3)CC2=O)cc1] | 526.2 |
| 196 | 1-(4-(pyridin-4-yl)phenyl)-4-(4-(1,3-thiazol-2-ylcarbonyl)piperazin-1-yl)pyrrolidin-2-one | 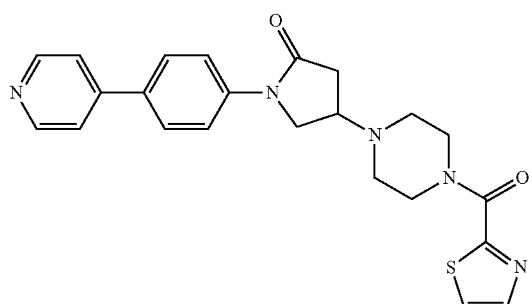 | 434.1 |
| 197 | 1-(4-(pyridin-3-yl)phenyl)-4-(4-(1,3-thiazol-2-ylcarbonyl)piperazin-1-yl)pyrrolidin-2-one | 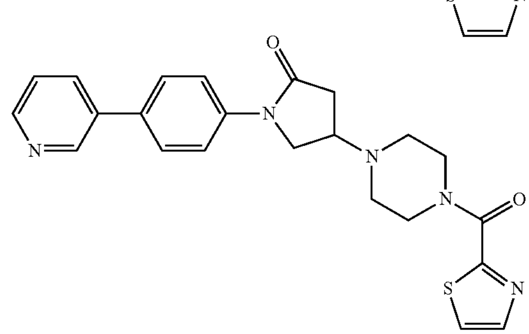 | 434.1 |
| 198 | 1-(4-(1-methyl-1H-pyrazol-5-yl)phenyl)-4-(4-(1,3-thiazol-2-ylcarbonyl)piperazin-1-yl)pyrrolidin-2-one | 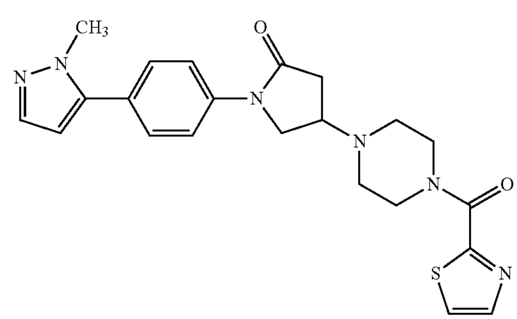 [SMILES: Cn1nccc1-c1ccc(N2CC(N3CCN(C(=O)c4nccs4)CC3)CC2=O)cc1] | 437.2 |

TABLE 1-23

| 199 | 1-(3-(2-chloropyridin-3-yl)phenyl)-4-(4-(1,3-thiazol-2-ylcarbonyl)piperazin-1-yl)pyrrolidin-2-one | 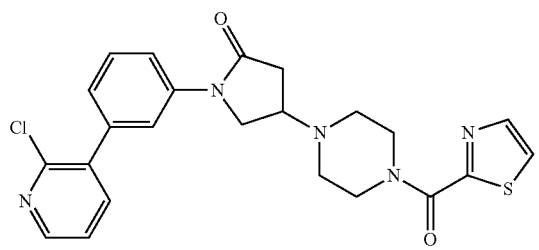 | 468.1 |
| 200 | 6-(3-(2-oxo-4-(4-(1,3-thiazol-2-ylcarbonyl)piperazin-1-yl)pyrrolidin-1-yl)phenyl)-1,3-dihydro-2H-indol-2-one | 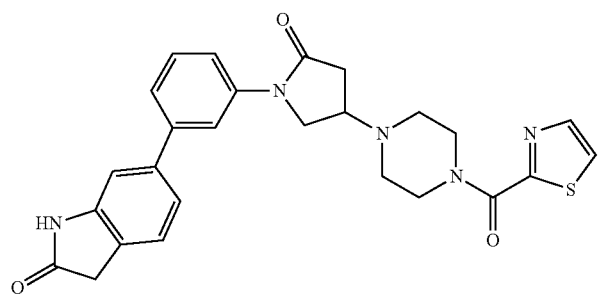 [SMILES: O=C1Cc2ccc(-c3cccc(N4CC(N5CCN(C(=O)c6nccs6)CC5)CC4=O)c3)cc2N1] | 488.2 |
| 201 | 1-(2-phenylpyridin-4-yl)-4-(4-(1,3-thiazol-2-ylcarbonyl)piperazin-1-yl)pyrrolidin-2-one | 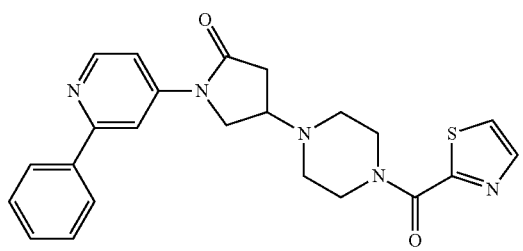 [SMILES: O=C(c1nccs1)N1CCN(C2CC(=O)N(c3ccnc(-c4ccccc4)c3)C2)CC1] | 434.1 |
| 202 | 1-(3-(4-methylpyridin-3-yl)phenyl)-4-(4-(1,3-thiazol-2-ylcarbonyl)piperazin-1-yl)pyrrolidin-2-one | 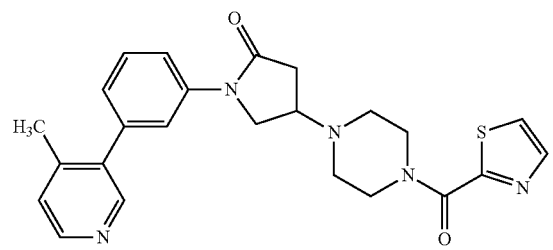 [SMILES: Cc1ccncc1-c1cccc(N2CC(N3CCN(C(=O)c4nccs4)CC3)CC2=O)c1] | 448.2 |
| 203 | 1-(3-(3-methylpyridin-4-yl)phenyl)-4-(4-(1,3-thiazol-2-ylcarbonyl)piperazin-1-yl)pyrrolidin-2-one | 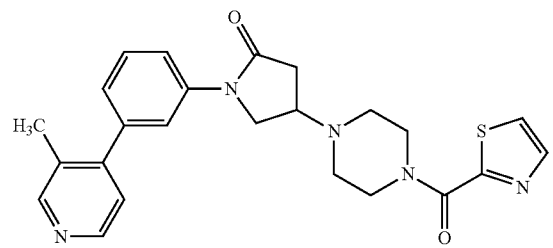 [SMILES: Cc1cnccc1-c1cccc(N2CC(N3CCN(C(=O)c4nccs4)CC3)CC2=O)c1] | 448.2 |
| 204 | 1-(3-(2-methylpyridin-4-yl)phenyl)-4-(4-(1,3-thiazol-2-ylcarbonyl)piperazin-1-yl)pyrrolidin-2-one | 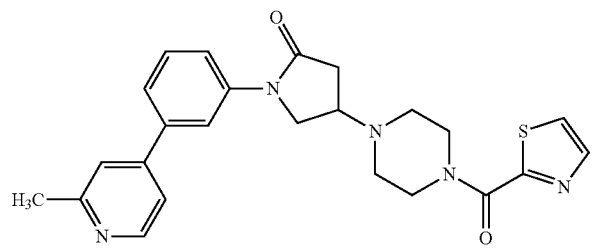 [SMILES: Cc1cc(-c2cccc(N3CC(N4CCN(C(=O)c5nccs5)CC4)CC3=O)c2)ccn1] | 448.1 |

TABLE 1-23-continued

| | | | |
|---|---|---|---|
| 205 | (4R)-1-(1-(4-fluorophenyl)-1H-indazol-5-yl)-4-(4-(1,3-thiazol-2-ylcarbonyl)piperazin-1-yl)pyrrolidin-2-one | 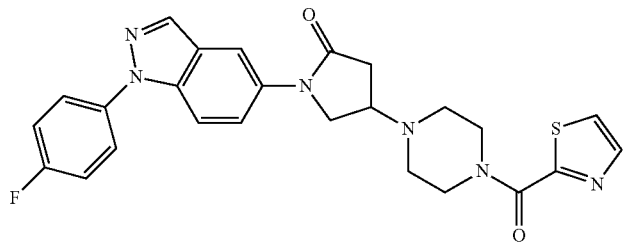 [SMILES: O=C(c1nccs1)N1CCN(C2CC(=O)N(c3ccc4c(cnn4-c4ccc(F)cc4)c3)C2)CC1] | 491.2 |
| 206 | 1-(3-(5-methylpyridin-3-yl)phenyl)-4-(4-(1,3-thiazol-2-ylcarbonyl)piperazin-1-yl)pyrrolidin-2-one | 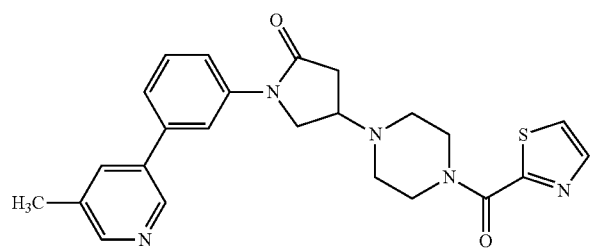 [SMILES: Cc1cncc(-c2cccc(N3CC(N4CCN(C(=O)c5nccs5)CC4)CC3=O)c2)c1] | 448.2 |
| 207 | 1-(4-(2-furyl)phenyl)-4-(4-(1,3-thiazol-2-ylcarbonyl)piperazin-1-yl)pyrrolidin-2-one | 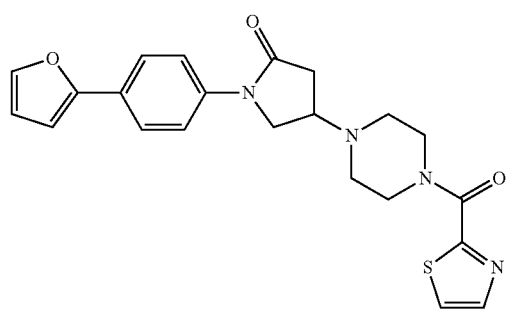 [SMILES: O=C(c1nccs1)N1CCN(C2CC(=O)N(c3ccc(-c4ccco4)cc3)C2)CC1] | 423.1 |

TABLE 1-24

| | | | |
|---|---|---|---|
| 208 | 1-(3'-methylpyridin-4-yl)-4-(4-(1,3-thiazol-2-ylcarbonyl)piperazin-1-yl)pyrrolidin-2-one | 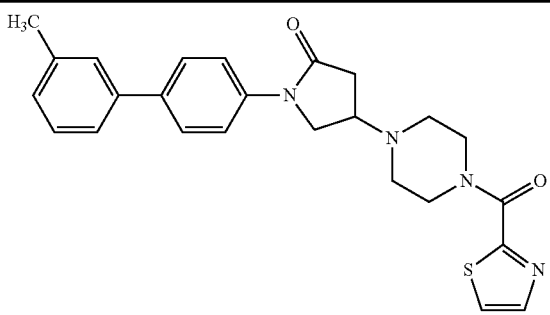 | 447.1 |
| 209 | 4'-(2-oxo-4-(4-(1,3-thiazol-2-ylcarbonyl)piperazin-1-yl)pyrrolidin-1-yl)biphenyl-2-carbonitrile | 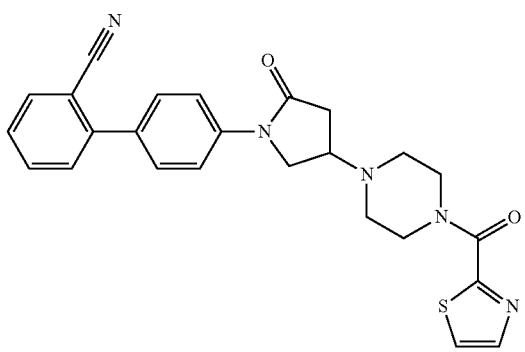 [SMILES: N#Cc1ccccc1-c1ccc(N2CC(N3CCN(C(=O)c4nccs4)CC3)CC2=O)cc1] | 458.2 |

TABLE 1-24-continued

| 210 | 4'-(2-oxo-4-(4-(1,3-thiazol-2-ylcarbonyl)piperazin-1-yl)pyrrolidin-1-yl)biphenyl-4-carbonitrile | 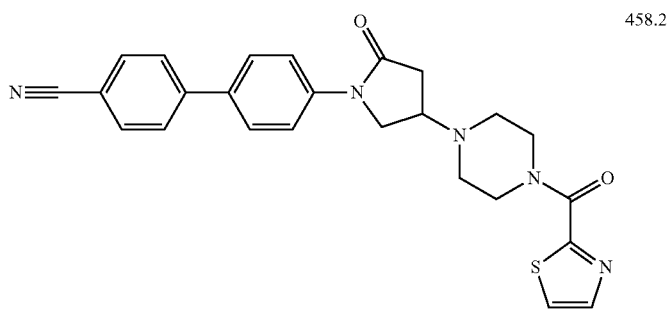 | 458.2 |
| 211 | 1-methyl-5-(4-(2-oxo-4-(4-(1,3-thiazol-2-ylcarbonyl)piperazin-1-yl)pyrrolidin-1-yl)phenyl)pyridin-2(1H)-one | 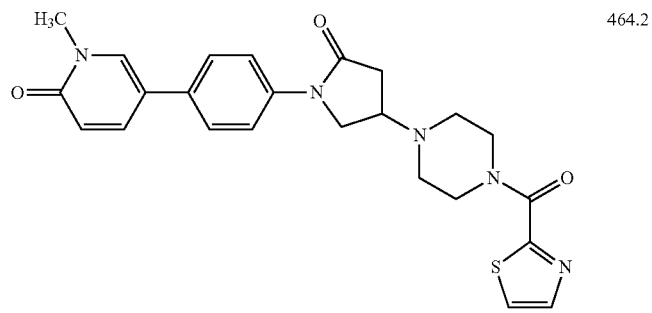 | 464.2 |
| 212 | 1-(4-(pyrazolo[1,5-a]pyridin-3-yl)phenyl)-4-(4-(1,3-thiazol-2-ylcarbonyl)piperazin-1-yl)pyrrolidin-2-one | 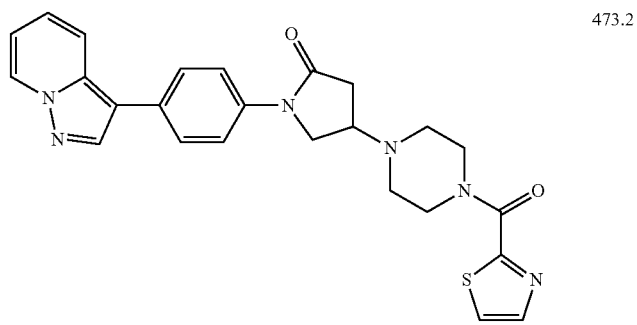 | 473.2 |
| 213 | 1-(biphenyl-4-yl)-4-(4-(1,3-thiazol-2-ylcarbonyl)piperazin-1-yl)pyrrolidin-2-one | 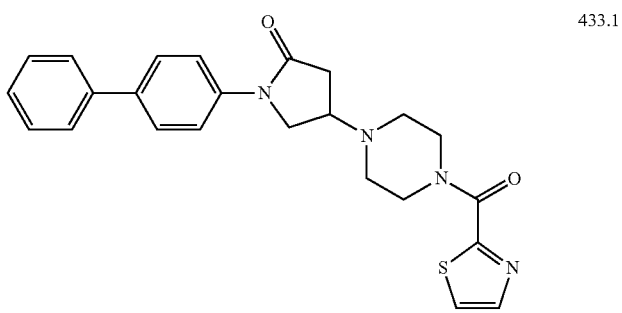 | 433.1 |
| 214 | 2-(4'-(2-oxo-4-(4-(1,3-thiazol-2-ylcarbonyl)piperazin-1-yl)pyrrolidin-1-yl)biphenyl-3-yl)acetamide | 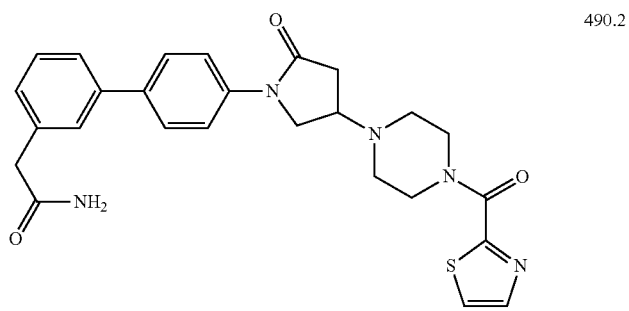 | 490.2 |

TABLE 1-24-continued
| 215 | 4-(4-(1,3-thiazol-2-ylcarbonyl)piperazin-1-yl)-1-(2'-(trifluoromethyl)biphenyl-4-yl)pyrrolidin-2-one | 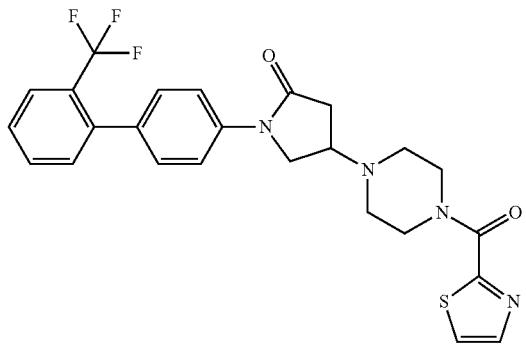 [SMILES: O=C(c1nccs1)N1CCN(C2CC(=O)N(c3ccc(-c4ccccc4C(F)(F)F)cc3)C2)CC1] | 501.2 |
| --- | --- | --- | --- |
| 216 | N-(4'-(2-oxo-4-(4-(1,3-thiazol-2-ylcarbonyl)piperazin-1-yl)pyrrolidin-1-yl)biphenyl-3-yl)methanesulfonamide | 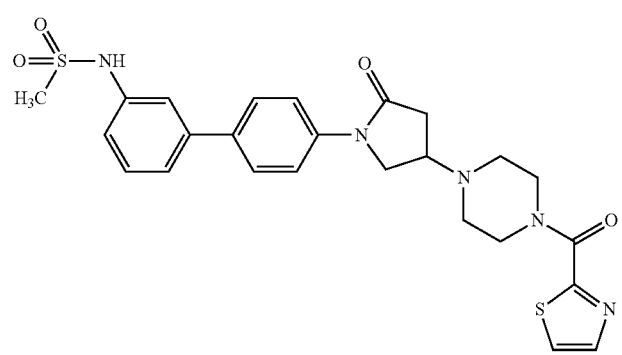 [SMILES: CS(=O)(=O)Nc1cccc(-c2ccc(N3CC(N4CCN(C(=O)c5nccs5)CC4)CC3=O)cc2)c1] | 526.2 |
TABLE 1-25
| 217 | 4-(4-(1,3-thiazol-2-ylcarbonyl)piperazin-1-yl)-1-(4-(3-thienyl)phenyl)pyrrolidin-2-one | 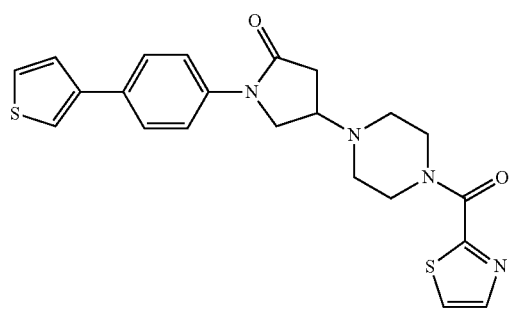 [SMILES: O=C(c1nccs1)N1CCN(C2CC(=O)N(c3ccc(-c4ccsc4)cc3)C2)CC1] | 439.1 |
| --- | --- | --- | --- |
| 218 | 4-(4-(1,3-thiazol-2-ylcarbonyl)piperazin-1-yl)-1-(4-(2-thienyl)phenyl)pyrrolidin-2-one | 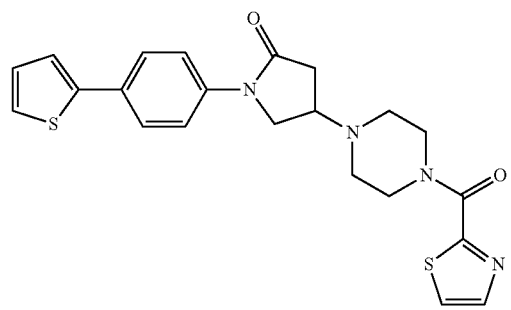 [SMILES: O=C(c1nccs1)N1CCN(C2CC(=O)N(c3ccc(-c4cccs4)cc3)C2)CC1] | 439.1 |

| | | | |
|---|---|---|---|
| 219 | 1-(4'-methylbiphenyl-4-yl)-4-(4-(1,3-thiazol-2-ylcarbonyl)piperazin-1-yl)pyrrolidin-2-one | 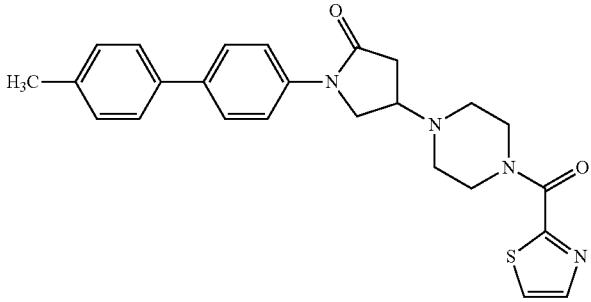 [SMILES: Cc1ccc(-c2ccc(N3CC(N4CCN(C(=O)c5nccs5)CC4)CC3=O)cc2)cc1] | 447.2 |
| 220 | 1-(2'-methylbiphenyl-3-yl)-4-(4-(1,3-thiazol-4-ylcarbonyl)piperazin-1-yl)pyrrolidin-2-one | 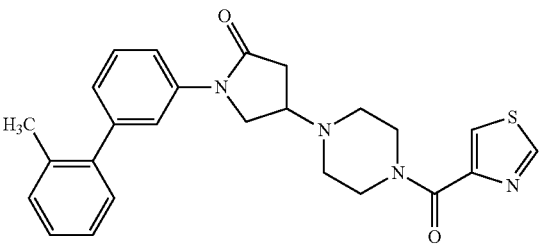 | 447.1 |
| 221 | 1-(2'-methylbiphenyl-3-yl)-4-(4-(1,3-oxazol-2-ylcarbonyl)piperazin-1-yl)pyrrolidin-2-one | 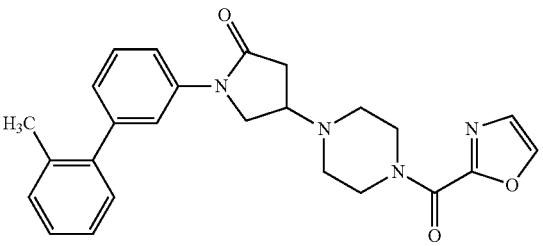 | 431.2 |
| 222 | 7-(3-(2-oxo-4-(4-(1,3-thiazol-2-ylcarbonyl)piperazin-1-yl)pyrrolidin-1-yl)phenyl)-1,3-dihydro-2H-indol-2-one | 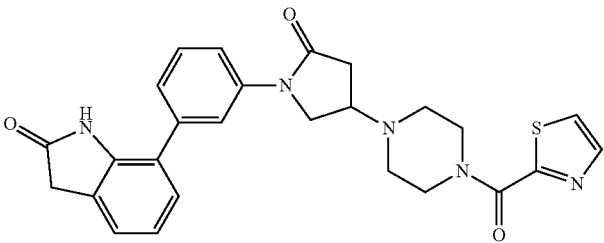 [SMILES: O=C1Cc2cccc(-c3cccc(N4CC(N5CCN(C(=O)c6nccs6)CC5)CC4=O)c3)c2N1] | 488.1 |
| 223 | 1-(3-(2-chloropyridin-3-yl)phenyl)-4-(4-(1,3-thiazol-4-ylcarbonyl)piperazin-1-yl)pyrrolidin-2-one | 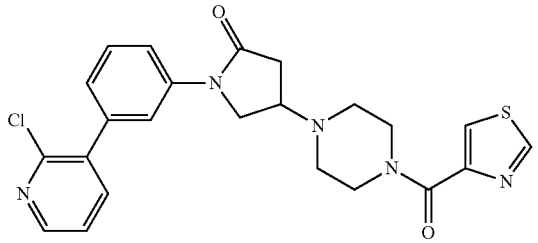 [SMILES: O=C(c1cscn1)N1CCN(C2CC(=O)N(c3cccc(-c4cccnc4Cl)c3)C2)CC1] | 468.1 |
| 224 | 1-(3-(2-chloropyridin-3-yl)phenyl)-4-(4-(1,3-oxazol-2-ylcarbonyl)piperazin-1-yl)pyrrolidin-2-one | 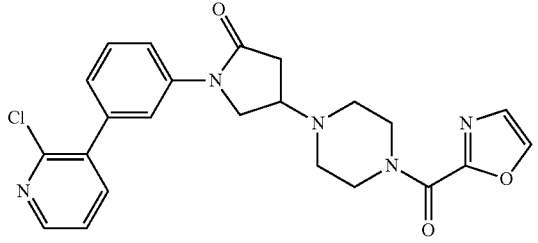 | 452.1 |

TABLE 1-25-continued

| 225 | 1-(2'-chlorobiphenyl-3-yl)-3-methyl-4-(4-(1,3-thiazol-2-ylcarbonyl)piperazin-1-yl)pyrrolidin-2-one | 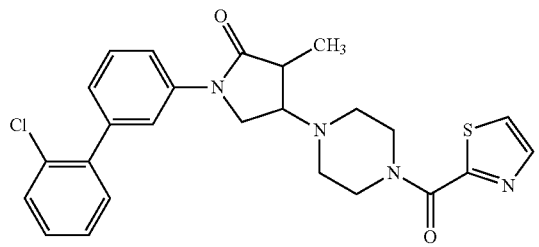 [SMILES: CC1C(=O)N(c2cccc(-c3ccccc3Cl)c2)CC1N1CCN(C(=O)c2nccs2)CC1] | 481.1 |

TABLE 1-26

| 226 | 1-(2'-chlorobiphenyl-3-yl)-3,3-dimethyl-4-(4-(1,3-thiazol-2-ylcarbonyl)piperazin-1-yl)pyrrolidin-2-one | 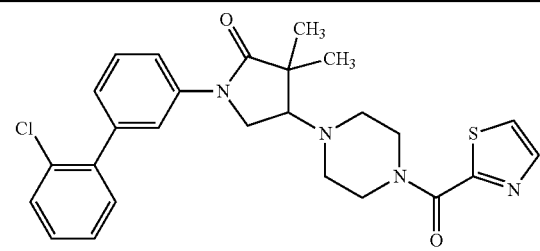 | 495.0 |
| 227 | 3-methyl-1-(3-(2-methylpyridin-3-yl)phenyl)-4-(4-(1,3-thiazol-2-ylcarbonyl)piperazin-1-yl)pyrrolidin-2-one | 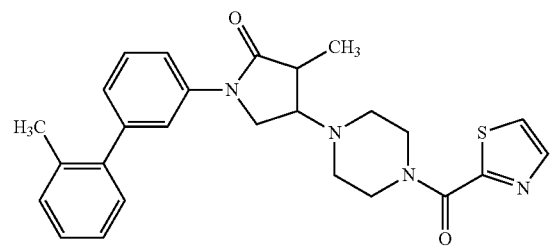 [SMILES: Cc1ccccc1-c1cccc(N2CC(N3CCN(C(=O)c4nccs4)CC3)C(C)C2=O)c1] | 462.1 |
| 228 | 5-methyl-1-(4-phenoxyphenyl)-4-(4-(1,3-thiazol-2-ylcarbonyl)piperazin-1-yl)pyrrolidin-2-one | 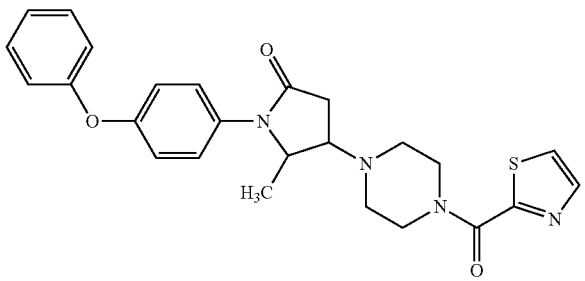 [SMILES: CC1C(N2CCN(C(=O)c3nccs3)CC2)CC(=O)N1c1ccc(Oc2ccccc2)cc1] | 463.0 |
| 229 | 1-methyl-7-(3-(2-oxo-4-(4-(1,3-thiazol-2-ylcarbonyl)piperazin-1-yl)pyrrolidin-1-yl)phenyl)-1,3-dihydro-2H-indol-2-one | 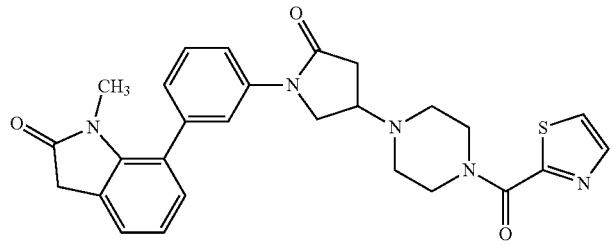 | 502.1 |
| 230 | 1-methyl-4-(3-(2-oxo-4-(4-(1,3-thiazol-2-ylcarbonyl)piperazin-1-yl)pyrrolidin-1-yl)phenyl)-1,3-dihydro-2H-indol-2-one | 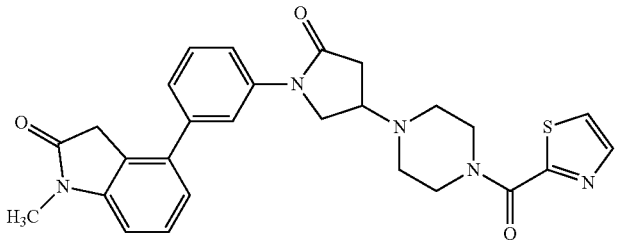 [SMILES: CN1C(=O)Cc2c(-c3cccc(N4CC(N5CCN(C(=O)c6nccs6)CC5)CC4=O)c3)cccc21] | 502.1 |

TABLE 1-26-continued

| 231 | 3,3-dimethyl-4-(3-(2-oxo-4-(4-(1,3-thiazol-2-ylcarbonyl)piperazin-1-yl)pyrrolidin-1-yl)phenyl)-1,3-dihydro-2H-indol-2-one | 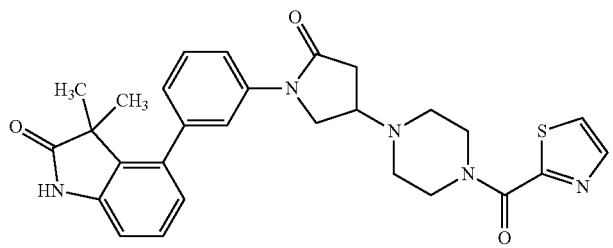 [SMILES: CC1(C)C(=O)Nc2cccc(-c3cccc(N4CC(N5CCN(C(=O)c6nccs6)CC5)CC4=O)c3)c21] | 516.1 |
|---|---|---|---|
| 232 | 1-(2'-chlorobiphenyl-3-yl)-4-(4-(1,3-thiazol-4-ylcarbonyl)piperazin-1-yl)pyrrolidin-2-one(optical isomer) | 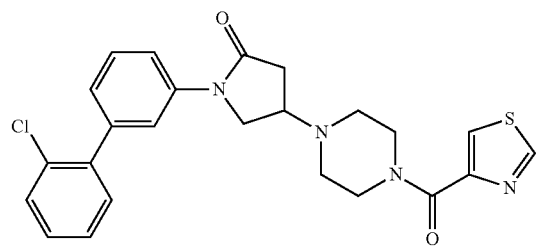 | 467.0 |
| 233 | 1-(2'-chlorobiphenyl-3-yl)-4-(4-(1,3-thiazol-4-ylcarbonyl)piperazin-1-yl)pyrrolidin-2-one(optical isomer) | 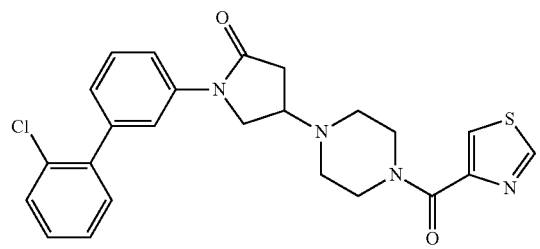 | 467.0 |
| 234 | (4R)-4-(4-(1,3-thiazol-2-ylcarbonyl)piperazin-1-yl)-1-(1-(6-(trifluoromethyl)pyridazin-3-yl)-1H-indol-5-yl)pyrrolidin-2-one | 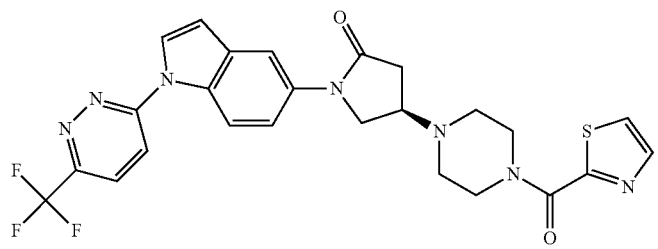 [SMILES: O=C(c1nccs1)N1CCN([C@@H]2CC(=O)N(c3ccc4c(ccn4-c4ccc(C(F)(F)F)nn4)c3)C2)CC1] | 542.1 |

TABLE 1-27

| 235 | 1-(1-(4-methylphenyl)-1H-indol-5-yl)-4-(4-(1,3-thiazol-2-ylcarbonyl)piperazin-1-yl)pyrrolidin-2-one | 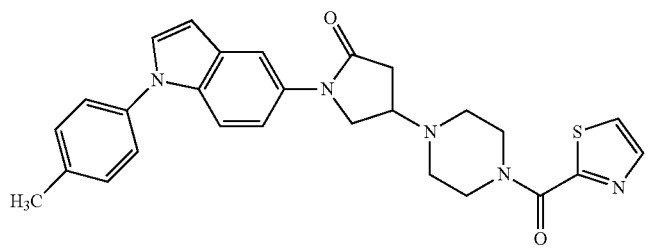 [SMILES: Cc1ccc(-n2ccc3cc(N4CC(N5CCN(C(=O)c6nccs6)CC5)CC4=O)ccc32)cc1] | 486.1 |
|---|---|---|---|
| 236 | 3-methyl-1-(4-phenoxyphenyl)-4-(4-(1,3-thiazol-2-ylcarbonyl)piperazin-1-yl)pyrrolidin-2-one | 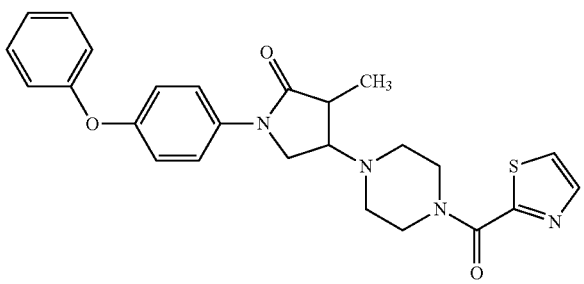 | 463.0 |

TABLE 1-27-continued

| | | | |
|---|---|---|---|
| 237 | 3,3-dimethyl-1-(4-phenoxyphenyl)-4-(4-(1,3-thiazol-2-ylcarbonyl)piperazin-1-yl)pyrrolidin-2-one | 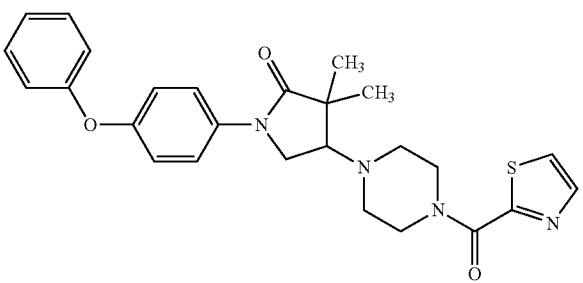 [SMILES: CC1(C)C(=O)N(c2ccc(Oc3ccccc3)cc2)CC1N1CCN(C(=O)c2nccs2)CC1] | 477.1 |
| 238 | 1-(1-(6-methylpyridin-2-yl)-1H-indol-5-yl)-4-(4-(1,3-thiazol-2-ylcarbonyl)piperazin-1-yl)pyrrolidin-2-one | 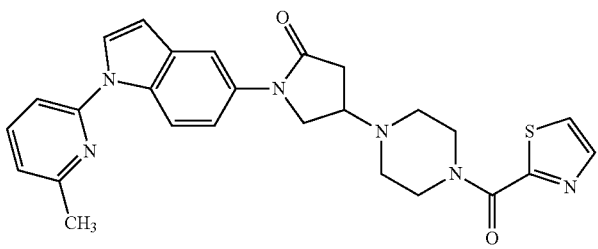 | 487.1 |
| 239 | 1-(1-(5-methylpyridin-2-yl)-1H-indol-5-yl)-4-(4-(1,3-thiazol-2-ylcarbonyl)piperazin-1-yl)pyrrolidin-2-one | 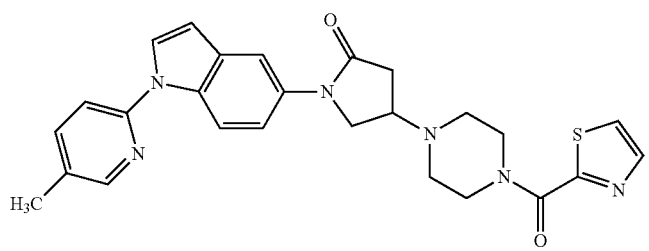 | 487.0 |
| 240 | 1-(5-methylbiphenyl-3-yl)-4-(4-(1,3-thiazol-2-ylcarbonyl)piperazin-1-yl)pyrrolidin-2-one | 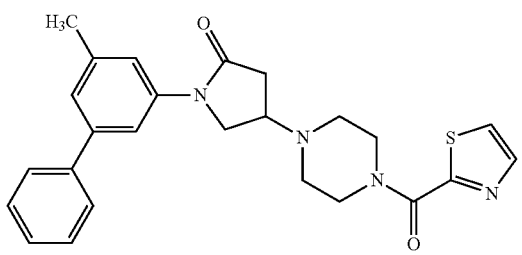 [SMILES: Cc1cc(-c2ccccc2)cc(N2CC(N3CCN(C(=O)c4nccs4)CC3)CC2=O)c1] | 447.0 |
| 241 | 1-(4-fluorobiphenyl-3-yl)-4-(4-(1,3-thiazol-2-ylcarbonyl)piperazin-1-yl)pyrrolidin-2-one | 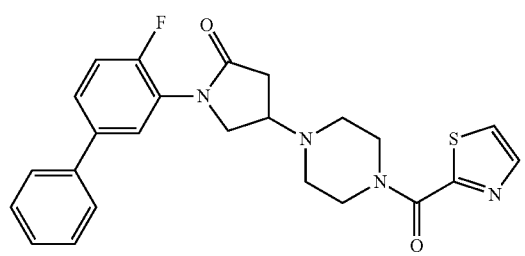 [SMILES: O=C(c1nccs1)N1CCN(C2CC(=O)N(c3cc(-c4ccccc4)ccc3F)C2)CC1] | 451.0 |
| 242 | 1-(5-fluorobiphenyl-3-yl)-4-(4-(1,3-thiazol-2-ylcarbonyl)piperazin-1-yl)pyrrolidin-2-one | 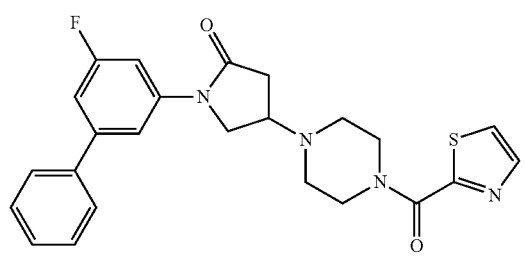 [SMILES: O=C(c1nccs1)N1CCN(C2CC(=O)N(c3cc(F)cc(-c4ccccc4)c3)C2)CC1] | 451.0 |

TABLE 1-27-continued

| 243 | 1-(6-fluorobiphenyl-3-yl)-4-(4-(1,3-thiazol-2-ylcarbonyl)piperazin-1-yl)pyrrolidin-2-one | 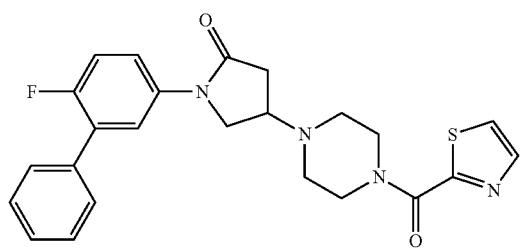 [SMILES: O=C(c1nccs1)N1CCN(C2CC(=O)N(c3ccc(F)c(-c4ccccc4)c3)C2)CC1] | 451.0 |

TABLE 1-28

| 244 | 1-(2-fluorobiphenyl-3-yl)-4-(4-(1,3-thiazol-2-ylcarbonyl)piperazin-1-yl)pyrrolidin-2-one | 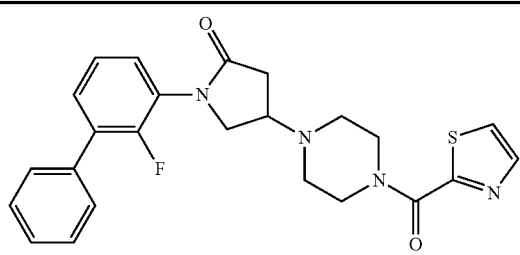 | 451.0 |
| 245 | (4R)-4-(4-(1,3-thiazol-2-ylcarbonyl)piperazin-1-yl)-1-(1-(5-(trifluoromethyl)pyrazin-2-yl)-1H-indol-5-yl)pyrrolidin-2-one | 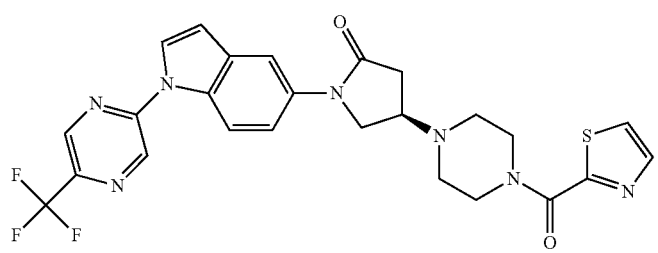 [SMILES: O=C(c1nccs1)N1CCN([C@@H]2CC(=O)N(c3ccc4c(ccn4-c4cnc(C(F)(F)F)cn4)c3)C2)CC1] | 542.1 |
| 246 | (4R)-4-(4-(1,3-thiazol-2-ylcarbonyl)piperazin-1-yl)-1-(1-(2-(trifluoromethyl)pyridin-4-yl)-1H-indol-5-yl)pyrrolidin-2-one | 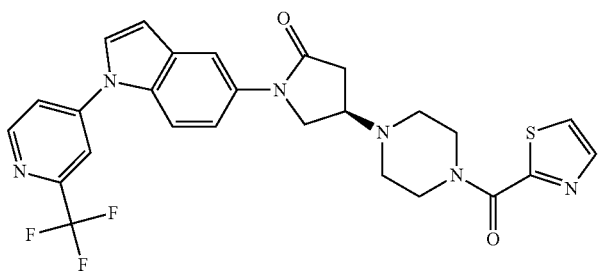 [SMILES: O=C(c1nccs1)N1CCN([C@@H]2CC(=O)N(c3ccc4c(ccn4-c4ccnc(C(F)(F)F)c4)c3)C2)CC1] | 541.1 |
| 247 | 1-(4-methylbiphenyl-3-yl)-4-(4-(1,3-thiazol-2-ylcarbonyl)piperazin-1-yl)pyrrolidin-2-one | 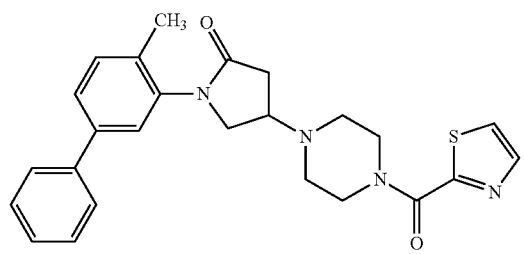 [SMILES: Cc1ccc(-c2ccccc2)cc1N1CC(N2CCN(C(=O)c3nccs3)CC2)CC1=O] | 447.0 |
| 248 | 1-(6-methylbiphenyl-3-yl)-4-(4-(1,3-thiazol-2-ylcarbonyl)piperazin-1-yl)pyrrolidin-2-one | 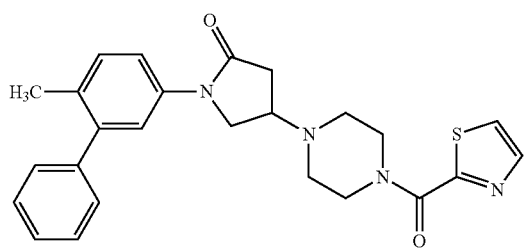 | 447.0 |

TABLE 1-28-continued

| | | | |
|---|---|---|---|
| 249 | 1-(2-methylbiphenyl-3-yl)-4-(4-(1,3-thiazol-2-ylcarbonyl)piperazin-1-yl)pyrrolidin-2-one | 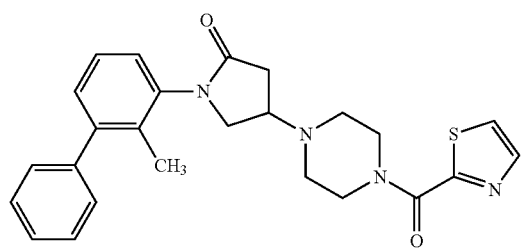 | 447.0 |
| 250 | 1-(1-phenyl-1H-indol-5-yl)-4-(4-(1,3-thiazol-2-ylcarbonyl)piperazin-1-yl)pyrrolidin-2-one | 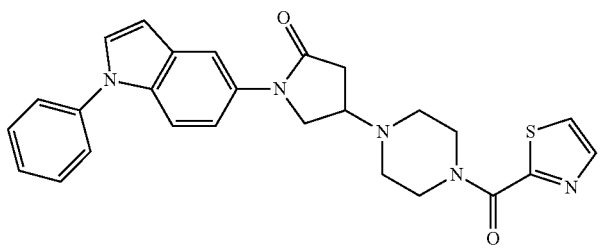 [SMILES: O=C(c1nccs1)N1CCN(C2CC(=O)N(c3ccc4c(ccn4-c4ccccc4)c3)C2)CC1] | 472.0 |
| 251 | 1-(1-(3-methylphenyl)-1H-indol-5-yl)-4-(4-(1,3-thiazol-2-ylcarbonyl)piperazin-1-yl)pyrrolidin-2-one | 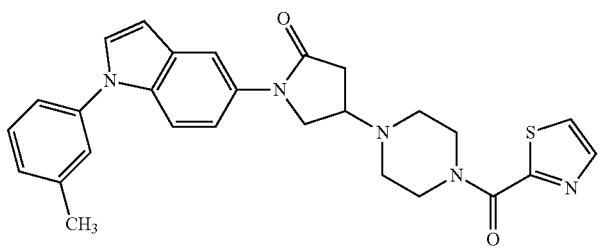 [SMILES: Cc1cccc(-n2ccc3cc(N4CC(N5CCN(C(=O)c6nccs6)CC5)CC4=O)ccc32)c1] | 486.1 |
| 252 | 1-(1-(4-methylpyridin-2-yl)-1H-indol-5-yl)-4-(4-(1,3-thiazol-2-ylcarbonyl)piperazin-1-yl)pyrrolidin-2-one | 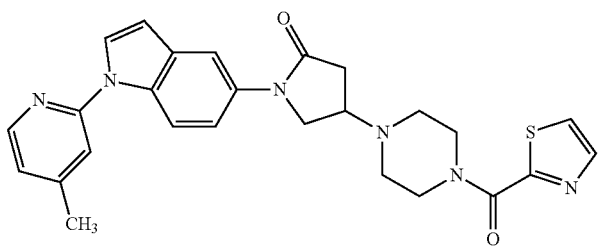 [SMILES: Cc1ccnc(-n2ccc3cc(N4CC(N5CCN(C(=O)c6nccs6)CC5)CC4=O)ccc32)c1] | 487.0 |

TABLE 1-29

| | | | |
|---|---|---|---|
| 253 | 1-(1-(2-methylphenyl)-1H-indol-5-yl)-4-(4-(1,3-thiazol-2-ylcarbonyl)piperazin-1-yl)pyrrolidin-2-one | 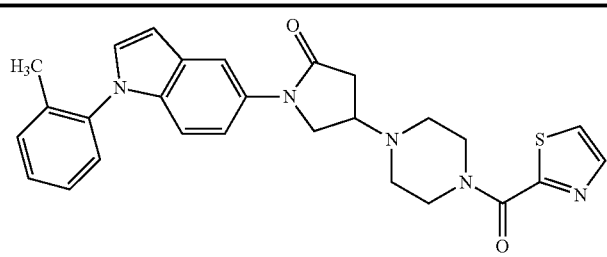 | 486.1 |
| 254 | 1-(3-iodophenyl)-4-(4-(pyrimidin-2-yl)piperazin-1-yl)pyrrolidin-2-one | 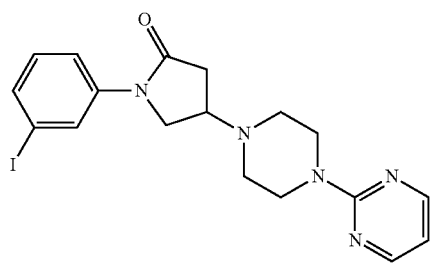 [SMILES: O=C1CC(N2CCN(c3ncccn3)CC2)CN1c1cccc(I)c1] | 449.8 |

TABLE 1-29-continued

| 255 | 1-(1-(2-methylpyridin-4-yl)-1H-indol-5-yl)-4-(4-(1,3-thiazol-2-ylcarbonyl)piperazin-1-yl)pyrrolidin-2-one | | 487.0 |
|---|---|---|---|
| 256 | 1-(3-(2-methylpyridin-3-yl)phenyl)-4-(4-(pyrimidin-2-yl)piperazin-1-yl)pyrrolidin-2-one | | 415.2 |
| 257 | (4R)-4-(4-(1,3-thiazol-2-ylcarbonyl)piperazin-1-yl)-1-(1-(5-(trifluoromethyl)pyrimidin-2-yl)-1H-indol-5-yl)pyrrolidin-2-one | | HCl 542.1 |
| 258 | 1-(3-(2,4-dimethyl-1,3-thiazol-5-yl)phenyl)-4-(4-(1,3-thiazol-2-ylcarbonyl)piperazin-1-yl)pyrrolidin-2-one(optical isomer) | | 468.0 |
| 259 | 3,3-difluoro-1-(4-phenoxyphenyl)-4-(4-(1,3-thiazol-2-ylcarbonyl)piperazin-1-yl)pyrrolidin-2-one | | 385.1 |
| 260 | 3-hydroxy-1-(4-phenoxyphenyl)-4-(4-(1,3-thiazol-2-ylcarbonyl)piperazin-1-yl)pyrrolidin-2-one | | 465.0 |

TABLE 1-29-continued

| 261 | 3-fluoro-1-(4-phenoxyphenyl)-4-(4-(1,3-thiazol-2-ylcarbonyl)piperazin-1-yl)pyrrolidin-2-one | | 467.0 |
|---|---|---|---|

TABLE 1-30

| 262 | 1-(3,4'-difluorobiphenyl-4-yl)-4-(4-(1,3-thiazol-2-ylcarbonyl)piperazin-1-yl)pyrrolidin-2-one | | 469.0 |
|---|---|---|---|
| 263 | 1-(2,4'-difluorobiphenyl-4-yl)-4-(4-(1,3-thiazol-2-ylcarbonyl)piperazin-1-yl)pyrrolidin-2-one | | 469.1 |
| 264 | 1-(4-(2-methylpyridin-4-yl)phenyl)-4-(4-(1,3-thiazol-2-ylcarbonyl)piperazin-1-yl)pyrrolidin-2-one | | 448.0 |
| 265 | 1-(4-(6-methylpyridin-3-yl)phenyl)-4-(4-(1,3-thiazol-2-ylcarbonyl)piperazin-1-yl)pyrrolidin-2-one | | 448.0 |
| 266 | 1-(3-(2-chloropyridin-3-yl)phenyl)-4-(4-(1,3-thiazol-2-ylcarbonyl)piperazin-1-yl)pyrrolidin-2-one(optical isomer) | | 468.0 |

TABLE 1-30-continued

| | | | |
|---|---|---|---|
| 267 | 6-(3-(2-oxo-4-(4-(1,3-thiazol-2-ylcarbonyl)piperazin-1-yl)pyrrolidin-1-yl)phenyl)-1,3-dihydro-2H-indol-2-one(optical isomer) | 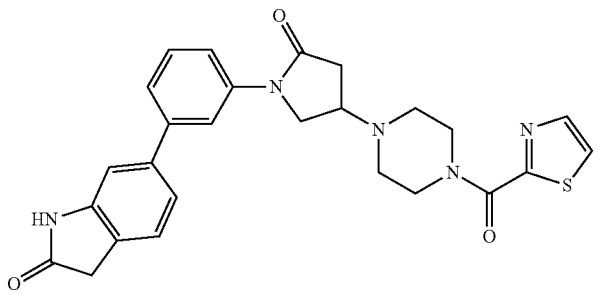 [SMILES: O=C1Cc2ccc(-c3cccc(N4CC(N5CCN(C(=O)c6nccs6)CC5)CC4=O)c3)cc2N1] | 488.0 |
| 268 | 1-(2'-methylbiphenyl-3-yl)-4-(4-(pyrimidin-2-yl)piperazin-1-yl)pyrrolidin-2-one | 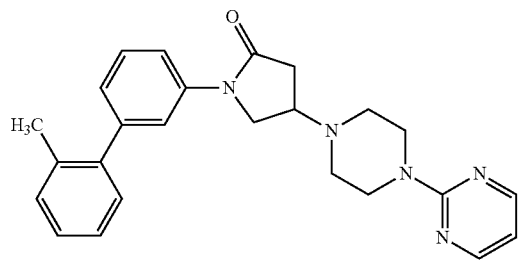 [SMILES: Cc1ccccc1-c1cccc(N2CC(N3CCN(c4ncccn4)CC3)CC2=O)c1] | 414.0 |
| 269 | 1-(2'-chlorobiphenyl-3-yl)-4-(4-(pyrimidin-2-yl)piperazin-1-yl)pyrrolidin-2-one | 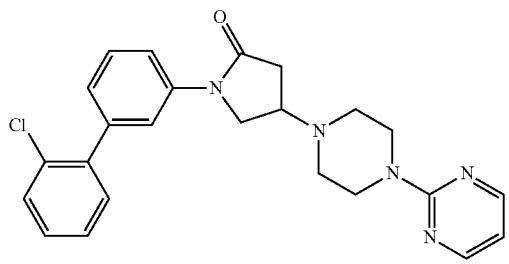 [SMILES: O=C1CC(N2CCN(c3ncccn3)CC2)CN1c1cccc(-c2ccccc2Cl)c1] | 434.0 |
| 270 | 1-(1-(4-fluorophenyl)-1H-indol-5-yl)-4-(4-(1,3-thiazol-4-ylcarbonyl)piperazin-1-yl)pyrrolidin-2-one | 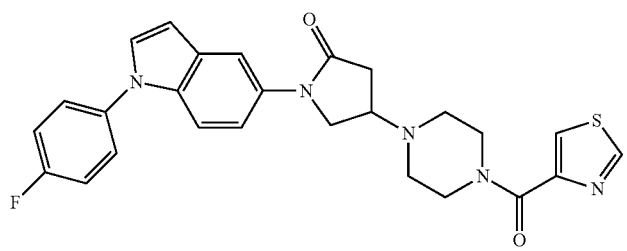 [SMILES: O=C(c1cscn1)N1CCN(C2CC(=O)N(c3ccc4c(ccn4-c4ccc(F)cc4)c3)C2)CC1] | 490.0 |

TABLE 1-31

| | | | |
|---|---|---|---|
| 271 | (4R)-4-(4-(1,3-thiazol-2-ylcarbonyl)piperazin-1-yl)-1-(1-(5-(trifluoromethyl)pyrimidin-2-yl)-2,3-dihydro-1H-indol-5-yl)pyrrolidin-2-one | 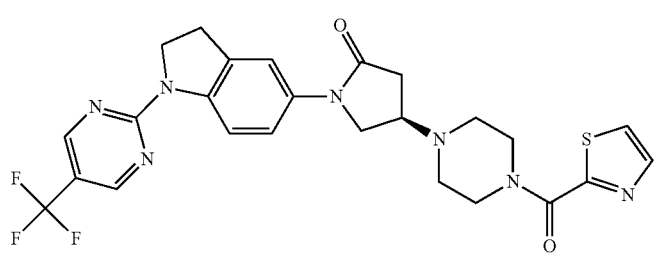 [SMILES: O=C(c1nccs1)N1CCN([C@@H]2CC(=O)N(c3ccc4c(c3)CCN4c3ncc(C(F)(F)F)cn3)C2)CC1] | 544.0 |

TABLE 1-31-continued

| | | | | |
|---|---|---|---|---|
| 272 | (4R)-4-(4-(1,3-thiazol-2-ylcarbonyl)piperazin-1-yl)-1-(1-(5-(trifluoromethyl)pyrimidin-2-yl)-2,3-dihydro-1H-indol-5-yl)pyrrolidin-2-one | | HCl | 544.0 |
| 273 | 1-(3-(4,6-dimethylpyrimidin-5-yl)phenyl)-4-(4-(1,3-thiazol-2-ylcarbonyl)piperazin-1-yl)pyrrolidin-2-one | | | 463.1 |
| 274 | 1-(4-(6-methylpyridin-2-yl)phenyl)-4-(4-(1,3-thiazol-2-ylcarbonyl)piperazin-1-yl)pyrrolidin-2-one | | | 448.0 |
| 275 | 1-(2'-chloro-4'-fluorobiphenyl-3-yl)-4-(4-(1,3-thiazol-2-ylcarbonyl)piperazin-1-yl)pyrrolidin-2-one | | | 485.0 |
| 276 | 1-(2'-chloro-4',6-difluorobiphenyl-3-yl)-4-(4-(1,3-thiazol-2-ylcarbonyl)piperazin-1-yl)pyrrolidin-2-one | | | 503.0 |
| 277 | 1-(2'-chloro-6-fluorobiphenyl-3-yl)-4-(4-(1,3-thiazol-2-ylcarbonyl)piperazin-1-yl)pyrrolidin-2-one | | | 485.0 |

TABLE 1-31-continued

| | | | |
|---|---|---|---|
| 278 | 1-(3-fluoro-5-(2-methylpyridin-3-yl)phenyl)-4-(4-(1,3-thiazol-2-ylcarbonyl)piperazin-1-yl)pyrrolidin-2-one | 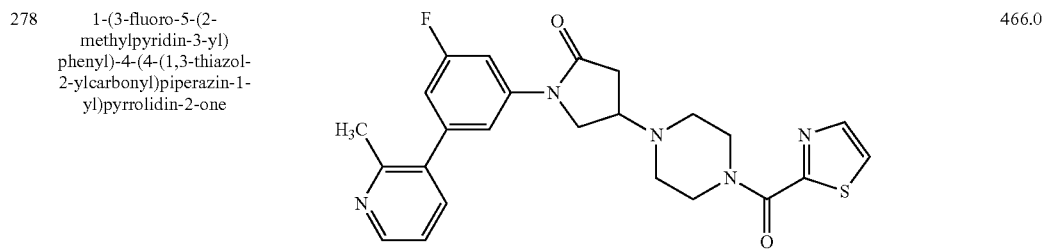 | 466.0 |
| 279 | 1-(1-(3,5-dimethylphenyl)-1H-indol-5-yl)-4-(4-(1,3-thiazol-2-ylcarbonyl)piperazin-1-yl)pyrrolidin-2-one | 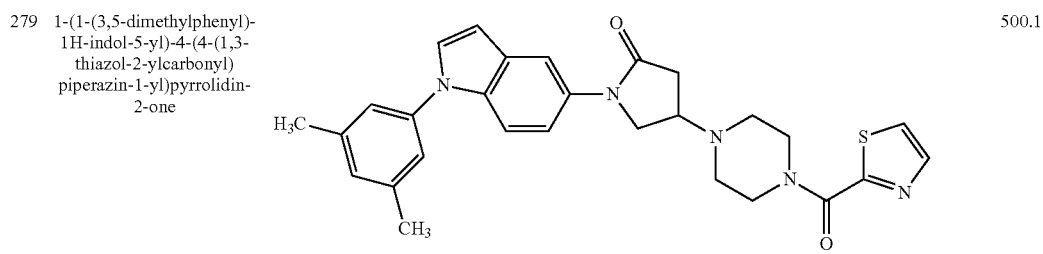 | 500.1 |

TABLE 1-32

| | | | |
|---|---|---|---|
| 280 | 4-(4-(1,3-thiazol-2-ylcarbonyl)piperazin-1-yl)-1-(1-(3-(trifluoromethyl)phenyl)-1H-indol-5-yl)pyrrolidin-2-one | 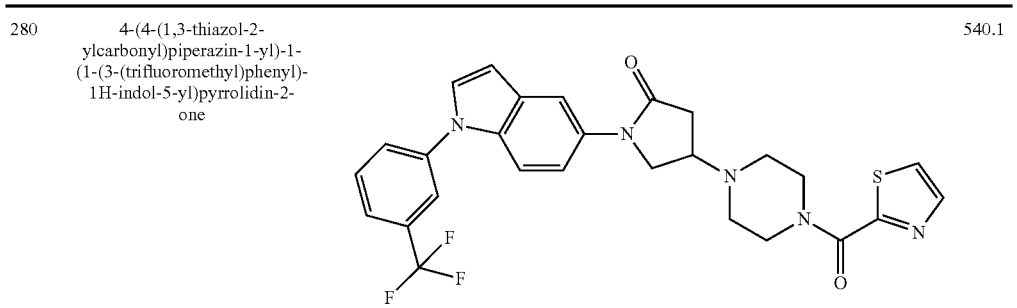 | 540.1 |
| 281 | 4-(4-(1,3-thiazol-2-ylcarbonyl)piperazin-1-yl)-1-(1-(4-(trifluoromethyl)pyrimidin-2-yl)-1H-indol-5-yl)pyrrolidin-2-one | 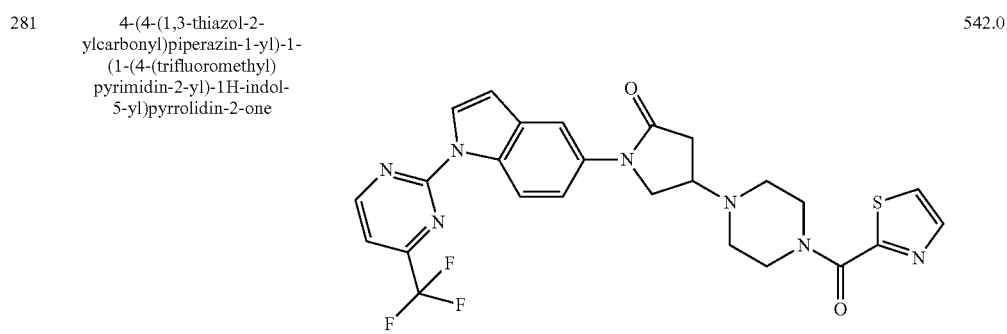 | 542.0 |
| 282 | 4-(4-(1,3-thiazol-2-ylcarbonyl)piperazin-1-yl)-1-(2',4',6'-trifluorobiphenyl-3-yl)pyrrolidin-2-one | 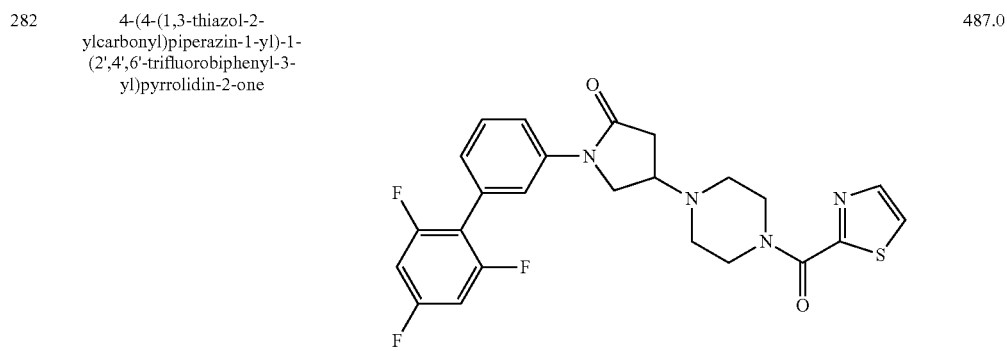 | 487.0 |

TABLE 1-32-continued

| 283 | 1-(2',4'-dichlorobiphenyl-3-yl)-4-(4-(1,3-thiazol-2-ylcarbonyl)piperazin-1-yl)pyrrolidin-2-one | 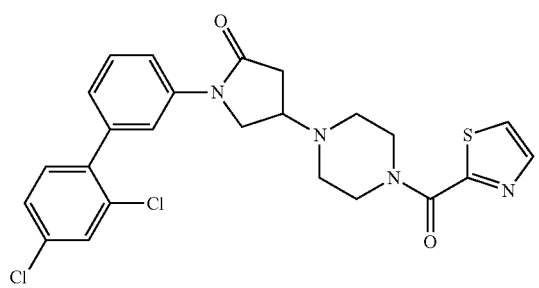 [SMILES: O=C(c1nccs1)N1CCN(C2CC(=O)N(c3cccc(-c4ccc(Cl)cc4Cl)c3)C2)CC1] | 501.0 |
| 284 | 1-(3'-chloro-4'-fluorobiphenyl-3-yl)-4-(4-(1,3-thiazol-2-ylcarbonyl)piperazin-1-yl)pyrrolidin-2-one | 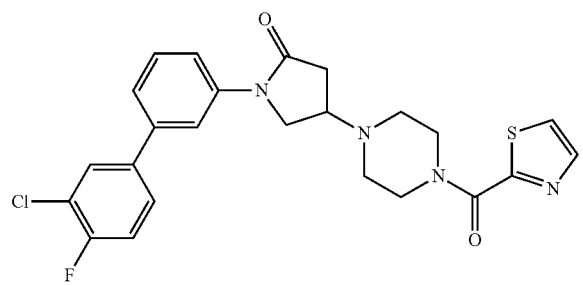 [SMILES: O=C(c1nccs1)N1CCN(C2CC(=O)N(c3cccc(-c4ccc(F)c(Cl)c4)c3)C2)CC1] | 485.0 |
| 285 | 1-(1,1':2',1''-terphenyl-3-yl)-4-(4-(1,3-thiazol-2-ylcarbonyl)piperazin-1-yl)pyrrolidin-2-one | 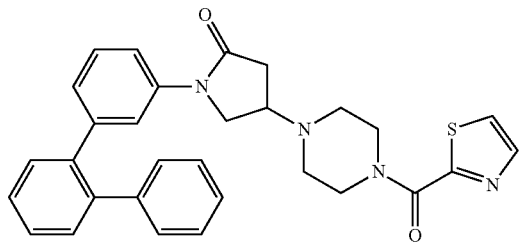 [SMILES: O=C(c1nccs1)N1CCN(C2CC(=O)N(c3cccc(-c4ccccc4-c4ccccc4)c3)C2)CC1] | 509.2 |
| 286 | 3'-(2-oxo-4-(4-(1,3-thiazol-2-ylcarbonyl)piperazin-1-yl)pyrrolidin-1-yl)biphenyl-4-carboxylic acid | 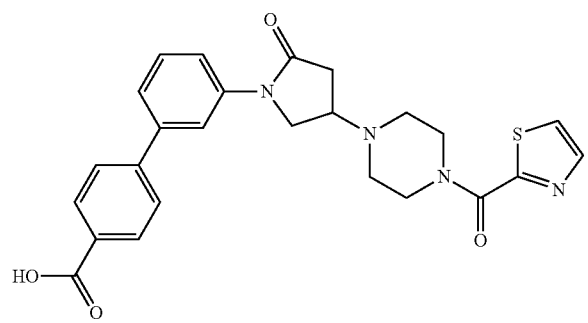 [SMILES: O=C(O)c1ccc(-c2cccc(N3CC(N4CCN(C(=O)c5nccs5)CC4)CC3=O)c2)cc1] | 477.1 |
| 287 | 4-(4-(1,3-thiazol-2-ylcarbonyl)piperazin-1-yl)-1-(3'-(trifluoromethyl)biphenyl-3-yl)pyrrolidin-2-one | 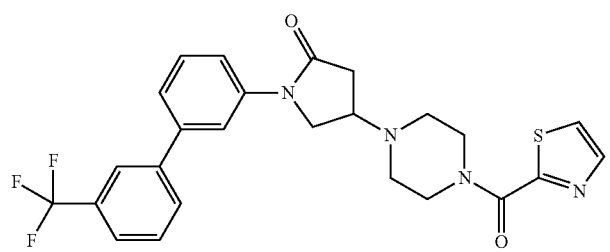 [SMILES: O=C(c1nccs1)N1CCN(C2CC(=O)N(c3cccc(-c4cccc(C(F)(F)F)c4)c3)C2)CC1] | 501.1 |

TABLE 1-32-continued

| 288 | 4-(4-(1,3-thiazol-2-ylcarbonyl)piperazin-1-yl)-1-(4'-(trifluoromethyl)biphenyl-3-yl)pyrrolidin-2-one | 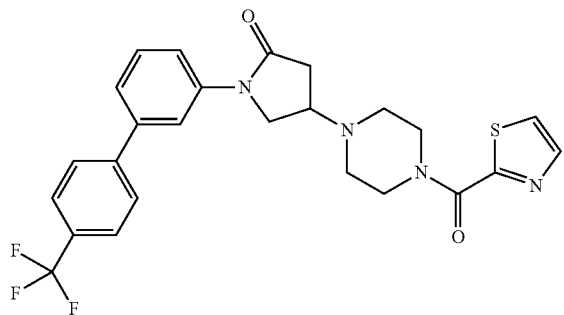 [SMILES: O=C(c1nccs1)N1CCN(C2CC(=O)N(c3cccc(-c4ccc(C(F)(F)F)cc4)c3)C2)CC1] | 501.1 |

TABLE 1-33

| 289 | 1-(2'-ethoxybiphenyl-3-yl)-4-(4-(1,3-thiazol-2-ylcarbonyl)piperazin-1-yl)pyrrolidin-2-one | 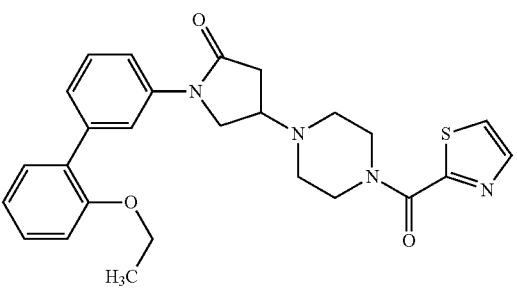 [SMILES: CCOc1ccccc1-c1cccc(N2CC(N3CCN(C(=O)c4nccs4)CC3)CC2=O)c1] | 477.1 |
| 290 | 1-(3',4'-difluorophenyl-3-yl)-4-(4-(1,3-thiazol-2-ylcarbonyl)piperazin-1-yl)pyrrolidin-2-one | 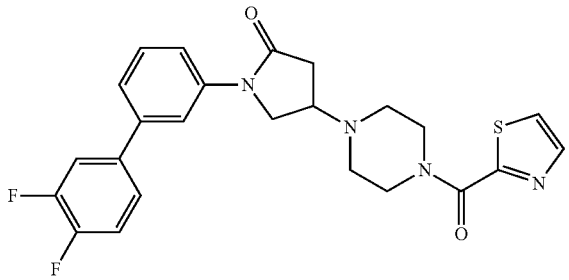 [SMILES: O=C(c1nccs1)N1CCN(C2CC(=O)N(c3cccc(-c4ccc(F)c(F)c4)c3)C2)CC1] | 469.1 |
| 291 | 1-(2'-phenoxybiphenyl-3-yl)-4-(4-(1,3-thiazol-2-ylcarbonyl)piperazin-1-yl)pyrrolidin-2-one | 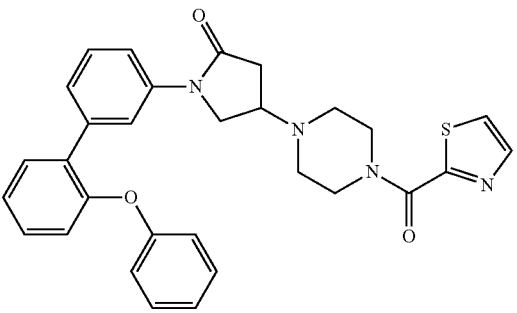 [SMILES: O=C(c1nccs1)N1CCN(C2CC(=O)N(c3cccc(-c4ccccc4Oc4ccccc4)c3)C2)CC1] | 525.2 |
| 292 | 4-(4-(1,3-thiazol-2-ylcarbonyl)piperazin-1-yl)-1-(4'-(trifluoromethoxy)biphenyl-3-yl)pyrrolidin-2-one | 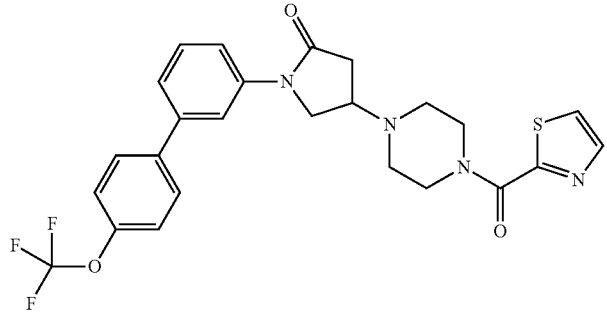 [SMILES: O=C(c1nccs1)N1CCN(C2CC(=O)N(c3cccc(-c4ccc(OC(F)(F)F)cc4)c3)C2)CC1] | 517.1 |

TABLE 1-33-continued

| | | | |
|---|---|---|---|
| 293 | 1-(2',3'-dichlorophenyl-3-yl)-4-(4-(1,3-thiazol-2-ylcarbonyl)piperazin-1-yl)pyrrolidin-2-one | 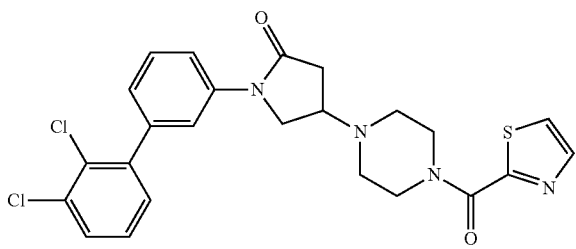 [SMILES: O=C(c1nccs1)N1CCN(C2CC(=O)N(c3cccc(-c4cccc(Cl)c4Cl)c3)C2)CC1] | 501.0 |
| 294 | 1-(3-(1-benzothiophen-3-yl)phenyl)-4-(4-(1,3-thiazol-2-ylcarbonyl)piperazin-1-yl)pyrrolidin-2-one | 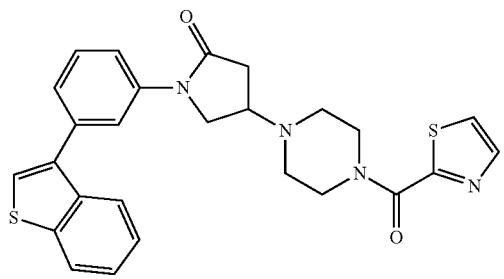 [SMILES: O=C(c1nccs1)N1CCN(C2CC(=O)N(c3cccc(-c4csc5ccccc45)c3)C2)CC1] | 489.0 |
| 295 | 3'-(2-oxo-4-(4-(1,3-thiazol-2-ylcarbonyl)piperazin-1-yl)pyrrolidin-1-yl)biphenyl-4-carbonitrile | 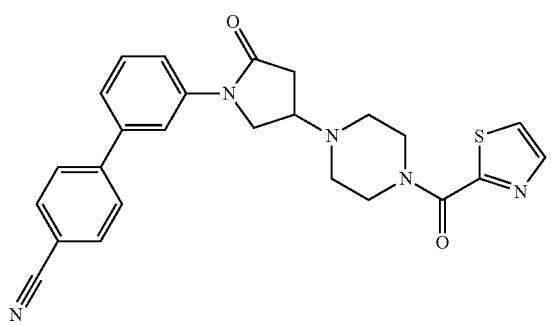 [SMILES: N#Cc1ccc(-c2cccc(N3CC(N4CCN(C(=O)c5nccs5)CC4)CC3=O)c2)cc1] | 458.0 |
| 296 | 1-(2',4'-difluorobiphenyl-3-yl)-4-(4-(1,3-thiazol-2-ylcarbonyl)piperazin-1-yl)pyrrolidin-2-one | 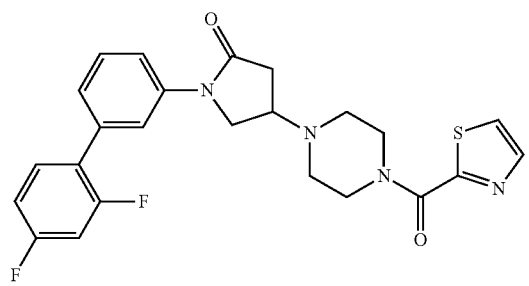 [SMILES: O=C(c1nccs1)N1CCN(C2CC(=O)N(c3cccc(-c4ccc(F)cc4F)c3)C2)CC1] | 469.1 |
| 297 | 4-(4-(1,3-thiazol-2-ylcarbonyl)piperazin-1-yl)-1-(3'-(trifluoromethoxy)biphenyl-3-yl)pyrrolidin-2-one | 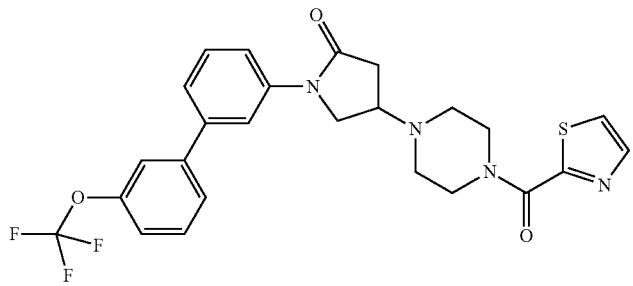 [SMILES: O=C(c1nccs1)N1CCN(C2CC(=O)N(c3cccc(-c4cccc(OC(F)(F)F)c4)c3)C2)CC1] | 517.1 |

TABLE 1-34

| | | | |
|---|---|---|---|
| 298 | 4-(4-(1,3-thiazol-2-ylcarbonyl)piperazin-1-yl)-1-(2'-(trifluoromethoxy)biphenyl-3-yl)pyrrolidin-2-one | | 517.1 |
| 299 | 1-(2',3'-difluorobiphenyl-3-yl)-4-(4-(1,3-thiazol-2-ylcarbonyl)piperazin-1-yl)pyrrolidin-2-one | | 469.1 |
| 300 | 1-(2',5'-dichlorobiphenyl-3-yl)-4-(4-(1,3-thiazol-2-ylcarbonyl)piperazin-1-yl)pyrrolidin-2-one | | 501.1 |
| 301 | 1-(4'-fluoro-2'-methylbiphenyl-3-yl)-4-(4-(1,3-thiazol-2-ylcarbonyl)piperazin-1-yl)pyrrolidin-2-one | | 465.1 |
| 302 | N-(3'-(2-oxo-4-(4-(1,3-thiazol-2-ylcarbonyl)piperazin-1-yl)pyrrolidin-1-yl)biphenyl-2-yl)methanesulfonamide | | 526.1 |
| 303 | N-(3'-(2-oxo-4-(4-(1,3-thiazol-2-ylcarbonyl)piperazin-1-yl)pyrrolidin-1-yl)biphenyl-2-yl)acetamide | | 490.1 |

TABLE 1-34-continued

| 304 | 1-(4'-chloro-2'-fluorobiphenyl-3-yl)-4-(4-(1,3-thiazol-2-ylcarbonyl)piperazin-1-yl)pyrrolidin-2-one | 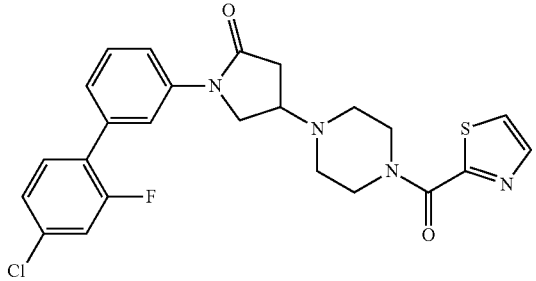 [SMILES: O=C(c1nccs1)N1CCN(C2CC(=O)N(c3cccc(-c4ccc(Cl)cc4F)c3)C2)CC1] | 485.0 |
|---|---|---|---|
| 305 | 1-(2'-chloro-4'-(trifluoromethyl)biphenyl-3-yl)-4-(4-(1,3-thiazol-2-ylcarbonyl)piperazin-1-yl)pyrrolidin-2-one | 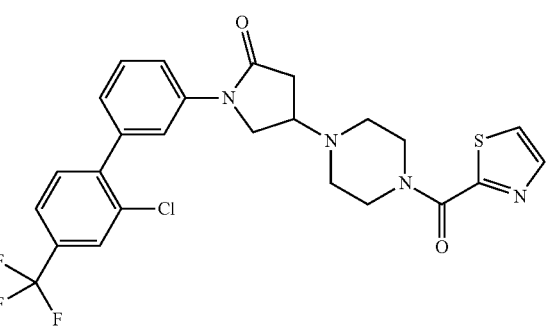 | 535.0 |
| 306 | 1-(2'-(morpholin-4-yl)biphenyl-3-yl)-4-(4-(1,3-thiazol-2-ylcarbonyl)piperazin-1-yl)pyrrolidin-2-one | 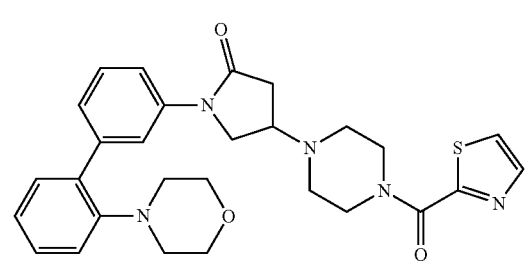 [SMILES: O=C(c1nccs1)N1CCN(C2CC(=O)N(c3cccc(-c4ccccc4N4CCOCC4)c3)C2)CC1] | 518.1 |

TABLE 1-35

| 307 | 1-(3-(1H-indol-4-yl)phenyl)-4-(4-(1,3-thiazol-2-ylcarbonyl)piperazin-1-yl)pyrrolidin-2-one | 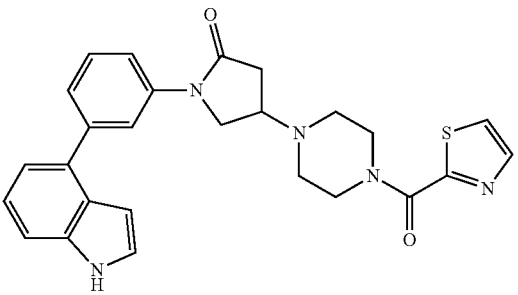 [SMILES: O=C(c1nccs1)N1CCN(C2CC(=O)N(c3cccc(-c4cccc5[nH]ccc45)c3)C2)CC1] | 472.0 |
|---|---|---|---|
| 308 | 3'-(2-oxo-4-(4-(1,3-thiazol-2-ylcarbonyl)piperazin-1-yl)pyrrolidin-1-yl)biphenyl-3-carboxylic acid | 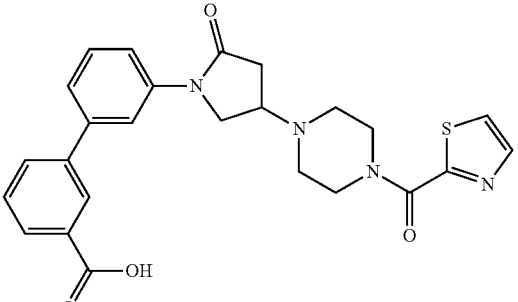 | 477.0 |

TABLE 1-35-continued

| | | | |
|---|---|---|---|
| 309 | 1-(2'-isopropoxybiphenyl-3-yl)-4-(4-(1,3-thiazol-2-ylcarbonyl)piperazin-1-yl)pyrrolidin-2-one | 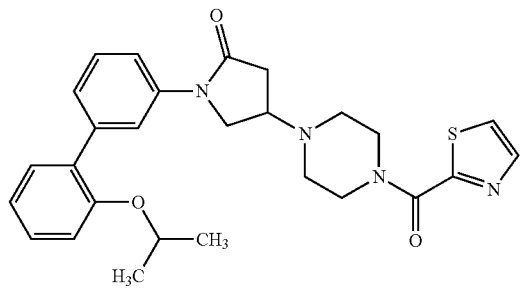 [SMILES: CC(C)Oc1ccccc1-c1cccc(N2CC(N3CCN(C(=O)c4nccs4)CC3)CC2=O)c1] | 491.1 |
| 310 | 1-(2'-methoxy-4'-(trifluoromethyl)biphenyl-3-yl)-4-(4-(1,3-thiazol-2-ylcarbonyl)piperazin-1-yl)pyrrolidin-2-one | 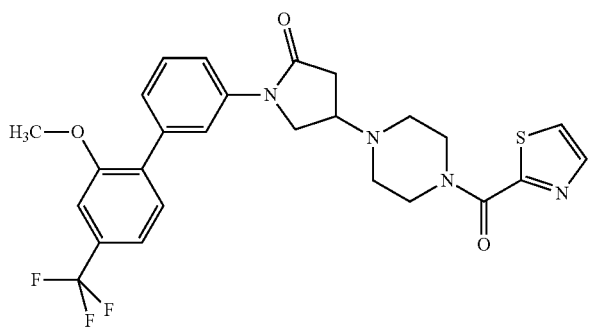 [SMILES: COc1cc(C(F)(F)F)ccc1-c1cccc(N2CC(N3CCN(C(=O)c4nccs4)CC3)CC2=O)c1] | 531.0 |
| 311 | 1-(3-(1-naphthyl)phenyl)-4-(4-(1,3-thiazol-2-ylcarbonyl)piperazin-1-yl)pyrrolidin-2-one | 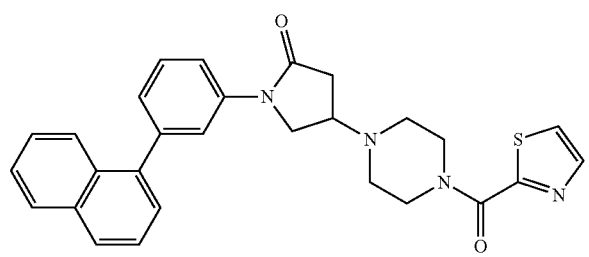 [SMILES: O=C(c1nccs1)N1CCN(C2CC(=O)N(c3cccc(-c4cccc5ccccc45)c3)C2)CC1] | 483.0 |
| 312 | 4-(4-(1,3-thiazol-2-ylcarbonyl)piperazin-1-yl)-1-(3-(1,3,5-trimethyl-1H-pyrazol-4-yl)phenyl)pyrrolidin-2-one | 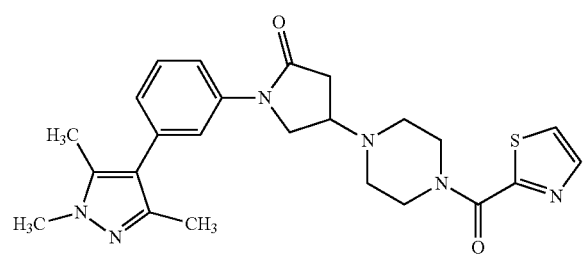 [SMILES: Cc1nn(C)c(C)c1-c1cccc(N2CC(N3CCN(C(=O)c4nccs4)CC3)CC2=O)c1] | 465.0 |
| 313 | 1-(3-(1-benzothiophen-7-yl)phenyl)-4-(4-(1,3-thiazol-2-ylcarbonyl)piperazin-1-yl)pyrrolidin-2-one | 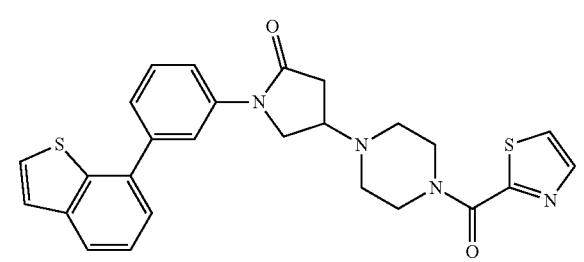 [SMILES: O=C(c1nccs1)N1CCN(C2CC(=O)N(c3cccc(-c4cccc5ccsc45)c3)C2)CC1] | 489.0 |

TABLE 1-35-continued

| | | | |
|---|---|---|---|
| 314 | 1-(3-(2,3-dihydro-1-benzofuran-7-yl)phenyl)-4-(4-(1,3-thiazol-2-ylcarbonyl)piperazin-1-yl)pyrrolidin-2-one | 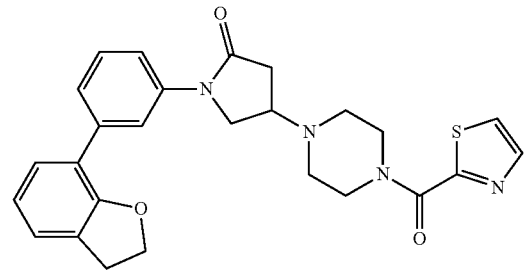 [SMILES: O=C(c1nccs1)N1CCN(C2CC(=O)N(c3cccc(-c4cccc5c4OCC5)c3)C2)CC1] | 475.1 |
| 315 | 1-(4'-fluoro-3'-(trifluoromethyl)biphenyl-3-yl)-4-(4-(1,3-thiazol-2-ylcarbonyl)piperazin-1-yl)pyrrolidin-2-one | 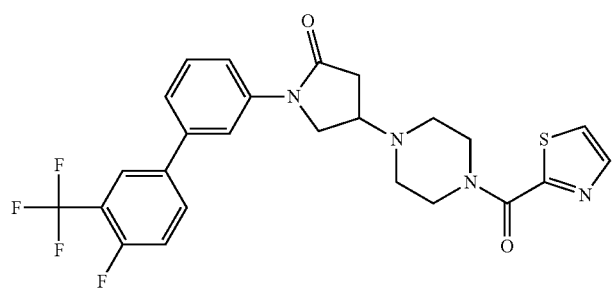 [SMILES: O=C(c1nccs1)N1CCN(C2CC(=O)N(c3cccc(-c4ccc(F)c(C(F)(F)F)c4)c3)C2)CC1] | 519.0 |

TABLE 1-36

| | | | |
|---|---|---|---|
| 316 | 2-fluoro-3'-(2-oxo-4-(4-(1,3-thiazol-2-ylcarbonyl)piperazin-1-yl)pyrrolidin-1-yl)biphenyl-4-carbonitrile | 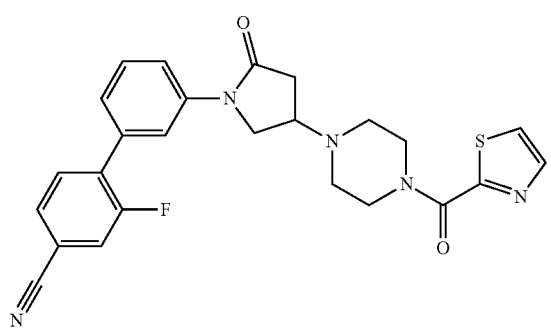 [SMILES: N#Cc1ccc(-c2cccc(N3CC(N4CCN(C(=O)c5nccs5)CC4)CC3=O)c2)c(F)c1] | 476.1 |
| 317 | 1-(3-(1H-indazol-7-yl)phenyl)-4-(4-(1,3-thiazol-2-ylcarbonyl)piperazin-1-yl)pyrrolidin-2-one | 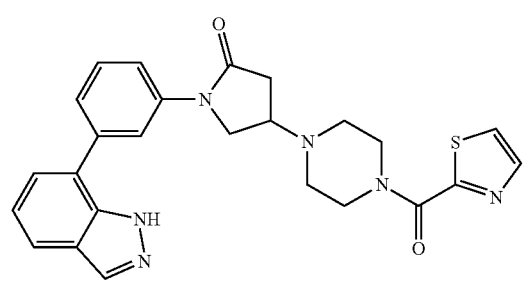 [SMILES: O=C(c1nccs1)N1CCN(C2CC(=O)N(c3cccc(-c4cccc5cn[nH]c45)c3)C2)CC1] | 473.0 |
| 318 | 1-(3-(1H-indazol-4-yl)phenyl)-4-(4-(1,3-thiazol-2-ylcarbonyl)piperazin-1-yl)pyrrolidin-2-one | 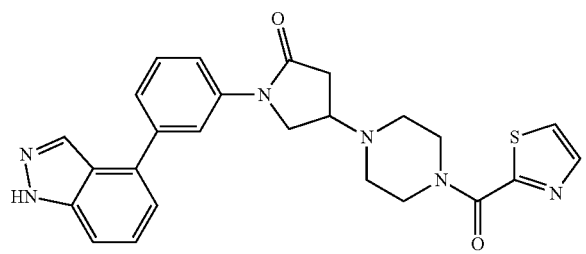 [SMILES: O=C(c1nccs1)N1CCN(C2CC(=O)N(c3cccc(-c4cccc5[nH]ncc45)c3)C2)CC1] | 473.0 |

TABLE 1-36-continued

| | | | |
|---|---|---|---|
| 319 | 2-(3'-(2-oxo-4-(4-(1,3-thiazol-2-ylcarbonyl)piperazin-1-yl)pyrrolidin-1-yl)biphenyl-3-yl)acetamide | 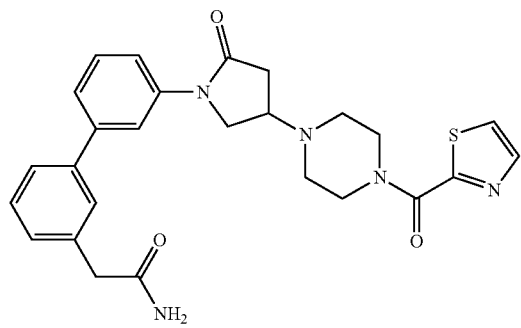 [SMILES: NC(=O)Cc1cccc(-c2cccc(N3CC(N4CCN(C(=O)c5nccs5)CC4)CC3=O)c2)c1] | 490.1 |
| 320 | 1-(3-(1H-indol-7-yl)phenyl)-4-(4-(1,3-thiazol-2-ylcarbonyl)piperazin-1-yl)pyrrolidin-2-one | 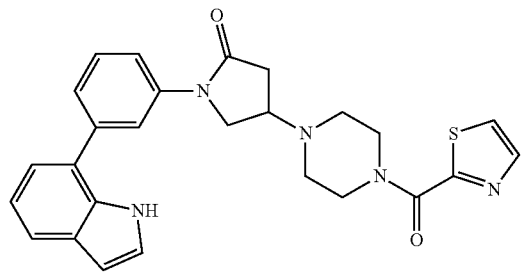 [SMILES: O=C(c1nccs1)N1CCN(C2CC(=O)N(c3cccc(-c4cccc5cc[nH]c45)c3)C2)CC1] | 472.0 |
| 321 | 1-(3'-(pyrrolidin-1-ylcarbonyl)biphenyl-3-yl)-4-(4-(1,3-thiazol-2-ylcarbonyl)piperazin-1-yl)pyrrolidin-2-one | 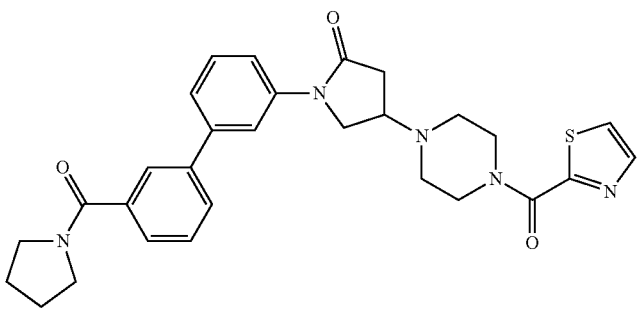 [SMILES: O=C(c1cccc(-c2cccc(N3CC(N4CCN(C(=O)c5nccs5)CC4)CC3=O)c2)c1)N1CCCC1] | 530.1 |
| 322 | 2-methyl-3'-(2-oxo-4-(4-(1,3-thiazol-2-ylcarbonyl)piperazin-1-yl)pyrrolidin-1-yl)biphenyl-4-carbonitrile | 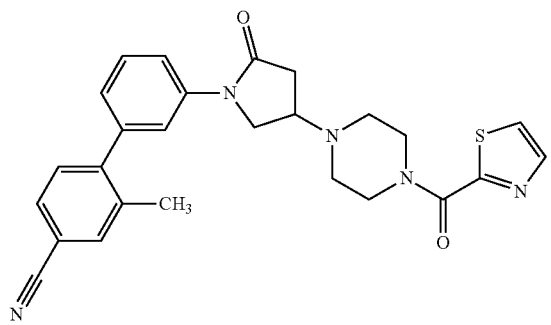 [SMILES: Cc1cc(C#N)ccc1-c1cccc(N2CC(N3CCN(C(=O)c4nccs4)CC3)CC2=O)c1] | 472.0 |
| 323 | 1-(3-(3-methoxy-2-thienyl)phenyl)-4-(4-(1,3-thiazol-2-ylcarbonyl)piperazin-1-yl)pyrrolidin-2-one | 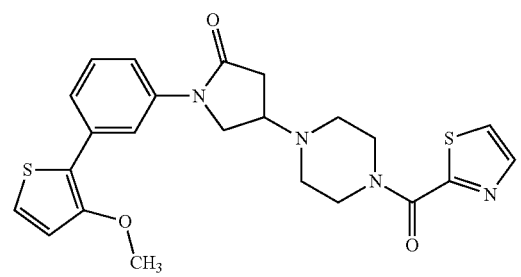 [SMILES: COc1ccsc1-c1cccc(N2CC(N3CCN(C(=O)c4nccs4)CC3)CC2=O)c1] | 469.0 |

TABLE 1-36-continued

| 324 | 1-(3-(1,5-dimethyl-1H-pyrazol-4-yl)phenyl)-4-(4-(1,3-thiazol-2-ylcarbonyl)piperazin-1-yl)pyrrolidin-2-one | 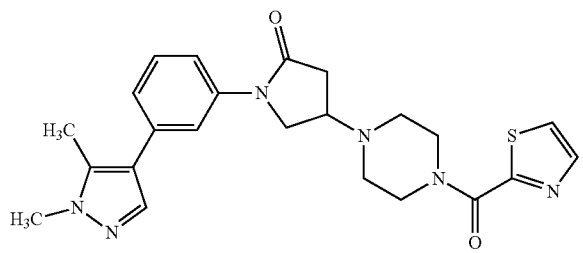 [SMILES: Cc1c(-c2cccc(N3CC(N4CCN(C(=O)c5nccs5)CC4)CC3=O)c2)cnn1C] | 451.0 |

TABLE 1-37

| 325 | 1-(3-(1,3-dimethyl-1H-pyrazol-4-yl)phenyl)-4-(4-(1,3-thiazol-2-ylcarbonyl)piperazin-1-yl)pyrrolidin-2-one | 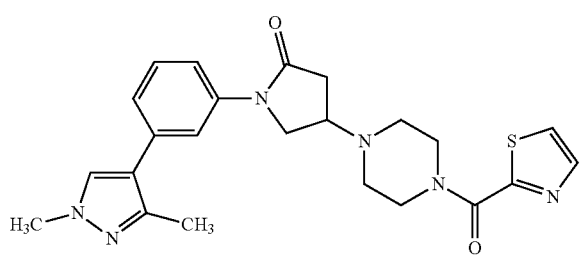 [SMILES: Cc1nn(C)cc1-c1cccc(N2CC(N3CCN(C(=O)c4nccs4)CC3)CC2=O)c1] | 451.0 |
| 326 | 1-(3-(1-methyl-1H-indazol-4-yl)phenyl)-4-(4-(1,3-thiazol-2-ylcarbonyl)piperazin-1-yl)pyrrolidin-2-one | 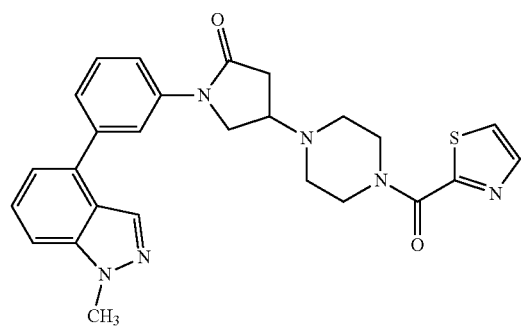 [SMILES: Cn1ncc2c(-c3cccc(N4CC(N5CCN(C(=O)c6nccs6)CC5)CC4=O)c3)cccc21] | 487.0 |
| 327 | 4-(4-(1,3-thiazol-2-ylcarbonyl)piperazin-1-yl)-1-(3-(3-(trifluoromethyl)-1H-pyrazol-4-yl)phenyl)pyrrolidin-2-one | 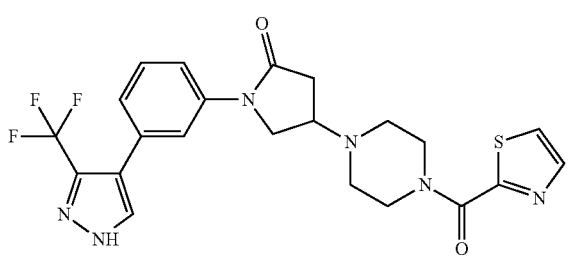 [SMILES: O=C(c1nccs1)N1CCN(C2CC(=O)N(c3cccc(-c4c[nH]nc4C(F)(F)F)c3)C2)CC1] | 491.0 |
| 328 | 1-(3-(1-benzofuran-3-yl)phenyl)-4-(4-(1,3-thiazol-2-ylcarbonyl)piperazin-1-yl)pyrrolidin-2-one | 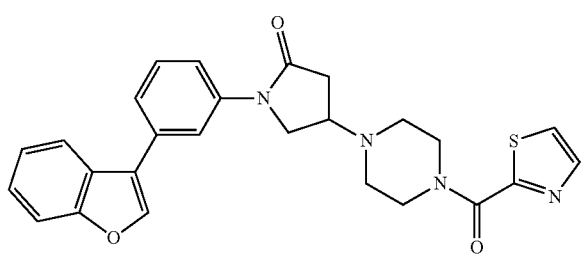 [SMILES: O=C(c1nccs1)N1CCN(C2CC(=O)N(c3cccc(-c4coc5ccccc45)c3)C2)CC1] | 473.0 |

TABLE 1-37-continued

| | | | |
|---|---|---|---|
| 329 | 1-(3-(1-benzofuran-7-yl)phenyl)-4-(4-(1,3-thiazol-2-ylcarbonyl)piperazin-1-yl)pyrrolidin-2-one | 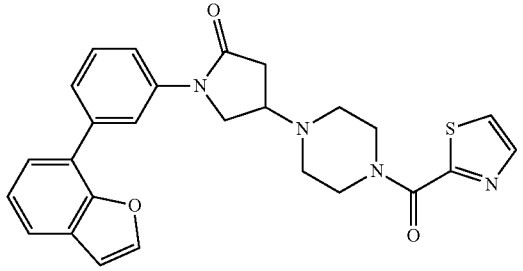 [SMILES: O=C(c1nccs1)N1CCN(C2CC(=O)N(c3cccc(-c4cccc5ccoc45)c3)C2)CC1] | 473.0 |
| 330 | 1-(2',3',4',5',6'-pentafluorobiphenyl-3-yl)-4-(4-(1,3-thiazol-2-ylcarbonyl)piperazin-1-yl)pyrrolidin-2-one | 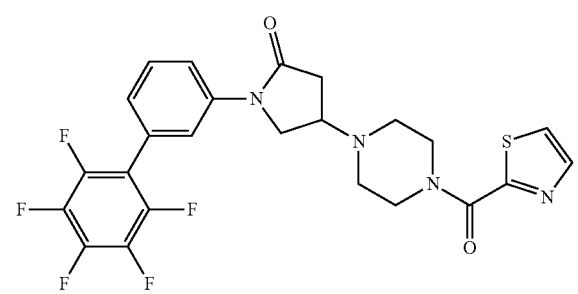 [SMILES: O=C(c1nccs1)N1CCN(C2CC(=O)N(c3cccc(-c4c(F)c(F)c(F)c(F)c4F)c3)C2)CC1] | 523.0 |
| 331 | 1-(3-(imidazo[1,2-a]pyridin-3-yl)phenyl)-4-(4-(1,3-thiazol-2-ylcarbonyl)piperazin-1-yl)pyrrolidin-2-one | 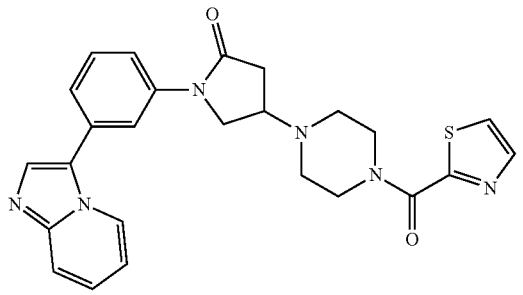 [SMILES: O=C(c1nccs1)N1CCN(C2CC(=O)N(c3cccc(-c4cnc5ccccn45)c3)C2)CC1] | 473.0 |
| 332 | 1-(3-(1H-indazol-3-yl)phenyl)-4-(4-(1,3-thiazol-2-ylcarbonyl)piperazin-1-yl)pyrrolidin-2-one | 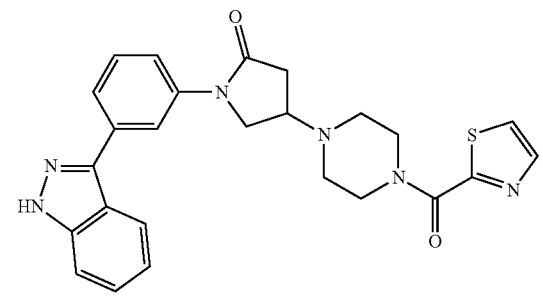 [SMILES: O=C(c1nccs1)N1CCN(C2CC(=O)N(c3cccc(-c4n[nH]c5ccccc45)c3)C2)CC1] | 473.0 |
| 333 | 1-(3-(1-methyl-1H-imidazol-2-yl)phenyl)-4-(4-(1,3-thiazol-2-ylcarbonyl)piperazin-1-yl)pyrrolidin-2-one | 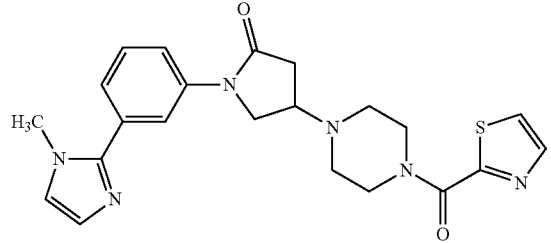 [SMILES: Cn1ccnc1-c1cccc(N2CC(N3CCN(C(=O)c4nccs4)CC3)CC2=O)c1] | 437.0 |

TABLE 1-38

| | | | |
|---|---|---|---|
| 334 | 1-(3-(1,2-benzothiazol-3-yl)phenyl)-4-(4-(1,3-thiazol-2-ylcarbonyl)piperazin-1-yl)pyrrolidin-2-one | 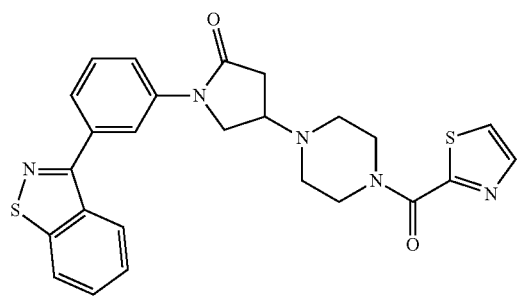 [SMILES: O=C(c1nccs1)N1CCN(C2CC(=O)N(c3cccc(-c4nsc5ccccc45)c3)C2)CC1] | 490.1 |
| 335 | 1-(3-(2-methylimidazo[1,2-a]pyridin-3-yl)phenyl)-4-(4-(1,3-thiazol-2-ylcarbonyl)piperazin-1-yl)pyrrolidin-2-one | 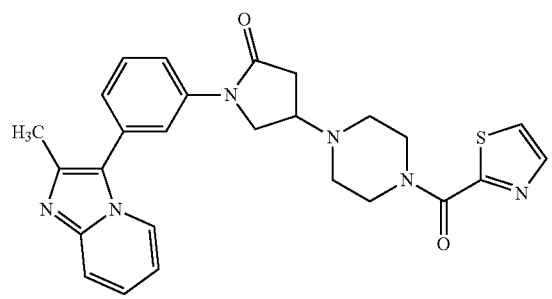 [SMILES: Cc1nc2ccccn2c1-c1cccc(N2CC(N3CCN(C(=O)c4nccs4)CC3)CC2=O)c1] | 487.1 |
| 336 | 6-fluoro-3'-(2-oxo-4-(4-(1,3-thiazol-2-ylcarbonyl)piperazin-1-yl)pyrrolidin-1-yl)biphenyl-2-carbonitrile | 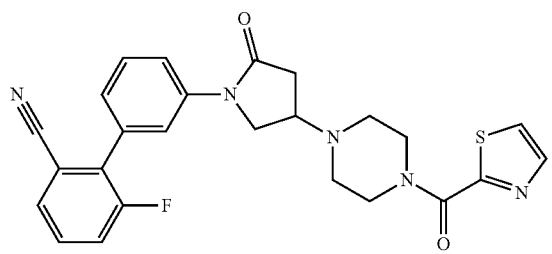 [SMILES: N#Cc1cccc(F)c1-c1cccc(N2CC(N3CCN(C(=O)c4nccs4)CC3)CC2=O)c1] | 476.1 |
| 337 | 1-(3-(1H-pyrrolo[2,3-b]pyridin-3-yl)phenyl)-4-(4-(1,3-thiazol-2-ylcarbonyl)piperazin-1-yl)pyrrolidin-2-one | 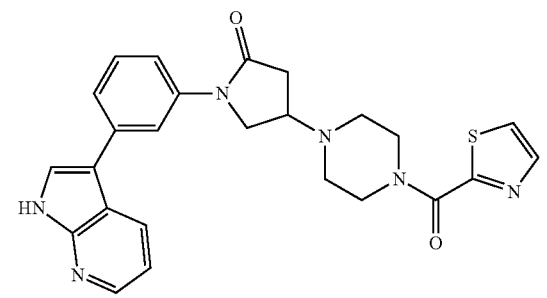 [SMILES: O=C(c1nccs1)N1CCN(C2CC(=O)N(c3cccc(-c4c[nH]c5ncccc45)c3)C2)CC1] | 473.1 |
| 338 | 1-(3-(pyrazolo[1,5-a]pyridin-7-yl)phenyl)-4-(4-(1,3-thiazol-2-ylcarbonyl)piperazin-1-yl)pyrrolidin-2-one | 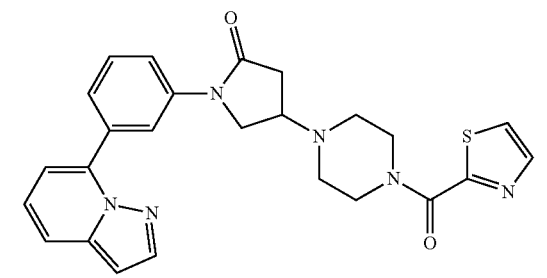 [SMILES: O=C(c1nccs1)N1CCN(C2CC(=O)N(c3cccc(-c4cccc5ccnn45)c3)C2)CC1] | 473.0 |

TABLE 1-38-continued

| | | | |
|---|---|---|---|
| 339 | 1-(3-(2-methoxy-4-methylpyridin-3-yl)phenyl)-4-(4-(1,3-thiazol-2-ylcarbonyl)piperazin-1-yl)pyrrolidin-2-one | 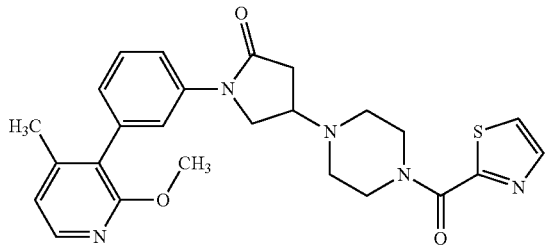 [SMILES: COc1nccc(C)c1-c1cccc(N2CC(N3CCN(C(=O)c4nccs4)CC3)CC2=O)c1] | 478.1 |
| 340 | 1-(3-(imidazo[1,2-a]pyridin-5-yl)phenyl)-4-(4-(1,3-thiazol-2-ylcarbonyl)piperazin-1-yl)pyrrolidin-2-one | 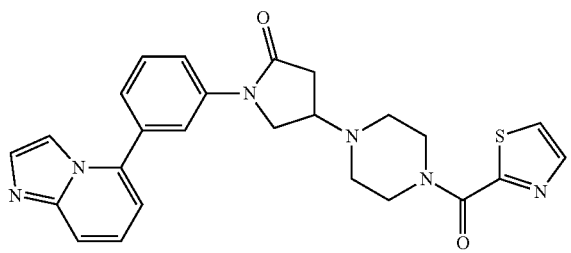 [SMILES: O=C(c1nccs1)N1CCN(C2CC(=O)N(c3cccc(-c4cccc5nccn45)c3)C2)CC1] | 473.0 |
| 341 | 4-(4-(1,3-thiazol-2-ylcarbonyl)piperazin-1-yl)-1-(3-(2-(trifluoromethyl)-3-thienyl)phenyl)pyrrolidin-2-one | 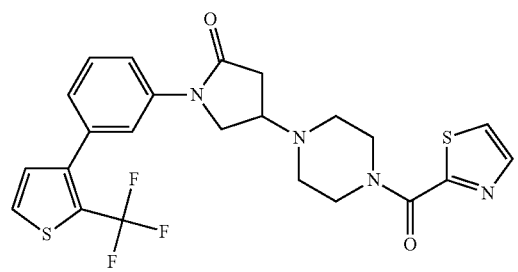 [SMILES: O=C(c1nccs1)N1CCN(C2CC(=O)N(c3cccc(-c4ccsc4C(F)(F)F)c3)C2)CC1] | 507.1 |
| 342 | 1-(3-(imidazo[1,2-a]pyridin-8-yl)phenyl)-4-(4-(1,3-thiazol-2-ylcarbonyl)piperazin-1-yl)pyrrolidin-2-one | 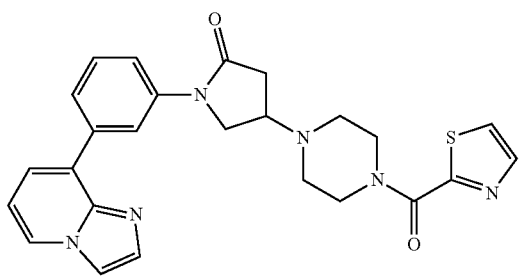 [SMILES: O=C(c1nccs1)N1CCN(C2CC(=O)N(c3cccc(-c4cccn5ccnc45)c3)C2)CC1] | 473.0 |

TABLE 1-39

| | | | |
|---|---|---|---|
| 343 | 1-(3-(4-methoxy-1H-pyrrolo[3,2-c]pyridin-3-yl)phenyl)-4-(4-(1,3-thiazol-2-ylcarbonyl)piperazin-1-yl)pyrrolidin-2-one | 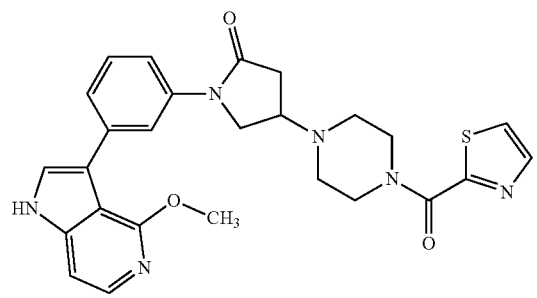 [SMILES: COc1nccc2[nH]cc(-c3cccc(N4CC(N5CCN(C(=O)c6nccs6)CC5)CC4=O)c3)c12] | 503.1 |

TABLE 1-39-continued

| | | | |
|---|---|---|---|
| 344 | 1-(2'-chloro-6'-fluorobiphenyl-3-yl)-4-(4-(1,3-thiazol-2-ylcarbonyl)piperazin-1-yl)pyrrolidin-2-one | | 485.0 |
| 345 | 1-(3-(2-methylimidazo[1,2-a]pyridin-5-yl)phenyl)-4-(4-(1,3-thiazol-2-ylcarbonyl)piperazin-1-yl)pyrrolidin-2-one | | 487.0 |
| 346 | 4-(4-(1,3-thiazol-2-ylcarbonyl)piperazin-1-yl)-1-(3-(thieno[2,3-b]pyridin-4-yl)phenyl)pyrrolidin-2-one | | 490.1 |
| 347 | 4-(4-(1,3-thiazol-2-ylcarbonyl)piperazin-1-yl)-1-(3-(thieno[2,3-b]pyridin-3-yl)phenyl)pyrrolidin-2-one | | 490.1 |
| 348 | 4-(3-(2-oxo-4-(4-(1,3-thiazol-2-ylcarbonyl)piperazin-1-yl)pyrrolidin-1-yl)phenyl)-1,3-dihydro-2H-pyrrolo[2,3-b]pyridin-2-one | | 489.1 |
| 349 | 4-(4-(1,3-thiazol-2-ylcarbonyl)piperazin-1-yl)-1-(3-(4-(trifluoromethyl)-1,3-thiazol-2-yl)phenyl)pyrrolidin-2-one | | 508.0 |

TABLE 1-39-continued

| 350 | 1-(2'-chloro-5-fluorobiphenyl-3-yl)-4-(4-(1,3-thiazol-2-ylcarbonyl)piperazin-1-yl)pyrrolidin-2-one | 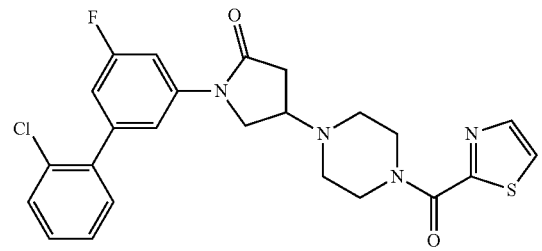 [SMILES: O=C(c1nccs1)N1CCN(C2CC(=O)N(c3cc(F)cc(-c4ccccc4Cl)c3)C2)CC1] | 485.0 |

| 351 | 7-methoxy-6-(3-(2-oxo-4-(4-(1,3-thiazol-2-ylcarbonyl)piperazin-1-yl)pyrrolidin-1-yl)phenyl)-1,3-dihydro-2H-indol-2-one | 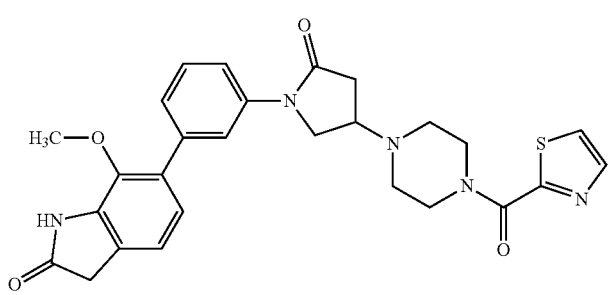 [SMILES: COc1c(-c2cccc(N3CC(N4CCN(C(=O)c5nccs5)CC4)CC3=O)c2)ccc2c1NC(=O)C2] | 518.1 |

TABLE 1-40

| 352 | 1-(3-(2,4-dimethylpyridin-3-yl)phenyl)-4-(4-(1,3-thiazol-2-ylcarbonyl)piperazin-1-yl)pyrrolidin-2-one | 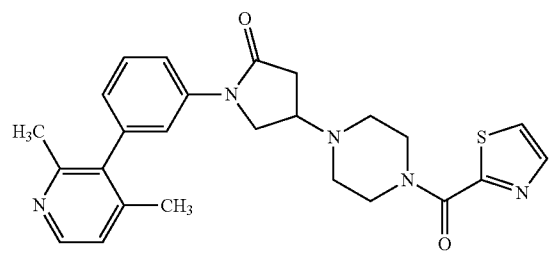 [SMILES: Cc1ccnc(C)c1-c1cccc(N2CC(N3CCN(C(=O)c4nccs4)CC3)CC2=O)c1] | 462.1 |

| 353 | 1-(7-(2-fluorophenyl)-1H-indol-5-yl)-4-(4-(1,3-thiazol-2-ylcarbonyl)piperazin-1-yl)pyrrolidin-2-one | 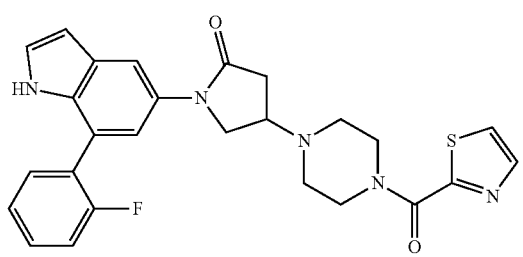 [SMILES: O=C(c1nccs1)N1CCN(C2CC(=O)N(c3cc(-c4ccccc4F)c4[nH]ccc4c3)C2)CC1] | 490.1 |

| 354 | 1-(7-(2-methoxyphenyl)-1H-indol-5-yl)-4-(4-(1,3-thiazol-2-ylcarbonyl)piperazin-1-yl)pyrrolidin-2-one | 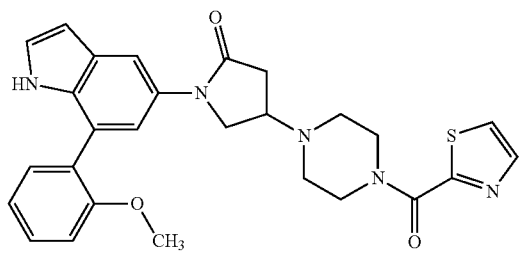 [SMILES: COc1ccccc1-c1cc(N2CC(N3CCN(C(=O)c4nccs4)CC3)CC2=O)cc2cc[nH]c12] | 502.1 |

TABLE 1-40-continued

| | | | |
|---|---|---|---|
| 355 | 1-(7-(2-methoxyphenyl)-1H-indazol-5-yl)-4-(4-(1,3-thiazol-2-ylcarbonyl)piperazin-1-yl)pyrrolidin-2-one | | 503.1 |
| 356 | 1-(4'-chloro-2'-methylbiphenyl-3-yl)-4-(4-(1,3-thiazol-2-ylcarbonyl)piperazin-1-yl)pyrrolidin-2-one | | 481.0 |
| 357 | 1-(4'-chloro-5-fluoro-2'-methylbiphenyl-3-yl)-4-(4-(1,3-thiazol-2-ylcarbonyl)piperazin-1-yl)pyrrolidin-2-one | | 499.0 |
| 358 | 1-(1-(5-methylpyrimidin-2-yl)-1H-indol-5-yl)-4-(4-(1,3-thiazol-2-ylcarbonyl)piperazin-1-yl)pyrrolidin-2-one | | 488.2 |
| 359 | 1-(1-(4-fluorophenyl)-1H-indol-5-yl)-4-((2R)-2-methyl-4-(1,3-thiazol-2-ylcarbonyl)piperazin-1-yl)pyrrolidin-2-one | | 504.1 |
| 360 | 1-(1-(4-fluorophenyl)-1H-indol-5-yl)-4-((3R)-3-methyl-4-(1,3-thiazol-2-ylcarbonyl)piperazin-1-yl)pyrrolidin-2-one | | 504.1 |

TABLE 1-41

| | | | |
|---|---|---|---|
| 361 | 4-(4-(pyrimidin-2-yl)piperazin-1-yl)-1-(1-(2-(trifluoromethyl)pyridin-4-yl)-1H-indol-5-yl)pyrrolidin-2-one | 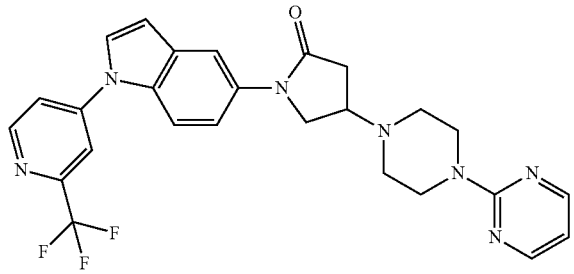 [SMILES: O=C1CC(N2CCN(c3ncccn3)CC2)CN1c1ccc2c(ccn2-c2ccnc(C(F)(F)F)c2)c1] | 508.1 |
| 362 | 1-(3-(3-methylpyrazin-2-yl)phenyl)-4-(4-(1,3-thiazol-2-ylcarbonyl)piperazin-1-yl)pyrrolidin-2-one | 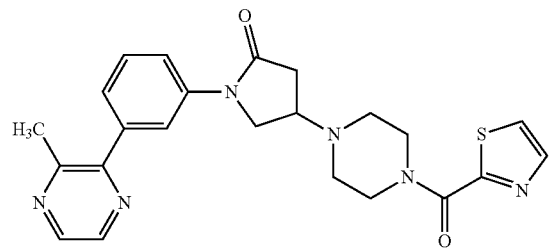 [SMILES: Cc1nccnc1-c1cccc(N2CC(N3CCN(C(=O)c4nccs4)CC3)CC2=O)c1] | 449.0 |
| 363 | 1-(1-(4-fluorophenyl)-1H-indol-5-yl)-4-((3S)-3-methyl-4-(1,3-thiazol-2-ylcarbonyl)piperazin-1-yl)pyrrolidin-2-one | 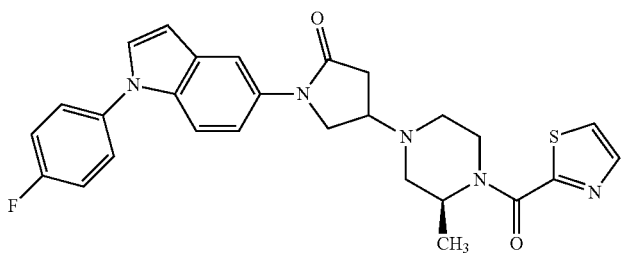 [SMILES: C[C@H]1CN(C2CC(=O)N(c3ccc4c(ccn4-c4ccc(F)cc4)c3)C2)CCN1C(=O)c1nccs1] | 504.1 |
| 364 | 1-(1-(4-fluorophenyl)-1H-indol-5-yl)-4-((2S)-2-methyl-4-(1,3-thiazol-2-ylcarbonyl)piperazin-1-yl)pyrrolidin-2-one | 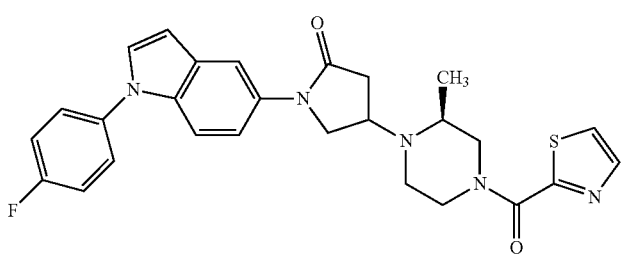 | 504.1 |
| 365 | 4-(4-(1,3-thiazol-2-ylcarbonyl)piperazin-1-yl)-1-(1-(2-(trifluoromethyl)pyridin-4-yl)-2,3-dihydro-1H-indol-5-yl)pyrrolidin-2-one | 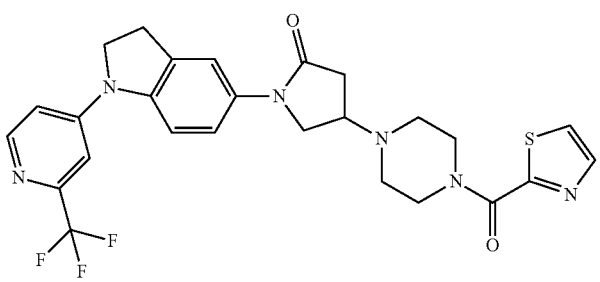 [SMILES: O=C(c1nccs1)N1CCN(C2CC(=O)N(c3ccc4c(c3)CCN4c3ccnc(C(F)(F)F)c3)C2)CC1] | 543.1 |
| 366 | 1-(3-chloro-6-fluoro-1-benzothiophen-2-yl)-4-(4-(1,3-thiazol-2-ylcarbonyl)piperazin-1-yl)pyrrolidin-2-one | 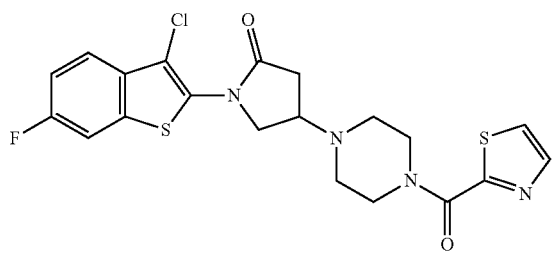 [SMILES: O=C(c1nccs1)N1CCN(C2CC(=O)N(c3sc4cc(F)ccc4c3Cl)C2)CC1] | 464.9 |

TABLE 1-41-continued

| | | | |
|---|---|---|---|
| 368 | 1-(3-(2,6-dimethylpyridin-3-yl)phenyl)-4-(4-(1,3-thiazol-2-ylcarbonyl)piperazin-1-yl)pyrrolidin-2-one | 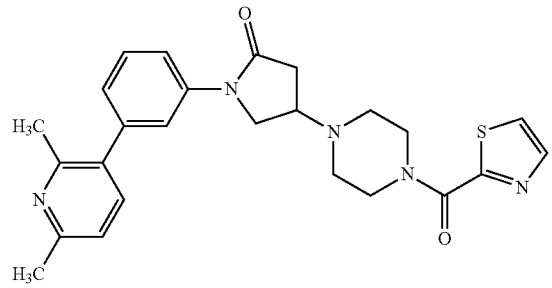 [SMILES: Cc1ccc(-c2cccc(N3CC(N4CCN(C(=O)c5nccs5)CC4)CC3=O)c2)c(C)n1] | 462.1 |
| 369 | 1-(cyclohex-2-en-1-yl)-4-(4-(1,3-thiazol-2-ylcarbonyl)piperazin-1-yl)pyrrolidin-2-one | 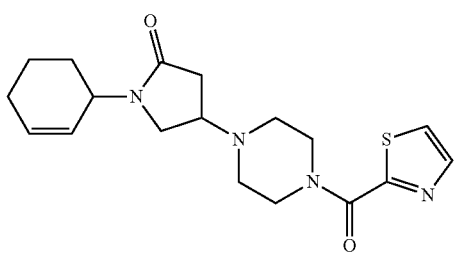 [SMILES: O=C(c1nccs1)N1CCN(C2CC(=O)N(C3C=CCCC3)C2)CC1] | 361.0 |
| 370 | 1-(3-(4-chloropyridin-3-yl)phenyl)-4-(4-(1,3-thiazol-2-ylcarbonyl)piperazin-1-yl)pyrrolidin-2-one | 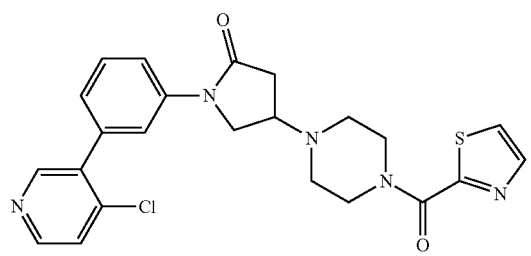 [SMILES: O=C(c1nccs1)N1CCN(C2CC(=O)N(c3cccc(-c4cnccc4Cl)c3)C2)CC1] | 468.0 |

TABLE 1-42

| | | | |
|---|---|---|---|
| 371 | 4-(4-(1,3-thiazol-2-ylcarbonyl)piperazin-1-yl)-1-(3-(4-(trifluoromethyl)pyridin-3-yl)phenyl)pyrrolidin-2-one | 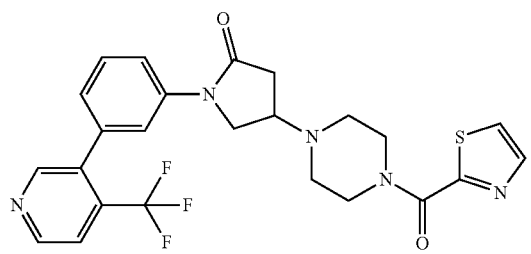 [SMILES: O=C(c1nccs1)N1CCN(C2CC(=O)N(c3cccc(-c4cnccc4C(F)(F)F)c3)C2)CC1] | 502.1 |
| 372 | tert-butyl 5-(2-oxo-4-(4-(1,3-thiazol-2-ylcarbonyl)piperazin-1-yl)pyrrolidin-1-yl)indoline-1-carboxylate | 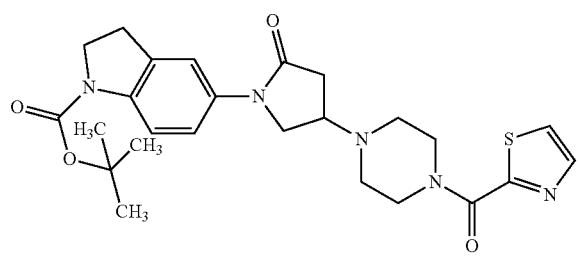 [SMILES: CC(C)(C)OC(=O)N1CCc2cc(N3CC(N4CCN(C(=O)c5nccs5)CC4)CC3=O)ccc21] | 498.0 |

TABLE 1-42-continued

| | | | |
|---|---|---|---|
| 373 | 4-(4-(1,3-thiazol-2-ylcarbonyl)piperazin-1-yl)-1-(1-(trifluoroacetyl)-2,3-dihydro-1H-indol-5-yl)pyrrolidin-2-one | 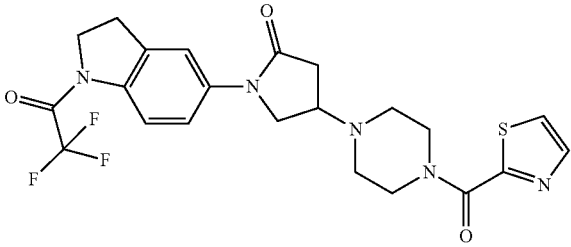 [SMILES: O=C(c1nccs1)N1CCN(C2CC(=O)N(c3ccc4c(c3)CCN4C(=O)C(F)(F)F)C2)CC1] | 494.0 |
| 374 | 1-(2,3-dihydro-1H-indol-5-yl)-4-(4-(1,3-thiazol-2-ylcarbonyl)piperazin-1-yl)pyrrolidin-2-one | 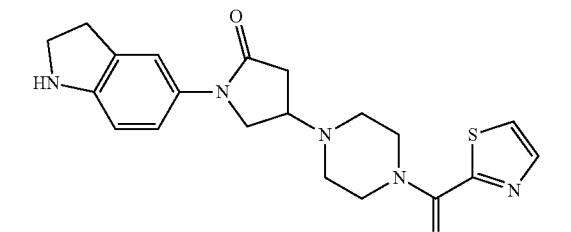 | 398.0 |
| 375 | 1-(1-cyclopropyl-2,3-dihydro-1H-indol-5-yl)-4-(4-(1,3-thiazol-2-ylcarbonyl)piperazin-1-yl)pyrrolidin-2-one | 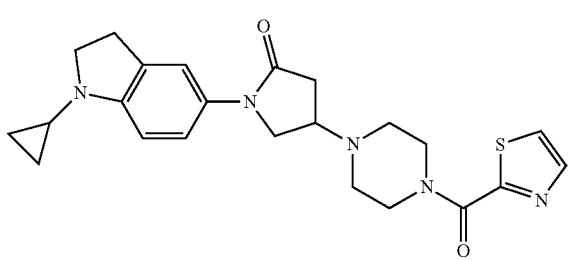 [SMILES: O=C(c1nccs1)N1CCN(C2CC(=O)N(c3ccc4c(c3)CCN4C3CC3)C2)CC1] | 438.0 |
| 377 | 4-(4-(pyrimidin-2-yl)piperazin-1-yl)-1-(1-(2-(trifluoromethyl)pyridin-4-yl)-2,3-dihydro-1H-indol-5-yl)pyrrolidin-2-one | 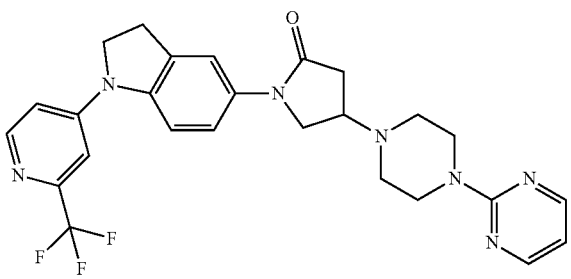 [SMILES: O=C1CC(N2CCN(c3ncccn3)CC2)CN1c1ccc2c(c1)CCN2c1ccnc(C(F)(F)F)c1] | 510.1 |
| 378 | 4-(4-(pyrimidin-2-yl)piperazin-1-yl)-1-(1-(5-(trifluoromethyl)pyrimidin-2-yl)-2,3-dihydro-1H-indol-5-yl)pyrrolidin-2-one | 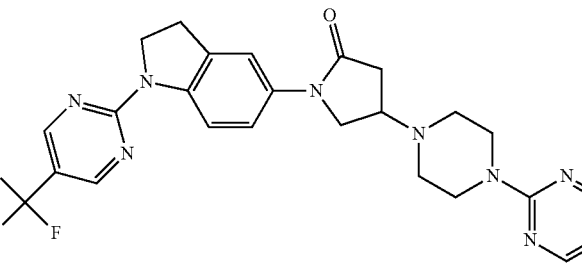 | 511.1 |
| 379 | 1-(1-(2-methylpyridin-3-yl)-1H-indol-5-yl)-4-(4-(1,3-thiazol-2-ylcarbonyl)piperazin-1-yl)pyrrolidin-2-one | 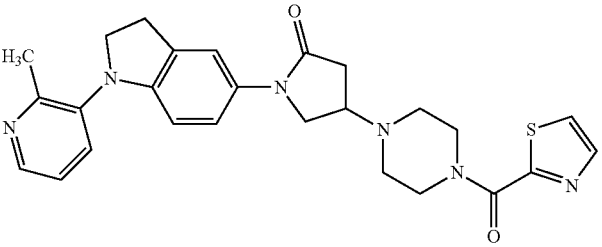 [SMILES: Cc1ncccc1N1CCc2cc(N3CC(N4CCN(C(=O)c5nccs5)CC4)CC3=O)ccc21] | 487.0 |

TABLE 1-42-continued

| 380 | 1-(3-(2-methylpyridin-3-yl)phenyl)-4-(4-(pyrimidin-2-yl)piperazin-1-yl)pyrrolidin-2-one (optical isomer) | 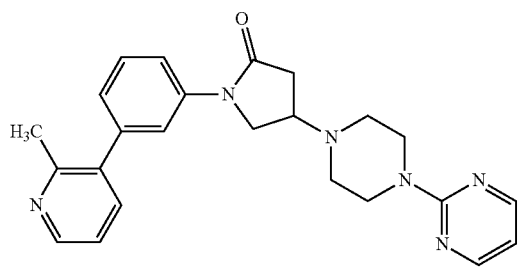 [SMILES: Cc1ncccc1-c1cccc(N2CC(N3CCN(c4ncccn4)CC3)CC2=O)c1] | 415.2 |

TABLE 1-43

| 381 | 1-(3-(2-methylpyridin-3-yl)phenyl)-4-(4-(pyrimidin-2-yl)piperazin-1-yl)pyrrolidin-2-one (optical isomer) | 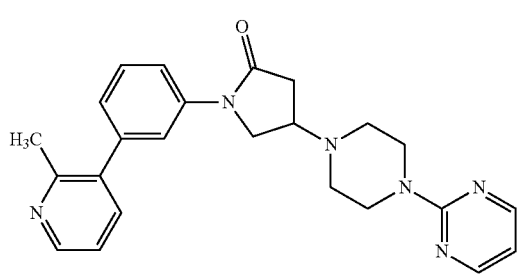 [SMILES: Cc1ncccc1-c1cccc(N2CC(N3CCN(c4ncccn4)CC3)CC2=O)c1] | 415.2 |
| 382 | 1-(1-(3,3-dimethylbutanoyl)-2,3-dihydro-1H-indol-5-yl)-4-(4-(1,3-thiazol-2-ylcarbonyl)piperazin-1-yl)pyrrolidin-2-one | 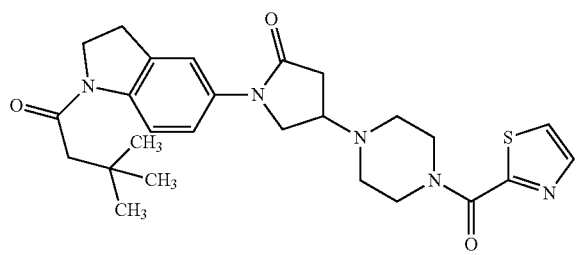 [SMILES: CC(C)(C)CC(=O)N1CCc2cc(N3CC(N4CCN(C(=O)c5nccs5)CC4)CC3=O)ccc21] | 496.2 |
| 383 | 4-(4-(1,3-thiazol-2-ylcarbonyl)piperazin-1-yl)-1-(1-(5-(trifluoromethyl)pyridin-2-yl)-2,3-dihydro-1H-indol-5-yl)pyrrolidin-2-one | 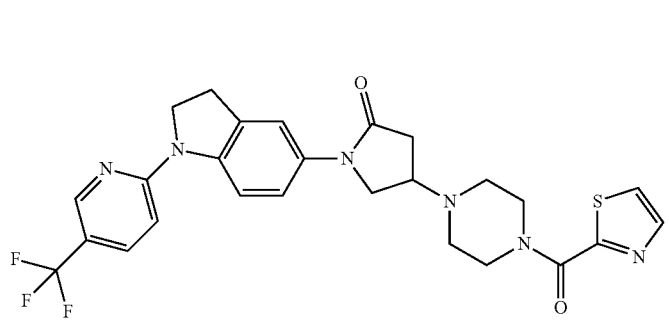 [SMILES: O=C(c1nccs1)N1CCN(C2CC(=O)N(c3ccc4c(c3)CCN4c3ccc(C(F)(F)F)cn3)C2)CC1] | 543.1 |
| 384 | (4R)-4-(4-(1,3-thiazol-4-ylcarbonyl)piperazin-1-yl)-1-(1-(5-(trifluoromethyl)pyrimidin-2-yl)-2,3-dihydro-1H-indol-5-yl)pyrrolidin-2-one | 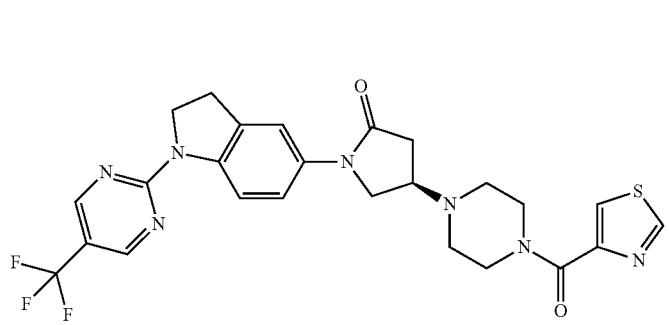 [SMILES: O=C(c1cscn1)N1CCN([C@@H]2CC(=O)N(c3ccc4c(c3)CCN4c3ncc(C(F)(F)F)cn3)C2)CC1] | 544.2 |

TABLE 1-43-continued

| | | | |
|---|---|---|---|
| 385 | (4R)-4-(4-(1,3-thiazol-2-ylcarbonyl)piperazin-1-yl)-1-(1-(6-(trifluoromethyl)pyrimidin-4-yl)-2,3-dihydro-1H-indol-5-yl)pyrrolidin-2-one | 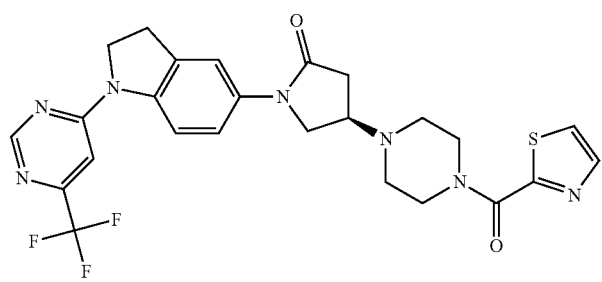 [SMILES: O=C(c1nccs1)N1CCN([C@@H]2CC(=O)N(c3ccc4c(c3)CCN4c3cc(C(F)(F)F)ncn3)C2)CC1] | 544.2 |
| 386 | 1-(2-(4-fluorophenyl)-1,3-benzoxazol-5-yl)-4-(4-(1,3-thiazol-2-ylcarbonyl)piperazin-1-yl)pyrrolidin-2-one | 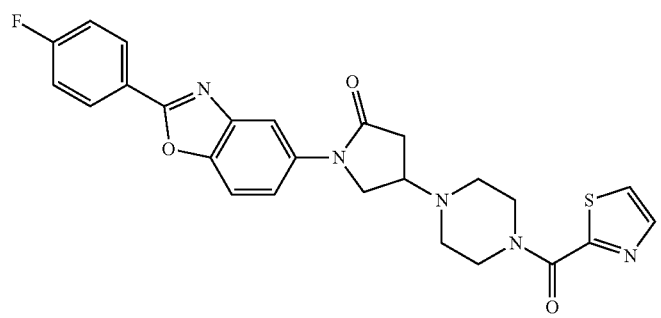 [SMILES: O=C(c1nccs1)N1CCN(C2CC(=O)N(c3ccc4oc(-c5ccc(F)cc5)nc4c3)C2)CC1] | 492.2 |
| 387 | 1-(2-phenyl-1,3-benzoxazol-6-yl)-4-(4-(1,3-thiazol-2-ylcarbonyl)piperazin-1-yl)pyrrolidin-2-one | 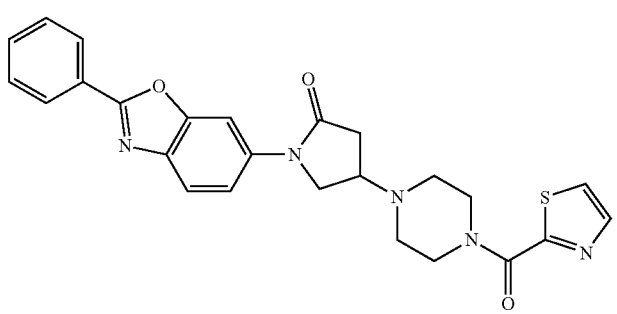 [SMILES: O=C(c1nccs1)N1CCN(C2CC(=O)N(c3ccc4nc(-c5ccccc5)oc4c3)C2)CC1] | 474.2 |
| 388 | (4R)-4-(4-(1,3-thiazol-2-ylcarbonyl)piperazin-1-yl)-1-(1-(2-(trifluoromethyl)pyrimidin-4-yl)-2,3-dihydro-1H-indol-5-yl)pyrrolidin-2-one | 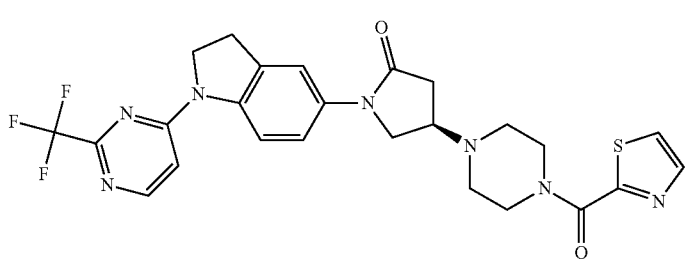 [SMILES: O=C(c1nccs1)N1CCN([C@@H]2CC(=O)N(c3ccc4c(c3)CCN4c3ccnc(C(F)(F)F)n3)C2)CC1] | 544.2 |
| 389 | tert-butyl 5-(2-oxo-4-(4-(pyrimidin-2-yl)piperazin-1-yl)pyrrolidin-1-yl)indoline-1-carboxylate | 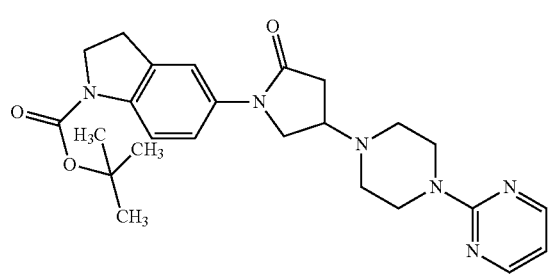 [SMILES: CC(C)(C)OC(=O)N1CCc2cc(N3CC(N4CCN(c5ncccn5)CC4)CC3=O)ccc21] | 465.2 |

TABLE 1-44

| 390 | (4R)-4-(4-(1,3-thiazol-2-ylcarbonyl)piperazin-1-yl)-1-(1-(5-(trifluoromethyl)pyrazin-2-yl)-2,3-dihydro-1H-indol-5-yl)pyrrolidin-2-one | | 544.2 |
|---|---|---|---|
| 391 | (4R)-4-(4-(1,3-thiazol-2-ylcarbonyl)piperazin-1-yl)-1-(1-(2-(trifluoromethyl)pyrimidin-5-yl)-2,3-dihydro-1H-indol-5-yl)pyrrolidin-2-one | | 544.2 |
| 392 | 1-(1-(phenylacetyl)-2,3-dihydro-1H-indol-5-yl)-4-(4-(1,3-thiazol-2-ylcarbonyl)piperazin-1-yl)pyrrolidin-2-one | | 516.2 |
| 393 | 1-(1-((4-chlorophenyl)acetyl)-2,3-dihydro-1H-indol-5-yl)-4-(4-(1,3-thiazol-2-ylcarbonyl)piperazin-1-yl)pyrrolidin-2-one | | 550.1 |
| 394 | 1-(1-((3-chlorophenyl)acetyl)-2,3-dihydro-1H-indol-5-yl)-4-(4-(1,3-thiazol-2-ylcarbonyl)piperazin-1-yl)pyrrolidin-2-one | | 550.2 |
| 395 | 1-(1-((2-chlorophenyl)acetyl)-2,3-dihydro-1H-indol-5-yl)-4-(4-(1,3-thiazol-2-ylcarbonyl)piperazin-1-yl)pyrrolidin-2-one | | 550.2 |

TABLE 1-44-continued

| | | | |
|---|---|---|---|
| 396 | 1-(1-benzoyl-2,3-dihydro-1H-indol-5-yl)-4-(4-(1,3-thiazol-2-ylcarbonyl)piperazin-1-yl)pyrrolidin-2-one | | 502.2 |
| 397 | 1-(1-(3-methylbutanoyl)-2,3-dihydro-1H-indol-5-yl)-4-(4-(1,3-thiazol-2-ylcarbonyl)piperazin-1-yl)pyrrolidin-2-one | | 482.2 |
| 398 | 1-(1-(cyclopropylacetyl)-2,3-dihydro-1H-indol-5-yl)-4-(4-(1,3-thiazol-2-ylcarbonyl)piperazin-1-yl)pyrrolidin-2-one | | 480.2 |

TABLE 1-45

| | | | |
|---|---|---|---|
| 399 | 4-(4-(1,3-thiazol-2-ylcarbonyl)piperazin-1-yl)-1-(1-(3,3,3-trifluoropropanoyl)-2,3-dihydro-1H-indol-5-yl)pyrrolidin-2-one | | 508.3 |
| 400 | 1-(1-(tetrahydro-2H-pyran-4-ylcarbonyl)-2,3-dihydro-1H-indol-5-yl)-4-(4-(1,3-thiazol-2-ylcarbonyl)piperazin-1-yl)pyrrolidin-2-one | | 510.2 |
| 401 | 1-(1-(tetrahydro-2H-pyran-4-ylacetyl)-2,3-dihydro-1H-indol-5-yl)-4-(4-(1,3-thiazol-2-ylcarbonyl)piperazin-1-yl)pyrrolidin-2-one | | 524.3 |

TABLE 1-45-continued

| | | | |
|---|---|---|---|
| 402 | (4R)-4-(4-(1,3-thiazol-2-ylcarbonyl)piperazin-1-yl)-1-(1-(5-(trifluoromethyl)pyridin-2-yl)-1H-pyrrolo[2,3-c]pyridin-5-yl)pyrrolidin-2-one | 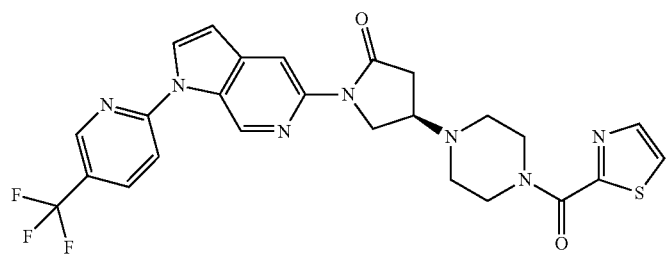 [SMILES: O=C(c1nccs1)N1CCN([C@@H]2CC(=O)N(c3cc4ccn(-c5ccc(C(F)(F)F)cn5)c4cn3)C2)CC1] | 542.2 |
| 403 | 1-(3-bromo-5-fluorophenyl)-4-(4-(pyrimidin-2-yl)piperazin-1-yl)pyrrolidin-2-one | 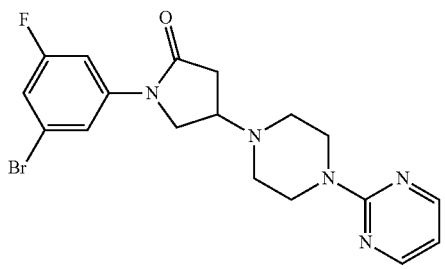 [SMILES: O=C1CC(N2CCN(c3ncccn3)CC2)CN1c1cc(F)cc(Br)c1] | 420.1 |
| 404 | 1-(4-fluoro-3-(2-methylpyridin-3-yl)phenyl)-4-(4-(pyrimidin-2-yl)piperazin-1-yl)pyrrolidin-2-one | 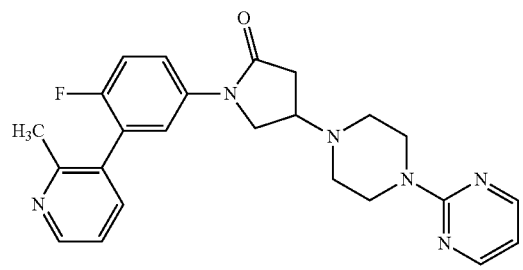 [SMILES: Cc1ncccc1-c1cc(N2CC(N3CCN(c4ncccn4)CC3)CC2=O)ccc1F] | 433.2 |
| 405 | (4R)-4-(4-(1,3-thiazol-4-ylcarbonyl)piperazin-1-yl)-1-(1-(4-(trifluoromethyl)phenyl)-2,3-dihydro-1H-indol-5-yl)pyrrolidin-2-one | 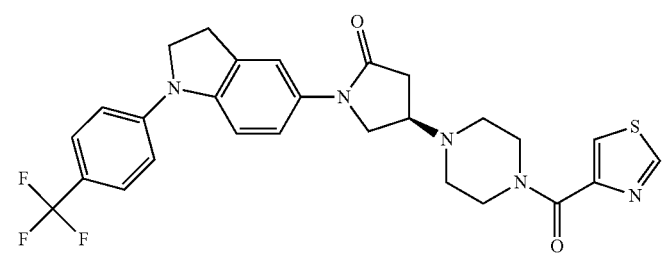 | 542.3 |
| 406 | 1-(3-fluoro-5-(2-methylpyridin-3-yl)phenyl)-4-(4-(pyrimidin-2-yl)piperazin-1-yl)pyrrolidin-2-one | 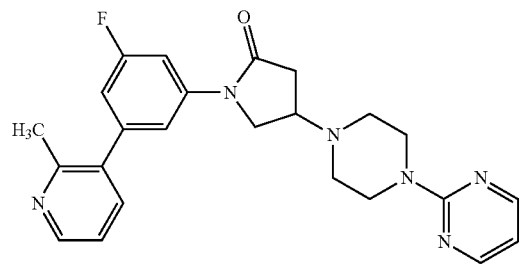 [SMILES: Cc1ncccc1-c1cc(F)cc(N2CC(N3CCN(c4ncccn4)CC3)CC2=O)c1] | 433.1 |
| 407 | (4R)-1-(1-(5-methoxypyrimidin-2-yl)-2,3-dihydro-1H-indol-5-yl)-4-(4-(1,3-thiazol-2-ylcarbonyl)piperazin-1-yl)pyrrolidin-2-one | 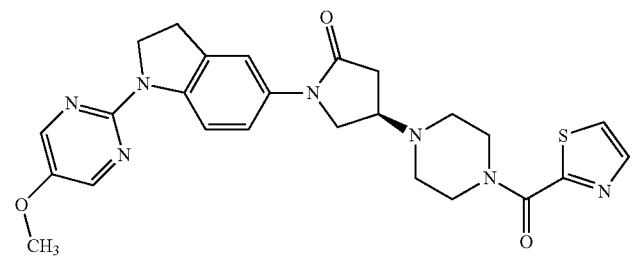 [SMILES: COc1cnc(N2CCc3cc(N4C[C@H](N5CCN(C(=O)c6nccs6)CC5)CC4=O)ccc32)nc1] | 506.2 |

TABLE 1-46

| | | | |
|---|---|---|---|
| 408 | tert-butyl 5-((4R)-2-oxo-4-(4-(1,3-thiazol-4-ylcarbonyl)piperazin-1-yl)pyrrolidin-1-yl)indoline-1-carboxylate | 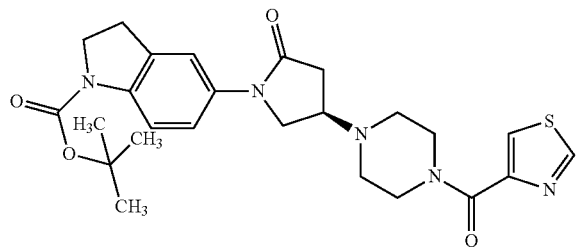 [SMILES: CC(C)(C)OC(=O)N1CCc2cc(N3C[C@H](N4CCN(C(=O)c5cscn5)CC4)CC3=O)ccc21] | 497.9 |
| 409 | 1-(1-(3,3-dimethylbutanoyl)-2,3-dihydro-1H-indol-5-yl)-4-(4-(pyrimidin-2-yl)piperazin-1-yl)pyrrolidin-2-one | 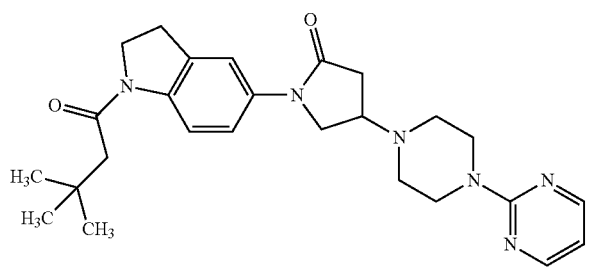 [SMILES: CC(C)(C)CC(=O)N1CCc2cc(N3CC(N4CCN(c5ncccn5)CC4)CC3=O)ccc21] | 463.2 |
| 410 | 1-(1-((6-methoxypyridin-3-yl)acetyl)-2,3-dihydro-1H-indol-5-yl)-4-(4-(pyrimidin-2-yl)piperazin-1-yl)pyrrolidin-2-one | 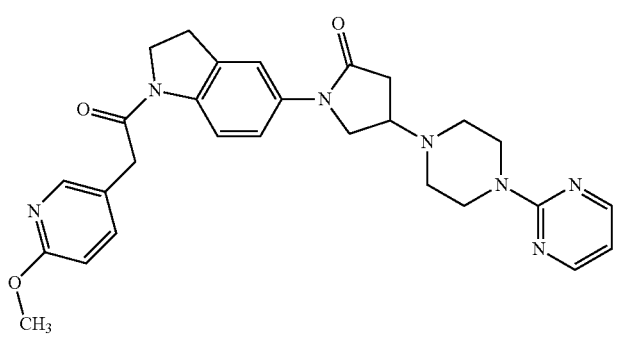 [SMILES: COc1ccc(CC(=O)N2CCc3cc(N4CC(N5CCN(c6ncccn6)CC5)CC4=O)ccc32)cn1] | 514.2 |
| 411 | 1-(1-((2-chloropyridin-4-yl)acetyl)-2,3-dihydro-1H-indol-5-yl)-4-(4-(pyrimidin-2-yl)piperazin-1-yl)pyrrolidin-2-one | 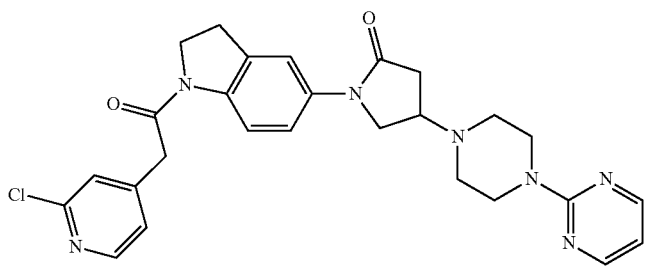 [SMILES: O=C1CC(N2CCN(c3ncccn3)CC2)CN1c1ccc2c(c1)CCN2C(=O)Cc1ccnc(Cl)c1] | 518.2 |
| 412 | 1-(1-((3-fluorophenyl)acetyl)-2,3-dihydro-1H-indol-5-yl)-4-(4-(pyrimidin-2-yl)piperazin-1-yl)pyrrolidin-2-one | 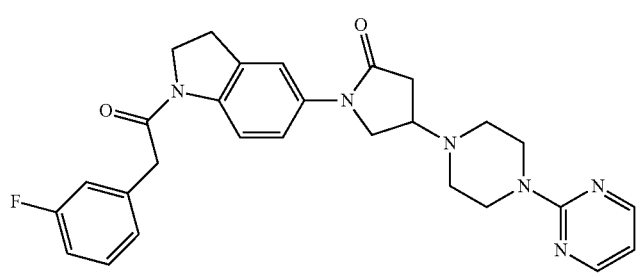 [SMILES: O=C1CC(N2CCN(c3ncccn3)CC2)CN1c1ccc2c(c1)CCN2C(=O)Cc1cccc(F)c1] | 501.2 |

TABLE 1-46-continued

| | | | |
|---|---|---|---|
| 413 | 1-(1-((4-fluorophenyl)acetyl)-2,3-dihydro-1H-indol-5-yl)-4-(4-(pyrimidin-2-yl)piperazin-1-yl)pyrrolidin-2-one | | 501.2 |
| 414 | (4R)-1-(1-(3,3-dimethylbutanoyl)-2,3-dihydro-1H-indol-5-yl)-4-(4-(1,3-thiazol-4-ylcarbonyl)piperazin-1-yl)pyrrolidin-2-one | | 496.2 |
| 415 | (4R)-1-(1-((4-chlorophenyl)acetyl)-2,3-dihydro-1H-indol-5-yl)-4-(4-(1,3-thiazol-4-ylcarbonyl)piperazin-1-yl)pyrrolidin-2-one | | 550.1 |
| 416 | (4R)-1-(1-((3-chlorophenyl)acetyl)-2,3-dihydro-1H-indol-5-yl)-4-(4-(1,3-thiazol-4-ylcarbonyl)piperazin-1-yl)pyrrolidin-2-one | | 550.1 |

TABLE 1-47

| | | | |
|---|---|---|---|
| 417 | 2-methyl-2-(4-(2-oxo-4-(4-(pyrimidin-2-yl)piperazin-1-yl)pyrrolidin-1-yl)phenyl)propanenitrile | | 391.2 |

TABLE 1-47-continued

| 418 | (4R)-4-(4-(1,3-thiazol-4-ylcarbonyl)piperazin-1-yl)-1-(1-(4-(trifluoromethyl)phenyl)-1H-indol-5-yl)pyrrolidin-2-one | | 540.2 |
| --- | --- | --- | --- |
| 419 | (4R)-4-(4-(1,3-thiazol-4-ylcarbonyl)piperazin-1-yl)-1-(1-(5-(trifluoromethyl)pyridin-2-yl)-1H-indol-5-yl)pyrrolidin-2-one | | 541.3 |
| 420 | (4R)-4-(4-(1,3-thiazol-4-ylcarbonyl)piperazin-1-yl)-1-(1-(5-(trifluoromethyl)pyridin-2-yl)-2,3-dihydro-1H-indol-5-yl)pyrrolidin-2-one | | 543.2 |
| 421 | (4R)-4-(4-(1,3-thiazol-4-ylcarbonyl)piperazin-1-yl)-1-(1-(3-(trifluoromethyl)phenyl)-1H-indol-5-yl)pyrrolidin-2-one | | 540.2 |
| 422 | (4R)-1-(1-(3-fluorophenyl)-1H-indol-5-yl)-4-(4-(1,3-thiazol-4-ylcarbonyl)piperazin-1-yl)pyrrolidin-2-one | | 490.1 |
| 423 | (4R)-1-(1-(4-chlorophenyl)-1H-indol-5-yl)-4-(4-(1,3-thiazol-4-ylcarbonyl)piperazin-1-yl)pyrrolidin-2-one | | 506.2 |

TABLE 1-47-continued

| 424 | (4R)-1-(3-fluoro-5-(2-methylpyridin-3-yl)phenyl)-4-(4-(1,3-thiazol-2-ylcarbonyl)piperazin-1-yl)pyrrolidin-2-one | 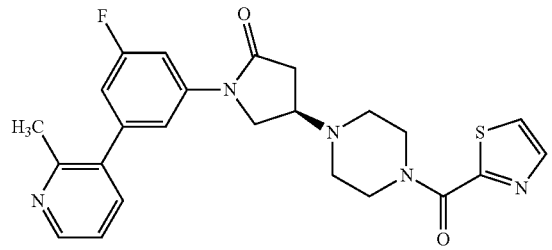 [SMILES: Cc1ncccc1-c1cc(F)cc(N2C[C@H](N3CCN(C(=O)c4nccs4)CC3)CC2=O)c1] | 466.1 |
| --- | --- | --- | --- |
| 425 | (4R)-4-(4-(1,3-thiazol-4-ylcarbonyl)piperazin-1-yl)-1-(1-(4-(trifluoromethyl)pyridin-2-yl)-1H-indol-5-yl)pyrrolidin-2-one | 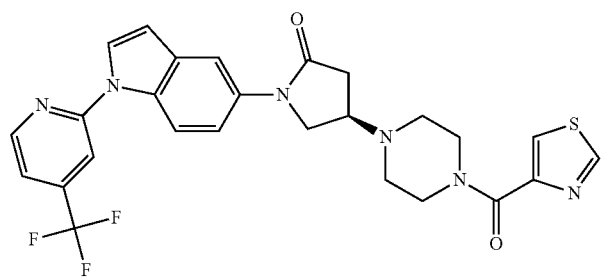 [SMILES: O=C(c1cscn1)N1CCN([C@@H]2CC(=O)N(c3ccc4c(ccn4-c4cc(C(F)(F)F)ccn4)c3)C2)CC1] | 541.3 |

TABLE 1-48

| 426 | (4R)-1-(3-fluoro-5-(2-methylpyridin-3-yl)phenyl)-4-(4-(pyrimidin-2-yl)piperazin-1-yl)pyrrolidin-2-one | 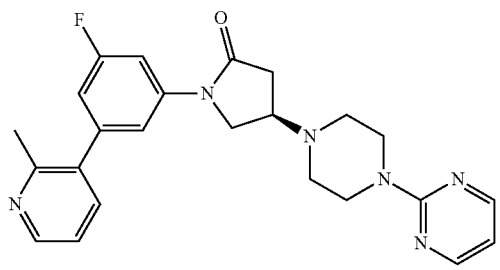 [SMILES: Cc1ncccc1-c1cc(F)cc(N2C[C@H](N3CCN(c4ncccn4)CC3)CC2=O)c1] | 433.2 |
| --- | --- | --- | --- |
| 427 | (4S)-1-(3-fluoro-5-(2-methylpyridin-3-yl)phenyl)-4-(4-(pyrimidin-2-yl)piperazin-1-yl)pyrrolidin-2-one | 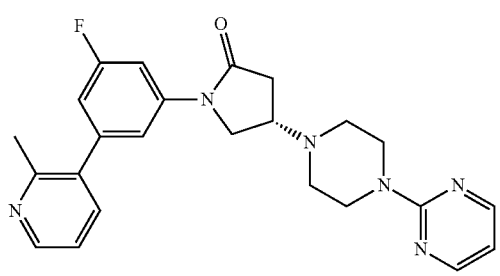 [SMILES: Cc1ncccc1-c1cc(F)cc(N2C[C@@H](N3CCN(c4ncccn4)CC3)CC2=O)c1] | 433.2 |
| 428 | (4R)-1-(1-(3-chlorophenyl)-1H-indol-5-yl)-4-(4-(1,3-thiazol-4-ylcarbonyl)piperazin-1-yl)pyrrolidin-2-one | 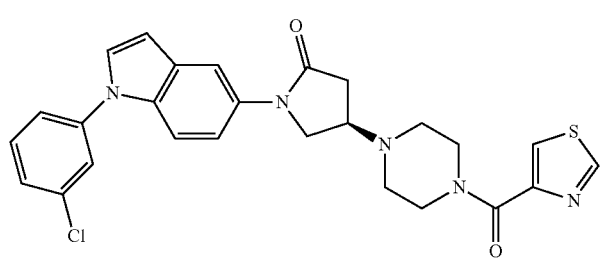 [SMILES: O=C(c1cscn1)N1CCN([C@@H]2CC(=O)N(c3ccc4c(ccn4-c4cccc(Cl)c4)c3)C2)CC1] | 506.2 |

TABLE 1-48-continued

| # | Name | Structure | MS |
|---|------|-----------|-----|
| 429 | (4R)-1-(1-(4-fluorophenyl)-2,3-dihydro-1H-indol-5-yl)-4-(4-(1,3-thiazol-4-ylcarbonyl)piperazin-1-yl)pyrrolidin-2-one | 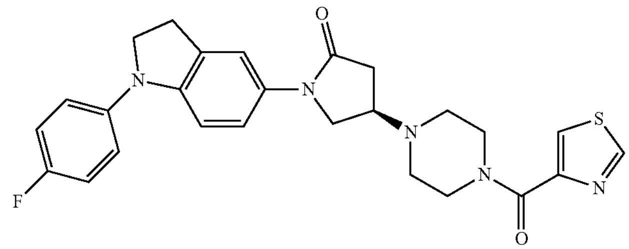 [SMILES: O=C(c1cscn1)N1CCN([C@@H]2CC(=O)N(c3ccc4c(c3)CCN4c3ccc(F)cc3)C2)CC1] | 492.2 |
| 430 | 4-(4-(pyrimidin-2-yl)piperazin-1-yl)-1-(1-(5-(trifluoromethyl)pyrimidin-2-yl)-2,3-dihydro-1H-indol-5-yl)pyrrolidin-2-one (optical isomer) | 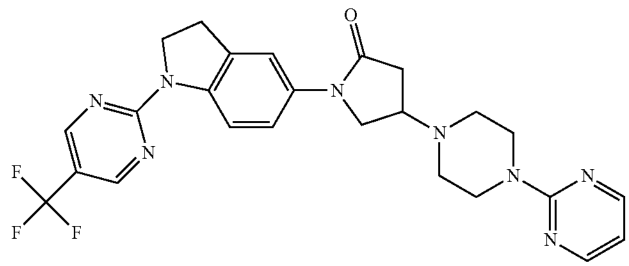 [SMILES: O=C1CC(N2CCN(c3ncccn3)CC2)CN1c1ccc2c(c1)CCN2c1ncc(C(F)(F)F)cn1] | 511.2 |
| 431 | 4-(4-(pyrimidin-2-yl)piperazin-1-yl)-1-(1-(5-(trifluoromethyl)pyrimidin-2-yl)-2,3-dihydro-1H-indol-5-yl)pyrrolidin-2-one (optical isomer) | 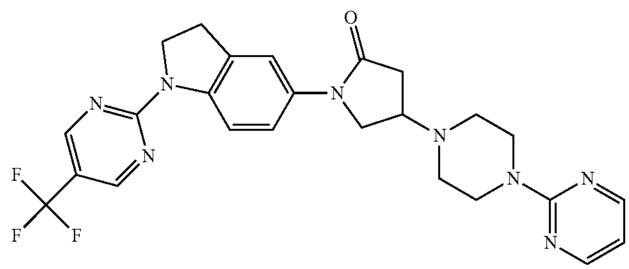 [SMILES: O=C1CC(N2CCN(c3ncccn3)CC2)CN1c1ccc2c(c1)CCN2c1ncc(C(F)(F)F)cn1] | 511.2 |
| 432 | (4R)-4-(4-(1,3-thiazol-4-ylcarbonyl)piperazin-1-yl)-1-(1-(5-(trifluoromethyl)pyrimidin-2-yl)-1H-indol-5-yl)pyrrolidin-2-one | 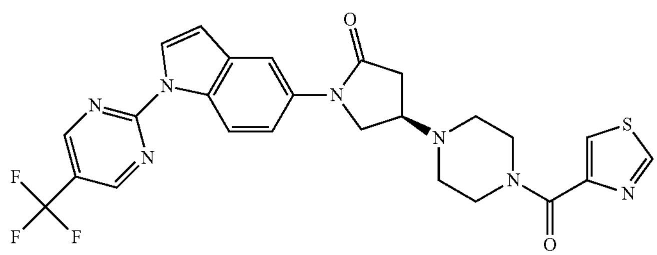 [SMILES: O=C(c1cscn1)N1CCN([C@@H]2CC(=O)N(c3ccc4c(ccn4-c4ncc(C(F)(F)F)cn4)c3)C2)CC1] | 542.2 |
| 433 | 4-(4-(pyrimidin-2-yl)piperazin-1-yl)-1-(1-(5-(trifluoromethyl)pyrimidin-2-yl)-1H-indol-5-yl)pyrrolidin-2-one | 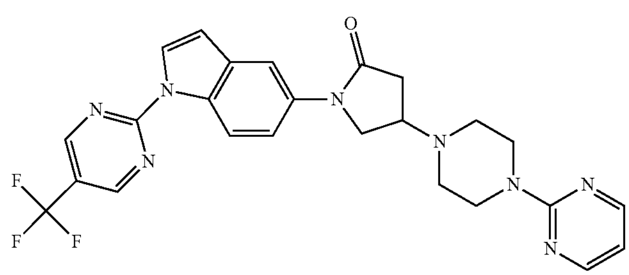 [SMILES: O=C1CC(N2CCN(c3ncccn3)CC2)CN1c1ccc2c(ccn2-c2ncc(C(F)(F)F)cn2)c1] | 509.3 |
| 434 | 5-methyl-4-(4-(1,3-thiazol-2-ylcarbonyl)piperazin-1-yl)-1-(1-(5-(trifluoromethyl)pyrimidin-2-yl)-1H-indol-5-yl)pyrrolidin-2-one | 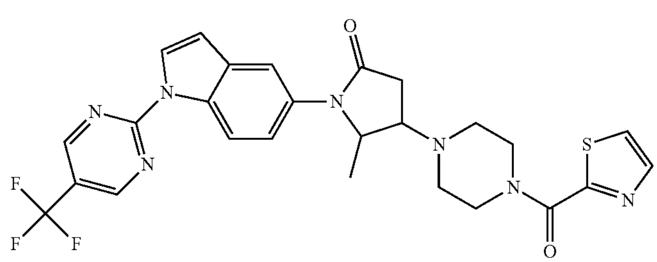 [SMILES: CC1C(N2CCN(C(=O)c3nccs3)CC2)CC(=O)N1c1ccc2c(ccn2-c2ncc(C(F)(F)F)cn2)c1] | 556.2 |

Experimental Example 1

Measurement of MAGL Inhibitory Activity

Experimental Example 1-1

Measurement of MAGL Inhibitory Activity by Absorbance (1) Cloning of Human MGLL Encoding MAGL Protein and Construction of Expression Plasmid Human MGLL cDNA was obtained by PCR using human ORF Clone (DNAForm; Clone ID: 100004585) as a template. For PCR, two kinds of primers:

[SEQ ID NO: 1]
5'-CCACCATCATCACGGATCCATGCCAGAGGAAAGTTCCCCCA-3'
and

[SEQ ID NO: 2]
5'-TGGTGCTCGAGTGCGGCCGCTCAGGGTGGGGACGCAGTTC-3' and PrimeSTAR MAX DNA Polymerase (Takara Bio Inc.) were used, and (1) reaction at 98° C. for 1 min, (2) 25 cycles of reaction at 98° C. for 10 sec and 68° C. for 10 sec as one cycle, and (3) reaction at 72° C. for 1 min were performed. The obtained PCR product was digested with Bam HI and Not I (Takara Bio Inc.), inserted into the Bam HI/Not I site of pET21HH(V) (pET21a (Novagen) inserted with His x6 and TEV Protease recognition sequence) by using Ligation High (Toyobo Co., Ltd.), and introduced into ECOS™ JM109 (Nippon Gene Co., Ltd.), whereby expression plasmid pET21HH(V)/His-hMGLLv2 for *Escherichia coli* was constructed.

(2) Preparation of Recombinant Polyhistidine Tagged Human MAGL Protein

Recombinant His-hMAGL protein was prepared by transforming ECOS™ Competent *E. coli* BL21(DE3) (Nippon Gene Co., Ltd.) with the pET21HH(V)/His-hMGLLv2 plasmid prepared above. *Escherichia coli* obtained by transformation was inoculated to 10 mL of LB medium (1% peptone, 0.5% yeast extract, 0.5% sodium chloride, 0.01% ampicillin), and cultured at 30° C. for 16 hr. The obtained culture medium (5 mL) was transplanted into a 2 L Sakaguchi flask containing 1 L of main fermentation medium (1.05% M9 MEDIUM BROTH (AMRESCO LLC), 0.5% yeast extract, 1.5% sorbitol, 1.5% casamino acid, 0.024% magnesium sulfate, 0.01% antifoaming agent PE-L (Wako Pure Chemical Industries, Ltd.), 0.01% ampicillin), and shaking culture at 37° C., 150 rpm was started. When the turbidity of the culture medium reached about 500 Klett unit, the culture temperature was lowered to 16° C., isopropyl-β-D-thiogalactopyranoside (IPTG) was added to a final concentration of 1 mM, and the mixture was further cultured for 19 hr. After the completion of culture, the culture medium was centrifuged (4° C., 6,000 rpm, 10 min) to give His-hMAGL expression *Escherichia coli*. Then, His-hMAGL expression *Escherichia coli* was suspended in 50 mM Tris-HCl (pH 8.0, 100 ml) containing 1% Triton X-100, 20 mM imidazole, 3 mM DTT, 5 U/mL Benzonase (Merck) and 150 mM NaCl, sufficiently cooled, and subjected to sonication at AMPLITUDE=60%, 15 sec/ON, 30 sec/OFF for 3 min using ¾" solid type crushed horn of BRANSON Digital Sonifier 450 (Central Scientific Commerce, Inc.). Furthermore, the homogenate was centrifuged (4° C., 15,000 rpm, 15 min) and the supernatant was obtained. As the purification apparatus, AKTA explorer 10s (GE Healthcare Japan Corporation) was used at 4° C. To the obtained supernatant was added 5M NaCl to the final salt concentration of 0.3 M, and the mixture was flown through and adsorbed to 5 mL of Ni-NTA Superflow Cartridges (QIAGEN) equilibrated in advance with buffer A (50 mM Tris-HCl (pH 8.0) containing 0.05% TritonX-100, 1 mM DTT, 300 mM NaCl). The column was sufficiently washed with buffer A containing 20 mM imidazole and His-hMAGL was eluted with buffer A containing imidazole at a final concentration of 250 mM. The eluate was further subjected to gel filtration using HiLoad 26/600 Superdex 200 pg (GE Healthcare Japan Corporation) equilibrated with 50 mM Tris-HCl pH 8.0 containing 10% glycerol, 0.05% TritonX-100, 1 mM DTT, 150 mM NaCl. The eluted fraction was concentrated by Amicon Ultra-15 10K (Merck Millipore) to give purified His-hMAGL protein. The protein concentration was measured by BCA Protein Assay Kit (Thermo Fisher Scientific) using BSA as the standard.

(3) Measurement of MAGL Inhibitory Activity

His-hMAGL obtained above was diluted with enzyme reaction buffer (10 mM Tris-HCl, pH 7.5, 1 mM EDTA, 0.1 (w/v) % Triton X-100) to a concentration of 60 ng/mL. To each well of a 384 well assay plate (Nunc 262160) was added a solution (5 μL) of a test compound dissolved in dimethyl sulfoxide (DMSO), which was diluted with the above-mentioned enzyme reaction buffer, then His-hMAGL solution (5 μL) diluted to a concentration of 60 ng/mL was added and the mixture was incubated at room temperature for 60 min. Thereafter, to each well was added 750 μM p-nitrophenyl acetate (Wako Pure Chemical Industries, Ltd.) by 5 μL, and the absorbance at 405 nm was measured every 2 minutes up to 10 minutes by EnVision (PerkinElmer). The amount of change was obtained by subtracting the absorbance measured immediately after the start of the reaction from the absorbance measured 10 min after the start of the reaction.

MAGL inhibitory rate (%) was calculated according to the following calculation formula.

(1−(absorbance change amount of test compound addition group−absorbance change amount of enzyme addition-free group)÷(absorbance change amount of test compound addition-free group−absorbance change amount of enzyme addition-free group))×100

The results are shown in the following Table 2.

TABLE 2

| Example | Inhibition at 10 μM (%) |
|---|---|
| 1 | 98 |
| 2 | 96 |
| 4 | 96 |
| 6 | 93 |
| 7 | 87 |
| 8 | 93 |
| 11 | 99 |
| 12 | 98 |
| 13 | 98 |
| 14 | 98 |
| 15 | 99 |
| 18 | 96 |
| 19 | 91 |
| 20 | 93 |
| 21 | 69 |
| 22 | 97 |
| 23 | 99 |
| 36 | 95 |
| 38 | 99 |
| 44 | 97 |
| 45 | 97 |

TABLE 2-continued

| Example | Inhibition at 10 μM (%) |
|---|---|
| 47 | 96 |
| 51 | 97 |
| 52 | 97 |
| 53 | 98 |
| 54 | 93 |
| 57 | 90 |
| 58 | 97 |
| 59 | 97 |
| 60 | 98 |
| 62 | 98 |
| 63 | 95 |
| 64 | 90 |
| 65 | 93 |
| 66 | 91 |
| 70 | 91 |
| 71 | 90 |
| 72 | 92 |
| 75 | 95 |
| 76 | 95 |
| 77 | 96 |
| 79 | 95 |
| 80 | 100 |
| 81 | 97 |
| 82 | 95 |
| 83 | 96 |
| 84 | 96 |
| 85 | 99 |
| 86 | 99 |
| 87 | 98 |

Experimental Example 1-2

Measurement of MAGL Inhibitory Activity by Mass Spectrometry

His-hMAGL obtained in the above-mentioned Experimental Example 1-1 (1) and (2) was diluted with enzyme reaction buffer (10 mM Tris-HCl, pH 7.5, 1 mM EDTA, 0.025 (w/v) % Triton X-100, 0.01% Bovine serum albumin) to a concentration of 7.5 ng/mL. To each well of a 384 well assay plate (Greiner 781280) was added a solution (5 μL) of a test compound dissolved in dimethyl sulfoxide (DMSO), which was diluted with the above-mentioned enzyme reaction buffer, then His-hMAGL solution (5 μL) diluted to a concentration of 7.5 ng/mL was added and the mixture was incubated at room temperature for 60 min. Thereafter, to each well was added 150 μM 2-arachidonylglycerol (Tocris Bioscience) by 5 μL, and the mixture was incubated at room temperature for 10 min. Then, 2% formic acid (Wako Pure Chemical Industries, Ltd.) was added by 10 μL to discontinue the reaction. Furthermore, acetonitrile (50 μL) containing 3 μM arachidonic acid-d8 (Cayman Chemical Company) was added and the mixture was stirred.

The amount of arachidonic acid in the obtained enzyme reaction mixture was calculated by measuring by RapidFire-mass spectrometry and correcting by the amount of arachidonic acid-d8. High Throughput online solid phase extraction was performed using RapidFire 300TM system (Agilent Technologies, Inc.). Samples were loaded on SPE C4 cartridge (Agilent Technologies, Inc.) and desalted with 0.2 (v/v) % acetic acid (Wako Pure Chemical Industries, Ltd.) in ultrapure water/acetonitrile (70/30, v/v) at a flow rate of 1.5 mL/min, eluted at a flow rate of 0.5 mL/min with 0.2 (v/v) % acetic acid dissolved in acetonitrile/ultrapure water (90/10, v/v), and injected into the mass spectrometry part. The injection needle was washed with ultrapure water (500 millisecond) and acetonitrile (500 millisecond) to minimize carry-over. The suction time (injection loop 5 μL), load/cleansing time, elution time, and re-equilibration time were adjusted to 300, 3000, 4250, and 1000 milliseconds, respectively, and the total cycle time was adjusted to about 10.0 seconds. The RapidFire300 system was controlled by RapidFire UI software version 3.6 (Agilent Technologies, Inc.).

The mass spectrometry of the resultant product was performed using API4000TM triple quadrupole mass spectrometer (AB SCIEX) equipped with an electrospray ion sauce (Turbolon Spray™) in a negative selected reaction monitoring (SRM) mode. The conditions of SRM are shown below. The parameters of the instrument were optimized as follows: capillary temperature 600° C., ion spray voltage −4.5 kV, collision gas 8, curtain gas 15 psi, ion source gas 1 60 psi, ion source gas 2 60 psi. The mass spectrometer was controlled by Analyst™ software version 1.5.1 (AB SCIEX). The peak area integration was analyzed using RapidFire integrator software version 3.6 (Agilent Technologies, Inc.).

MAGL inhibitory rate (%) was calculated according to the following calculation formula.

(1−(arachidonic acid production amount of test compound addition group−arachidonic acid production amount of enzyme addition-free group)+(arachidonic acid production amount of test compound addition-free group−arachidonic acid production amount of enzyme addition-free group))×100

The 50% inhibitory concentration (IC50) was calculated by fitting using Xlfit (IDBS Ltd.) and dose response one site 4 parameter logistic model.

The results are shown in the following Tables 3-1-3-4.

TABLE 3-1

| Exampe | % inhibition at 10 μM |
|---|---|
| 80 | 97 |
| 89 | 99 |
| 90 | 102 |
| 91 | 102 |
| 92 | 100 |
| 93 | 101 |
| 94 | 99 |
| 95 | 99 |
| 96 | 99 |
| 97 | 97 |
| 98 | 100 |
| 99 | 102 |
| 100 | 101 |
| 101 | 99 |
| 102 | 96 |
| 103 | 100 |
| 104 | 95 |
| 105 | 101 |
| 106 | 99 |
| 108 | 97 |
| 109 | 100 |
| 110 | 99 |
| 111 | 99 |
| 112 | 06 |
| 113 | 80 |
| 114 | 98 |
| 115 | 97 |
| 116 | 99 |
| 117 | 99 |
| 118 | 99 |
| 119 | 100 |
| 122 | 98 |
| 123 | 97 |
| 126 | 97 |
| 127 | 99 |
| 128 | 101 |
| 129 | 101 |
| 131 | 91 |

TABLE 3-1-continued

| Exampe | % inhibition at 10 μM |
|---|---|
| 132 | 101 |
| 133 | 102 |
| 134 | 100 |
| 135 | 100 |
| 136 | 102 |
| 137 | 101 |
| 138 | 101 |
| 139 | 101 |
| 140 | 100 |
| 141 | 98 |
| 142 | 100 |
| 143 | 102 |
| 144 | 101 |
| 145 | 102 |
| 146 | 100 |
| 148 | 95 |
| 149 | 96 |
| 150 | 96 |
| 151 | 99 |
| 152 | 99 |
| 153 | 97 |
| 154 | 101 |
| 155 | 99 |
| 156 | 100 |
| 157 | 99 |
| 158 | 99 |
| 150 | 83 |
| 160 | 91 |
| 161 | 100 |
| 162 | 99 |
| 165 | 100 |
| 166 | 99 |
| 167 | 94 |
| 168 | 101 |
| 169 | 97 |
| 170 | 98 |
| 171 | 99 |
| 172 | 102 |
| 173 | 91 |
| 174 | 100 |
| 175 | 101 |
| 176 | 100 |
| 177 | 80 |
| 178 | 81 |

TABLE 3-2

| Example | % inhibition at 10 μM |
|---|---|
| 179 | 98 |
| 180 | 94 |
| 181 | 94 |
| 182 | 92 |
| 184 | 98 |
| 185 | 100 |
| 186 | 98 |
| 187 | 96 |
| 188 | 99 |
| 189 | 97 |
| 191 | 96 |
| 193 | 97 |
| 194 | 96 |
| 196 | 83 |
| 197 | 89 |
| 199 | 101 |
| 200 | 98 |
| 201 | 84 |
| 202 | 102 |
| 203 | 99 |
| 204 | 101 |
| 205 | 100 |
| 206 | 98 |
| 207 | 97 |
| 208 | 101 |
| 209 | 96 |

TABLE 3-2-continued

| Example | % inhibition at 10 μM |
|---|---|
| 210 | 91 |
| 212 | 100 |
| 213 | 100 |
| 214 | 93 |
| 215 | 101 |
| 216 | 97 |
| 217 | 98 |
| 218 | 99 |
| 219 | 102 |
| 220 | 103 |
| 221 | 101 |
| 222 | 98 |
| 223 | 101 |
| 224 | 100 |
| 228 | 96 |
| 229 | 100 |
| 230 | 101 |
| 231 | 100 |
| 232 | 99 |
| 234 | 98 |
| 235 | 100 |
| 238 | 100 |
| 239 | 100 |
| 240 | 99 |
| 241 | 96 |
| 242 | 99 |
| 243 | 100 |
| 244 | 98 |
| 245 | 98 |
| 246 | 98 |
| 247 | 99 |
| 248 | 103 |
| 249 | 96 |
| 250 | 101 |
| 251 | 102 |
| 252 | 103 |
| 253 | 101 |
| 254 | 95 |
| 255 | 101 |
| 256 | 102 |
| 257 | 99 |
| 258 | 102 |
| 260 | 84 |
| 261 | 100 |
| 262 | 97 |
| 263 | 87 |
| 264 | 92 |
| 265 | 97 |
| 266 | 99 |
| 267 | 102 |
| 268 | 101 |
| 269 | 101 |
| 270 | 100 |
| 271 | 101 |
| 272 | 101 |
| 273 | 100 |

TABLE 3-3

| Example | % inhibition at 10 μM |
|---|---|
| 274 | 96 |
| 275 | 103 |
| 276 | 102 |
| 277 | 98 |
| 278 | 100 |
| 279 | 101 |
| 280 | 101 |
| 281 | 99 |
| 282 | 100 |
| 283 | 101 |
| 284 | 101 |
| 285 | 101 |
| 286 | 91 |
| 287 | 103 |

TABLE 3-3-continued

| Example | % inhibition at 10 μM |
|---|---|
| 288 | 97 |
| 289 | 103 |
| 290 | 101 |
| 291 | 104 |
| 292 | 93 |
| 293 | 103 |
| 294 | 100 |
| 295 | 98 |
| 296 | 102 |
| 297 | 103 |
| 298 | 101 |
| 299 | 102 |
| 300 | 101 |
| 301 | 104 |
| 302 | 98 |
| 303 | 88 |
| 304 | 100 |
| 305 | 96 |
| 306 | 102 |
| 307 | 103 |
| 308 | 98 |
| 309 | 103 |
| 310 | 98 |
| 311 | 103 |
| 312 | 101 |
| 313 | 101 |
| 314 | 104 |
| 315 | 101 |
| 316 | 97 |
| 317 | 99 |
| 318 | 103 |
| 319 | 102 |
| 320 | 100 |
| 321 | 102 |
| 322 | 103 |
| 323 | 100 |
| 324 | 101 |
| 325 | 101 |
| 326 | 105 |
| 327 | 100 |
| 328 | 102 |
| 329 | 104 |
| 330 | 101 |
| 331 | 101 |
| 332 | 100 |
| 333 | 83 |
| 334 | 103 |
| 335 | 101 |
| 336 | 100 |
| 337 | 99 |
| 338 | 98 |
| 339 | 100 |
| 340 | 99 |
| 341 | 101 |
| 342 | 100 |
| 343 | 101 |
| 344 | 98 |
| 345 | 97 |
| 346 | 99 |
| 347 | 100 |
| 348 | 99 |
| 349 | 98 |
| 350 | 104 |
| 351 | 100 |
| 352 | 102 |
| 353 | 101 |
| 354 | 101 |
| 355 | 98 |

TABLE 3-4

| Example | % inhibition at 10 μM |
|---|---|
| 356 | 98 |
| 357 | 101 |
| 358 | 102 |
| 359 | 96 |
| 361 | 92 |
| 362 | 92 |
| 363 | 96 |
| 365 | 98 |
| 366 | 100 |
| 368 | 97 |
| 370 | 101 |
| 371 | 104 |
| 372 | 101 |
| 373 | 96 |
| 374 | 81 |
| 375 | 95 |
| 377 | 97 |
| 378 | 95 |
| 379 | 97 |
| 380 | 102 |
| 382 | 99 |
| 383 | 98 |
| 384 | 99 |
| 385 | 100 |
| 386 | 99 |
| 387 | 97 |
| 388 | 99 |
| 389 | 98 |
| 390 | 96 |
| 391 | 90 |
| 392 | 99 |
| 393 | 93 |
| 394 | 98 |
| 395 | 102 |
| 396 | 97 |
| 397 | 101 |
| 398 | 100 |
| 399 | 95 |
| 400 | 96 |
| 401 | 94 |
| 402 | 94 |
| 403 | 91 |
| 404 | 96 |
| 405 | 103 |
| 406 | 98 |
| 407 | 104 |
| 408 | 103 |
| 409 | 94 |
| 410 | 80 |
| 413 | 94 |
| 414 | 100 |
| 415 | 97 |
| 416 | 99 |
| 418 | 96 |
| 419 | 96 |
| 420 | 89 |
| 421 | 100 |
| 422 | 99 |
| 423 | 98 |
| 424 | 98 |
| 425 | 100 |
| 426 | 99 |
| 428 | 100 |
| 429 | 100 |
| 430 | 85 |
| 432 | 100 |
| 433 | 83 |
| 434 | 100 |

Experimental Example 2

Measurement of Intracerebral 2-AG and AA

As the mouse, 8-week-old male C57BL/6J mice (CLEA Japan, Inc.) were used (3 mice/group). Administration solutions were prepared by suspending the test compounds (compound 1 (Example 80), compound 2 (Example 205), compound 3 (Example 418), compound 4 (Example 426)) in 0.5% methylcellulose solution (Wako Pure Chemical Industries, Ltd.). The dose of the test compound was prepared to be 10 mg/kg/10 mL (compounds 1, 3 and 4) or 30 mg/kg/10 mL (compound 2). The test compounds were administered by gavage at 10 mg/kg or 30 mg/kg. The cerebrum was isolated 1 hr after the administration of the test compound, and the cerebrum hemisphere was extracted. The obtained cerebrum hemisphere was frozen on dry ice, and the frozen tissue weight was measured.

The cerebrum hemisphere was homogenized with 9-fold (v/w) of isopropanol, and then centrifuged by 15000 rpm for 5 min. The supernatant, 5 µL, was mixed with 5 µL of internal standard solution (5Z, 8Z, 11Z, 14Z-eicosatetraenoic-5, 6, 8, 9, 11, 12, 14, 15-$d_8$ acid (AA-$d_8$, 10 nmol/mL) and 5Z, 8Z, 11Z, 14Z-eicosatetraenoic-5, 6, 8, 9, 11, 12, 14, 15-$d_8$ acid 2-glyceryl ester (2-AG-$d_8$, 10 nmol/mL) in isopropanol) and 90 µl of isopropanol. The sample solution was applied to a high-performance liquid chromatography/tandem mass spectrometry (LC/MS/MS) analysis. Five microliter of the sample solution was injected to the liquid chromatography system, for which Ultimate 3000 RSLC system (Thermo Fisher Scientific, San Jose, Calif.) was selected. Chromatographic separation was performed by a gradient elution on a reverse phase column, Xbridge C18 (2.5 µm, 2.1×50 mm, Waters, Milford, Mass.), under the column temperature of 60° C. The solvent system consisted of 0.01% acetic acid-1 mM $NH_3$-2 µM EDTA-2Na in distilled water (solvent A) and 0.001% acetic acid-0.2 mM $NH_3$ in ethanol-isopropanol (3:2, v/v) (solvent B) with a flow rate of 0.5 mL/min. The following gradient program was applied to the chromatographic separation: 0-1 min, 1% solvent B; 1-1.2 min, 1 to 55% solvent B; 1.2-2.7 min, 55 to 75% solvent B; 2.7-3.5 min, 75 to 99% solvent B; 3.5-6 min, 99% solvent B; and 6-8 min, 1% solvent B. The eluate from the liquid chromatography system was directly introduced to an electrospray ionization on TSQ Vantage mass spectrometer (Thermo Fisher Scientific, San Jose, Calif.) with a simultaneous polarity switching, where arachidonic acid (AA) and its internal standard (AA-$d_8$) were ionized by negative ionization mode, and 2-arachidonyl glycerol (2-AG) and its internal standard (2-AG-$d_8$) were ionized by positive ionization mode. Detection condition of the mass spectrometer is shown in Table 4.

Working solution for a calibration curve was prepared by dilution of a stock solution to the final concentration of 0.1, 0.5, 1, 2, 5, 10, 25, 50 and 100 nmol/mL of isopropanol. Five microliter of the working solution was mixed with 5 µL of the internal standard solution and 90 µL of isopropanol, and then the mixed solution was applied to the preparation of calibration curve. The calibration curve was drawn with a weighting of 1/x, and confirmed by assessing the accuracy within a range of ±15% and the linearity of $R^2>0.995$.

TABLE 4

Selected-ion-monitoring (SRM) parameters for specific detection of analytes by mass spectrometer

| Analytes | polarity | Q1 | Q3 | CE | S-Lens |
|---|---|---|---|---|---|
| Arachidonic acid | − | 303.2 | 303.2 | 12 | 90 |
| Arachidonic acid-$d_8$ | − | 311.3 | 311.3 | 13 | 90 |

TABLE 4-continued

Selected-ion-monitoring (SRM) parameters for specific detection of analytes by mass spectrometer

| Analytes | polarity | Q1 | Q3 | CE | S-Lens |
|---|---|---|---|---|---|
| 2-Arachidonyl glycerol | + | 379.3 | 91 | 46 | 70 |
| 2-Arachidonyl glycerol-$d_8$ | + | 387.3 | 294.3 | 12 | 80 |

Q1: Precursor ion (m/z),
Q3: Product ion (m/z),
CE: Collision energy (V),
S-Lens: Stacked lens (V)

The amount of change was calculated based on the value obtained for the control group (0.5% methylcellulose solution administration group) as 1.

Figure 2:
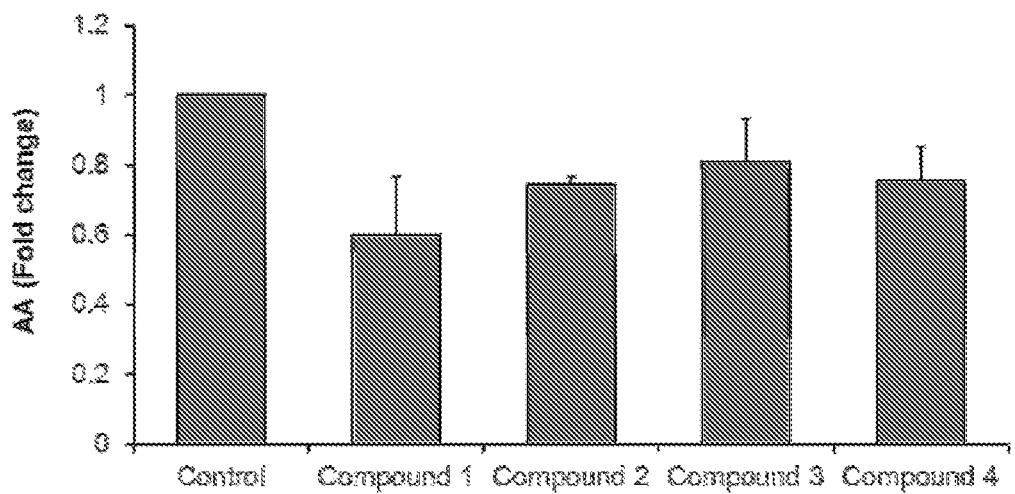
FIG. 2 shows an effect of compounds 1-4 to decrease AA.

The results are shown in FIGS. 1 and 2.

Experimental Example 3

Measurement of Gene Expression in Hippocampus of Kainic Acid Intraventricular Administration Rat As the rat, 5-week-old male SD rats (Charles River Laboratories Japan, Inc.) were used (5 rats/group). Saline (0.2 mg/mL, Otsuka Pharmaceutical Co., Ltd.) or kainic acid (0.2 mg/mL, Sigma-Aldrich Co. LLC) were each administered (1.5 µL, 0.2 µL/min) into the lateral cerebral ventricle by using an infusion pump. The test compound (compound 1 (Example 80)) was suspended in 0.5% methylcellulose solution (Wako Pure Chemical Industries, Ltd.) at 30 mg/kg/5 mL and administered by gavage into the lateral cerebral ventricle immediately before administration of kainic acid.

The cerebrum was isolated 24 hr after the administration of the test compound, and hippocampus was extracted. The obtained cerebrum hemisphere was frozen on dry ice. Frozen hippocampus was placed in a tube, 700 µL of QIAzol solution (QIAGEN) was added, and the mixture was homogenized. 280 µL of chloroform (Wako Pure Chemical Industries, Ltd.) was added, and the mixture was stirred. The mixture was centrifuged (4° C., 15,000 rpm, 15 min), and the upper layer was recovered. An equal amount of 70% ethanol solution was added, and the mixture was stirred. The mixture was applied to RNeasy column (QIAGEN) and centrifuged (10,000 rpm, 1 min). 350 µL of RW1 solution (QIAGEN) was added to the column, and the mixture was centrifuged (10,000 rpm, 1 min). 80 µL of DNase solution (QIAGEN) was added to the column, and the mixture was reacted at room temperature for 15 min. 350 µL of RW1 solution was added to the column, and the mixture was centrifuged (10,000 rpm, 1 min). 500 µL of RPE solution (QUIAGEN) was added to the column, and the mixture was centrifuged (10,000 rpm, 1 min). 60 µL RNase-free water (QUIAGEN) was added to the column, and the mixture was stood at room temperature for 5 min and centrifuged (10,000 rpm, 1 min). The concentration of the obtained RNA was quantified by Nanodrop ND-8000 (Thermo Fisher Scientific).

The reaction mixture was prepared using TaqMan RNA-to-CT 1-Step Kit (Life Technologies) and the obtained RNA as a template. As an endogenous control gene, Gapdh gene was used. For one reaction, 3 µL RNA solution (200 ng/µL), 5 µL TaqMan RT-PCR Mix (2×), 0.25 µL TaqMan RT Enzyme Mix (40×), 0.75 µL sterilization distilled water, 0.5 µL TaqMan Gene Expression Assay (Life Technologies), 0.5 µL Rat Gapdh TaqMan Endogenous Control (Life Technologies), total 10 µL, were prepared, and dispensed to one well of a 384 well plate. TaqMan probe set used for the real-time PCR analysis was TaqMan Gene Expression Assay (Life Technologies). ID corresponding to each gene is as follows.

Gfap: Rn00566603_m1
IL-1β: Rn00580432_m1
IL-6: Rn01410330_m1

The real-time PCR reaction was performed using ViiA 7 real-time PCR system (Life Technologies). After reaction at 48° C. for 15 min, 95° C. for 10 min, the reactions of 1) 95° C. for 10 sec and 2) 60° C. for 1 min were repeated 40 times. Analysis was performed using ViiA 7 software (Life Technologies). The gene expression level was calculated by subtracting the Ct value of Gapdh gene which is an endogenous control gene from the Ct value of each gene obtained by real-time PCR reaction (ΔCt), and further multiplying the value by 2(-ΔCt). The amount of change was calculated based on the value obtained for the control group (0.5% methylcellulose solution and saline in the lateral cerebral ventricle administration group) as 1.

Figure 3:
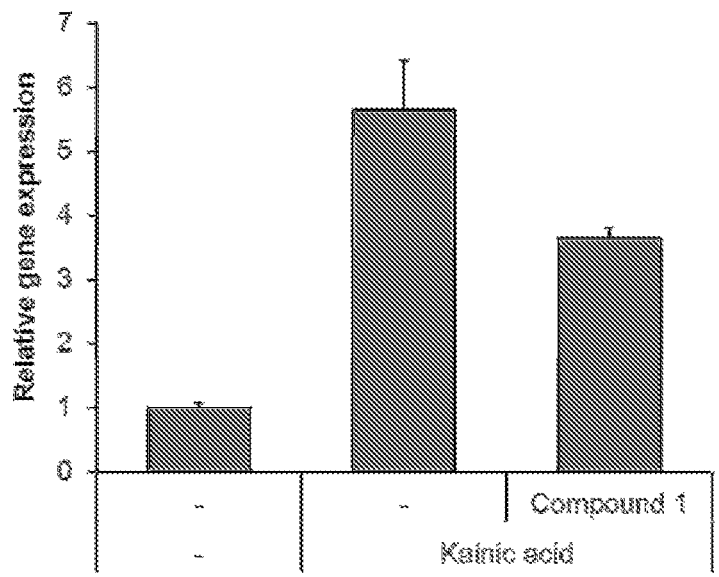
FIG. 3 shows an effect of compound 1 to decrease expression of a gene of glial fibrillary acidic protein (GFAP).
Figure 4:
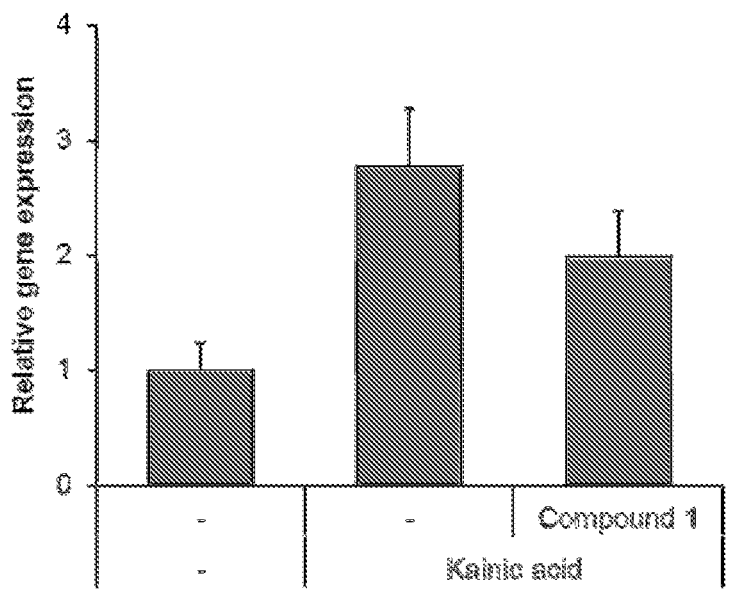
FIG. 4 shows an effect of compound 1 to decrease expression of a gene of interleukin 1β (IL-1β).
Figure 5:
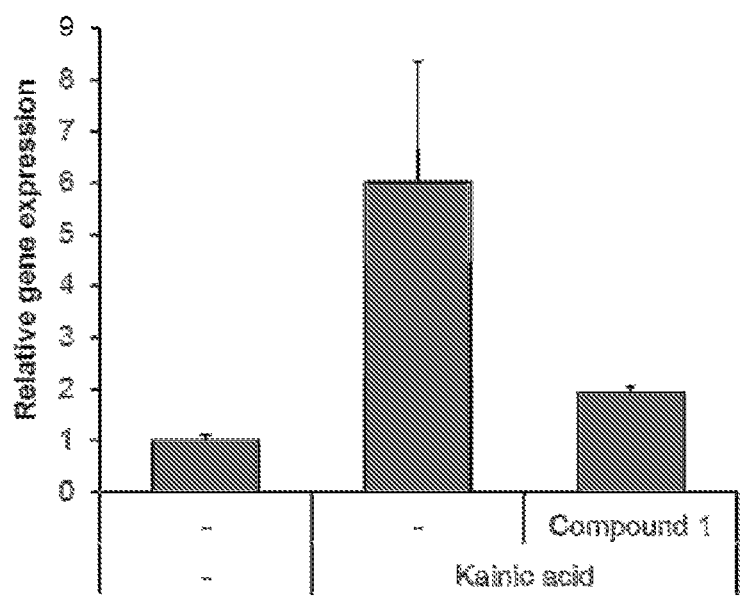
FIG. 5 shows an effect of compound 1 to decrease expression of a gene of interleukin 6 (IL-6).

The results are shown in FIGS. 3-5.

Preparation Examples

Medicaments containing the compound of the present invention as an active ingredient can be produced, for example, by the following formulations.

2. tablet

| | |
|---|---|
| (1) compound obtained in Example 1 | 10 mg |
| (2) lactose | 35 mg |
| (3) cornstarch | 150 mg |
| (4) microcrystalline cellulose | 30 mg |
| (5) magnesium stearate | 5 mg |
| 1 tablet | 230 mg |

The total amount of the above-mentioned (1), (2) and (3), 20 mg of (4) and 2.5 mg of (5) are blended and granulated, and 10 mg of the remaining (4) and 2.5 mg of (5) are added and the mixture is compression formed to give a tablet.

INDUSTRIAL APPLICABILITY

According to the present invention, a compound having an MAGL inhibitory action, and useful as a prophylactic or therapeutic agent neurodegenerative diseases (e.g., Alzheimer's disease, Huntington's disease, Parkinson's disease, amyotrophic lateral sclerosis, traumatic brain injury, glaucoma, multiple sclerosis and the like), anxiety disorder, pain (e.g., inflammatory pain, carcinomatous pain, nervous pain and the like), epilepsy and the like can be provided.

This application is based on a patent application No. 2013-269244 filed in Japan (filing date: Dec. 26, 2013), the contents of which are incorporated in full herein.

SEQUENCE LISTING

```
<160> NUMBER OF SEQ ID NOS: 2

<210> SEQ ID NO 1
<211> LENGTH: 41
<212> TYPE: DNA
<213> ORGANISM: Artificial Sequence
<220> FEATURE:
<223> OTHER INFORMATION: primer

<400> SEQUENCE: 1
ccaccatcat cacggatcca tgccagagga aagttccccc a                          41

<210> SEQ ID NO 2
<211> LENGTH: 40
<212> TYPE: DNA
<213> ORGANISM: Artificial Sequence
<220> FEATURE:
<223> OTHER INFORMATION: primer

<400> SEQUENCE: 2
tggtgctcga gtgcggccgc tcagggtggg gacgcagttc                            40
```

1. capsule

| | |
|---|---|
| (1) compound obtained in Example 1 | 10 mg |
| (2) lactose | 90 mg |
| (3) microcrystalline cellulose | 70 mg |
| (4) magnesium stearate | 10 mg |
| 1 capsule | 180 mg |

The total amount of the above-mentioned (1), (2) and (3) and 5 mg of (4) are blended and granulated, and 5 mg of the remaining (4) is added. The whole mixture is sealed in a gelatin capsule.

The invention claimed is:

1. A compound represented by the formula (I):

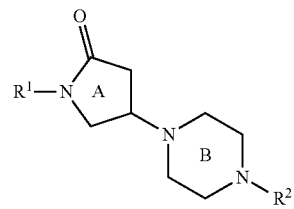

(I)

wherein ring A is a pyrrolidin-2-one ring optionally substituted by 1 or 2 additional substituents selected from a halogen atom, a cyano group, a hydroxy group, a $C_{1-6}$ alkoxy group, a $C_{2-6}$ alkenyloxy group, a $C_{3-10}$ cycloalkyloxy group, a $C_{6-14}$ aryloxy group, a $C_{7-16}$ aralkyloxy group, a $C_{1-6}$ alkyl-carbonyloxy group, a $C_{6-14}$ aryl-carbonyloxy group, a $C_{7-16}$ aralkyl-carbonyloxy group, a 5- to 14-membered aromatic heterocyclylcarbonyloxy group, a 3- to 14-membered non-aromatic heterocyclylcarbonyloxy group, a $C_{1-6}$ alkoxy-carbonyloxy group, a 5- to 14-membered aromatic heterocyclyloxy group, a carbamoyloxy group, a $C_{1-6}$ alkyl-carbamoyloxy group, a $C_{7-16}$ aralkyl-carbamoyloxy group, a $C_{1-6}$ alkylsulfonyloxy group, a $C_{6-14}$ arylsulfonyloxy group, an optionally substituted amino group, an optionally substituted sulfanyl group, an acyl group, an optionally substituted hydrocarbon group, and an optionally substituted heterocyclic group, ring B is a piperazine ring optionally substituted by 1 to 3 additional substituents selected from a halogen atom, a cyano group, a hydroxy group, a $C_{1-6}$ alkoxy group, a $C_{2-6}$ alkenyloxy group, a $C_{3-10}$ cycloalkyloxy group, a $C_{6-14}$ aryloxy group, a $C_{7-16}$ aralkyloxy group, a $C_{1-6}$ alkyl-carbonyloxy group, a $C_{6-14}$ aryl-carbonyloxy group, a $C_{7-16}$ aralkyl-carbonyloxy group, a 5- to 14-membered aromatic heterocyclylcarbonyloxy group, a 3- to 14-membered non-aromatic heterocyclylcarbonyloxy group, a $C_{1-6}$ alkoxy-carbonyloxy group, a 5- to 14-membered aromatic heterocyclyloxy group, a carbamoyloxy group, a $C_{1-6}$ alkyl-carbamoyloxy group, a $C_{7-16}$ aralkyl-carbamoyloxy group, a $C_{1-6}$ alkylsulfonyloxy group, a $C_{6-14}$ arylsulfonyloxy group, an optionally substituted amino group, an optionally substituted sulfanyl group, an acyl group, an optionally substituted hydrocarbon group, and an optionally substituted heterocyclic group, $R^1$ is an optionally substituted hydrocarbon group or an optionally substituted heterocyclic group, and $R^2$ is an acyl group, an optionally substituted $C_{6-14}$ aryl group, or an optionally substituted heterocyclic group, or a salt thereof.

2. The compound or salt according to claim 1, wherein ring A is a pyrrolidin-2-one ring optionally substituted by 1 or 2 additional substituents selected from a halogen atom, a hydroxy group and a $C_{1-6}$ alkyl group; and ring B is a piperazine ring optionally further substituted by 1 to 3 $C_{1-6}$ alkyl groups.

3. The compound or salt according to claim 1, wherein the both ring A and ring B are not substituted by the additional substituents.

4. The compound or salt according to claim 1, wherein $R^1$ is (1) a $C_{6-14}$ aryl group optionally substituted by 1 to 3 substituents selected from
  (i) an optionally substituted hydrocarbon group,
  (ii) an optionally substituted heterocyclic group,
  (iii) an acyl group,
  (iv) an optionally substituted amino group,
  (v) a hydroxy group, a $C_{1-6}$ alkoxy group, a $C_{2-6}$ alkenyloxy group, a $C_{3-10}$ cycloalkyloxy group, a $C_{6-14}$ aryloxy group, a $C_{7-16}$ aralkyloxy group, a $C_{1-6}$ alkyl-carbonyloxy group, a $C_{6-14}$ aryl-carbonyloxy group, a $C_{7-16}$ aralkyl-carbonyloxy group, a 5- to 14-membered aromatic heterocyclylcarbonyloxy group, a 3- to 14-membered non-aromatic heterocyclylcarbonyloxy group, a $C_{1-6}$ alkoxy-carbonyloxy group, a 5- to 14-membered aromatic heterocyclyloxy group, a carbamoyloxy group, a $C_{1-6}$ alkyl-carbamoyloxy group, a $C_{7-16}$ aralkyl-carbamoyloxy group, a $C_{1-6}$ alkylsulfonyloxy group and a $C_{6-14}$ arylsulfonyloxy group,
  (vi) a halogen atom, and
  (vii) a cyano group;

(2) a 5- to 14-membered aromatic heterocyclic group optionally substituted by 1 to 3 substituents selected from
  (i) an optionally substituted hydrocarbon group,
  (ii) an optionally substituted heterocyclic group,
  (iii) an acyl group,
  (iv) an optionally substituted amino group,
  (v) a hydroxy group, a $C_{1-6}$ alkoxy group, a $C_{2-6}$ alkenyloxy group, a $C_{3-10}$ cycloalkyloxy group, a $C_{6-14}$ aryloxy group, a $C_{7-16}$ aralkyloxy group, a $C_{1-6}$ alkyl-carbonyloxy group, a $C_{6-14}$ aryl-carbonyloxy group, a $C_{7-16}$ aralkyl-carbonyloxy group, a 5- to 14-membered aromatic heterocyclylcarbonyloxy group, a 3- to 14-membered non-aromatic heterocyclylcarbonyloxy group, a $C_{1-6}$ alkoxy-carbonyloxy group, a 5- to 14-membered aromatic heterocyclyloxy group, a carbamoyloxy group, a $C_{1-6}$ alkyl-carbamoyloxy group, a $C_{7-16}$ aralkyl-carbamoyloxy group, a $C_{1-6}$ alkylsulfonyloxy group and a $C_{6-14}$ arylsulfonyloxy group, and
  (vi) a halogen atom;

(3) a 3- to 14-membered non-aromatic heterocyclic group optionally substituted by 1 to 3 substituents selected from
  (i) an optionally substituted hydrocarbon group,
  (ii) an optionally substituted heterocyclic group,
  (iii) an acyl group, and
  (iv) a halogen atom;

(4) a $C_{1-6}$ alkyl group optionally substituted by 1 to 3 optionally substituted hydrocarbon groups, or (5) a $C_{3-10}$ cycloalkenyl group.

5. The compound or salt according to claim 1, wherein $R^1$ is (1) a $C_{6-14}$ aryl group optionally substituted by 1 to 3 substituents selected from
  (i) a $C_{6-14}$ aryloxy group optionally substituted by 1 to 3 substituents selected from
    (a) a $C_{1-6}$ alkoxy group, and
    (b) a halogen atom,
  (ii) a halogen atom,
  (iii) a cyano group,
  (iv) an optionally halogenated $C_{1-6}$ alkoxy group,
  (v) a $C_{1-6}$ alkyl group optionally substituted by 1 to 3 substituents selected from
    (a) a halogen atom,
    (b) a cyano group,
    (c) a $C_{6-14}$ aryl group, and
    (d) a 3- to 14-membered non-aromatic heterocyclic group optionally substituted by 1 to 3 $C_{1-6}$ alkyl groups,
  (vi) a $C_{7-16}$ aralkyloxy group,
  (vii) a $C_{3-10}$ cycloalkyl group,
  (viii) a $C_{6-14}$ aryl group optionally substituted by 1 to 5 substituents selected from
    (a) a halogen atom,
    (b) a cyano group,
    (c) a $C_{1-6}$ alkyl group optionally substituted by 1 to 3 substituents selected from a halogen atom, a hydroxy group and a carbamoyl group,
    (d) an optionally halogenated $C_{1-6}$ alkoxy group,
    (e) a carboxy group, (f) a mono- or di-$C_{1-6}$ alkyl-carbonylamino group,
(g) a mono- or di-$C_{1-6}$ alkylsulfonylamino group,
(h) a sulfamoyl group,
(i) a mono- or di-$C_{1-6}$ alkylsulfamoyl group,
(j) a carbamoyl group,
(k) a mono- or di-$C_{1-6}$ alkyl-carbamoyl group,
(l) a 3- to 14-membered non-aromatic heterocyclyl-carbonyl group,
(m) a $C_{6-14}$ aryl group,
(n) a $C_{6-14}$ aryloxy group, and
(o) a 3- to 14-membered non-aromatic heterocyclic group,
(ix) a 5- to 14-membered aromatic heterocyclic group optionally substituted by 1 to 3 substituents selected from
(a) a halogen atom,
(b) an optionally halogenated $C_{1-6}$ alkyl group, and
(c) a $C_{1-6}$ alkoxy group,
(x) a 3- to 14-membered non-aromatic heterocyclic group optionally substituted by 1 to 3 substituents selected from
(a) a $C_{1-6}$ alkyl group,
(b) a $C_{1-6}$ alkoxy group, and
(c) an oxo group,
(xi) a 5- to 14-membered aromatic heterocyclyloxy group,
(xii) a mono- or di-$C_{6-14}$ arylamino group optionally substituted by 1 to 3 substituents selected from
(a) a halogen atom,
(b) a mono- or di-$C_{1-6}$ alkyl-carbonylamino group,
(c) a ($C_{1-6}$ alkyl)($C_{1-6}$ alkyl-carbonyl)amino group, and
(d) a pyrrolidinyl group optionally substituted by 1 to 3 oxo groups,
(xiii) a mono- or di-$C_{6-14}$ aryl-carbamoyl group,
(xiv) a $C_{3-10}$ cycloalkylamino group, and
(xv) a 3- to 14-membered non-aromatic heterocyclylamino group optionally substituted by 1 to 3 substituents selected from
(a) a $C_{1-6}$ alkyl group,
(b) a $C_{1-6}$ alkyl-carbonyl group, and
(c) an oxo group,
(2) a 5- or 6-membered monocyclic aromatic heterocyclic group optionally substituted by 1 to 3 substituents selected from
(i) a halogen atom,
(ii) a $C_{6-14}$ aryl group,
(iii) a $C_{6-14}$ aryloxy group, and
(iv) a 5- to 14-membered aromatic heterocyclic group optionally substituted by 1 to 3 $C_{1-6}$ alkyl groups,
(3) a 8- to 14-membered fused polycyclic aromatic heterocyclic group or a 9- to 14-membered fused polycyclic non-aromatic heterocyclic group, each of which is optionally substituted by 1 to 3 substituents selected from
(i) a halogen atom,
(ii) a $C_{6-14}$ aryl group optionally substituted by 1 to 3 substituents selected from
(a) a halogen atom,
(b) an optionally halogenated $C_{1-6}$ alkyl group, and
(c) a $C_{1-6}$ alkoxy group,
(iii) a 5- to 14-membered aromatic heterocyclic group optionally substituted by 1 to 3 substituents selected from
(a) a halogen atom,
(b) an optionally halogenated $C_{1-6}$ alkyl group, and
(c) a $C_{1-6}$ alkoxy group,
(iv) a $C_{1-6}$ alkyl group optionally substituted by 1 to 3 $C_{6-14}$ aryl groups optionally substituted by 1 to 3 halogen atoms,
(v) a $C_{1-6}$ alkyl-carbonyl group optionally substituted by 1 to 3 substituents selected from
(a) a halogen atom,
(b) a $C_{6-14}$ aryl group optionally substituted by 1 to 3 halogen atoms,
(c) a $C_{3-10}$ cycloalkyl group,
(d) a 5- to 14-membered aromatic heterocyclic group optionally substituted by 1 to 3 substituents selected from a halogen atom and a $C_{1-6}$ alkoxy group, and
(e) a 3- to 14-membered non-aromatic heterocyclic group,
(vi) a $C_{1-6}$ alkoxy-carbonyl group,
(vii) a $C_{6-14}$ aryl-carbonyl group,
(viii) a 3- to 14-membered non-aromatic heterocyclyl-carbonyl group, and
(ix) a $C_{3-10}$ cycloalkyl group,
(4) a $C_{1-6}$ alkyl group optionally substituted by 1 to 3 $C_{6-14}$ aryl groups, or
(5) a $C_{3-10}$ cycloalkenyl group.

6. The compound or salt according to claim 1, wherein $R^2$ is
(1) a 5- to 14-membered aromatic heterocyclylcarbonyl group optionally substituted by 1 to 3 substituents selected from
(i) a halogen atom, and
(ii) a $C_{1-6}$ alkyl group,
(2) a 3- to 14-membered non-aromatic heterocyclylcarbonyl group,
(3) a $C_{1-6}$ alkyl-carbonyl group optionally substituted by 1 to 3 substituents selected from
(i) a halogen atom,
(ii) a mono- or di-$C_{1-6}$ alkylamino group, and
(iii) a 5- to 14-membered aromatic heterocyclic group,
(4) a $C_{6-14}$ aryl-carbonyl group,
(5) an optionally halogenated $C_{3-10}$ cycloalkyl-carbonyl group,
(6) a $C_{1-6}$ alkoxy-carbonyl group,
(7) a 5- to 14-membered aromatic heterocyclylsulfonyl group,
(8) a $C_{6-14}$ aryl group, or
(9) a 5- to 14-membered aromatic heterocyclic group optionally substituted by 1 to 3 cyano groups.

7. The compound or salt according to claim 1, wherein ring A is a pyrrolidin-2-one ring optionally substituted by 1 or 2 additional substituents selected from a halogen atom, a hydroxy group and a $C_{1-6}$ alkyl group;
ring B is a piperazine ring optionally further substituted by 1 to 3 $C_{1-6}$ alkyl groups;
$R^1$ is
(1) a $C_{6-14}$ aryl group optionally substituted by 1 to 3 substituents selected from
(i) a $C_{6-14}$ aryloxy group optionally substituted by 1 to 3 substituents selected from
(a) a $C_{1-6}$ alkoxy group, and
(b) a halogen atom,
(ii) a halogen atom,
(iii) a cyano group,
(iv) an optionally halogenated $C_{1-6}$ alkoxy group,
(v) a $C_{1-6}$ alkyl group optionally substituted by 1 to 3 substituents selected from
(a) a halogen atom,
(b) a cyano group,
(c) a $C_{6-14}$ aryl group, and (d) a 3- to 14-membered non-aromatic heterocyclic group optionally substituted by 1 to 3 $C_{1-6}$ alkyl groups,
(vi) a $C_{7-16}$ aralkyloxy group,
(vii) a $C_{3-10}$ cycloalkyl group,
(viii) a $C_{6-14}$ aryl group optionally substituted by 1 to 5 substituents selected from
  (a) a halogen atom,
  (b) a cyano group,
  (c) a $C_{1-6}$ alkyl group optionally substituted by 1 to 3 substituents selected from a halogen atom, a hydroxy group and a carbamoyl group,
  (d) an optionally halogenated $C_{1-6}$ alkoxy group,
  (e) a carboxy group,
  (f) a mono- or di-$C_{1-6}$ alkyl-carbonylamino group,
  (g) a mono- or di-$C_{1-6}$ alkylsulfonylamino group,
  (h) a sulfamoyl group,
  (i) a mono- or di-$C_{1-6}$ alkylsulfamoyl group,
  (j) a carbamoyl group,
  (k) a mono- or di-$C_{1-6}$ alkyl-carbamoyl group,
  (l) a 3- to 14-membered non-aromatic heterocyclyl-carbonyl group,
  (m) a $C_{6-14}$ aryl group,
  (n) a $C_{6-14}$ aryloxy group, and
  (o) a 3- to 14-membered non-aromatic heterocyclic group,
(ix) a 5- to 14-membered aromatic heterocyclic group optionally substituted by 1 to 3 substituents selected from
  (a) a halogen atom,
  (b) an optionally halogenated $C_{1-6}$ alkyl group, and
  (c) a $C_{1-6}$ alkoxy group,
(x) a 3- to 14-membered non-aromatic heterocyclic group optionally substituted by 1 to 3 substituents selected from
  (a) a $C_{1-6}$ alkyl group,
  (b) a $C_{1-6}$ alkoxy group, and
  (c) an oxo group,
(xi) a 5- to 14-membered aromatic heterocyclyloxy group,
(xii) a mono- or di-$C_{6-14}$ arylamino group optionally substituted by 1 to 3 substituents selected from
  (a) a halogen atom,
  (b) a mono- or di-$C_{1-6}$ alkyl-carbonylamino group,
  (c) a ($C_{1-6}$ alkyl)($C_{1-6}$ alkyl-carbonyl)amino group, and
  (d) a pyrrolidinyl group optionally substituted by 1 to 3 oxo groups,
(xiii) a mono- or di-$C_{6-14}$ aryl-carbamoyl group,
(xiv) a $C_{3-10}$ cycloalkylamino group, and
(xv) a 3- to 14-membered non-aromatic heterocyclylamino group optionally substituted by 1 to 3 substituents selected from
  (a) a $C_{1-6}$ alkyl group,
  (b) a $C_{1-6}$ alkyl-carbonyl group, and
  (c) an oxo group,
(2) a 5- or 6-membered monocyclic aromatic heterocyclic group optionally substituted by 1 to 3 substituents selected from
  (i) a halogen atom,
  (ii) a $C_{6-14}$ aryl group,
  (iii) a $C_{6-14}$ aryloxy group, and
  (iv) a 5- to 14-membered aromatic heterocyclic group optionally substituted by 1 to 3 $C_{1-6}$ alkyl groups,
(3) a 8- to 14-membered fused polycyclic aromatic heterocyclic group or a 9- to 14-membered fused polycyclic non-aromatic heterocyclic group, each of which is optionally substituted by 1 to 3 substituents selected from
  (i) a halogen atom,
  (ii) a $C_{6-14}$ aryl group optionally substituted by 1 to 3 substituents selected from
    (a) a halogen atom,
    (b) an optionally halogenated $C_{1-6}$ alkyl group, and
    (c) a $C_{1-6}$ alkoxy group,
  (iii) a 5- to 14-membered aromatic heterocyclic group optionally substituted by 1 to 3 substituents selected from
    (a) a halogen atom,
    (b) an optionally halogenated $C_{1-6}$ alkyl group, and
    (c) a $C_{1-6}$ alkoxy group,
  (iv) a $C_{1-6}$ alkyl group optionally substituted by 1 to 3 $C_{6-14}$ aryl groups optionally substituted by 1 to 3 halogen atoms,
  (v) a $C_{1-6}$ alkyl-carbonyl group optionally substituted by 1 to 3 substituents selected from
    (a) a halogen atom,
    (b) a $C_{6-14}$ aryl group optionally substituted by 1 to 3 halogen atoms,
    (c) a $C_{3-10}$ cycloalkyl group,
    (d) a 5- to 14-membered aromatic heterocyclic group optionally substituted by 1 to 3 substituents selected from a halogen atom and a $C_{1-6}$ alkoxy group, and
    (e) a 3- to 14-membered non-aromatic heterocyclic group,
  (vi) a $C_{1-6}$ alkoxy-carbonyl group,
  (vii) a $C_{6-14}$ aryl-carbonyl group,
  (viii) a 3- to 14-membered non-aromatic heterocyclyl-carbonyl group, and
  (ix) a $C_{3-10}$ cycloalkyl group,
(4) a $C_{1-6}$ alkyl group optionally substituted by 1 to 3 $C_{6-14}$ aryl groups, or
(5) a $C_{3-10}$ cycloalkenyl group; and
$R^2$ is
(1) a 5- to 14-membered aromatic heterocyclylcarbonyl group optionally substituted by 1 to 3 substituents selected from
  (i) a halogen atom, and
  (ii) a $C_{1-6}$ alkyl group,
(2) a 3- to 14-membered non-aromatic heterocyclylcarbonyl group,
(3) a $C_{1-6}$ alkyl-carbonyl group optionally substituted by 1 to 3 substituents selected from
  (i) a halogen atom,
  (ii) a mono- or di-$C_{1-6}$ alkylamino group, and
  (iii) a 5- to 14-membered aromatic heterocyclic group,
(4) a $C_{6-14}$ aryl-carbonyl group,
(5) an optionally halogenated $C_{3-10}$ cycloalkyl-carbonyl group,
(6) a $C_{1-6}$ alkoxy-carbonyl group,
(7) a 5- to 14-membered aromatic heterocyclylsulfonyl group,
(8) a $C_{6-14}$ aryl group, or
(9) a 5- to 14-membered aromatic heterocyclic group optionally substituted by 1 to 3 cyano groups.

8. The compound or salt according to claim 1, wherein ring A is a pyrrolidin-2-one ring optionally substituted by 1 or 2 additional substituents selected from a halogen atom, a hydroxy group and a $C_{1-6}$ alkyl group;
ring B is a piperazine ring optionally further substituted by 1 to 3 $C_{1-6}$ alkyl groups;

R¹ is
(1) a phenyl group or a naphthyl group, each of which is optionally substituted by 1 to 3 substituents selected from
  (i) a phenoxy group optionally substituted by 1 to 3 substituents selected from
    (a) a $C_{1-6}$ alkoxy group, and
    (b) a halogen atom,
  (ii) a halogen atom,
  (iii) a cyano group,
  (iv) an optionally halogenated $C_{1-6}$ alkoxy group,
  (v) a $C_{1-6}$ alkyl group optionally substituted by 1 to 3 substituents selected from
    (a) a halogen atom,
    (b) a cyano group,
    (c) a phenyl group,
    (d) a piperazinyl group optionally substituted by 1 to 3 $C_{1-6}$ alkyl groups, and
    (e) a morpholinyl group,
  (vi) a benzyloxy group,
  (vii) a $C_{3-10}$ cycloalkyl group,
  (viii) a phenyl group optionally substituted by 1 to 5 substituents selected from
    (a) a halogen atom,
    (b) a cyano group,
    (c) a $C_{1-6}$ alkyl group optionally substituted by 1 to 3 substituents selected from a halogen atom, a hydroxy group and a carbamoyl group,
    (d) an optionally halogenated $C_{1-6}$ alkoxy group,
    (e) a carboxy group,
    (f) a mono- or di-$C_{1-6}$ alkyl-carbonylamino group,
    (g) a mono- or di-$C_{1-6}$ alkylsulfonylamino group,
    (h) a sulfamoyl group,
    (i) a mono- or di-$C_{1-6}$ alkylsulfamoyl group,
    (j) a carbamoyl group,
    (k) a mono- or di-$C_{1-6}$ alkyl-carbamoyl group,
    (l) a pyrrolidinylcarbonyl group,
    (m) a phenyl group,
    (n) a phenoxy group, and
    (o) a morpholinyl group,
  (ix) a pyridyl group optionally substituted by 1 to 3 substituents selected from
    (a) a halogen atom,
    (b) an optionally halogenated $C_{1-6}$ alkyl group, and
    (c) a $C_{1-6}$ alkoxy group,
  (x) a dihydropyridyl group optionally substituted by 1 to 3 substituents selected from
    (a) a $C_{1-6}$ alkyl group, and
    (b) an oxo group,
  (xi) a thiazolyl group optionally substituted by 1 to 3 optionally halogenated $C_{1-6}$ alkyl groups,
  (xii) a morpholinyl group,
  (xiii) a pyridyloxy group,
  (xiv) a mono- or di-phenylamino group optionally substituted by 1 to 3 substituents selected from
    (a) a halogen atom,
    (b) a mono- or di-$C_{1-6}$ alkyl-carbonylamino group,
    (c) a ($C_{1-6}$ alkyl)($C_{1-6}$ alkyl-carbonyl)amino group, and
    (d) a pyrrolidinyl group optionally substituted by 1 to 3 oxo groups,
  (xv) a mono- or di-phenylcarbamoyl group,
  (xvi) a thienyl group optionally substituted by 1 to 3 substituents selected from
    (a) an optionally halogenated $C_{1-6}$ alkyl group, and
    (b) a $C_{1-6}$ alkoxy group,
  (xvii) a furyl group,
  (xviii) a pyrazinyl group optionally substituted by 1 to 3 $C_{1-6}$ alkyl groups,
  (xix) a pyrazolyl group optionally substituted by 1 to 3 optionally halogenated $C_{1-6}$ alkyl groups,
  (xx) a pyrimidinyl group optionally substituted by 1 to 3 $C_{1-6}$ alkyl groups,
  (xxi) an isoxazolyl group optionally substituted by 1 to 3 $C_{1-6}$ alkyl groups,
  (xxii) an imidazolyl group optionally substituted by 1 to 3 $C_{1-6}$ alkyl groups,
  (xxiii) a naphthyl group,
  (xxiv) a dihydroindolyl group optionally substituted by 1 to 3 substituents selected from
    (a) a $C_{1-6}$ alkyl group,
    (b) a $C_{1-6}$ alkoxy group, and
    (c) an oxo group,
  (xxv) an indolyl group,
  (xxvi) an indazolyl group optionally substituted by 1 to 3 $C_{1-6}$ alkyl groups,
  (xxvii) an imidazopyridyl group optionally substituted by 1 to 3 $C_{1-6}$ alkyl groups,
  (xxviii) an isobenzothiazolyl group,
  (xxix) a pyrazolopyridyl group,
  (xxx) a thienopyridyl group,
  (xxxi) a dihydropyrrolopyridyl group optionally substituted by 1 to 3 oxo group,
  (xxxii) a pyrrolopyridyl group optionally substituted by 1 to 3 $C_{1-6}$ alkoxy groups,
  (xxxiii) a benzothiophenyl group,
  (xxxiv) a benzofuranyl group,
  (xxxv) a dihydrobenzofuranyl group,
  (xxxvi) a $C_{3-10}$ cycloalkylamino group,
  (xxxvii) a piperidylamino group optionally substituted by 1 to 3 substituents selected from
    (a) a $C_{1-6}$ alkyl group,
    (b) a $C_{1-6}$ alkyl-carbonyl group, and
    (c) an oxo group,
  (xxxviii) a tetrahydropyranylamino group,
  (xxxix) a 1,4-dihydrobenzoxazinylamino group optionally substituted by 1 to 3 oxo groups, and
  (xxxx) a tetrahydroquinolylamino group optionally substituted by 1 to 3 oxo groups,
(2) a pyridyl group, an imidazolyl group or a pyrazolyl group, each of which is optionally substituted by 1 to 3 substituents selected from
  (i) a halogen atom,
  (ii) a phenyl group,
  (iii) a phenoxy group, and
  (iv) a pyridyl group optionally substituted by 1 to 3 $C_{1-6}$ alkyl groups,
(3) an indolyl group, an indazolyl group, a pyrrolopyridyl group, a dibenzofuranyl group, an imidazopyridyl group, a dihydroindolyl group, a benzothiophenyl group or a benzoxazolyl group, each of which is optionally substituted by 1 to 3 substituents selected from
  (i) a halogen atom,
  (ii) a phenyl group optionally substituted by 1 to 3 substituents selected from
    (a) a halogen atom,
    (b) an optionally halogenated $C_{1-6}$ alkyl group, and
    (c) a $C_{1-6}$ alkoxy group,
  (iii) a pyridyl group optionally substituted by 1 to 3 substituents selected from
    (a) a halogen atom, and
    (b) an optionally halogenated $C_{1-6}$ alkyl group, (iv) a pyrimidinyl group optionally substituted by 1 to 3 substituents selected from
  (a) a halogen atom,
  (b) an optionally halogenated $C_{1-6}$ alkyl group, and
  (c) a $C_{1-6}$ alkoxy group,
(v) a pyridazinyl group optionally substituted by 1 to 3 optionally halogenated $C_{1-6}$ alkyl groups,
(vi) a pyrazinyl group optionally substituted by 1 to 3 optionally halogenated $C_{1-6}$ alkyl groups,
(vii) a $C_{1-6}$ alkyl group optionally substituted by 1 to 3 phenyl groups optionally substituted by 1 to 3 halogen atoms,
(viii) a $C_{1-6}$ alkyl-carbonyl group optionally substituted by 1 to 3 substituents selected from
  (a) a halogen atom,
  (b) a phenyl group optionally substituted by 1 to 3 halogen atoms,
  (c) a $C_{3-10}$ cycloalkyl group,
  (d) a pyridyl group optionally substituted by 1 to 3 substituents selected from a halogen atom and a $C_{1-6}$ alkoxy group, and
  (e) a tetrahydropyranyl group,
(ix) a $C_{1-6}$ alkoxy-carbonyl group,
(x) a benzoyl group,
(xi) a tetrahydropyranylcarbonyl group, and
(xii) a $C_{3-10}$ cycloalkyl group,
(4) a $C_{1-6}$ alkyl group optionally substituted by 1 to 3 phenyl groups, or
(5) a $C_{3-10}$ cycloalkenyl group; and
$R^2$ is
(1) a thiazolylcarbonyl group, a thienylcarbonyl group, a furylcarbonyl group, a pyrrolylcarbonyl group, a pyrazolylcarbonyl group, an imidazolylcarbonyl group, an oxazolylcarbonyl group or a quinolylcarbonyl group, each of which is optionally substituted by 1 to 3 substituents selected from
  (i) a halogen atom, and
  (ii) a $C_{1-6}$ alkyl group,
(2) a pyrrolidinylcarbonyl group,
(3) a $C_{1-6}$ alkyl-carbonyl group optionally substituted by 1 to 3 substituents selected from
  (i) a halogen atom,
  (ii) a mono- or di-$C_{1-6}$ alkylamino group, and
  (iii) a pyridyl group,
(4) a benzoyl group,
(5) an optionally halogenated $C_{3-10}$ cycloalkyl-carbonyl group,
(6) a $C_{1-6}$ alkoxy-carbonyl group,
(7) a pyridylsulfonyl group,
(8) a phenyl group, or
(9) a pyridyl group or a pyrimidinyl group, each of which is optionally substituted by 1 to 3 cyano groups.

9. The compound or salt according to claim 1, wherein ring A is a pyrrolidin-2-one ring optionally substituted by 1 or 2 additional substituents selected from a halogen atom, a hydroxy group and a $C_{1-6}$ alkyl group;
ring B is a piperazine ring optionally further substituted by 1 to 3 $C_{1-6}$ alkyl groups;
$R^1$ is
(1) a phenyl group or a naphthyl group, each of which is optionally substituted by 1 to 3 substituents selected from
  (i) a phenoxy group optionally substituted by 1 to 3 substituents selected from
    (a) a $C_{1-6}$ alkoxy group, and
    (b) a halogen atom,
  (ii) a halogen atom,
  (iii) an optionally halogenated $C_{1-6}$ alkoxy group,
  (iv) a $C_{1-6}$ alkyl group optionally substituted by 1 to 3 phenyl groups,
  (v) a benzyloxy group,
  (vi) a $C_{3-10}$ cycloalkyl group,
  (vii) a phenyl group optionally substituted by 1 to 5 substituents selected from
    (a) a halogen atom,
    (b) a cyano group,
    (c) a $C_{1-6}$ alkyl group optionally substituted by 1 to 3 substituents selected from a halogen atom, a hydroxy group and a carbamoyl group,
    (d) an optionally halogenated $C_{1-6}$ alkoxy group,
    (e) a carboxy group,
    (f) a mono- or di-$C_{1-6}$ alkyl-carbonylamino group,
    (g) a mono- or di-$C_{1-6}$ alkylsulfonylamino group,
    (h) a sulfamoyl group,
    (i) a mono- or di-$C_{1-6}$ alkylsulfamoyl group,
    (j) a carbamoyl group,
    (k) a mono- or di-$C_{1-6}$ alkyl-carbamoyl group,
    (l) a pyrrolidinylcarbonyl group,
    (m) a phenyl group,
    (n) a phenoxy group, and
    (o) a morpholinyl group,
  (viii) a pyridyl group optionally substituted by 1 to 3 substituents selected from
    (a) a halogen atom,
    (b) an optionally halogenated $C_{1-6}$ alkyl group, and
    (c) a $C_{1-6}$ alkoxy group,
  (ix) a thiazolyl group optionally substituted by 1 to 3 optionally halogenated $C_{1-6}$ alkyl groups,
  (x) a pyridyloxy group,
  (xi) a mono- or di-phenylamino group optionally substituted by 1 to 3 substituents selected from
    (a) a halogen atom,
    (b) a mono- or di-$C_{1-6}$ alkyl-carbonylamino group,
    (c) a ($C_{1-6}$ alkyl)($C_{1-6}$ alkyl-carbonyl)amino group, and
    (d) a pyrrolidinyl group optionally substituted by 1 to 3 oxo groups,
  (xii) a thienyl group optionally substituted by 1 to 3 substituents selected from
    (a) an optionally halogenated $C_{1-6}$ alkyl group, and
    (b) a $C_{1-6}$ alkoxy group,
  (xiii) a furyl group,
  (xiv) a pyrazinyl group optionally substituted by 1 to 3 $C_{1-6}$ alkyl groups,
  (xv) a pyrazolyl group optionally substituted by 1 to 3 optionally halogenated $C_{1-6}$ alkyl groups,
  (xvi) a pyrimidinyl group optionally substituted by 1 to 3 $C_{1-6}$ alkyl groups,
  (xvii) an isoxazolyl group optionally substituted by 1 to 3 $C_{1-6}$ alkyl groups,
  (xviii) an imidazolyl group optionally substituted by 1 to 3 $C_{1-6}$ alkyl groups,
  (xix) a naphthyl group,
  (xx) a dihydroindolyl group optionally substituted by 1 to 3 substituents selected from
    (a) a $C_{1-6}$ alkyl group,
    (b) a $C_{1-6}$ alkoxy group, and
    (c) an oxo group,
  (xxi) an indolyl group,
  (xxii) an indazolyl group optionally substituted by 1 to 3 $C_{1-6}$ alkyl groups,
  (xxiii) an imidazopyridyl group optionally substituted by 1 to 3 $C_{1-6}$ alkyl groups,
  (xxiv) an isobenzothiazolyl group, (xxv) a pyrazolopyridyl group,
(xxvi) a thienopyridyl group,
(xxvii) a dihydropyrrolopyridyl group optionally substituted by 1 to 3 oxo groups,
(xxviii) a pyrrolopyridyl group optionally substituted by 1 to 3 $C_{1-6}$ alkoxy groups,
(xxix) a benzothiophenyl group,
(xxx) a benzofuranyl group,
(xxxi) a dihydrobenzofuranyl group,
(xxxii) a $C_{3-10}$ cycloalkylamino group,
(xxxiii) a piperidylamino group optionally substituted by 1 to 3 substituents selected from
  (a) a $C_{1-6}$ alkyl group, and
  (b) an oxo group,
(xxxiv) a 1,4-dihydrobenzoxazinylamino group optionally substituted by 1 to 3 oxo groups, and
(xxxv) a tetrahydroquinolylamino group optionally substituted by 1 to 3 oxo groups,
(2) a pyridyl group optionally substituted by 1 to 3 substituents selected from
  (i) a halogen atom,
  (ii) a phenyl group,
  (iii) a phenoxy group, and
  (iv) a pyridyl group optionally substituted by 1 to 3 $C_{1-6}$ alkyl groups, or
(3) an indolyl group, an indazolyl group, a pyrrolopyridyl group, a dibenzofuranyl group, a dihydroindolyl group, a benzothiophenyl group or a benzoxazolyl group, each of which is optionally substituted by 1 to 3 substituents selected from
  (i) a halogen atom,
  (ii) a phenyl group optionally substituted by 1 to 3 substituents selected from
    (a) a halogen atom,
    (b) an optionally halogenated $C_{1-6}$ alkyl group, and
    (c) a $C_{1-6}$ alkoxy group,
  (iii) a pyridyl group optionally substituted by 1 to 3 substituents selected from
    (a) a halogen atom, and
    (b) an optionally halogenated $C_{1-6}$ alkyl group,
  (iv) a pyrimidinyl group optionally substituted by 1 to 3 substituents selected from
    (a) a halogen atom,
    (b) an optionally halogenated $C_{1-6}$ alkyl group, and
    (c) a $C_{1-6}$ alkoxy group,
  (v) a pyridazinyl group optionally substituted by 1 to 3 optionally halogenated $C_{1-6}$ alkyl groups,
  (vi) a pyrazinyl group optionally substituted by 1 to 3 optionally halogenated $C_{1-6}$ alkyl groups,
  (vii) a $C_{1-6}$ alkyl group optionally substituted by 1 to 3 phenyl groups optionally substituted by 1 to 3 halogen atoms,
  (viii) a $C_{1-6}$ alkyl-carbonyl group optionally substituted by 1 to 3 substituents selected from
    (a) a halogen atom,
    (b) a phenyl group optionally substituted by 1 to 3 halogen atoms,
    (c) a $C_{3-10}$ cycloalkyl group,
    (d) a pyridyl group optionally substituted by 1 to 3 substituents selected from a halogen atom and a $C_{1-6}$ alkoxy group, and
    (e) a tetrahydropyranyl group,
  (ix) a $C_{1-6}$ alkoxy-carbonyl group,
  (x) a benzoyl group,
  (xi) a tetrahydropyranylcarbonyl group, and
  (xii) a $C_{3-10}$ cycloalkyl group; and
$R^2$ is
(1) a thiazolylcarbonyl group, a thienylcarbonyl group, a furylcarbonyl group or an oxazolylcarbonyl group, each of which is optionally substituted by 1 to 3 halogen atoms,
(2) a pyrrolidinylcarbonyl group, or
(3) a pyridyl group or a pyrimidinyl group, each of which is optionally substituted by 1 to 3 cyano groups.

10. The compound or salt according to claim 1, wherein ring A is a pyrrolidin-2-one ring not substituted by the additional substituents;
ring B is a piperazine ring not substituted by the additional substituents;
$R^1$ is
(1) a phenyl group substituted by 1 to 3 substituents selected from
  (i) a halogen atom, and
  (ii) a pyridyl group substituted by 1 to 3 $C_{1-6}$ alkyl groups, or
(2) an indolyl group or an indazolyl group, each of which is substituted by 1 to 3 substituents selected from
  (i) a phenyl group substituted by 1 to 3 substituents selected from
    (a) a halogen atom, and
    (b) a halogenated $C_{1-6}$ alkyl group, and
  (ii) a pyrimidinyl group substituted by 1 to 3 halogenated $C_{1-6}$ alkyl groups; and
$R^2$ is a thiazolylcarbonyl group or a pyrimidinyl group.

11. (4R)-4-(4-(1,3-thiazol-2-ylcarbonyl)piperazin-1-yl)-1-(1-(5-(trifluoromethyl) pyrimidin-2-yl)-1H-indol-5-yl) pyrrolidin-2-one, or a salt thereof.

12. (4R)-4-(4-(1,3-thiazol-4-ylcarbonyl)piperazin-1-yl)-1-(1-(4-(trifluoromethyl) phenyl)-1H-indol-5-yl)pyrrolidin-2-one, or a salt thereof.

13. (4R)-1-(3-fluoro-5-(2-methylpyridin-3-yl)phenyl)-4-(4-(pyrimidin-2-yl) piperazin-1-yl)pyrrolidin-2-one, or a salt thereof.

14. A medicament comprising the compound or salt according to claim 1.

15. A method of inhibiting monoacylglycerol lipase in a mammal, comprising administering an effective amount of the compound or salt according to claim 1 to the mammal.

16. A method of treating Alzheimer's disease, Parkinson's disease, pain or epilepsy in a mammal, comprising administering an effective amount of the compound or salt according to claim 1 to the mammal.

* * * * *